US007410777B2

United States Patent

(12) United States Patent
Liaw et al.
(10) Patent No.: US 7,410,777 B2
(45) Date of Patent: *Aug. 12, 2008

(54) NON-ENDOGENOUS, CONSTITUTIVELY ACTIVATED HUMAN G PROTEIN-COUPLED RECEPTORS

(75) Inventors: Chen W. Liaw, San Diego, CA (US); Dominic P. Behan, San Diego, CA (US); Derek T. Chalmers, Riverside, CT (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 660 days.

This patent is subject to a terminal disclaimer.

(21) Appl. No.: 10/251,385

(22) Filed: Sep. 20, 2002

(65) Prior Publication Data

US 2003/0105292 A1 Jun. 5, 2003

Related U.S. Application Data

(63) Continuation of application No. 09/170,496, filed on Oct. 13, 1998, now Pat. No. 6,555,339, which is a continuation-in-part of application No. 09/060,188, filed on Apr. 14, 1998, which is a continuation-in-part of application No. 08/839,449, filed on Apr. 14, 1997, now abandoned.

(60) Provisional application No. 60/090,783, filed on Jun. 26, 1998, provisional application No. 60/095,677, filed on Aug. 7, 1998.

(51) Int. Cl.

| | |
|---|---|
| ***C07K 14/435*** | (2006.01) |
| ***C07K 14/705*** | (2006.01) |
| ***C07K 14/72*** | (2006.01) |
| ***G01N 33/566*** | (2006.01) |
| ***C07D 409/12*** | (2006.01) |
| ***C07D 409/00*** | (2006.01) |
| ***C07D 231/16*** | (2006.01) |
| ***C07D 231/00*** | (2006.01) |
| ***C07D 231/12*** | (2006.01) |

(52) U.S. Cl. .................. 435/69.1; 435/320.1; 435/325; 435/252.3; 435/172.3; 435/68.1; 530/333; 530/350; 702/19; 702/20; 702/22; 536/23.1; 536/24.31

(58) Field of Classification Search ....................... None
See application file for complete search history.

(56) References Cited

U.S. PATENT DOCUMENTS

| | | | | |
|---|---|---|---|---|
| 5,514,578 | A | 5/1996 | Hogness et al. | |
| 5,532,157 | A | 7/1996 | Fink | |
| 5,573,944 | A | 11/1996 | Kirschner et al. | |
| 5,639,616 | A | 6/1997 | Liao et al. | |
| 5,750,353 | A | 5/1998 | Kopin et al. | |
| 5,861,309 | A | 1/1999 | Bard et al. | |
| 5,891,720 | A | 4/1999 | Moore et al. | |
| 5,955,308 | A | 9/1999 | Bergsma et al. | |
| 6,555,339 | B1 * | 4/2003 | Liaw et al. | 435/69.1 |

FOREIGN PATENT DOCUMENTS

| | | | |
|---|---|---|---|
| CA | 2135253 | | 5/1996 |
| EP | 0 612 845 | A2 | 8/1994 |
| EP | 0 878 542 | A3 | 11/1998 |
| EP | 1 094 076 | A1 | 4/2001 |
| EP | 1 090 989 | A1 | 11/2001 |
| WO | WO96/05302 | | 2/1996 |
| WO | WO97/11159 | | 3/1997 |
| WO | WO 97/021731 | | 6/1997 |
| WO | WO97/21731 | | 6/1997 |
| WO | WO98/00552 | | 1/1998 |
| WO | WO98/29439 | | 7/1998 |
| WO | WO98/34948 | | 8/1998 |
| WO | WO98/38217 | | 9/1998 |
| WO | WO98/46620 | | 10/1998 |
| WO | WO98/46995 | | 10/1998 |

(Continued)

OTHER PUBLICATIONS

Samama et. al., The Journal of Biological Chemistry, vol. 268, No. 7, pp. 4625-4636, 1993.*

(Continued)

*Primary Examiner*—Gary B. Nickol
*Assistant Examiner*—Nirmal S Basi
(74) *Attorney, Agent, or Firm*—David C. Scherer; Bozicevic Field & Francis LLP.

(57) ABSTRACT

Disclosed herein are constitutively activated, non-endogenous versions of endogenous human G protein-coupled receptors comprising (a) the following amino acid sequence region (C-terminus to N-terminus orientation) and/or (b) the following nucleic acid sequence region (3' to 5' orientation) transversing the transmembrane-6 (TM6) and intracellular loop-3 (IC3) regions of the GPCR:

(a) $P^1$ $AA_{15}X$ and/or (b) $p^{codon}$ $(AA\text{-codon})_{15}$ $X_{codon}$, respectively. In a most preferred embodiment, $P^1$ and $P^{codon}$ are endogenous proline and an endogenous nucleic acid encoding region encoding proline, respectively, located within TM6 of the non-endogenous GPCR; $AA_{15}$ and $(AA\text{-codon})_{15}$ are 15 endogenous amino acid residues and 15 codons encoding endogenous amino acid residues, respectively; and X and $X_{codon}$ are non-endogenous lysine and a non-endogenous nucleic acid encoding region encoding lysine, respectively, located within IC3 of the non-endogenous GPCR. Because it is most preferred that the non-endogenous human GPCRs which incorporate these mutations are incorporated into mammalian cells and utilized for the screening of candidate compounds, the non-endogenous human GPCR incorporating the mutation need not be purified and isolated per se (i.e., these are incorporated within the cellular membrane of a mammalian cell), although such purified and isolated non-endogenous human GPCRs are well within the purview of this disclosure.

10 Claims, 17 Drawing Sheets

FOREIGN PATENT DOCUMENTS

| | | |
|---|---|---|
| WO | WO98/56820 | 12/1998 |
| WO | WO99/06552 | 2/1999 |
| WO | WO99/24569 | 5/1999 |
| WO | WO99/32519 | 7/1999 |
| WO | WO99/48921 | 9/1999 |
| WO | WO99/52927 | 10/1999 |
| WO | WO00/14229 | 3/2000 |
| WO | WO00/22131 | 4/2000 |
| WO | WO00/49046 | 8/2000 |
| WO | WO01/07606 | 2/2001 |
| WO | WO01/09184 | 2/2001 |
| WO | WO01/12673 | 2/2001 |
| WO | WO01/14577 | 3/2001 |
| WO | WO01/16159 | 3/2001 |
| WO | WO01/31014 | 5/2001 |
| WO | WO01/36471 | 5/2001 |

OTHER PUBLICATIONS

Kjelsberg et. al., The Journal of Biological Chemistry, vol. 267, No. 3, pp. 1430-1433, 1992.*
Pei et al, Proc. Natl. Acad. Sci. USA. vol. 91 pp. 2699-2702,1994.*
Abola, et al. EMBL Accession No. AC026756, Apr. 24, 2001.
Adams et al, EMBL Accession No. AQ001459, Aug. 24, 2001.
Birren et al, EMBL Accession No. AC027026, Apr. 27, 2000.
Birren et al, EMBL Accession No. AC011780, Oct. 18, 1999.
Birren et al, EMBL Acession No. AC016468, Dec. 1, 1999.
Boyer, et al, "Molecular cloning and expression of an avian G protein-coupledP2Y receptor," Am. Soc. Pharmacol. Exptal. Therapeutics (1997) 928-934.
Burton et al., EMBL Accession No. A1161458, Apr. 16, 2000.
Burton, et al., EMBL Accession No. AL136106, Jan. 7, 2000.
Collier, R., EMBL Accession No. Q9NTTO, Jan. 10, 2001.
Doe Joint Genome Institute, EMBL Accession No. AC008547, Aug. 4, 1999.
Doe Joint Genome Institute, EMBL Accession No. AC008754, Aug. 4, 1999.
Doe Joint Genome Institute, EMBL Accession No. AC008728, Aug. 4, 1999.
Hattori, M., et al., EMBL Accession No. AP000808, Dec. 3, 1999.
Heise, C.E., et al., "Characterization of the human cysteinyl leukotriene 2 receptor," J. Biological Chemistry, Sep. 29, 2000, 275(39), 30531-30536.
Kjelsberg, M.A., et al., "constitutive activation of the α1B-adrenergic receptor by all amino acid substitutions at a single site," J. Biological Chemistry, XP-002135768, 1992, 265(3), 1430-1433.
Mahairas, G.G., et al., "Sequence-tagged connectors: A sequence approach to mapping and scanning the human genome," Proc. Natl. Acad. Sci. USA, Aug. 1999, 96, 9739-9744.
Marchese, A., et al., "Novel GPCRs and their endogenous ligands: expanding the boundaries of physiology and pharmacology," TiPS, Sep. 1999, 20, 370-375.
O'Dowd, B.F., et al., "Discovery of three novel G-protein-coupled receptor genes," Genomics, XP-000863786, 1998, 310-313.
Ohono, M., et al., EMBL Accession No. AB038237, May 4, 2000.
Stadel, J.M., et al., "Orphan G protein-coupled receptors: a neglected opportunity for pioneer drug discovery," TiPS, Nov. 1997, 18, 430-437.
Stone, N., et al., EMBL Accession No. AC007104, Apr. 23, 1999.
Wallis, J., EMBL Accession No. AL355310, May 5, 2000.
Waterson, R.H., EMBL Accession No. AC010984, Sep. 29, 1999.
Weinshank, R.H., EMBL Accession No. AC 008892, Jul. 15, 1998.
Zhao, S., et al., EMBL Accession No. AQ532303, May 18, 1999.
Shryock, John et al., "Inverse Agonists and Neutral Antagonists of Recombinant Human A1 Adenosine Receptors Stably Expressed in Chinese Hamseter Overy Cells," Molecular Pharmacology, 1998, 53 pp. 886-893.
Wenzel-Seifert et al., "High Constitutve Activity of the Human Formyl Peptide Receptor", Journal of Biological Chem., 1998, 273 pp. 24181-24189.
Forman, B.M., et al., "Androstane Metabolities Bind to and Deactivate the Nuclear Receptor CAR-B", Nature, 1998 395, pp. 612-615.
Seifert R. et al., Different Effects of Gxa Splice Variants on B2-Adrenoreceptor-mediated Signaling, Journal of Biological Chem., 1998, 273, pp. 5109-5116.
Pauwels, P.J., et al., "Review: Amino Acid Domains Involved in Constitutive Activation of G-Protein-Coupled Receptors", Molecular Neurobiology, 1998, 17 pp. 109-135.
Alla, S.A. et al., "Extracellular domains of the bradykinin B2 receptor involved in ligand binding and agonist sensing defined by anti-peptide antibodies," J. Biol. Chem., 1996, 271, 1748-1755.
Advenier, C. et al., "Effects on the isolated human bronchus of SR 48968, a potent and selective nonpeptide antagonist of the neurokinin A (NK2) receptors," Am. Rev. Respir. Dis., 1992, 146 (5, Pt. 1), 1177-1181.
Alexander, W.S. et a., "Point mutations within the dimer interfact homology domain of c-Mpl include constitutive receptor activity and tumorigenicity," EMBO J., 1995, 14(22) 5569-5578.
Arvanitkis, L. et al., "Human herpesvirus KSHV encodes a constitutively actige G-protein-coupled receptor agonist activity of receptor ligands," J. Biol. Chem. 1994, 269(16), 11687-11690.
Barker, E.L. et al., "Constitutively active 5-hydroxytryptamine 2c receptors reveal novel inverse agonist activity of receptor ligands," J. Biol. Chem., 1994, 269(16), 11687-11690.
Baxter, G., "5-HT2 receptors: a family re-united?" Trends Pharmacol. Sci. 1995, 16, 105-110.
Besmer, P. et al., "A new acute transforming feline retrovirus and relationship of its oncogene v-kit with the protein kinase gene family," Nature, 1986, 320, 415.
Blin, N. et al., "Mapping of single amino acid residues required for selective activation of G_by the m3 muscarinic acetylcholine reeptor," J. Biol. Chem., 1995, 270, 17741-17748.
Bond, R.A. et al., "Inverse agonists an G-protein-coupled receptors," in Receptor-Based Drug Design, Leff, P. (ed.), New York, M. Dekker, 1998, 363-377.
Boone, C. et al., "Mutuations that alter the third cytoplasmic loop of the a-factor receptor lead to a constitutive and hypersensitive phenotype," Proc. Natl. Acad. Sci. USA, 1993, 90(21), 9921-9925.
Burstein, E.S. et al., "Constitutive activation of chimeric m2/m5 muscarinic receptors and delineation of G-protein coupling selectivity domains," Biochem. Pharmacol., 1996, 51(4), 539-544.
Kjelsbergt, M., "Constitutive Activation of the gamma-Adrenergic Receptor by All Amino Acid Substitutions at a Single Site"; 1992; The Journal of Biological Chemistry; vol. 267, No. 3, Issue of Jan. 25, pp. 1430-1433.
Cotecchia, S., "Regions of the gamma -adrenergic receptor involved in coupling to phosphatidylinositol hydrolysis and enhanced sensitivity of biological function"; 1990, Proc. Natl. Acad. Sci. USA, vol. 87 pp. 2896-2900.
Bergsma, D.J., et al., "Cloning and characterization of a human angiotensin II type 1 receptor," Biochem. & Biophy. Res. Comm., 1992, XP-002145165, 183(3), 989-995.
Gantz, I., et al., "Molecular cloning expression, and gene localization of a fourth melanocortin receptor," J. Biol. Chem., 1993, XP-002051983, 268(20), 15174-15178.
Groblewski, T., et al., "Mutation of Asn111 in the third transmembrane domain of the AT1a angiotensin II receptor inductes its constitutive activation," J. Biol. Chem., 1997, XP-002145162, 272(3), 1822-1826.
Koike, G., et al., "Human type 2 angiotensin II receptor gene: cloned, mapped to the X chromosome, and its mRNA is expressed in the human lung," Biochem. And Biophy. Res., Comm., 1994, XP-002145166, 203(3), 1842-1850.
Kyaw, H., et al., "Cloning, characterization, and mapping of human homolog of mouse T-cell death-associated gene," DNA and Cell Biology, 1998, XP000929737, 17(6), 493-500.
Noda, K., et al., "The active state of the AT1 angiotensin receptor is generated by angiotensin II induction," Biochem., 1996, XP-002145163, 35, 16435-16442.
Reppert, S.M., et al., "Cloning of a melatonin-related receptor from human pituitary," FEBS Letts., 1996 XP-002145161, 219-2254.

Scheer, A., et al., "Constitutively active G protein-coupled receptors: potential mechanisms of receptor activation," J. Receptor & Signal Transduction Res., 1997, XP-000867531, 17(1-3), 57-73.

Burstein, E.S. et al., "Amino acid side chains that define muscarinic receptor/G-protein coupling. Studies of the third intercellular loop," J. Biol. Chem., 1996, 271(6), 2882-2885.

Burstein, E.S. et al., "Constitutive activitation of muscarinic receptors by the G-protein Gq" FEBS Lett., 1995, 363(3), 261-263.

Bylund, D., "International union of pharmacology nomenclature of adrenoceptors," Pharmacol. Rev., 1994, 46, 121-136.

Casey, C. et al., "Constitutively active mutant 5-HT2A serotonic receptors: inverse agonists activity of classical 5HT2A antagonists," Soc. Neurosci., 1996, Abstract #699.10.

Cheatham, B. et al., "Substitution of the erB-2 oncoprotein transmembrane domain activates the insulin receptor and modulates the action of insulin-receptor substrate 1," Proc. Natl. Acad. Sci. USA, 1993, 90, 7336-7340.

Chen, J., et al., "Tethered Ligand Library for Discovery of Peptide Agonists," J. Biol. Chem., 1995 270, 23398-23401.

Chen, T.S. et al., "Microbial hydroxylation and glucuronidation of the angiotensin II (AII) receptor antagonist MK 954," J. Antiobiot. (Tokyo), 1993, 46(1), 131-134.

Chen, W., et al., "A colorimetric assay for the measuring activation of Gs- and Gq-coupled signaling pathways," Anal. Biochem., 1995, 226(2), 349-354.

Chidiac P. et al., "Inverse agonist activity of □-adregenic antagonists," J. Pharm. Exp. Ther., 1994 45, 490-499.

Clozel, M. et al., "In vivo pharmacology of Ro 46-2005, the first synthetic nonpeptide endothelin receptor antagonist: implications of endothelin physiology," J. Cardiovas. Pharmacol., 1993, 22(Suppl. 8), S377-S379.

Collesi, C. et al., "A splicing variant of the RON transcript induces constitutic tyrosine kinase activity and an invasive phenotype," Mol. Cell. Biol., 1996, 16(2), 5518-5526.

Cooper, C.S. et al., "Molecular cloning of a new transforming gene from a chemically transformed human cell line," Nature, 1984, 311, 29-33.

De Dios, I., et al., "Effect of L-364, 718 (CCK Receptor Antagonist) on Exocrine Pancreatic Secretion of Hydrocortison-Treated Rats," Pancreas, 1994, 9(2), 212-218.

Desbios-Mouthon, C. et al., "Deletion of Asn281 in the □-subunit of the human insulin receptor causes constitutive activation of the receptor and insulin desensitization," J. Clin, Endocrinol. Metab., 1996, 81(2), 719-727.

Di Renzo, M.F. et al., "Expression of the Met/HGF receptor in normal and neoplastic human tissues," Ongogene, 1991, 6(11) 1997-2003.

Di Renzo, M. F. et al., "Overexpression of the c-MET/HGF receptor gene in human thyroid carcinomas," Oncogene, 1992, 7, 2549-2553.

Duprez, L. et al., "Germline mutations of the thyrotropin receptor gene cause non-autoimmune autosomal dominant hyperethyroidism," Nature Genetics, 1994, 7, 396-401.

Eggericksx, D. et al., "Molecular Cloning of an Orphan G-Protein-Coupled Receptor that Constitutively Activates Adenylate Cyclase," Biochem, J., 1995, 309, 837-843.

Evans, B.E. et al., "Orally Active, Nonpeptide Oxytocin Antagonists," J. Med. Chem., 1992, 35, 3919-3927.

Fu, M et al., "Functional autoimmune epitope on □1-adrenergic receptors in patients with malignant hypertension," Lancet, 1994, 344, 1660-1663.

Furitsu, T. et al., "Identification of Mutations in the Coding Sequence of the Proto-oncogene c-kit in a Human Mast Cell Leukemia Cell Line Causing Ligand-independent Activation of c-kit Product," J. Clin. Invest., 1993, 92, 1736-1744.

Gellai, M. et al., "Nonpeptide Endothelin Receptor Antagonists V: Prevention and Reversal of Acute Renal Failure in the Rat by SB 290670" J. Pharm. Exp. Therap., 1995, 275(1), 200-206.

Gitter, B., et al., "Pharmacological Characterization of LY303870: A Novel Potent and Selective Nonpeptide Substance P (Neurokinin-1) Receptor Antagonists," J. Pharm. Exp. Therp., 1995, 275(2) 737-744.

Gouilleux-Gruart, V. et al., "STAT-Related Transcription Factors are Constitutively Activated in Peripheral Blood Cells from Acute Leukemia Patients," Blood, 1996, 87(5), 1692-1697.

Hansson, J.H. et al., "Hypertension caused by a truncated epithelial sodium channel Y subunit: genetic heterogeneity of Liddle syndrome," Nat. Genet., 1995, 11(1), 76-82.

Hasegawa, H. et al., "Two Isoforms of the Prostaglandin E Receptor EP3 Subtype Different in Angonist-independent Constitituve Activity," J. Biol. Chem., 1996, 271(4), 1857-1860.

Hendler, F. et al., "Human Squamous Cell Lung Cancers Express Increased Epidermal Growth Factor Receptors," J. Clin. Invest., 1984, 74, 647-651.

Herrick-Davis, K. et al., "Constitutively Active 5HT2C Serotonin Receptor Created by Site-Directed Mutagenesis," Soc. Neurosci, Abstract No. 699.18.

Hieble, J., "International union of pharmacology, X. Recommendation for nomenclature of 1-adrenoceptors," Pharm. Rev., 1995, 47, 267-270.

Hills, S., "Distribution, Properties and Functional Characteristics of Three Classes of Histamine Receptor," Am. Soc. Pharm. Exp. Therap., 1990 42(1), 45-83.

Hogger, P. et al., "Activating and Inactivating Mutations in—and C-terminal i3 Loop Junctions of Muscarinic Acetylcholine Hml Receptors," J. Biol. Chem., 1995, 270(13), 7405-7410.

Ikeda, H. et al., "Expression and Functional Role of the Proto-oncogene c-kit in Acute Myeloblastic Leukemia Cells," Blood, 1991, 78(11), 2962-2968.

Imura, R. et al., "Inhibition by HS-142-1, a novel nonpeptide atrial natriuretic peptide antagonist of microbial origin, or atrial natriuretic peptide-indicated relaxation of isolated rabbit aorta through the blockade of guanyly cyclase-linked receptors," Mol. Pharm., 1992, 42, 982-990.

Jakubik. J et al., "Constitutive activity of the M1-M4 subtypes of muscarinic receptors in transfected CHO cells and of muscarinic receptors in the heart cells revealed by negative antagonists," FEBS Letts., 1995, 377, 275-279.

Knapp, R. et al., "Molecular biology and pharmacology of cloned opiod receptors," FASEB J., 1995, 9, 516-525.

Kosugi, S. et al., "Identification of Thyroid-Stimulating Antibody-Specific Interaction Sites in the N-Terminal Region of the Thyrotropin Receptor," Mol. Endocrinology, 1993, 7, 114-130.

Kraus, M. et al., "Demonstration of ligand-dependent signaling by the erbB-3 tyrosine kinase and its constitutive activation in human breast tumor cells," Proc. Natl. Acad. Sci. USA, 1993, 90, 2900-2904.

Kudlacz, E. et al., "In Vitro and In Vivo Characterization of MDL 105,212A, a Nonpeptide NK-1/NK-2 Tachykinin Receptor Antagonist," J. Pharm. Exp. Therap., 1996, 277(2), 840-851.

Kuriu, A. et al., Proliferation of Human Myeloid Leukemia Cell Line Associated with the Tyrosine-Phosphorylation and Activation of the Proto-oncogene c-kit Product, Blood, 1991, 78(11), 2834-2840.

Labbe-Jullie, C et al., "Effect of the nonpeptide neurotensin antagonist, SR 48692, and two enantiomeric analogs, SR 48527 and SR 49711, on neurotensis binding and contractile responses in guinea pig ileum and colon," J. Pharm. Exp. Therap., 1994, 271(1), 267-276.

Latronico, A. et al., "A novel mutation of the luteinizing hormone receptor gene causing male gonadotropin-independent precocious puberty," J. Clin. Endorcinol. Metabl., 1995, 80(8), 2490-2494.

Laue, L. et al., "Genetic heterogeneity of constitutively activating mutations of the human luteinizing hormone receptor in familial male-limited precocious puberty," Proc. Natl. Acad. Sci. USA, 1995, 92, 1906-1910.

Lovlie, R. et al., "The Ca2+ -sensing receptor gene (PCAR1) mutation T151M in isolated autosomal dominant hypoparathyrodism," Human Genet. 1996, 98, 129-133.

Lefkowitz, R. et al., "Constitutive activity of receptors coupled to guanine nucleotide regulatory proteins," Trends Pharmacol. Sci., 1993, 14, 300-307.

Libermann, T. et al., "Amplification, enhanced expression and possible rearrangement of EGF receptor gene in primary human brain tumours in glial origin," Nature, 1985, 313, 144-47.

Liu, C. et al., "Overexpression of c-met proto-oncongene but not epidermal growth factor receptors or c-erbB-2 in primary human colorectal carcinomas,"Oncogene, 1992, 7, 181-185.

Liu, J. et al., "Molecular mechanisms involved in muscarinic acetylcholine receptor-mediated G protein activation studied by insertion mutagenesis," J. Biol. Chem., 1996, 271(11), 6172-6178.

Lonardo, F. et al., "The normal erbB-2 product in an atypical receptor-like tyrosine kinase with constitutive activity in the absence of ligand," New Biologist, 1990, 2(11), 992-1003.
Maenhaut, C. et al., "RDC8 codes for an adenosine A2 receptor with physiological constitutively activity," Biochem. Biophys. Res. Comm., 1990, 173(3), 1169-1178.
Mann, J. et al., "Increased serotonin2 and □-adrenergic receptor binding in the frontal cortices of suicide victims," Arch. Gen. Psychiatry, 1986, 43, 954-959.
Marone, R.L. et al., "Human CRF receptors chimeras: Mapping of ligand binding determinants," 26th Meeting of the Society of Neurosciencce, Washington, D.C. Nov. 66-21, 1996, Abstract No. 609.8.
Magnusson, Y. et al., "Autoimmunity in idiopathic dilated cardiomyopathy," Circulation, 1994, 89-2760-2767.
Matus-Leibovitch, N. et al., "Truncation of the thyrotropin-releasing hormone receptor carboxyl tail causes constitutive and leads to impaired responsiveness in *Xenopus oocytes* and AtT20 Cells," J. Biol. Chem., 1995, 270(3), 1041-1047.
Myles, G.M. et a., "Tyrosine 569 in the c-Fms Juxtamembrane domain is essential for kinase activity and macrophage colony-stimulating factor-dependent internalization," Mol. Cell. Biol, 1994, 14(7), 4843-4854.
Nanevicz, T., et al., "Thrombin receptor activating mutations," J. Biol. Chem., 1996, 271(2), 702-706.
Natali, P.G. et al., "Expression of the c-Met/HGF receptor in human melanocytic neoplasms: demonstration of the relationship to malignant melanoma tumour progression," Br. J. Cancer, 1993, 68-746-750.
Neilson, K.M. et al., "Constitutive activation of fibroblast growth factor receptor-2 by a point mutation associated with Crouzon syndrome," J. Biol. Chem., 1995, 270(44), 26037-26040.
Oda, S. et al., Pharmacological profile of HS-142-1, a novel nonpeptide atrial natriueretic peptide (ANP) antagonist of microbial origin. II. Restoration of HS-142-1 of ANP-induced inhibition of aldosterone production in adrenal glomerulosa cells, J. Pharm. Exp. Ther., 1992, 263(1), 241-245.
Pettibone, D.J. et al., "Development and pharmacological assessment of novel peptide and nonpeptide oxytocin antagonists," Regul. Pept., 1993, 45, 289-293.
Prat, M.P. et al., "The receptor encoded by the human c-Met oncogene is expressed in hepatocytes, epithelial cells and solid tumors," Int. J. Cancer, 1991, 49, 323-328.
Prezeua, L. et al., "Changes in the carboxy-terminal domain of metabotropic glutamate receptor 1 by alternate splicing generate receptors with differing agonist-independent activity." Mol. Pharmacol., 1996, 49, 422-429.
Rakovska, A. et al., "Effect of loxiglumide (CR 1505) on CCK-induced contractions and 3H—acetylcholine release from guinea-pig gallbladder," Neuropeptides, 1993, 25(5), 271-276.
Ren, Q. et al., "Constitutive active mutants of the □-adrenergic receptor," J. Biol. Chem., 1993, 268, 16483-16487.
Reynolds, E.E. et al., "Pharmacological characterization of PD 156707, an orally active ETA receptor antagonist," J. Pharmacol. Exp. Ther., 1995, 273(3), 1410-1417.
Robbins, L.S. et al., "Pigmentation phenotypes of variant extension locus alleles result from point mutations that alter MSH receptor function," Cell, 1993, 72, 827-834.
Rong, S. et al., "Met expression and sarcoma tumorigenicity," Cancer, 1993, 53(22), 5355, 5360.
Samama, P. et al., "A mutation-induced activation state of the □2-adrenergic receptor," J. Biol. Chem., 1993, 268(7), 4625-4636.
Sautel, M. et al., "Neuropeptide Y and the nonpeptide antagonist BIBP 3226 share an overlapping binding site at the human Y1 receptor," Am. Soc. Pharm. Exp. Ther., 1996, 50, 285-292.
Sawutz, D.G. et al., "Pharmacology and structure-activity relationships of the nonpeptide bradykinin receptor antagonist WIN 64338," Can J. Physiol. Pharmacol., 1995, 73, 805-811.
Scheer, A. et al., "Constitutively active G-protein-coupled receptors: potential mechanisms of receptor activation," J. Rec. Signal Transduct Res., 1997, 17(1-3), 57-73.
Scheer, A. et al., "The activation process of the □1B-adrenergic receptor: Potential role of protonation and hydrophobicity of a highly conserved aspartate," Proc. Natl. Acad. Sci. USA, 1997, 94, 808-813.
Schwinn, D.A. et al., "Cloning and pharmacological characterization of human Alpha-1 adrenergic receptors: sequence correction and direct comparison with other species homologues," J. Pharmacol., 1995, 272(1), 134-142.
Schild, L. et al., "A mutation in the epithelial sodium channel causing Liddle disease increases channel activity in the *Xenopus laevis* oocyte expression system," Proc. Natl. Acad. Sci. USA, 1995, 92, 5699-5703.
Seeman, P. et al., "Dopanine receptor pharmacology," Trends Pharmacol. Sci., 1994, 15, 264-270.
Seeman, P. et al., "Dopamine D4 receptors elevated in schizophrenia," Nature, 1993, 365, 441-445.
Serradeil-Le Gale, C. et al., "Biochemical and pharmacological properties of SR 49059, a new potent, nonpeptide antagonist of rat and human vasopressin V1a receptors,"J. Clin. Inves.,, 1993, 92, 224-231.
Sharif, J. et al., "Malignant transformation by G protein-coupled hormone receptors," Mol. Cell. Endocrinology, 1994, 100, 115-119.
Showers, M. O. et al., "Activation of the erythropoietin receptor by the Friend spleen focus-forming virus gp55 glycoprotein induces constitutive protein tyrosine phosphorylation,"Blood, 1992, 80(12), 3070-3078.
Skinner, R.H. et al., "Direct measurement of the binding of the RAS to neurofibromin using scintillation proximity assay,"Anal. Biochem., 1994, 223, 259-265.
Slamon, D.J. et al., "Human Breast cancer: correlation of relapse and survival with amplification of HER-2/neu oncogene," Science, 1987, 235, 177-182.
Slamon, D. et al., "Studies of the HER-2/neu proto-oncogene in human breast and ovarian cancer,"Science, 1989, 244, 707-712.
Solomon, Y. et al., "A highly sensitive adenylate cyclase assay," Anal. Biochem. 1974, 58, 541-548.
Spiegel, A.M., "Defects in G protein-coupled signal transduction in human disease," Ann. Rev. Physiol, 1995, 58, 143-170.
Ter Laak, A. et al., "Modelling and mutation studies on the histamine H1-receptor agonist binding site reveal different modes for H1-agonists: Asp116 (TM3) has a constitutive role in receptor stimulation," J. Computer-Aided Mol. Design., 1995, 9, 319-330.
Tiberi, M. et al., "High agonist-independent activity is a distinguishing feature of the dopamine D1B receptor subtype," J. Biol. Chem., 1994, 269(45) 27925-27931.
Tsujimura T. et al., "Constitutive activation of c-kit in FMA3 murine mastocytoma cells caused by deletion of seven amino acids at the juxtamembrane domain,"Blood,, 1996, 87(1), 273-283.
Wang, Z. et al., "Constitutive □ opioid receptor activation as a regulatory mechanism underlying narcotic tolerance and dependence," Life Sci., 1994, 54(20), 339-350.
Watowich, S.S. et al., "Homodimerization and constitutive activation of the erythropoietin receptor," Proc. Natl. Acad. Sci USA, 1992, 89, 2140-2144.
Weber-Nordt, R.M. et al., "Constitutive activation of STAT proteins in primary lymphoid and myeloid leukemia cells and in Epstein-Barr virus (EBV)-related lymphoma cell lines," Blood, 1996, 88(3), 809-816.
Webster, M.K. et al., "Constitutive activation of fibroblast growth factor receptor 3 by the transmembrane point mutation found in achondroplasia," EMBO J., 1996, 15, 520-527.
Xu, Y., et al., "Characterization of epidermal growth factor gene expression in maligant and normal human cell lines," Proc. Natl. Acad. Sci. USA, 1984, 81, 7308-7312.
Yamada, K. et al., "Substitution of the insulin receptor transmembrane domain with the c-neu/erbB2 transmembrane domain constitutively activates the insulin receptor kinas in vitro," J. Biol. Chem., 1992, 267 (18), 12452-12461.
Zhang, S. et al., "Identification of Dynorphins as Endogenous Ligands for an Opioid Receptor-Like Orphan Receptor," J. Biol. Chem., 1995, 270-22772-22778.
Zhang, S. et al., Structural and functional domains critical for constructive activation of the HGF-receptor (Met), Oncogene, 1994, 9, 1691-1697.

* cited by examiner

SEQ.ID.NO.287 TTTGCTCAGAAGAAATGCCATCTAGTGATGATGAGGCTACTGCTGACTCTCAACATTCTACTCCTCCAAAAAAGAAGAGA 400
SEQ.ID.NO.288 AAACGAGTCTTCTTTACGGTAGATCACTACTACTCCGATGACGACTGAGAGTTGTAAGATGAGGAGGTTTTTTCTTCTCT

SEQ.ID.NO.289 L L R R N A I · · · · G Y C · L S T F Y S S K K E E
SEQ.ID.NO.290 F C S E E M P S S D D E A T A D S Q H S T P P K K K R
SEQ.ID.NO.291 F A Q K K C H L V M M R L L L T L N I L L L Q K R R E
SEQ.ID.NO.292 K S L L F A M · H H H P · Q Q S E V N · E E L F S S F
SEQ.ID.NO.293 Q E S S I G D L S S S A V A S E · C E V G G F F F L
SEQ.ID.NO.294 K A F F H W R T I I L S S S V R L M R S R W F L L S

Sty I

SEQ.ID.NO.287 AAGGTAGAAGACCCCAAGGACTTTCCTTCAGAATTGCTAAGTTTTTTGAGTCATGCTGTGTTTAGTAATAGAACTCTTGC 480
SEQ.ID.NO.288 TTCCATCTTCTGGGGTTCCTGAAAGGAAGTCTTAACGATTCAAAAAACTCAGTACGACACAAATCATTATCTTGAGAACG

SEQ.ID.NO.289 K G R R P Q G L S F R I A K F F E S C C V · · · N S C
SEQ.ID.NO.290 K V E D P K D F P S E L L S F L S H A V F S N R T L A
SEQ.ID.NO.291 R · K T P R T F L Q N C · V F · V M L C L V I E L L
SEQ.ID.NO.292 P L L G W P S E K L I A L N K S D H Q T · Y Y F E Q
SEQ.ID.NO.293 F T S S G L S K G E S N S L K K L · A T N L L L V R A
SEQ.ID.NO.294 L Y F V G L V K R · F Q · T K Q T M S H K T I S S K S

SEQ.ID.NO.287 TTGCTTTGCTATTTACACCACAAAGGAAAAAGCTGCACTGCTATACAAGAAAATTATGGAAAAATATTCTGTAACCTTTA 560
SEQ.ID.NO.288 AACGAAACGATAAATGTGGTGTTTCCTTTTTCGACGTGACGATATGTTCTTTTAATACCTTTTTATAAGACATTGGAAAT

SEQ.ID.NO.289 L L C Y L H H K G K S C T A I Q E N Y G K I F C N L Y
SEQ.ID.NO.290 C F A I Y T T K E K A A L L Y K K I M E K Y S V T F
SEQ.ID.NO.291 L A L L F T P Q R K K L H C Y T R K L W K N I L · P L
SEQ.ID.NO.292 K S Q · K C W L P F L Q V A I C S F · P F I N Q L R ·
SEQ.ID.NO.293 Q K A I · V V F S F A A S S Y L F I I S F Y E T V K I
SEQ.ID.NO.294 A K S N V G C L F F S C Q · V L F N H F F I R Y G K

AseI

SEQ.ID.NO.287 TAAGTAGGCATAACAGTTATAATCATAACATACTGTTTTTTCTTACTCCACACAGGCATAGAGTGTCTGCTATTAATAAC 640
SEQ.ID.NO.288 ATTCATCCGTATTGTCAATATTAGTATTGTATGACAAAAAAGAATGAGGTGTGTCCGTATCTCACAGACGATAATTATTG

SEQ.ID.NO.289 K · A · Q L · S · H T V F S Y S T Q A · S V C Y · ·
SEQ.ID.NO.290 I S R H N S Y N H N I L F F L T P H R H R V S A I N N
SEQ.ID.NO.291 · V G I T V I I I T Y C F F L L H T G I E C L L L I T
SEQ.ID.NO.292 L Y A Y C N Y D Y C V T K E · E V C A Y L T Q · · Y S
SEQ.ID.NO.293 L L C L L · L · L M S N K R V G C L C L T D A I L L
SEQ.ID.NO.294 Y T P M V T I I M V Y Q K K K S W V P M S H R S N I V

Rsa I

SEQ.ID.NO.287 TATGCTCAAAAATTGTGTACCTTTAGCTTTTTAATTTGTAAAGGGGTTAATAAGGAATATTTGATGTATAGTGCCTTGAC 720
SEQ.ID.NO.288 ATACGAGTTTTTAACACATGGAAATCGAAAAATTAAACATTTCCCCAATTATTCCTTATAAACTACATATCACGGAACTG

SEQ.ID.NO.289 L C S K I V Y L · L F N L · R G · · G I F D Y · C L D
SEQ.ID.NO.290 Y A Q K L C T F S F L I C K G V N K E Y L M Y S A L T
SEQ.ID.NO.291 M L K N C V P L A F · F V K G L I R N I · C I V P ·
SEQ.ID.NO.292 H E F I T Y R · S K L K Y L P · Y P I N S T Y H R S
SEQ.ID.NO.293 · A · F N H V K L K K I Q L P T L L S Y K I Y L A K V
SEQ.ID.NO.294 I S L F Q T G K A K · N T F P N I L F I Q H I T G Q S

*FIG. 3B*

Bsrb I

SEQ.ID.NO.287 GTTATCCGCTCACAATTCCACACAACATACGAGCCGGAAGCATAAAGTGTAAAGCCTGGGGTGCCTAATGAGTGAGCTAA 1440
SEQ.ID.NO.288 CAATAGGCGAGTGTTAAGGTGTGTTGTATGCTCGGCCTTCGTATTTCACATTTCGGACCCCACGGATTACTCACTCGATT

SEQ.ID.NO.289 C Y P L T I P H N I R A G S I K C K A W G A · · V S ·
SEQ.ID.NO.290 V I R S Q F H T T Y E P E A · S V K P G V P N E · A N
SEQ.ID.NO.291 L S A H N S T Q H T S R K H K V · S L G C L M S E L
SEQ.ID.NO.292 · G S V I G C L M R A P L M F H L A Q P A · H T L ·
SEQ.ID.NO.293 T I R E C N W V V Y S G S A Y L T F G P T G L S H A I
SEQ.ID.NO.294 N D A · L E V C C V L R F C L T Y L R P H R I L S S V

Asel Pvu II Asel Hae III

SEQ.ID.NO.287 CTCACATTAATTGCGTTGCGCTCACTGCCCGCTTTCCAGTCGGGAAACCTGTCGTGCCAGCTGCATTAATGAATCGGCCA 1520
SEQ.ID.NO.288 GAGTGTAATTAACGCAACGCGAGTGACGGGCGAAAGGTCAGCCCTTTGGACAGCACGGTCGACGTAATTACTTAGCCGGT

SEQ.ID.NO.289 L T L I A L R S L P A F Q S G N L S C Q L H · · I G Q
SEQ.ID.NO.290 S H · L R C A H C P L S S R E T C R A S C I N E S A
SEQ.ID.NO.291 T H I N C V A L T A R F P V G K P V V P A A L M N R P
SEQ.ID.NO.292 S V N I A N R E S G A K W D P F R D H W S C · H I P W
SEQ.ID.NO.293 E C · N R Q A · Q G S E L R S V Q R A L Q M L S D A L
SEQ.ID.NO.294 · M L Q T A S V A R K G T P F G T T G A A N I F R G

Sap I

SEQ.ID.NO.287 ACGCGCGGGGAGAGGCGGTTTGCGTATTGGGCGCTCTTCCGCTTCCTCGCTCACTGACTCGCTGCGCTCGGTCGTTCGGC 1600
SEQ.ID.NO.288 TGCGCGCCCCTCTCCGCCAAACGCATAACCCGCGAGAAGGCGAAGGAGCGAGTGACTGAGCGACGCGAGCCAGCAAGCCG

SEQ.ID.NO.289 R A G R G G L R I G R S S A S S L T D S L R S V V R
SEQ.ID.NO.290 N A R G E A V C V L G A L P L P R S L T R C A R S F G
SEQ.ID.NO.291 T R G E R R F A Y W A L F R F L A H · L A A L G R S A
SEQ.ID.NO.292 R A P L P P K R I P R E E A E E S V S E S R E T T R S
SEQ.ID.NO.293 A R P S A T Q T N P A R G S G R E S V R Q A R D N P
SEQ.ID.NO.294 V R P S L R N A Y Q A S K R K R A · Q S A A S P R E A

BsrB I

SEQ.ID.NO.287 TGCGGCGAGCGGTATCAGCTCACTCAAAGGCGGTAATACGGTTATCCACAGAATCAGGGGATAACGCAGGAAAGAACATG 1680
SEQ.ID.NO.288 ACGCCGCTCGCCATAGTCGAGTGAGTTTCCGCCATTATGCCAATAGGTGTCTTAGTCCCCTATTGCGTCCTTTCTTGTAC

SEQ.ID.NO.289 L R R A V S A H S K A V I R L S T E S G D N A G K N M
SEQ.ID.NO.290 C G E R Y Q L T Q R R · Y G Y P Q N Q G I T Q E R T C
SEQ.ID.NO.291 A A S G I S S L K G G N T V I H R I R G · R R K E H
SEQ.ID.NO.292 R R A T D A · E F A T I R N D V S D P S L A P F F M
SEQ.ID.NO.293 Q P S R Y · S V · L R Y Y P · G C F · P I V C S L V H
SEQ.ID.NO.294 A A L P I L E S L P P L V T I W L I L P Y R L F S C T

FIG. 3E

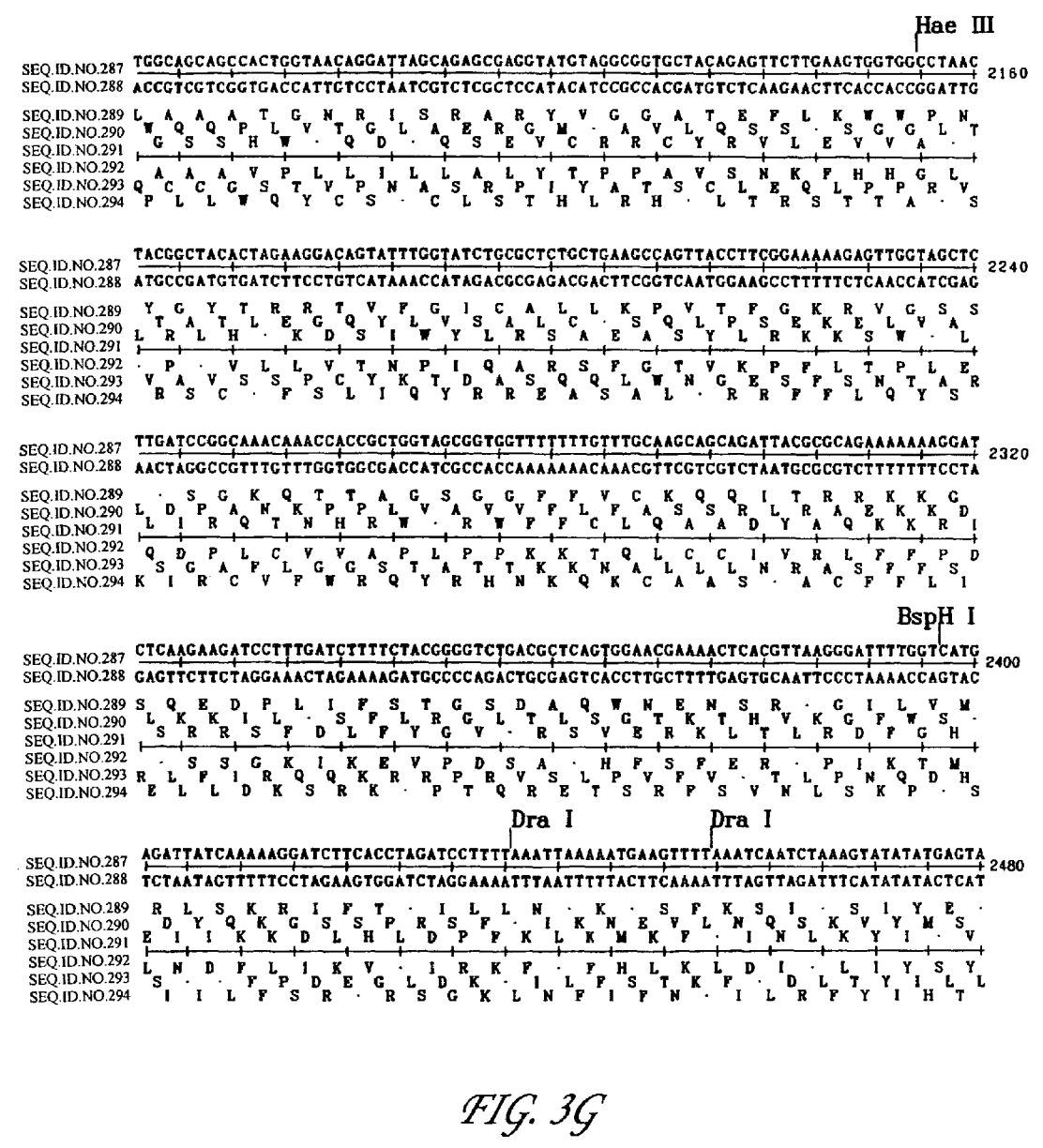

Hae III

SEQ.ID.NO.287 TGGCAGCAGCCACTGGTAACAGGATTAGCAGAGCGAGGTATGTAGGCGGTGCTACAGAGTTCTTGAAGTGGTGGCCTAAC 2160
SEQ.ID.NO.288 ACCGTCGTCGGTGACCATTGTCCTAATCGTCTCGCTCCATACATCCGCCACGATGTCTCAAGAACTTCACCACCGGATTG

SEQ.ID.NO.289 L A A A T G N R I S R A R Y V G G A T E F L K W W P N
SEQ.ID.NO.290 W Q Q P L V T G L A E R G M · A V L Q S S · S G G L T
SEQ.ID.NO.291 G S S H W · Q D · Q S E V C R R C Y R V L E V V A ·
SEQ.ID.NO.292 A A A V P L L I L L A L Y T P P A V S N K F H H G L
SEQ.ID.NO.293 Q C C G S T V P N A S R P I Y A T S C L E Q L P P R V
SEQ.ID.NO.294 P L L W Q Y C S · C L S T H L R H · L T R S T T A · S

SEQ.ID.NO.287 TACGGCTACACTAGAAGGACAGTATTTGGTATCTGCGCTCTGCTGAAGCCAGTTACCTTCGGAAAAAGAGTTGGTAGCTC 2240
SEQ.ID.NO.288 ATGCCGATGTGATCTTCCTGTCATAAACCATAGACGCGAGACGACTTCGGTCAATGGAAGCCTTTTTCTCAACCATCGAG

SEQ.ID.NO.289 Y G Y T R R T V F G I C A L L K P V T F G K R V G S S
SEQ.ID.NO.290 T A T L E G Q Y L V S A L C · S Q L P S E K E L V A
SEQ.ID.NO.291 L R L H · K D S I W Y L R S A E A S Y L R K K S W · L
SEQ.ID.NO.292 · P · V L L V T N P I Q A R S F G T V K P F L T P L E
SEQ.ID.NO.293 V A V S S P C Y K T D A S Q Q L W N G E S F S N T A R
SEQ.ID.NO.294 R S C · F S L I Q Y R R E A S A L · R R F F L Q Y S

SEQ.ID.NO.287 TTGATCCGGCAAACAAACCACCGCTGGTAGCGGTGGTTTTTTTGTTTGCAAGCAGCAGATTACGCGCAGAAAAAAAGGAT 2320
SEQ.ID.NO.288 AACTAGGCCGTTTGTTTGGTGGCGACCATCGCCACCAAAAAAACAAACGTTCGTCGTCTAATGCGCGTCTTTTTTTCCTA

SEQ.ID.NO.289 · S G K Q T T A G S G G F F V C K Q Q I T R R K K G
SEQ.ID.NO.290 L D P A N K P P L V A V V F L F A S S R L R A E K K D
SEQ.ID.NO.291 L I R Q T N H R W · R W F F C L Q A A D Y A Q K K R I
SEQ.ID.NO.292 Q D P L C V V A P L P P K K T Q L C C I V R L F F P D
SEQ.ID.NO.293 S G A F L G G S T A T T K K N A L L L N R A S F F S
SEQ.ID.NO.294 K I R C V F W R Q Y R H N K Q K C A A S · A C F F L I

BspH I

SEQ.ID.NO.287 CTCAAGAAGATCCTTTGATCTTTTCTACGGGGTCTGACGCTCAGTGGAACGAAAACTCACGTTAAGGGATTTTGGTCATG 2400
SEQ.ID.NO.288 GAGTTCTTCTAGGAAACTAGAAAAGATGCCCCAGACTGCGAGTCACCTTGCTTTTGAGTGCAATTCCCTAAAACCAGTAC

SEQ.ID.NO.289 S Q E D P L I F S T G S D A Q W N E N S R · G I L V M
SEQ.ID.NO.290 L K K I L · S F L R G L T L S G T K T H V K G F W S ·
SEQ.ID.NO.291 S R R S F D L F Y G V · R S V E R K L T L R D F G H
SEQ.ID.NO.292 · S S G K I K E V P D S A · H F S F E R · P I K T M
SEQ.ID.NO.293 R L F I R Q Q K R R P R V S L P V F V · T L P N Q D H
SEQ.ID.NO.294 E L L D K S R K · P T Q R E T S R F S V N L S K P · S

Dra I Dra I

SEQ.ID.NO.287 AGATTATCAAAAAGGATCTTCACCTAGATCCTTTTAAATTAAAAATGAAGTTTTAAATCAATCTAAAGTATATATGAGTA 2480
SEQ.ID.NO.288 TCTAATAGTTTTTCCTAGAAGTGGATCTAGGAAAATTTAATTTTTACTTCAAAATTTAGTTAGATTTCATATATACTCAT

SEQ.ID.NO.289 R L S K R I F T · I L L N · K · S F K S I · S I Y E ·
SEQ.ID.NO.290 D Y Q K G S S P R S F · I K N E V L N Q S K V Y M S
SEQ.ID.NO.291 E I I K K D L H L D P F K L K M K F · I N L K Y I · V
SEQ.ID.NO.292 L N D F L I K V · I R K F · F H L K L D I · L I Y S Y
SEQ.ID.NO.293 S · · F P D E G L D K · I L F S T K F · D L T Y I L L
SEQ.ID.NO.294 I I L F S R · R S G K L N F I F N · I L R F Y I H T

FIG. 3G

SEQ.ID.NO.287 AACTTGGTCTGACAGTTACCAATGCTTAATCAGTGAGGCACCTATCTCAGCGATCTGTCTATTTCGTTCATCCATAGTTG 2560
SEQ.ID.NO.288 TTGAACCAGACTGTCAATGGTTACGAATTAGTCACTCCGTGGATAGAGTCGCTAGACAGATAAAGCAAGTAGGTATCAAC

SEQ.ID.NO.289 T W S D S Y Q C L I S E A P I S A I C L F R S S I V
SEQ.ID.NO.290 K L G L T V T N A · S V R H L S Q R S V Y F V H P · L
SEQ.ID.NO.291 N L V · Q L P M L N Q · G T Y L S D L S I S P I H S C
SEQ.ID.NO.292 V Q D S L · W H K I L S A G I E A I Q R N R E D M T A
SEQ.ID.NO.293 S P R V T V L A · D T L C R D · R D T · K T · G Y N
SEQ.ID.NO.294 F K T Q C N G I S L · H P V · R L S R D I E N M W L Q

Hae III

SEQ.ID.NO.287 CCTGACTCCCCGTCGTGTAGATAACTACGATACGGGAGGGCTTACCATCTGGCCCCAGTGCTGCAATGATACCGCGAGAC 2640
SEQ.ID.NO.288 GGACTGAGGGGCAGCACATCTATTGATGCTATGCCCTCCCGAATGGTAGACCGGGGTCACGACGTTACTATGGCGCTCTG

SEQ.ID.NO.289 A · L P V V · I T T I R E G L P S G P S A A M I P R D
SEQ.ID.NO.290 P D S P S C R · L R Y G R A Y H L A P V L Q · Y R E T
SEQ.ID.NO.291 L T P R R V D N Y D T G G L T I W P Q C C N D T A R
SEQ.ID.NO.292 Q S G T T Y I V V I R S P K G D P G L A A I I G R S
SEQ.ID.NO.293 G S E G D H L Y S R Y P L A · W R A G T S C H Y R S V
SEQ.ID.NO.294 R V G R R T S L · S V P P S V M Q G W H Q L S V A L G

Bgl I Hae III Ava II

SEQ.ID.NO.287 CCACGCTCACCGGCTCCAGATTTATCAGCAATAAACCAGCCAGCCGGAAGGGCCGAGCGCAGAAGTGGTCCTGCAACTTT 2720
SEQ.ID.NO.288 GGTGCGAGTGGCCGAGGTCTAAATAGTCGTTATTTGGTCGGTCGGCCTTCCCGGCTCGCGTCTTCACCAGGACGTTGAAA

SEQ.ID.NO.289 P R S P A P D L S A I N Q P A G R A E R R S G P A T L
SEQ.ID.NO.290 H A H R L Q I Y Q Q · T S Q P E G P S A E V V L Q L
SEQ.ID.NO.291 P T L T G S R F I S N K P A S R K G R A Q K W S C N F
SEQ.ID.NO.292 G R E G A G S K D A I F W G A P L A S R L L P G A V K
SEQ.ID.NO.293 W A · R S W I · · C Y V L W G S P G L A S T T R C S ·
SEQ.ID.NO.294 V S V P E L N I L L L G A L R F P R A C F H D Q L K

AseI Nci I Fsp I

SEQ.ID.NO.287 ATCCGCCTCCATCCAGTCTATTAATTGTTGCCGGGAAGCTAGAGTAAGTAGTTCGCCAGTTAATAGTTTGCGCAACGTTG 2800
SEQ.ID.NO.288 TAGGCGGAGGTAGGTCAGATAATTAACAACGGCCCTTCGATCTCATTCATCAAGCGGTCAATTATCAAACGCGTTGCAAC

SEQ.ID.NO.289 S A S I Q S I N C C R E A R V S S S P V N S L R N V
SEQ.ID.NO.290 Y P P P S S L L I V A G K L E · V V R Q L I V C A T L
SEQ.ID.NO.291 I R L H P V Y · L L P G S · S K · F A S · · F A Q R C
SEQ.ID.NO.292 D A E M W D I L Q Q R S A L T L L E G T L L K R L T T
SEQ.ID.NO.293 G G G D L R N I T A P F S S Y T T R W N I T Q A V N
SEQ.ID.NO.294 I R R W G T · · N N G P L · L L Y N A L · Y N A C R Q

SEQ.ID.NO.287 TTGCCATTGCTACAGGCATCGTGGTGTCACGCTCGTCGTTTGGTATGGCTTCATTCAGCTCCGGTTCCCAACGATCAAGG 2880
SEQ.ID.NO.288 AACGGTAACGATGTCCGTAGCACCACAGTGCGAGCAGCAAACCATACCGAAGTAAGTCGAGGCCAAGGGTTGCTAGTTCC

SEQ.ID.NO.289 V A I A T G I V V S R S S F G M A S F S S G S Q R S R
SEQ.ID.NO.290 L P L L Q A S W C H A R R L V W L H S A P V P N D Q G
SEQ.ID.NO.291 C H C Y R H R G V T L V V W Y G F I Q L R F P T I K
SEQ.ID.NO.292 A M A V P M T T D R E D N P I A E N L E P E W R D L
SEQ.ID.NO.293 N G N S C A D H H · A R R K T H S · E A G T G L S · P
SEQ.ID.NO.294 Q W Q · L C R P T V S T T Q Y P K M · S R N G V I L A

*FIG. 3H*

Ava II Pvu I Hae III

SEQ.ID.NO.287 CGAGTTACATGATCCCCCATGTTGTGCAAAAAAGCGGTTAGCTCCTTCGGTCCTCCGATCGTTGTCAGAAGTAAGTTGGC 2960
SEQ.ID.NO.288 GCTCAATGTACTAGGGGGTACAACACGTTTTTTCGCCAATCGAGGAAGCCAGGAGGCTAGCAACAGTCTTCATTCAACCG

SEQ.ID.NO.289 R V T · S P M L C K K A V S S F G P P I V V R S K L A
SEQ.ID.NO.290 E L H D P P C C A K K R L A P S V L R S L S E V S W
SEQ.ID.NO.291 A S Y M I P H V V Q K S G · L L R S S D R C Q K · V G
SEQ.ID.NO.292 R T V H D G M N H L F A T L E K P G G I T T L L L N A
SEQ.ID.NO.293 S N C S G G H Q A F F R N A G E T R R D N D S T L Q G
SEQ.ID.NO.294 L · M I G W T T C F L P · S R R D E S R Q · F Y T P

SEQ.ID.NO.287 CGCAGTGTTATCACTCATGGTTATGGCAGCACTGCATAATTCTCTTACTGTCATGCCATCCGTAAGATGCTTTTCTGTGA 3040
SEQ.ID.NO.288 GCGTCACAATAGTGAGTACCAATACCGTCGTGACGTATTAAGAGAATGACAGTACGGTAGGCATTCTACGAAAAGACACT

SEQ.ID.NO.289 A V L S L M V M A A L H N S L T V M P S V R C F S V
SEQ.ID.NO.290 P Q C Y H S W L W Q H C I I L L L S C H P · D A F L ·
SEQ.ID.NO.291 R S V I T H G Y G S T A · F S Y C H A I R K M L F C D
SEQ.ID.NO.292 A T N D S M T I A A S C L E R V T M G D T L H K E T V
SEQ.ID.NO.293 C H · · E H N H C C Q M I R K S D H W G Y S A K R H
SEQ.ID.NO.294 R L T I V · P · P L V A Y N E · Q · A M R L I S K Q S

Rsa I
Sca I
Nci I Hinc II

SEQ.ID.NO.287 CTGGTGAGTACTCAACCAAGTCATTCTGAGAATAGTGTATGCGGCGACCGAGTTGCTCTTGCCCGGCGTCAACACGGGAT 3120
SEQ.ID.NO.288 GACCACTCATGAGTTGGTTCAGTAAGACTCTTATCACATACGCCGCTGGCTCAACGAGAACGGGCCGCAGTTGTGCCCTA

SEQ.ID.NO.289 T G E Y S T K S F · E · C M R R P S C S C P A S T R D
SEQ.ID.NO.290 L V S T Q P S H S E N S V C G D R V A L A R R Q H G I
SEQ.ID.NO.291 W · V L N Q V I L R I V Y A A T E L L L P G V N T G
SEQ.ID.NO.292 P S Y E V L D N Q S Y H I R R G L Q E Q G A D V R S
SEQ.ID.NO.293 S T L V · G L · E S F L T H P S R T A R A R R · C P I
SEQ.ID.NO.294 Q H T S L W T M R L I T Y A A V S N S K G P T L V P Y

Dra I Xmn I

SEQ.ID.NO.287 AATACCGCGCCACATAGCAGAACTTTAAAAGTGCTCATCATTGGAAAACGTTCTTCGGGGCGAAAACTCTCAAGGATCTT 3200
SEQ.ID.NO.288 TTATGGCGCGGTGTATCGTCTTGAAATTTTCACGAGTAGTAACCTTTTGCAAGAAGCCCCGCTTTTGAGAGTTCCTAGAA

SEQ.ID.NO.289 N T A P H S R T L K V L I I G K R S S G R K L S R I L
SEQ.ID.NO.290 I P R H I A E L · K C S S L E N V L R G E N S Q G S
SEQ.ID.NO.291 · Y R A T · Q N F K S A H H W K T F F G A K T L K D L
SEQ.ID.NO.292 L V A G C L L V K F T S M M P F R E E P R F S E L I K
SEQ.ID.NO.293 I G R W M A S S · F H E D N S F T R R P S F E · P D ·
SEQ.ID.NO.294 Y R A V Y C F K L L A · · Q F V N K P A F V R L S R

*FIG. 3I*

Aat II

SEQ.ID.NO.287 TGGCTGACCGCCCAACGACCCCCGCCCATTGACGTCAATAATGACGTATGTTCCCATAGTAACGCCAATAGGGACTTTCC 3600
SEQ.ID.NO.288 ACCGACTGGCGGGTTGCTGGGGGCGGGTAACTGCAGTTATTACTGCATACAAGGGTATCATTGCGGTTATCCCTGAAAGG

SEQ.ID.NO.289 L A D R P T T P A H · R Q · · R M F P · · R Q · G L S
SEQ.ID.NO.290 W L T A Q R P P P I D V N N D V C S H S N A N R D F P
SEQ.ID.NO.291 G · P P N D P R P L T S I M T Y V P I V T P I G T F
SEQ.ID.NO.292 A S R G V V G A W Q R · Y H R I N G Y Y R W Y P S E
SEQ.ID.NO.293 Q S V A W R G G G M S T L L S T H E W L L A L L S K G
SEQ.ID.NO.294 P Q G G L S G R G N V D I I V Y T G M T V G I P V K W

Aat II Bgl I Rsa I Nde I Rsa I

SEQ.ID.NO.287 ATTGACGTCAATGGGTGGACTATTTACGGTAAACTGCCCACTTGGCAGTACATCAAGTGTATCATATGCCAAGTACGCCC 3680
SEQ.ID.NO.288 TAACTGCAGTTACCCACCTGATAAATGCCATTTGACGGGTGAACCGTCATGTAGTTCACATAGTATACGGTTCATGCGGG

SEQ.ID.NO.289 I D V N G W T I Y G K L P T W Q Y I K C I I C Q V R P
SEQ.ID.NO.290 L T S M G G L F T V N C P L G S T S S V S Y A K Y A
SEQ.ID.NO.291 H · R Q W V D Y L R · T A H L A V H Q V Y H M P S T P
SEQ.ID.NO.292 M S T L P H V I · P L S G V Q C Y M L H I M H W T R G
SEQ.ID.NO.293 N V D I P P S N V T F Q G S P L V D L T D Y A L Y A G
SEQ.ID.NO.294 Q R · H T S · K R Y V A W K A T C · T Y · I G L V G

Hae III
Aat II Bgl I Rsa I

SEQ.ID.NO.287 CCTATTGACGTCAATGACGGTAAATGGCCCGCCTGGCATTATGCCCAGTACATGACCTTATGGGACTTTCCTACTTGGCA 3760
SEQ.ID.NO.288 GGATAACTGCAGTTACTGCCATTTACCGGGCGGACCGTAATACGGGTCATGTACTGGAATACCCTGAAAGGATGAACCGT

SEQ.ID.NO.289 L L T S M T V N G P P G I M P S T · P Y G T F L L G
SEQ.ID.NO.290 P Y · R Q · R · M A R L A L C P V H D L M G L S Y L A
SEQ.ID.NO.291 P I D V N D G K W P A W H Y A Q Y M T L W D F P T W Q
SEQ.ID.NO.292 R N V D I V T F P G G P M I G L V H G · P V K R S P L
SEQ.ID.NO.293 · Q R · H R Y I A R R A N H G T C S R I P S E · K A
SEQ.ID.NO.294 G I S T L S P L H G A Q C · A W Y M V K H S K G V Q C

BsaA I Nco I
Rsa I SnaB I Sty I Rsa I

SEQ.ID.NO.287 GTACATCTACGTATTAGTCATCGCTATTACCATGGTGATGCGGTTTTGGCAGTACATCAATGGGCGTGGATAGCGGTTTG 3840
SEQ.ID.NO.288 CATGTAGATGCATAATCAGTAGCGATAATGGTACCACTACGCCAAAACCGTCATGTAGTTACCCGCACCTATCGCCAAAC

SEQ.ID.NO.289 S T S T Y · S S L L P W · C G F G S T S M G V D S G L
SEQ.ID.NO.290 V H L R I S H R Y Y H G D A V L A V H Q W A W I A V
SEQ.ID.NO.291 Y I Y V L V I A I T M V M R F W Q Y I N G R G · R F
SEQ.ID.NO.292 V D V Y · D D S N G H H H P K P L V D I P T S L P K
SEQ.ID.NO.293 T C R R I L · R · · W P S A T K A T C · H A H I A T Q
SEQ.ID.NO.294 Y M · T N T M A I V M T I R N Q C Y M L P R P Y R N S

FIG. 3K

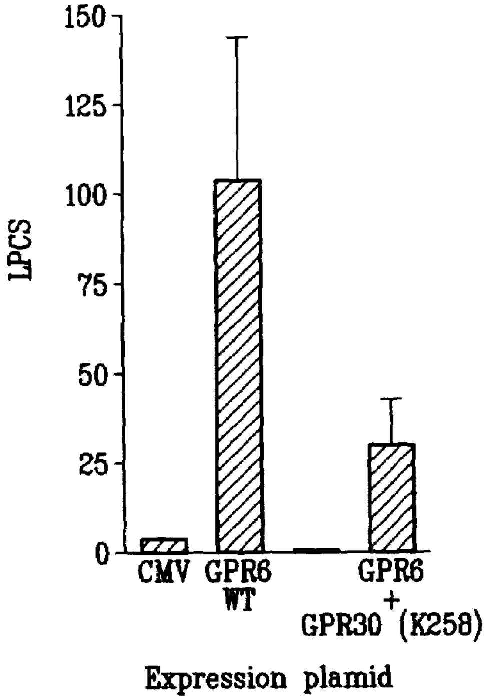
FIG. 4
FIG. 5
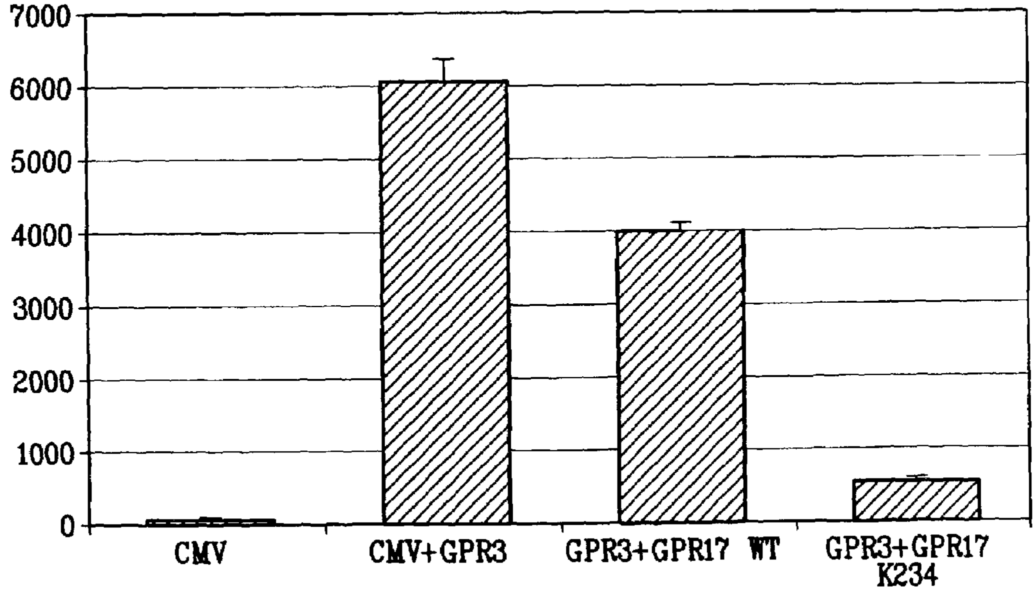

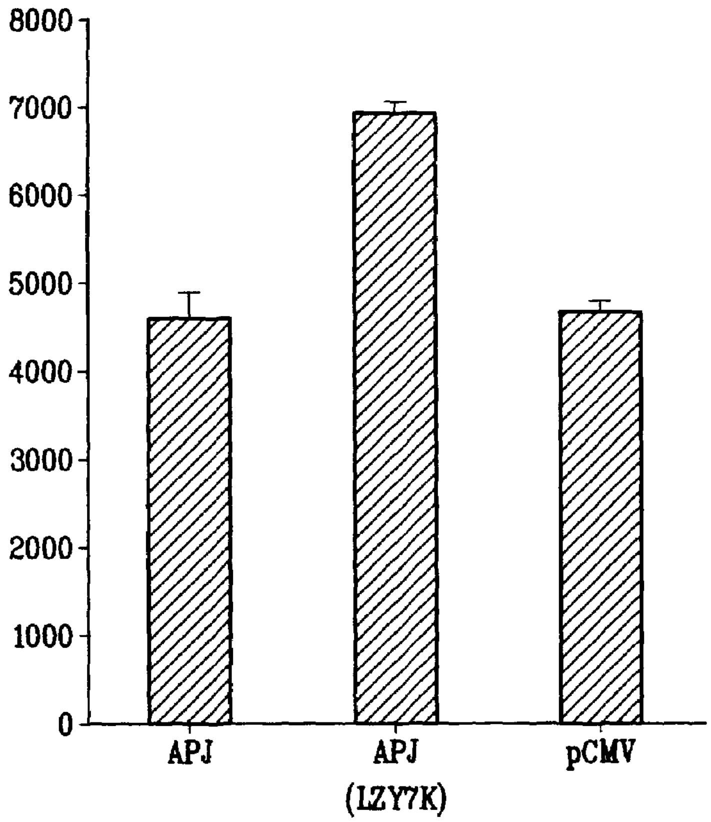
FIG. 6
FIG. 7
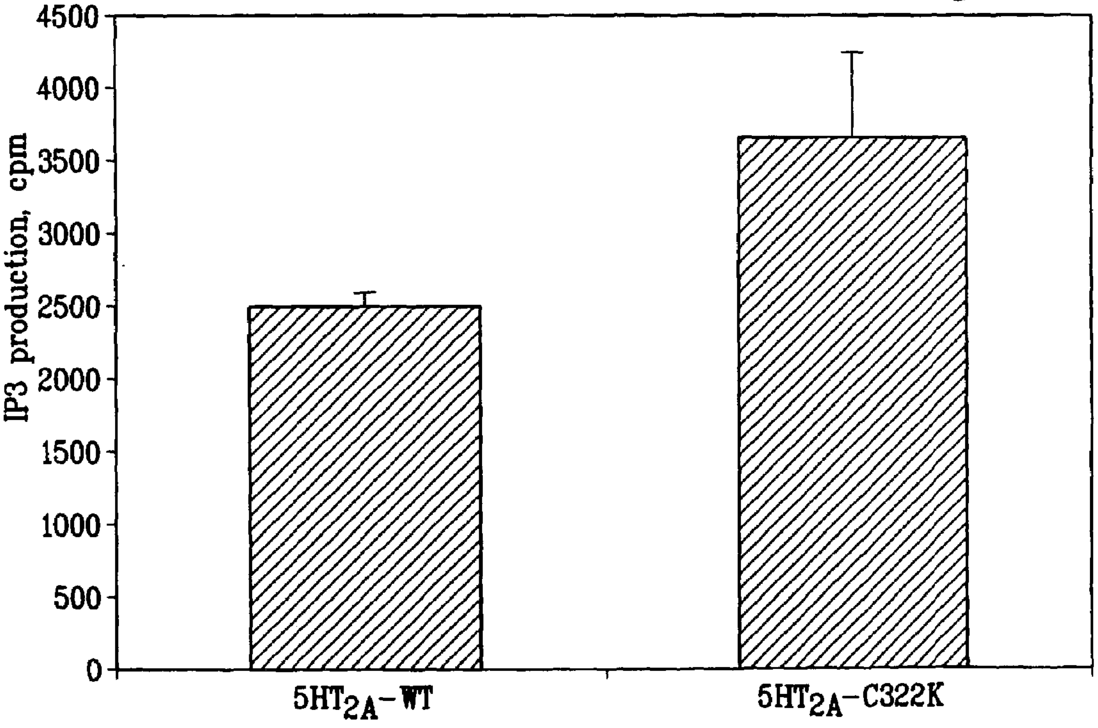

NON-ENDOGENOUS, CONSTITUTIVELY ACTIVATED HUMAN G PROTEIN-COUPLED RECEPTORS

This application is a continuation of U.S. Ser. No. 09/170,496 filed Oct. 13, 1998 (now U.S. Pat. No. 6,555,339) which is a continuation in part of U.S. Ser. No. 09/060,188, filed Apr. 14, 1998; which is a continuation in part of U.S. Ser. No. 08/839,449 filed Apr. 14, 1997 now abandoned. This application also claims benefit of priority to U.S. Provisional Number 60/090,783, filed Jun. 26, 1998; and U.S. Provisional No. 60/095,677, filed Aug. 7, 1998 since such priority is claimed by U.S. Ser. No. 09/170,496.

FIELD OF THE INVENTION

The invention disclosed in this patent document relates to transmembrane receptors, and more particularly to human G protein-coupled receptors (GPCRs) which have been altered such that altered GPCRs are constitutively activated. Most preferably, the altered human GPCRs are used for the screening of therapeutic compounds.

BACKGROUND OF THE INVENTION

Although a number of receptor classes exist in humans, by far the most abundant and therapeutically relevant is represented by the G protein-coupled receptor (GPCR or GPCRs) class. It is estimated that there are some 100,000 genes within the human genome, and of these, approximately 2% or 2,000 genes, are estimated to code for GPCRs. Of these, there are approximately 100 GPCRs for which the endogenous ligand that binds to the GPCR has been identified. Because of the significant time-lag that exists between the discovery of an endogenous GPCR and its endogenous ligand, it can be presumed that the remaining 1,900 GPCRs will be identified and characterized long before the endogenous ligands for these receptors are identified. Indeed, the rapidity by which the Human Genome Project is sequencing the 100,000 human genes indicates that the remaining human GPCRs will be fully sequenced within the next few years. Nevertheless, and despite the efforts to sequence the human genome, it is still very unclear as to how scientists will be able to rapidly, effectively and efficiently exploit this information to improve and enhance the human condition. The present invention is geared towards this important objective.

Receptors, including GPCRs, for which the endogenous ligand has been identified are referred to as "known" receptors, while receptors for which the endogenous ligand has not been identified are referred to as "orphan" receptors. This distinction is not merely semantic, particularly in the case of GPCRs. GPCRs represent an important area for the development of pharmaceutical products: from approximately 20 of the 100 known GPCRs, 60% of all prescription pharmaceuticals have been developed. Thus, the orphan GPCRs are to the pharmaceutical industry what gold was to California in the late $19^{th}$ century—an opportunity to drive growth, expansion, enhancement and development. A serious drawback exists, however, with orphan receptors relative to the discovery of novel therapeutics. This is because the traditional approach to the discovery and development of pharmaceuticals has required access to both the receptor and its endogenous ligand. Thus, heretofore, orphan GPCRs have presented the art with a tantalizing and undeveloped resource for the discovery of pharmaceuticals.

Under the traditional approach to the discovery of potential therapeutics, it is generally the case that the receptor is first identified. Before drug discovery efforts can be initiated, elaborate, time consuming and expensive procedures are typically put into place in order to identify, isolate and generate the receptor's endogenous ligand—this process can require from between 3 and ten years per receptor, at a cost of about $5 million (U.S.) per receptor. These time and financial resources must be expended before the traditional approach to drug discovery can commence. This is because traditional drug discovery techniques rely upon so-called "competitive binding assays" whereby putative therapeutic agents are "screened" against the receptor in an effort to discover compounds that either block the endogenous ligand from binding to the receptor ("antagonists"), or enhance or mimic the effects of the ligand binding to the receptor ("agonists"). The overall objective is to identify compounds that prevent cellular activation when the ligand binds to the receptor (the antagonists), or that enhance or increase cellular activity that would otherwise occur if the ligand was properly binding with the receptor (the agonists). Because the endogenous ligands for orphan GPCRs are by definition not identified, the ability to discover novel and unique therapeutics to these receptors using traditional drug discovery techniques is not possible. The present invention, as will be set forth in greater detail below, overcomes these and other severe limitations created by such traditional drug discovery techniques.

GPCRs share a common structural motif All these receptors have seven sequences of between 22 to 24 hydrophobic amino acids that form seven alpha helices, each of which spans the membrane (each span is identified by number, i.e., transmembrane-1 (TM-1), transmebrane-2 (TM-2), etc.). The transmembrane helices are joined by strands of amino acids between transmembrane-2 and transmembrane-3, transmembrane4 and transmembrane-5, and transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell. The general structure of G protein-coupled receptors is depicted in FIG. 1.

Generally, when an endogenous ligand binds with the receptor (often referred to as "activation" of the receptor), there is a change in the conformation of the intracellular region that allows for coupling between the intracellular region and an intracellular "G-protein." Although other G proteins exist, currently, Gq, Gs, Gi, and Go are G proteins that have been identified. Endogenous ligand-activated GPCR coupling with the G-protein begins a signaling cascade process (referred to as "signal transduction"). Under normal conditions, signal transduction ultimately results in cellular activation or cellular inhibition. It is thought that the IC-3 loop as well as the carboxy terminus of the receptor interact with the G protein. A principal focus of this invention is directed to the transmembrane-6 (TM6) region and the intracellular-3 (IC3) region of the GPCR.

Under physiological conditions, GPCRs exist in the cell membrane in equilibrium between two different conformations: an "inactive" state and an "active" state. As shown schematically in FIG. 2, a receptor in an inactive state is unable to link to the intracellular signaling transduction pathway to produce a biological response. Changing the receptor conformation to the active state allows linkage to the transduction pathway (via the G-protein) and produces a biological response.

A receptor may be stabilized in an active state by an endogenous ligand or a compound such as a drug. Recent discoveries, including but not exclusively limited to modifications to the amino acid sequence of the receptor, provide means other than endogenous ligands or drugs to promote and stabilize the receptor in the active state conformation. These means effectively stabilize the receptor in an active state by simulating the effect of an endogenous ligand binding to the receptor. Stabilization by such ligand-independent means is termed "constitutive receptor activation."

For instance, it was shown that interchange of a short homologous sequence of amino acids in the carboxy terminal of the third cytoplasmic loop of the $G_q$-phospholipase G protein coupled $\alpha_{1B}$ adrenoreceptor and the $G_s$-adenyl cyclase-coupled $\beta_2$ andrenergic receptor resulted in both receptors promoting intracellular activation levels comparable to the fully agonist-stimulated native receptors.

As noted above, the use of an orphan receptor for screening purposes has not been possible. This is because the traditional "dogma" regarding screening of compounds mandates that the ligand for the receptor be known. By definition, then, this approach has no applicability with respect to orphan receptors. Thus, by adhering to this dogmatic approach to the discovery of therapeutics, the art, in essence, has taught and has been taught to forsake the use of orphan receptors unless and until the endogenous ligand for the receptor is discovered. Given that there are an estimated 2,000 G protein coupled receptors, the majority of which are orphan receptors, such dogma castigates a creative, unique and distinct approach to the discovery of therapeutics.

Information regarding the nucleic acid and/or amino acid sequences of a variety of GPCRs is summarized below in Table A. Because an important focus of the invention disclosed herein is directed towards orphan GPCRs, many of the below-cited references are related to orphan GPCRs. However, this list is not intended to imply, nor is this list to be construed, legally or otherwise, that the invention disclosed herein is only applicable to orphan GPCRs or the specific GPCRs listed below. Additionally, certain receptors that have been isolated are not the subject of publications per se; for example, reference is made to a G Protein-Coupled Receptor database on the "world-wide web" (neither the named inventors nor the assignee have any affiliation with this site) that lists GPCRs. Other GPCRs are the subject of patent applications owned by the present assignee and these are not listed below (including GPR3, GPR6 and GPR12; see U.S. Provisional No. 60/094,879):

TABLE A

| Receptor Name | Publication Reference |
|---|---|
| GPR1 | 23 Genomics 609 (1994) |
| GPR4 | 14 DNA and Cell Biology 25 (1995) |
| GPR5 | 14 DNA and Cell Biology 25 (1995) |
| GPR7 | 28 Genomics 84 (1995) |
| GPR8 | 28 Genomics 84 (1995) |
| GPR9 | 184 J. Exp. Med. 963 (1996) |
| GPR10 | 29 Genomics 335 (1995) |
| GPR15 | 32 Genomics 462 (1996) |
| GPR17 | 70 J Neurochem. 1357 (1998) |
| GPR18 | 42 Genomics 462 (1997) |
| GPR20 | 187 Gene 75 (1997) |
| GPR21 | 187 Gene 75 (1997) |
| GPR22 | 187 Gene 75 (1997) |

TABLE A-continued

| Receptor Name | Publication Reference |
|---|---|
| GPR24 | 398 FEBS Lett. 253 (1996) |
| GPR30 | 45 Genomics 607 (1997) |
| GPR31 | 42 Genomics 519 (1997) |
| GPR32 | 50 Genomics 281 (1997) |
| GPR40 | 239 Biochem. Biophys. Res. Commun. 543 (1997) |
| GPR41 | 239 Biochem. Biophys. Res. Commun. 543 (1997) |
| GPR43 | 239 Biochem. Biophys. Res. Commun. 543 (1997) |
| APJ | 136 Gene 355 (1993) |
| BLR1 | 22 Eur. J. Immunol. 2759 (1992) |
| CEPR | 231 Biochem. Biophys. Res. Commun. 651 (1997) |
| EBI1 | 23 Genomics 643 (1994) |
| EBI2 | 67 J. Virol. 2209 (1993) |
| ETBR-LP2 | 424 FEBS Lett. 193 (1998) |
| GPCR-CNS | 54 Brain Res. Mol. Brain Res. 152 (1998); 45 Genomics 68 (1997) |
| GPR-NGA | 394 FEBS Lett. 325 (1996) |
| H9 | 386 FEBS Lett 219 (1996) |
| HBA954 | 1261 Biochim. Biophys. Acta 121 (1995) |
| HG38 | 247 Biochem. Biophys. Res. Commun. 266 (1998) |
| HM74 | 5 Int. Immunol. 1239 (1993) |
| OGR1 | 35 Genomics 397 (1996) |
| V28 | 163 Gene 295 (1995) |

As will be set forth and disclosed in greater detail below, utilization of a mutational cassette to modify the endogenous sequence of a human GPCR leads to a constitutively activated version of the human GPCR. These non-endogenous, constitutively activated versions of human GPCRs can be utilized, inter alia, for the screening of candidate compounds to directly identify compounds of, e.g., therapeutic relevance.

SUMMARY OF THE INVENTION

Disclosed herein is a non-endogenous, human G protein-coupled receptor comprising (a) as a most preferred amino acid sequence region (C-terminus to N-terminus orientation) and/or (b) as a most preferred nucleic acid sequence region (3' to 5' orientation) transversing the transmembrane-6 (TM6) and intracellular loop-3 (IC3) regions of the GPCR:

(a) $P^1$ $AA_{15}$ X wherein:

(1) $P^1$ is an amino acid residue located within the TM6 region of the GPCR, where $P^1$ is selected from the group consisting of (i) the endogenous GPCR's proline residue, and (ii) a non-endogenous amino acid residue other than proline;

(2) $AA_{15}$ are 15 amino acids selected from the group consisting of (a) the endogenous GPCR's amino acids (b) non-endogenous amino acid residues, and (c) a combination of the endogenous GPCR's amino acids and non-endogenous amino acids, excepting that none of the 15 endogenous amino acid residues that are positioned within the TM6 region of the GPCR is proline; and (3) X is a non-endogenous amino acid residue located within the IC3 region of said GPCR, preferably selected from the group consisting of lysine, hisitidine and arginine, and most preferably lysine, excepting that when the endogenous amino acid at position X is lysine, then X is an amino acid other than lysine, preferably alanine;

and/or (b) $P^{codon}$ (AA-codon)$_{15}$ $X_{codon}$ wherein:

(1) $P^{codon}$ is a nucleic acid sequence within the TM6 region of the GPCR, where $P^{codon}$ encodes an amino acid selected from the group consisting of (i) the endogenous GPCR's proline residue, and (ii) a non-endogenous amino acid residue other than proline;

(2) (AA-codon)$_{15}$ are 15 codons encoding 15 amino acids selected from the group consisting of (a) the endogenous GPCR's amino acids (b) non-endogenous amino acid residues and (c) a combination of the endogenous GPCR's amino acids and non-endogenous amino acids, excepting that none of the 15 endogenous codons within the TM6 region of the GPCR encodes a proline amino acid residue; and (3) $X_{codon}$ is a nucleic acid encoding region residue located within the IC3 region of said GPCR, where $X_{codon}$ encodes a non-endogenous amino acid, preferably selected from the group consisting of lysine, hisitidine and arginine, and most preferably lysine, excepting that when the endogenous encoding region at position $X_{codon}$ encodes the amino acid lysine, then $X_{codon}$ encodes an amino acid other than lysine, preferably alanine.

The terms endogenous and non-endogenous in reference to these sequence cassettes are relative to the endogenous GPCR. For example, once the endogenous proline residue is located within the TM6 region of a particular GPCR, and the $16^{th}$ amino acid therefrom is identified for mutation to constitutively activate the receptor, it is also possible to mutate the endogenous proline residue (i.e., once the marker is located and the $16^{th}$ amino acid to be mutated is identified, one may mutate the marker itself), although it is most preferred that the proline residue not be mutated. Similarly, and while it is most preferred that $AA_{15}$ be maintained in their endogenous forms, these amino acids may also be mutated. The only amino acid that must be mutated in the non-endogenous version of the human GPCR is X i.e., the endogenous amino acid that is 16 residues from $P^1$ cannot be maintained in its endogenous form and must be mutated, as further disclosed herein. Stated again, while it is preferred that in the non-endogenous version of the human GPCR, $P^1$ and $AA_{15}$ remain in their endogenous forms (i.e., identical to their wild-type forms), once X is identified and mutated, any and/or all of $P^1$ and $AA_{15}$ can be mutated. This applies to the nucleic acid sequences as well. In those cases where the endogenous amino acid at position X is lysine, then in the non-endogenous version of such GPCR, X is an amino acid other than lysine, preferably alanine.

Accordingly, and as a hypothetical example, if the endogenous GPCR has the following endogenous amino acid sequence at the above-noted positions:

P-AACCTTGGRRRDDDE-Q (SEQ.ID.NO.: 281)

then any of the following exemplary and hypothetical cassettes would fall within the scope of the disclosure (non-endogenous amino acids are set forth in bold):

P-AACCTTGGRRRDDDE-K (SEQ.ID.NO.282)
P-AACCTTHIGRRDDDE-K (SEQ.ID.NO.283)
P-ADEETTGGRRRDDDE-A (SEQ.ID.NO.284)
P-LLKFMSTWZLVAAPQ-K (SEQ.ID.NO.285)
A-LLKFMSTWZLVAAPQ-K (SEQ.ID.NO.286)

It is also possible to add amino acid residues within $AA_{15}$, but such an approach is not particularly advanced. Indeed, in the most preferred embodiments, the only amino acid that differs in the non-endogenous version of the human GPCR as compared with the endogenous version of that GPCR is the amino acid in position X; mutation of this amino acid itself leads to constitutive activation of the receptor.

Thus, in particularly preferred embodiments, $P^1$ and $P^{codon}$ are endogenous proline and an endogenous nucleic acid encoding region encoding proline, respectively; and X and $X_{codon}$ are non-endogenous lysine or alanine and a non-endogenous nucleic acid encoding region encoding lysine or alanine, respectively, with lysine being most preferred. Because it is most preferred that the non-endogenous versions of the human GPCRs which incorporate these mutations are incorporated into mammalian cells and utilized for the screening of candidate compounds, the non-endogenous human GPCR incorporating the mutation need not be purified and isolated per se (i.e., these are incorporated within the cellular membrane of a mammalian cell), although such purified and isolated non-endogenous human GPCRs are well within the purview of this disclosure. Gene-targeted and transgenic non-human mammals (preferably rats and mice) incorporating the non-endogenous human GPCRs are also within the purview of this invention; in particular, gene-targeted mammals are most preferred in that these animals will incorporate the non-endogenous versions of the human GPCRs in place of the non-human mammal's endogenous GPCR-encoding region (techniques for generating such non-human mammals to replace the non-human mammal's protein encoding region with a human encoding region are well known; see, for example, U.S. Pat. No. 5,777,194.)

It has been discovered that these changes to an endogenous human GPCR render the GPCR constitutively active such that, as will be further disclosed herein, the non-endogenous, constitutively activated version of the human GPCR can be utilized for, inter alia, the direct screening of candidate compounds without the need for the endogenous ligand. Thus, methods for using these materials, and products identified by these methods are also within the purview of the following disclosure.

BRIEF DESCRIPTION OF THE DRAWINGS

FIGS. 3A through 3L are is a sequence diagram of the preferred vector pCMV, including restriction enzyme site locations.

FIG. 4 is a diagrammatic representation of the signal measured comparing pCMV, non-endogenous, constitutively active GPR30 inhibition of GPR6-mediated activation of CRE-Luc reporter with endogenous GPR30 inhibition of GPR6-mediated activation of CRE-Luc reporter.

FIG. 5 is a diagrammatic representation of the signal measured comparing pCMV, non-endogenous, constitutively activated GPR17 inhibition of GPR3-mediated activation of CRE-Luc reporter with endogenous GPR17 inhibition of GPR3-mediated activation of CRE-Luc reporter.

FIG. 6 provides diagrammatic results of the signal measured comparing control pCMV, endogenous APJ and non-endogenous APJ.

FIG. 7 provides an illustration of $IP_3$ production from non-endogenous human 5-$HT_{2A}$ receptor as compared to the endogenous version of this receptor.

DETAILED DESCRIPTION

Figure 1:
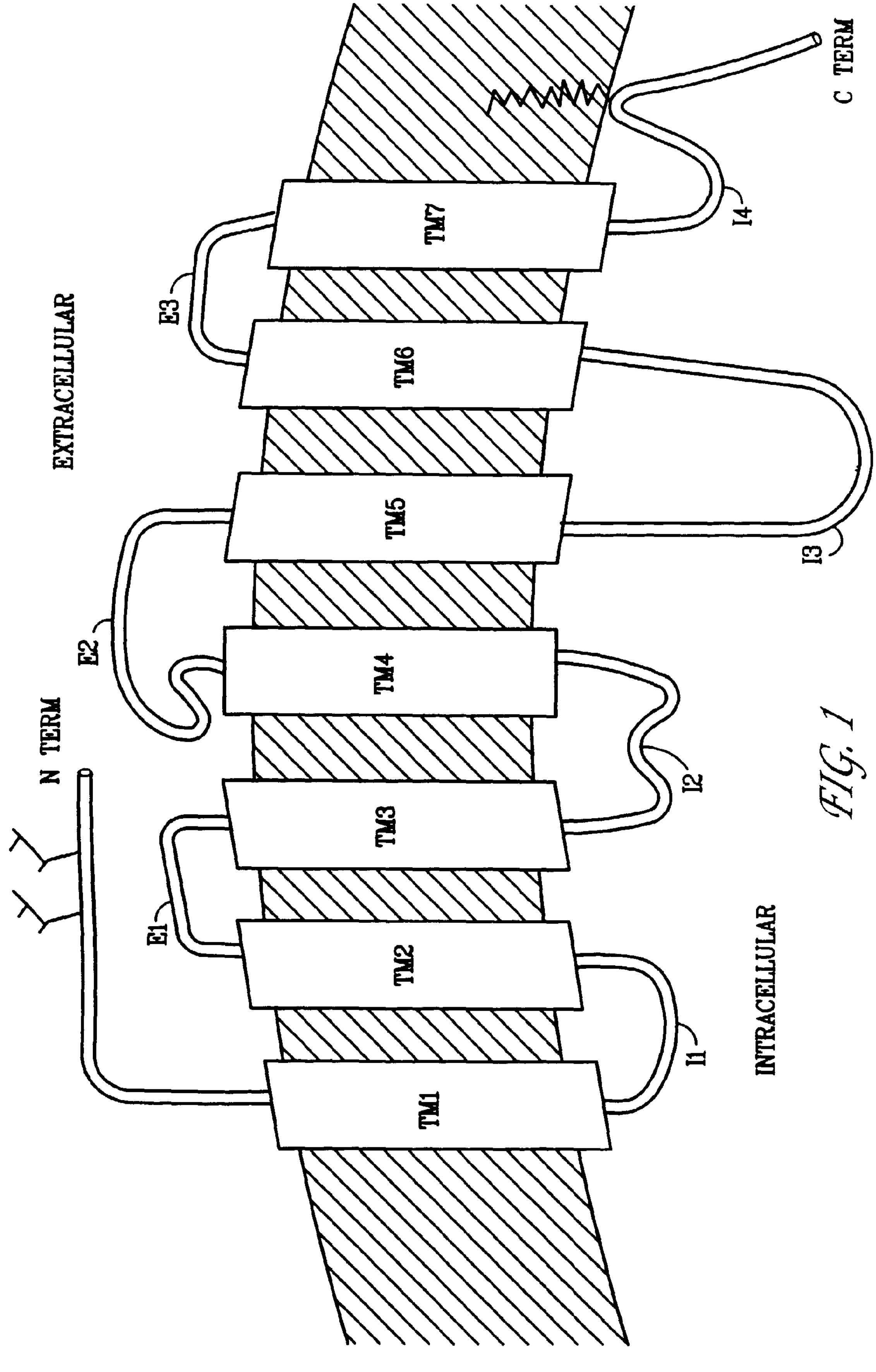
FIG. 1 shows a generalized structure of a G protein-coupled receptor with the numbers assigned to the transmembrane helixes, the intracellular loops, and the extracellular loops.
Figure 2:
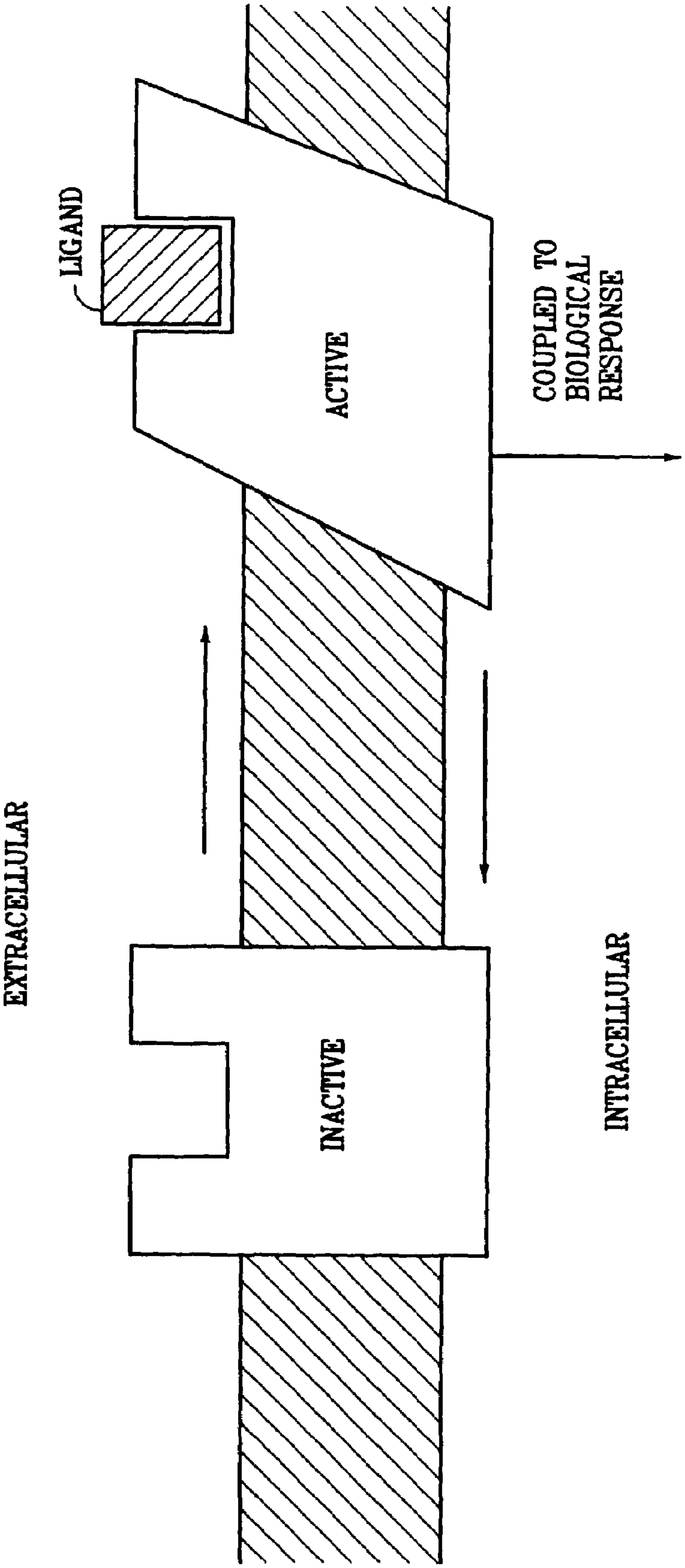
FIG. 2 schematically shows the two states, active and inactive, for a typical G protein coupled receptor and the linkage of the active state to the second messenger transduction pathway.
Figure 3A:
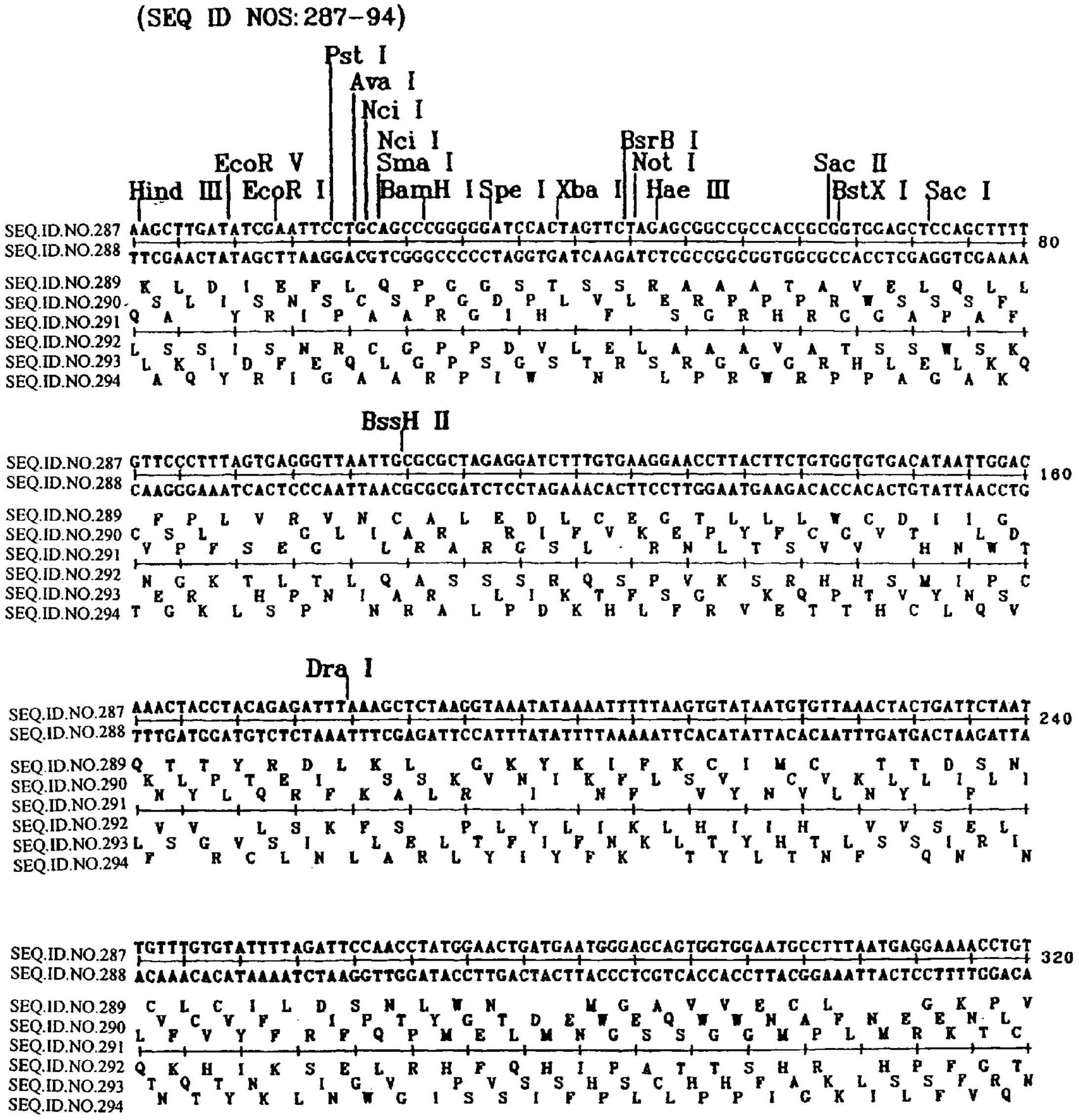
Figure 3C:
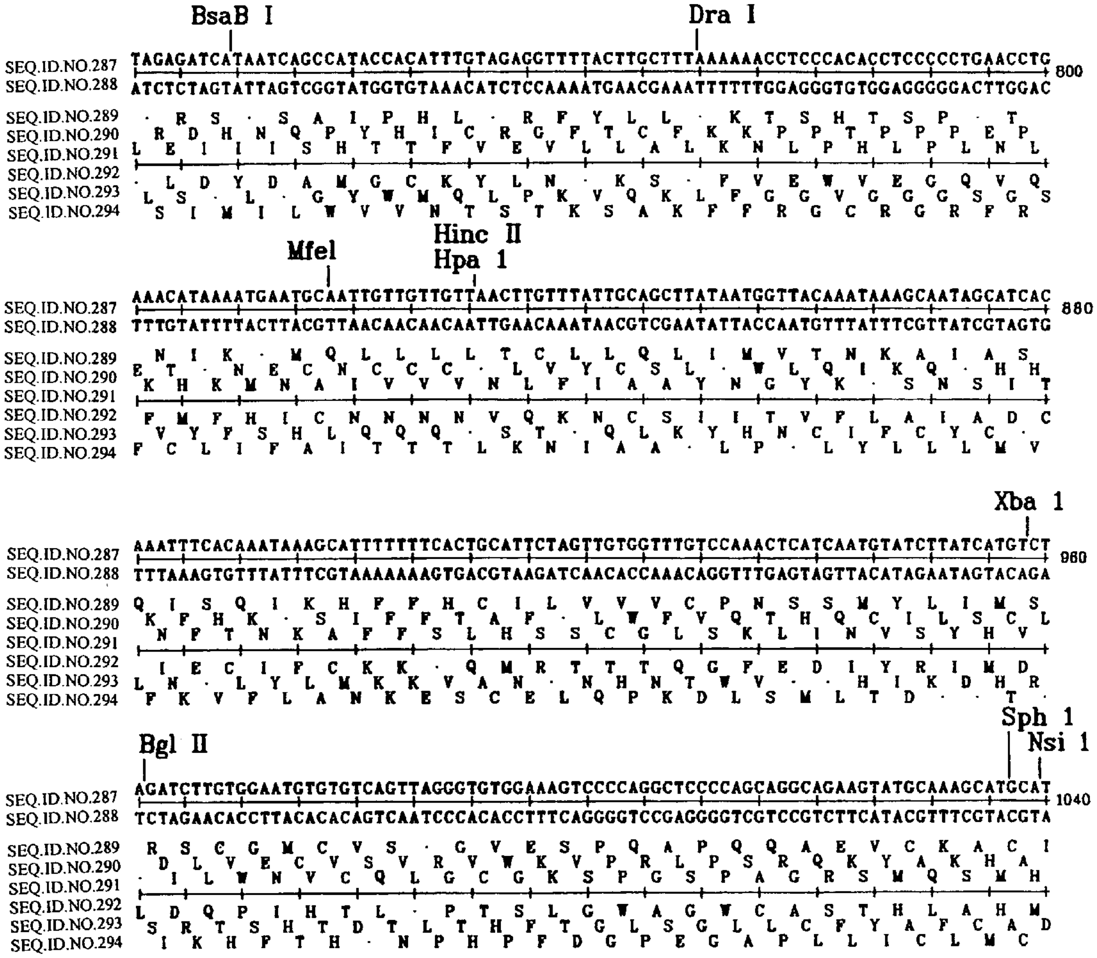
Figure 3D:
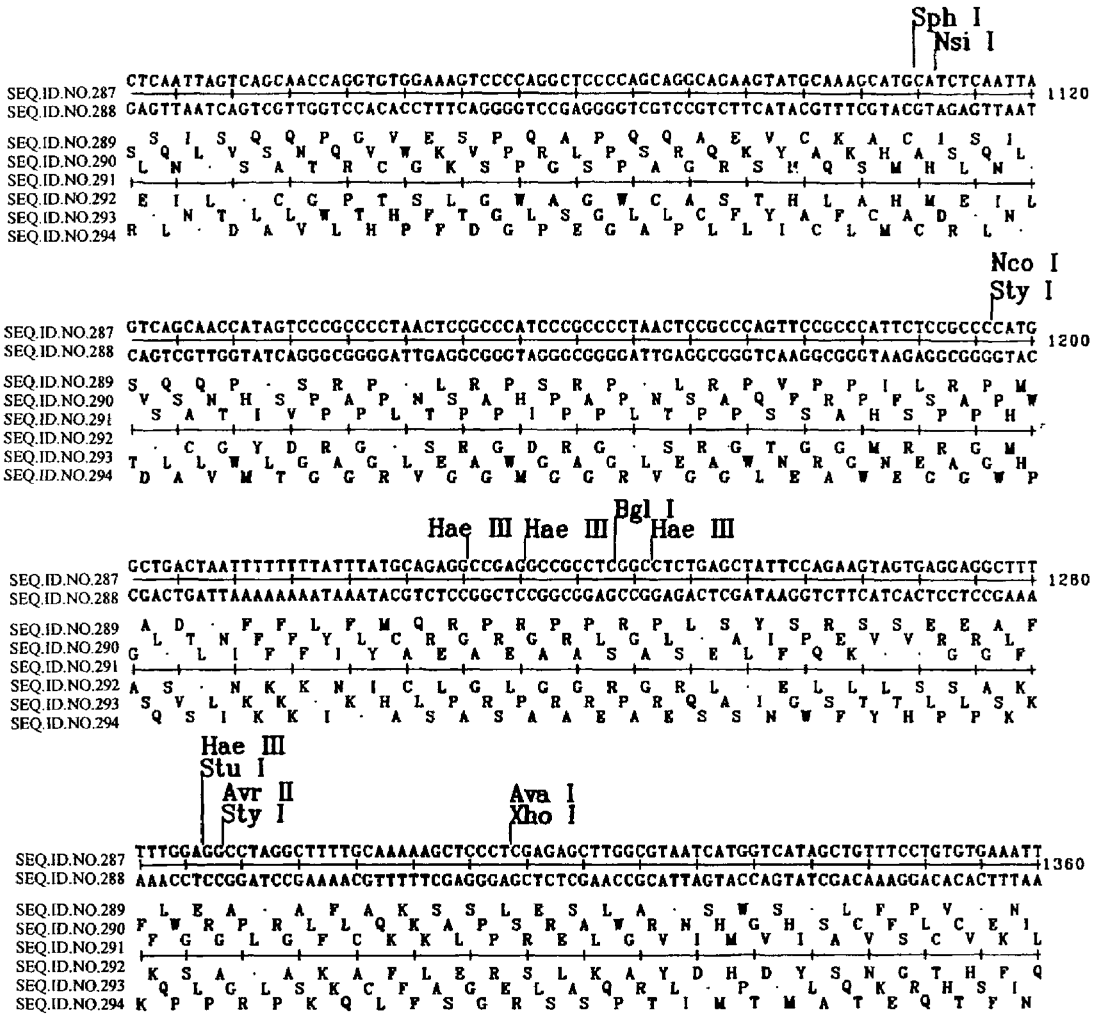
Figure 3F:
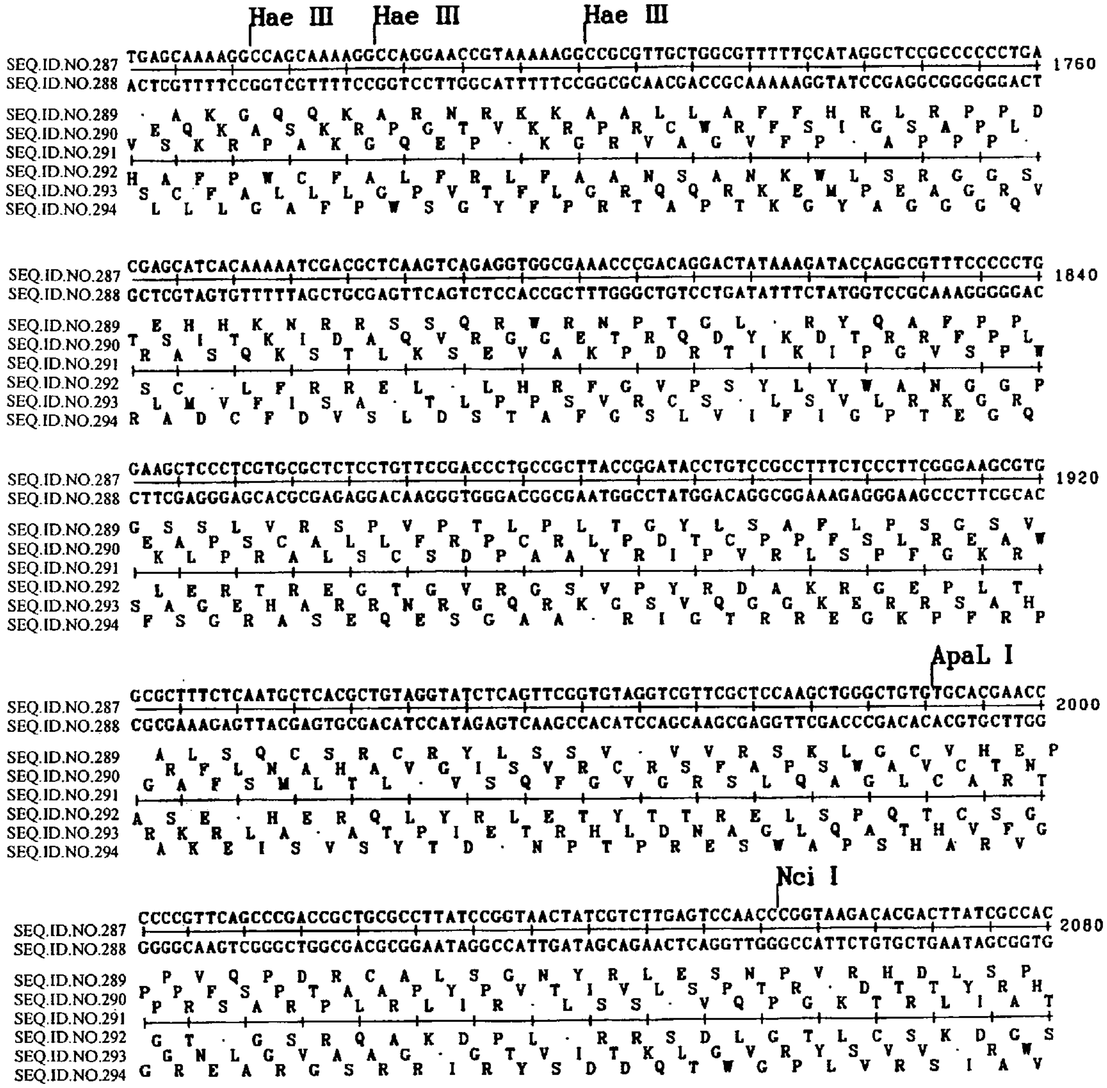
Figure 3J:
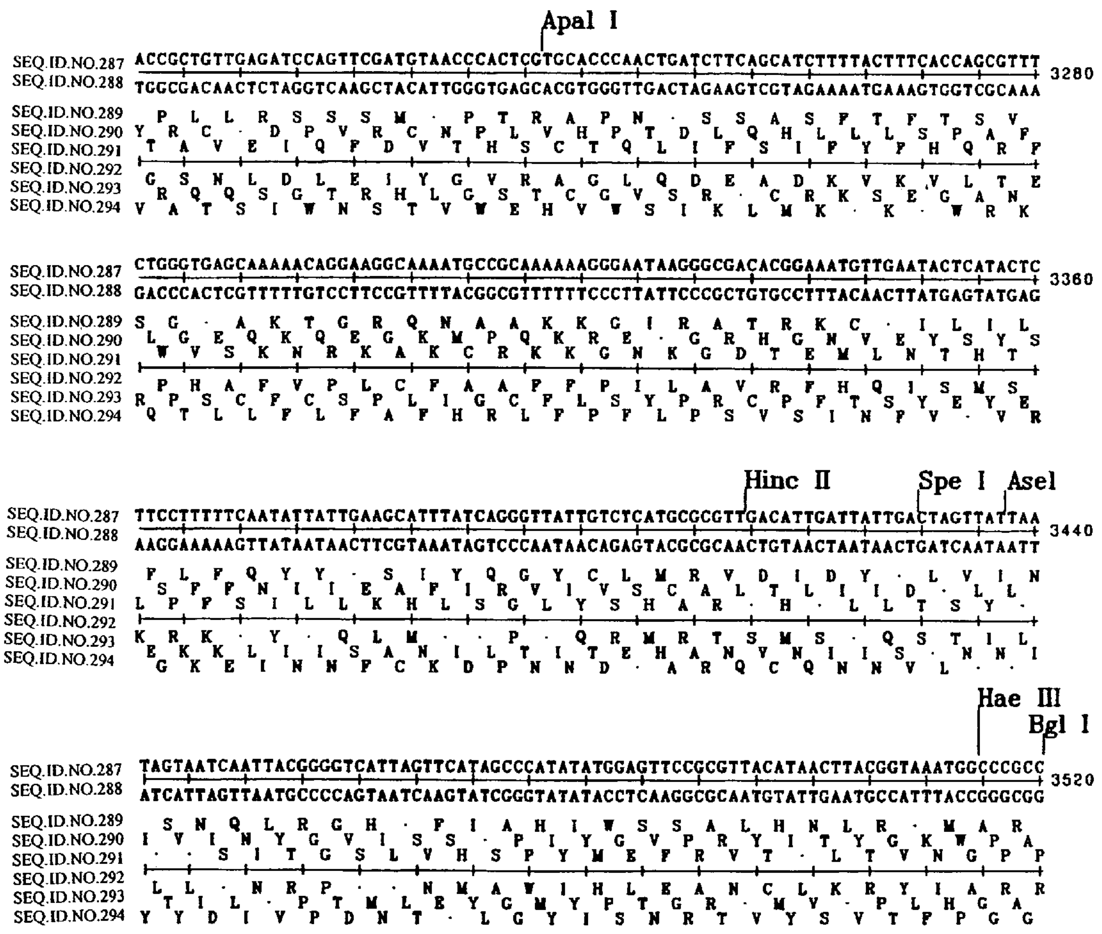
Figure 3L:
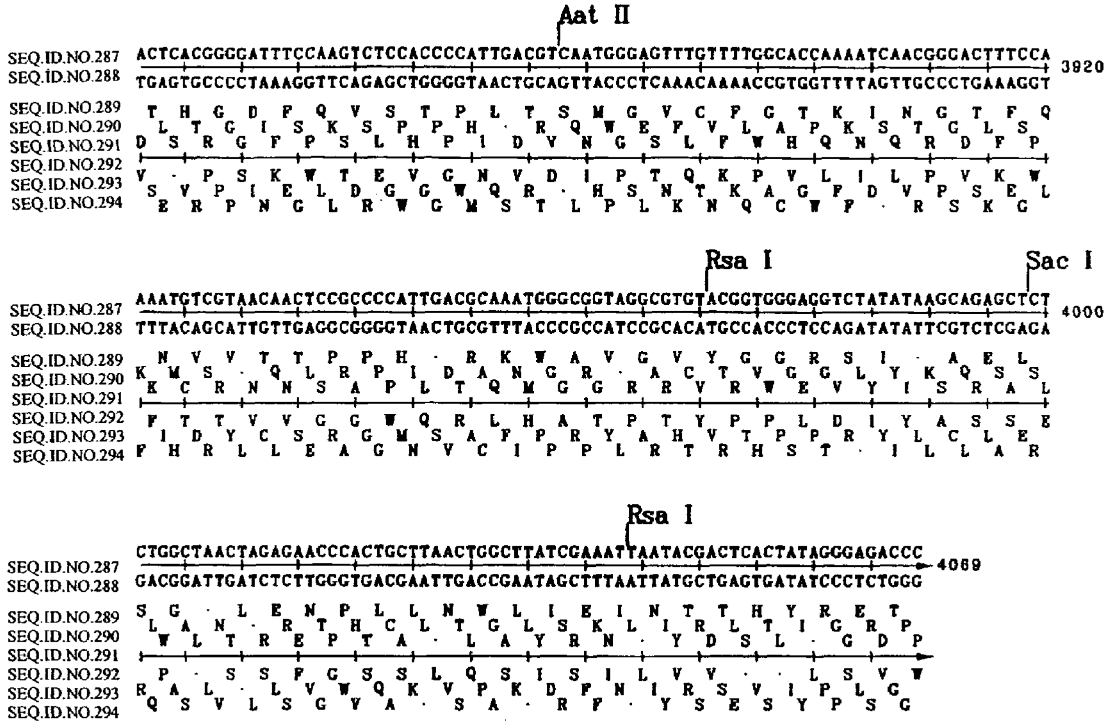

The scientific literature that has evolved around receptors has adopted a number of terms to refer to ligands having various effects on receptors. For clarity and consistency, the following definitions will be used throughout this patent document. To the extent that these definitions conflict with other definitions for these terms, the following definitions shall control:

AGONISTS shall mean compounds that activate the intracellular response when they bind to the receptor, or enhance GTP binding to membranes.

AMINO ACID ABBREVIATIONS used herein are set below:

| | | |
|---|---|---|
| ALANINE | ALA | A |
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

PARTIAL AGONISTS shall mean compounds which activate the intracellular response when they bind to the receptor to a lesser degree/extent than do agonists, or enhance GTP binding to membranes to a lesser degree/extent than do agonists ANTAGONIST shall mean compounds that competitively bind to the receptor at the same site as the agonists but which do not activate the intracellular response initiated by the active form of the receptor, and can thereby inhibit the intracellular responses by agonists or partial agonists. ANTAGONISTS do not diminish the baseline intracellular response in the absence of an agonist or partial agonist.

CANDIDATE COMPOUND shall mean a molecule (for example, and not limitation, a chemical compound) which is amenable to a screening technique. Preferably, the phrase "candidate compound" does not include compounds which were publicly known to be compounds selected from the group consisting of inverse agonist, agonist or antagonist to a receptor, as previously determined by an indirect identification process ("indirectly identified compound"); more preferably, not including an indirectly identified compound which has previously been determined to have therapeutic efficacy in at least one mammal; and, most preferably, not including an indirectly identified compound which has previously been determined to have therapeutic utility in humans.

CODON shall mean a grouping of three nucleotides (or equivalents to nucleotides) which generally comprise a nucleoside (adenosine (A), guanosine (G), cytidine (C), uridine (U) and thymidine (T)) coupled to a phosphate group and which, when translated, encodes an amino acid.

COMPOUND EFFICACY shall mean a measurement of the ability of a compound to inhibit or stimulate receptor functionality, as opposed to receptor binding affinity. A preferred means of detecting compound efficacy is via measurement of, e.g., $[^{35}S]GTP\gamma S$ binding, as further disclosed in the Example section of this patent document.

CONSTITUTIVELY ACTIVATED RECEPTOR shall mean a receptor subject to constitutive receptor activation. In accordance with the invention disclosed herein, a non-endogenous, human constitutively activated G protein-coupled receptor is one that has been mutated to include the amino acid cassette $P^1$ $AA_{15}X$, as set forth in greater detail below.

CONSTITUTIVE RECEPTOR ACTIVATION shall mean stabilization of a receptor in the active state by means other than binding of the receptor with its endogenous ligand or a chemical equivalent thereof. Preferably, a G protein-coupled receptor subjected to constitutive receptor activation in accordance with the invention disclosed herein evidences at least a 10% difference in response (increase or decrease, as the case may be) to the signal measured for constitutive activation as compared with the endogenous form of that GPCR, more preferably, about a 25% difference in such comparative response, and most preferably about a 50% difference in such comparative response. When used for the purposes of directly identifying candidate compounds, it is most preferred that the signal difference be at least about 50% such that there is a sufficient difference between the endogenous signal and the non-endogenous signal to differentiate between selected candidate compounds. In most instances, the "difference" will be an increase in signal; however, with respect to Gs-coupled GPCRS, the "difference" measured is preferably a decrease, as will be set forth in greater detail below.

CONTACT or CONTACTING shall mean bringing at least two moieties together, whether in an in vitro system or an in vivo system.

DIRECTLY IDENTIFYING or DIRECTLY IDENTIFIED, in relationship to the phrase "candidate compound", shall mean the screening of a candidate compound against a constitutively activated G protein-coupled receptor, and assessing the compound efficacy of such compound. This phrase is, under no circumstances, to be interpreted or understood to be encompassed by or to encompass the phrase "indirectly identifying" or "indirectly identified."

ENDOGENOUS shall mean a material that is naturally produced by the genome of the species. ENDOGENOUS in reference to, for example and not limitation, GPCR, shall mean that which is naturally produced by a human, an insect, a plant, a bacterium, or a virus. By contrast, the term NON-ENDOGENOUS in this context shall mean that which is not naturally produced by the genome of a species. For example, and not limitation, a receptor which is not constitutively active in its endogenous form, but when mutated by using the cassettes disclosed herein and thereafter becomes constitutively active, is most preferably referred to herein as a "non-endogenous, constitutively activated receptor." Both terms can be utilized to describe both "in vivo" and "in vitro" systems. For example, and not limitation, in a screening approach, the endogenous or non-endogenous receptor may be in reference to an in vitro screening system whereby the receptor is expressed on the cell-surface of a mammalian cell. As a further example and not limitation, where the genome of a mammal has been manipulated to include a non-endogenous constitutively activated receptor, screening of a candidate compound by means of an in vivo system is viable.

HOST CELL shall mean a cell capable of having a Plasmid and/or Vector incorporated therein. In the case of a prokaryotic Host Cell, a Plasmid is typically replicated as an autonomous molecule as the Host Cell replicates (generally, the Plasmid is thereafter isolated for introduction into a eukaryotic Host Cell); in the case of a eukaryotic Host Cell, a Plasmid is integrated into the cellular DNA of the Host Cell such that when the eukaryotic Host Cell replicates, the Plasmid replicates. Preferably, for the purposes of the invention disclosed herein, the Host Cell is eukaryotic, more preferably, mammalian, and most preferably selected from the group consisting of 293, 293T and COS-7 cells.

INDIRECTLY IDENTIFYING or INDIRECTLY IDENTIFIED means the traditional approach to the drug discovery process involving identification of an endogenous ligand specific for an endogenous receptor, screening of candidate compounds against the receptor for determination of those which interfere and/or compete with the ligand-receptor interaction, and assessing the efficacy of the compound for affecting at least one second messenger pathway associated with the activated receptor.

INHIBIT or INHIBITING, in relationship to the term "response" shall mean that a response is decreased or prevented in the presence of a compound as opposed to in the absence of the compound.

INVERSE AGONISTS shall mean compounds which bind to either the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding, to membranes. Preferably, the baseline intracellular response is inhibited in the presence of the inverse agonist by at least 30%, more preferably by at least 50%, and most preferably by at least 75%, as compared with the baseline response in the absence of the inverse agonist.

KNOWN RECEPTOR shall mean an endogenous receptor for which the endogenous ligand specific for that receptor has been identified.

LIGAND shall mean an endogenous, naturally occurring molecule specific for an endogenous, naturally occurring receptor.

MUTANT or MUTATION in reference to an endogenous receptor's nucleic acid and/or amino acid sequence shall mean a specified change or changes to such endogenous sequences such that a mutated form of an endogenous, non-constitutively activated receptor evidences constitutive activation of the receptor. In terms of equivalents to specific sequences, a subsequent mutated form of a human receptor is considered to be equivalent to a first mutation of the human receptor if (a) the level of constitutive activation of the subsequent mutated form of the receptor is substantially the same as that evidenced by the first mutation of the receptor; and (b) the percent sequence (amino acid and/or nucleic acid) homology between the subsequent mutated form of the receptor and the first mutation of the receptor is at least about 80%, more preferably at least about 90% and most preferably at least 95%. Ideally, and owing to the fact that the most preferred cassettes disclosed herein for achieving constitutive activation includes a single amino acid and/or codon change between the endogenous and the non-endogenous forms of the GPCR (i.e. X or $X_{codon}$), the percent sequence homology should be at least 98%.

ORPHAN RECEPTOR shall mean an endogenous receptor for which the endogenous ligand specific for that receptor has not been identified or is not known.

PHARMACEUTICAL COMPOSITION shall mean a composition comprising at least one active ingredient, whereby the composition is amenable to investigation for a specified, efficacious outcome in a mammal (for example, and not limitation, a human). Those of ordinary skill in the art will understand and appreciate the techniques appropriate for determining whether an active ingredient has a desired efficacious outcome based upon the needs of the artisan.

PLASMID shall mean the combination of a Vector and cDNA. Generally, a Plasmid is introduced into a Host Cell for the purpose of replication and/or expression of the cDNA as a protein.

STIMULATE or STIMULATING, in relationship to the term "response" shall mean that a response is increased in the presence of a compound as opposed to in the absence of the compound.

TRANSVERSE or TRANSVERSING, in reference to either a defined nucleic acid sequence or a defined amino acid sequence, shall mean that the sequence is located within at least two different and defined regions. For example, in an amino-acid sequence that is 10 amino acid moieties in length, where 3 of the 10 moieties are in the TM6 region of a GPCR and the remaining 7 moieties are in the IC3 region of the GPCR, the 10 amino acid moiety can be described as transversing the TM6 and IC3 regions of the GPCR.

VECTOR in reference to cDNA shall mean a circular DNA capable of incorporating at least one cDNA and capable of incorporation into a Host Cell.

The order of the following sections is set forth for presentational efficiency and is not intended, nor should be construed, as a limitation on the disclosure or the claims to follow.

A. Introduction

The traditional study of receptors has always proceeded from the a priori assumption (historically based) that the endogenous ligand must first be identified before discovery could proceed to find antagonists and other molecules that could affect the receptor. Even in cases where an antagonist might have been known first, the search immediately extended to looking for the endogenous ligand. This mode of thinking has persisted in receptor research even after the discovery of constitutively activated receptors. What has not been heretofore recognized is that it is the active state of the receptor that is most useful for discovering agonists, partial agonists, and inverse agonists of the receptor. For those diseases which result from an overly active receptor or an under-active receptor, what is desired in a therapeutic drug is a compound which acts to diminish the active state of a receptor or enhance the activity of the receptor, respectively, not necessarily a drug which is an antagonist to the endogenous ligand. This is because a compound that reduces or enhances the activity of the active receptor state need not bind at the same site as the endogenous ligand. Thus, as taught by a method of this invention, any search for therapeutic compounds should start by screening compounds against the ligand-independent active state.

Screening candidate compounds against non-endogenous, constitutively activated GPCRs allows for the direct identification of candidate compounds which act at these cell surface receptors, without requiring any prior knowledge or use of the receptor's endogenous ligand. By determining areas within the body where the endogenous version of such GPCRs are expressed and/or over-expressed, it is possible to determine related disease/disorder states which are associated with the expression and/or over-expression of these receptors; such an approach is disclosed in this patent document.

B. Disease/Disorder Identification and/or Selection

Most preferably, inverse agonists to the non-endogenous, constitutively activated GPCRs can be identified using the materials of this invention. Such inverse agonists are ideal candidates as lead compounds in drug discovery programs for treating diseases related to these receptors. Because of the ability to directly identify inverse agonists, partial agonists or agonists to these receptors, thereby allowing for the development of pharmaceutical compositions, a search, for diseases and disorders associated with these receptors is possible. For example, scanning both diseased and normal tissue samples for the presence of these receptor now becomes more than an academic exercise or one which might be pursued along the path of identifying, in the case of an orphan receptor, an endogenous ligand. Tissue scans can be conducted across a broad range of healthy and diseased tissues. Such tissue scans provide a preferred first step in associating a specific receptor with a disease and/or disorder.

Preferably, the DNA sequence of the endogenous GPCR is used to make a probe for either radiolabeled cDNA or RT-PCR identification of the expression of the GPCR in tissue samples. The presence of a receptor in a diseased tissue, or the presence of the receptor at elevated or decreased concentrations in diseased tissue compared to a normal tissue, can be preferably utilized to identify a correlation with that disease. Receptors can equally well be localized to regions of organs by this technique. Based on the known functions of the specific tissues to which the receptor is localized, the putative functional role of the receptor can be deduced.

C. A "Human GPCR Proline Marker" Algorithm and the Creation of Non-Endogenous, Constitutively-Active Human GPCRs Among the many challenges facing the biotechnology arts is the unpredictability in gleaning genetic information from one species and correlating that information to another species—nowhere in this art does this problem evidence more annoying exacerbation than in the genetic sequences that encode nucleic acids and proteins. Thus, for consistency and because of the highly unpredictable nature of this art, the following invention is limited, in terms of mammals, to human GPCRs—applicability of this invention to other mammalian species, while a potential possibility, is considered beyond mere rote application.

In general, when attempting to apply common "rules" from one related protein sequence to another or from one species to another, the art has typically resorted to sequence alignment, i.e., sequences are linearized and attempts are then made to find regions of commonality between two or more sequences. While useful, this approach does not always prove to result in meaningful information. In the case of GPCRs, while the general structural motif is identical for all GPCRs, the variations in lengths of the TMs, ECs and ICs make such alignment approaches from one GPCR to another difficult at best. Thus, while it may be desirable to apply a consistent approach to, e.g. constitutive activation from one GPCR to another, because of the great diversity in sequence length, fidelity, etc from one GPCR to the next, a generally applicable, and readily successful mutational alignment approach is in essence not possible. In an analogy, such an approach is akin to having a traveler start a journey at point A by giving the traveler dozens of different maps to point B, without any scale or distance markers on any of the maps, and then asking the traveler to find the shortest and most efficient route to destination B only by using the maps. In such a situation, the task can be readily simplified by having (a) a common "place-marker" on each map, and (b) the ability to measure the distance from the place-marker to destination B—this, then, will allow the traveler to select the most efficient from starting-point A to destination B.

In essence, a feature of the invention is to provide such coordinates within human GPCRs that readily allows for creation of a constitutively active form of the human GPCRs.

As those in the art appreciate, the transmembrane region of a cell is highly hydrophobic; thus, using standard hydrophobicity plotting techniques, those in the art are readily able to determine the TM regions of a GPCR, and specifically TM6 (this same approach is also applicable to determining the EC and IC regions of the GPCR). It has been discovered that within the TM6 region of human GPCRs, a common proline residue (generally near the middle of TM6), acts as a constitutive activation "marker." By counting 15 amino acids from the proline marker, the $16^{th}$ amino acid (which is located in the IC3 loop), when mutated from its endogenous form to a non-endogenous form, leads to constitutive activation of the receptor. For convenience, we refer to this as the "Human GPCR Proline Marker" Algorithm. Although the non-endogenous amino acid at this position can be any of the amino acids, most preferably, the non-endogenous amino acid is lysine. While not wishing to be bound by any theory, we believe that this position itself is unique and that the mutation at this location impacts the receptor to allow for constitutive activation.

We note that, for example, when the endogenous amino acid at the $16^{th}$ position is already lysine (as is the case with GPR4 and GPR32), then in order for X to be a non-endogenous amino acid, it must be other than lysine; thus, in those situations where the endogenous GPCR has an endogenous lysine residue at the $16^{th}$ position, the non-endogenous version of that GPCR preferably incorporates an amino acid other than lysine, preferably alanine, histidine and arginine, at this position. Of further note, it has been determined that GPR4 appears to be linked to Gs and active in its endogenous form (data not shown).

Because there are only 20 naturally occurring amino acids (although the use of non-naturally occurring amino acids is also viable), selection of a particular non-endogenous amino acid for substitution at this $16^{th}$ position is viable and allows for efficient selection of a non-endogenous amino acid that fits the needs of the investigator. However, as noted, the more preferred non-endogenous amino acids at the $16^{th}$ position are lysine, hisitidine, arginine and alanine, with lysine being most preferred. Those of ordinary skill in the art are credited with the ability to readily determine proficient methods for changing the sequence of a codon to achieve a desired mutation.

It has also been discovered that occasionally, but not always, the proline residue marker will be preceded in TM6 by W2 (i.e., $W2P^1AA_{15}X$) where W is tryptophan and 2 is any amino acid residue.

Our discovery, amongst other things, negates the need for unpredictable and complicated sequence alignment approaches commonly used by the art. Indeed, the strength of our discovery, while an algorithm in nature, is that it can be applied in a facile manner to human GPCRs, with dexterous simplicity by those in the art, to achieve a unique and highly useful end-product, i.e., a constitutively activated version of a human GPCR. Because many years and significant amounts of money will be required to determine the endogenous ligands for the human GPCRs that the Human Genome project is uncovering, the disclosed invention not only reduces the time necessary to positively exploit this sequence information, but at significant cost-savings. This approach truly validates the importance of the Human Genome Project because it allows for the utilization of genetic information to not only understand the role of the GPCRs in, e.g., diseases, but also provides the opportunity to improve the human condition.

D. Screening of Candidate Compounds

1. Generic GPCR Screening Assay Techniques

When a G protein receptor becomes constitutively active, it couples to a G protein (e.g., Gq, Gs, Gi, Go) and stimulates release and subsequent binding of GTP to the G protein. The G protein then acts as a GTPase and slowly hydrolyzes the GTP to GDP, whereby the receptor, under normal conditions, becomes deactivated. However, constitutively activated receptors, including the non-endogenous, human constitutively active GPCRs of the present invention, continue to exchange GDP for GTP. A non-hydrolyzable analog of GTP, $[^{35}S]GTP\gamma S$, can be used to monitor enhanced binding to G proteins present on membranes which express constitutively activated receptors. It is reported that $[^{35}S]GTP\gamma S$ can be used to monitor G protein coupling to membranes in the absence and presence of ligand. An example of this monitoring, among other examples well-known and available to those in the art, was reported by Traynor and Nahorski in 1995. The preferred use of this assay system is for initial screening of candidate compounds because the system is generically applicable to all G protein-coupled receptors regardless of the particular G protein that interacts with the intracellular domain of the receptor.

2. Specific GPCR Screening Assay Techniques

Once candidate compounds are identified using the "generic" G protein-coupled receptor assay (i.e., an assay to select compounds that are agonists, partial agonists, or inverse agonists), further screening to confirm that the compounds have interacted at the receptor site is preferred. For example, a compound identified by the "generic" assay may not bind to the receptor, but may instead merely "uncouple" the G protein from the intracellular domain.

a. Gs and Gi.

Gs stimulates the enzyme adenylyl cyclase. Gi (and Go), on the other hand, inhibit this enzyme. Adenylyl cyclase catalyzes the conversion of ATP to cAMP; thus, constitutively activated GPCRs that couple the Gs protein are associated with increased cellular levels of cAMP. On the other hand, constitutively activated GPCRs that couple the Gi (or Go) protein are associated with decreased cellular levels of cAMP. See, generally, "Indirect Mechanisms of Synaptic Transmission," Chpt. 8, *From Neuron To Brain* (3$^{rd}$ Ed.) Nichols, J. G. et al eds. Sinauer Associates, Inc. (1992). Thus, assays that detect cAMP can be utilized to determine if a candidate compound is, e.g., an inverse agonist to the receptor (i.e., such a compound would decrease the levels of cAMP). A variety of approaches known in the art for measuring cAMP can be utilized; a most preferred approach relies upon the use of anti-cAMP antibodies in an ELISA-based format. Another type of assay that can be utilized is a whole cell second messenger reporter system assay. Promoters on genes drive the expression of the proteins that a particular gene encodes. Cyclic AMP drives gene expression by promoting the binding of a cAMP-responsive DNA binding protein or transcription factor (CREB) which then binds to the promoter at specific sites called cAMP response elements and drives the expression of the gene. Reporter systems can be constructed which have a promoter containing multiple cAMP response elements before the reporter gene, e.g., β-galactosidase or luciferase. Thus, a constitutively activated Gs-linked receptor causes the accumulation of cAMP that then activates the gene and expression of the reporter protein. The reporter protein such as β-galactosidase or luciferase can then be detected using standard biochemical assays (Chen et al. 1995). With respect to GPCRs that link to Gi (or Go), and thus decrease levels of cAMP, an approach to the screening of, e.g., inverse agonists, based upon utilization of receptors that link to Gs (and thus increase levels of cAMP) is disclosed in the Example section with respect to GPR17 and GPR30.

b. Go and Gq.

Gq and Go are associated with activation of the enzyme phospholipase C, which in turn hydrolyzes the phospholipid $PIP_2$, releasing two intracellular messengers: diacycloglycerol (DAG) and inistol 1,4,5-triphoisphate ($IP_3$). Increased accumulation of $IP_3$ is associated with activation of Gq- and Go-associated receptors. See, generally, "Indirect Mechanisms of Synaptic Transmission," Chpt. 8, *From Neuron To Brain* (3$^{rd}$ Ed.) Nichols, J. G. et al eds. Sinauer Associates, Inc. (1992). Assays that detect $IP_3$ accumulation can be utilized to determine if a candidate compound is, e.g., an inverse agonist to a Gq- or Go-associated receptor (i.e., such a compound would decrease the levels of $IP_3$). Gq-associated receptors can also been examined using an AP1 reporter assay in that Gq-dependent phospholipase C causes activation of genes containing AP1 elements; thus, activated Gq-associated receptors will evidence an increase in the expression of such genes, whereby inverse agonists thereto will evidence a decrease in such expression, and agonists will evidence an increase in such expression. Commercially available assays for such detection are available.

E. Medicinal Chemistry

Generally, but not always, direct identification of candidate compounds is preferably conducted in conjunction with compounds generated via combinatorial chemistry techniques, whereby thousands of compounds are randomly prepared for such analysis. Generally, the results of such screening will be compounds having unique core structures; thereafter, these compounds are preferably subjected to additional chemical modification around a preferred core structure(s) to further enhance the medicinal properties thereof. Such techniques are known to those in the art and will not be addressed in detail in this patent document.

F. Pharmaceutical Compositions

Candidate compounds selected for further development can be formulated into pharmaceutical compositions using techniques well known to those in the art. Suitable pharmaceutically-acceptable carriers are available to those in the art; for example, see Remington's Pharmaceutical Sciences, 16$^{th}$ Edition, 1980, Mack Publishing Co., (Oslo et al., eds.)

G. Other Utility

Although a preferred use of the non-endogenous versions of the disclosed human GPCRs is for the direct identification of candidate compounds as inverse agonists, agonists or partial agonists (preferably for use as pharmaceutical agents), these receptors can also be utilized in research settings. For example, in vitro and in vivo systems incorporating these receptors can be utilized to further elucidate and understand the roles of the receptors in the human condition, both normal and diseased, as well understanding the role of constitutive activation as it applies to understanding the signaling cascade. A value in these non-endogenous receptors is that their utility as a research tool is enhanced in that, because of their unique features, the disclosed receptors can be used to understand the role of a particular receptor in the human body before the endogenous ligand therefor is identified. Other uses of the disclosed receptors will become apparent to those in the art based upon, inter alia, a review of this patent document.

EXAMPLES

The following examples are presented for purposes of elucidation, and not limitation, of the present invention. Following the teaching of this patent document that a mutational cassette may be utilized in the IC3 loop of human GPCRs based upon a position relative to a proline residue in TM6 to constitutively activate the receptor, and while specific nucleic acid and amino acid sequences are disclosed herein, those of ordinary skill in the art are credited with the ability to make minor modifications to these sequences while achieving the same or substantially similar results reported below. Particular approaches to sequence mutations are within the purview of the artisan based upon the particular needs of the artisan.

Example 1

Preparation of Endogenous Human GPCRs

A variety of GPCRs were utilized in the Examples to follow. Some endogenous human GPCRs were graciously provided in expression vectors (as acknowledged below) and other endogenous human GPCRs were synthesized de novo using publicly-available sequence information.

1. GPR1 (GenBank Accession Number: U13666)

The human cDNA sequence for GPR1 was provided in pRcCMV by Brian O'Dowd (University of Toronto). GPR1 cDNA (1.4 kB fragment) was excised from the pRcCMV vector as a NdeI-XbaI fragment and was subcloned into the NdeI-XbaI site of pCMV vector (see FIG. 3). Nucleic acid (SEQ.ID.NO.: 1) and amino acid (SEQ.ID.NO.: 2) sequences for human GPR1 were thereafter determined and verified.

2. GPR4 (GenBank Accession Numbers: L36148, U35399, U21051)

The human cDNA sequence for GPR4 was provided in pRcCMV by Brian O'Dowd (University of Toronto). GPR1 cDNA (1.4 kB fragment) was excised from the pRcCMV vector as an ApaI(blunted)-XbaI fragment and was subcloned (with most of the 5' untranslated region removed) into HindIII (blunted)-XbaI site of pCMV vector. Nucleic acid (SEQ.ID.NO.: 3) and amino acid (SEQ.ID.NO.: 4) sequences for human GPR4 were thereafter determined and verified.

3. GPR5 (GenBank Accession Number: L36149)

The cDNA for human GPR5 was generated and cloned into pCMV expression vector as follows: PCR was performed using genomic DNA as template and rTth polymerase (Perkin Elmer) with the buffer system provided by the manufacturer, 0.25 μM of each primer, and 0.2 mM of each of the 4 nucleotides. The cycle condition was 30 cycles of. 94° C. for 1 min; 64° C. for 1 min; and 72° C. for 1.5 min. The 5' PRC primer contained an EcoRI site with the sequence:

5'-TATGAATTCAGATGCTCTAAACGTCCCTGC-3' (SEQ.ID.NO.: 5)

and the 3' primer contained BamHI site with the sequence:

5'-TCCGGATCCACCTGCACCTGCGCCTGCACC-3' (SEQ.ID.NO.: 6).

The 1.1 kb PCR fragment was digested with EcoRI and BamHI and cloned into EcoRI-BamHI site of PCMV expression vector. Nucleic acid (SEQ.ID.NO.: 7) and amino acid (SEQ.ID.NO.: 8) sequences for human GPR5 were thereafter determined and verified.

4. GPR7 (GenBank Accession Number: U22491)

The cDNA for human GPR7 was generated and cloned into pCMV expression vector as follows: PCR condition-PCR was performed using genomic DNA as template and rTth polymerase (Perkin Elmer) with the buffer system provided by the manufacturer, 0.25 μM of each primer, and 0.2 mM of each of the 4 nucleotides. The cycle condition was 30 cycles of: 94° C. for 1 min; 62° C. for 1 min; and 72° C. for 1 min and 20 sec. The 5' PCR primer contained a HindIII site with the sequence:

5'-GCAAGCTTGGGGGACGCCAGGTCGCCGGCT-3' (SEQ.ID.NO.: 9)

and the 3' primer contained a BamHI site with the sequence:

5'-GCGGATCCGGACGCTGGGGGAGTCAGGCTGC-3' (SEQ.ID.NO.: 10).

The 1.1 kb PCR fragment was digested with HindIII and BamHI and cloned into HindIII-BamHI site of pCMV expression vector. Nucleic acid (SEQ.ID.NO.: 11) and amino acid (SEQ.ID.NO.: 12) sequences for human GPR7 were thereafter determined and verified.

5. GPR8 (GenBank Accession Number: U22492)

The cDNA for human GPR8 was generated and cloned into pCMV expression vector as follows: PCR was performed using genomic DNA as template and rTth polymerase (Perkin Elmer) with the buffer system provided by the manufacturer, 0.25 μM of each primer, and 0.2 mM of each of the 4 nucleotides. The cycle condition was 30 cycles of: 94° C. for 1 min; 62° C. for 1 min; and 72° C. for 1 min and 20 sec. The 5' PCR primer contained an EcoRI site with the sequence:

5'-CGGAATTCGTCAACGGTCCCAGCTACAATG-3' (SEQ.ID.NO.: 13).

and the 3' primer contained a BamHI site with the sequence:

5'-ATGGATCCCAGGCCCTTCAGCACCGCAATAT-3' (SEQ.ID.NO.: 14).

The 1.1 kb PCR fragment was digested with EcoRI and BamHI and cloned into EcoRI-BamHI site of PCMV expression vector. All 4 cDNA clones sequenced contained a possible polymorphism involving a change of amino acid 206 from Arg to Gln. Aside from this difference, nucleic acid (SEQ.ID.NO.: 15) and amino acid (SEQ.ID.NO.: 16) sequences for human GPR8 were thereafter determined and verified.

6. GPR9 (GenBank Accession Number: X95876)

The cDNA for human GPR9 was generated and cloned into pCMV expression vector as follows: PCR was performed using a clone (provided by Brian O'Dowd) as template and pfu polymerase (Stratagene) with the buffer system provided by the manufacturer supplemented with 10% DMSO, 0.25 μM of each primer, and 0.5 mM of each of the 4 nucleotides. The cycle condition was 25 cycles of: 94° C. for 1 min; 56° C. for 1 min; and 72° C. for 2.5 min. The 5' PCR primer contained an EcoRI site with the sequence:

5'-ACGAATTCAGCCATGGTCCTTGAGGT-GAGTGACCACCAAGTGCTAAAT-3' (SEQ.ID.NO.: 17)

and the 3' primer contained a BamHI site with the sequence:

5'-GAGGATCCTGGAATGCGGGGAAGTCAG-3' (SEQ.ID.NO.: 18).

The 1.2 kb PCR fragment was digested with EcoRI and cloned into EcoRI-SmaI site of PCMV expression vector. Nucleic acid (SEQ.ID.NO.: 19) and amino acid (SEQ.ID.NO.: 20) sequences for human GPR9 were thereafter determined and verified.

7. GPR9-6 (GenBank Accession Number: U45982)

The cDNA for human GPR9-6 was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each of the 4 nucleotides. The cycle condition was 30 cycles of: 94° C. for 1 min; 62° C. for 1 min; and 72° C. for 1 min and 20 sec. The 5' PCR primer was kinased with the sequence:

5'-TTAAGCTTGACCTAATGCCATCTTGTGTCC-3' (SEQ.ID.NO.: 21)

and the 3' primer contained a BamHI site with the sequence:

5'-TTGGATCCAAAAGAACCATGCACCTCAGAG-3' (SEQ.ID.NO.: 22).

The 1.2 kb PCR fragment was digested with BamHI and cloned into EcoRV-BamHI site of pCMV expression vector. Nucleic acid (SEQ.ID.NO.: 23) and amino acid (SEQ.ID.NO.: 24) sequences for human GPR9-6 were thereafter determined and verified.

8. GPR10 (GenBank Accession Number: U32672)

The human cDNA sequence for GPR10 was provided in pRcCMV by Brian O'Dowd (University of Toronto). GPR10 cDNA (1.3 kB fragment) was excised from the pRcCMV vector as an EcoRI-XbaI fragment and was subcloned into EcoRI-XbaI site of pCMV vector. Nucleic acid (SEQ.ID.NO.: 25) and amino acid (SEQ.ID.NO.: 26) sequences for human GPR10 were thereafter determined and verified.

9. GPR15 (GenBank Accession Number: U34806)

The human cDNA sequence for GPR15 was provided in pCDNA3 by Brian O'Dowd (University of Toronto). GPR15 cDNA (1.5 kB fragment) was excised from the pCDNA3 vector as a HindIII-Bam fragment and was subcloned into HindIII-Bam site of pCMV vector. Nucleic acid (SEQ.ID.NO.: 27) and amino acid (SEQ.ID.NO.: 28) sequences for human GPR15 were thereafter determined and verified.

10. GPR17 (GenBank Accession Number: Z94154)

The cDNA for human GPR17 was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each 4 nucleotides. The cycle condition was 30 cycles of: 94° C. for 1 min; 56° C. for 1 min and 72° C. for 1 min and 20 sec. The 5' PCR primer contained an EcoRI site with the sequence:

5'-CTAGAATTCTGACTCCAGCCAAAGCATGAAT-3' (SEQ.ID.NO.: 29) and the 3' primer contained a BamHI site with the sequence:

5'-GCTGGATCCTAAACAGTCTGCGCTCGGCCT-3' (SEQ.ID.NO.: 30).

The 1.1 kb PCR fragment was digested with EcoRI and BamHI and cloned into EcoRI-BamHI site of pCMV expression vector. Nucleic acid (SEQ.ID.NO.: 31) and amino acid (SEQ.ID.NO.: 32) sequences for human GPR17 were thereafter determined and verified.

11. GPR18 (GenBank Accession Number: L42324)

The cDNA for human GPR18 was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each of the 4 nucleotides. The cycle condition was 30 cycles of: 94° C. for 1 min; 54° C. for 1 min; and 72° C. for 1 min and 20 sec. The 5' PCR primer was kinased with the sequence:

5'-ATAAGATGATCACCCTGAACAATCAAGAT -3' (SEQ.ID.NO.: 33)

and the 3' primer contained an EcoRI site with the sequence:

5'-TCCGAATTCATAACATTTCACTGTTTATATTGC-3' (SEQ.ID.NO.: 34).

The 1.0 kb PCR fragment was digested with EcoRI and cloned into blunt-EcoRI site of pCMV expression vector. All 8 cDNA clones sequenced contained 4 possible polymorphisms involving changes of amino acid 12 from Thr to Pro, amino acid 86 from Ala to Glu, amino acid 97 from Ile to Leu and amino acid 310 from Leu to Met. Aside from these changes, nucleic acid (SEQ.ID.NO.: 35) and amino acid (SEQ.ID.NO.: 36) sequences for human GPR18 were thereafter determined and verified.

12. GPR20 (GenBank Accession Number: U66579)

The cDNA for human GPR20 was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each of the 4 nucleotides. The cycle condition was 30 cycles of. 94° C. for 1 min; 62° C. for 1 min; and 72° C. for 1 min and 20 sec. The 5' PCR primer was kinased with the sequence:

5'-CCAAGCTTCCAGGCCTGGGGTGTGCTGG-3' (SEQ.ID.NO.: 37)

and the 3' primer contained a BamHI site with the sequence:

5'-ATGGATCCTGACCTTCGGCCCCTGGCAGA-3' (SEQ. ID.NO.: 38).

The 1.2 kb PCR fragment was digested with BamHI and cloned into EcoRV-BamHI site of PCMV expression vector. Nucleic acid (SEQ.ID.NO.: 39) and amino acid (SEQ.ID.NO.: 40) sequences for human GPR20 were thereafter determined and verified.

13. GPR21 (GenBank Accession Number: U66580)

The cDNA for human GPR21 was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each of the 4 nucleotides. The cycle condition was 30 cycles of: 94° C. for 1 min; 62° C. for 1 min; and 72° C. for 1 min and 20 sec. The 5' PCR primer was kinased with the sequence:

5'-GAGAATTCACTCCTGAGCTCAAGATGAACT-3' (SEQ.ID.NO.: 41)

and the 3' primer contained a BamHI site with the sequence:

5'-CGGGATCCCCGTAACTGAGCCACTTCAGAT-3' (SEQ.ID.NO.: 42).

The 1.1 kb PCR fragment was digested with BamHI and cloned into EcoRV-BamHI site of pCMV expression vector. Nucleic acid (SEQ.ID.NO.: 43) and amino acid (SEQ.ID.NO.: 44) sequences for human GPR21 were thereafter determined and verified.

14. GPR22 (GenBank Accession Number: U66581)

The cDNA for human GPR22 was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each of the 4 nucleotides. The cycle condition was 30 cycles of: 94° C. for 1 min; 50° C. for 1 min; and 72° C. for 1.5 min. The 5' PC primer was kinased with the sequence:

5'-TCCCCCGGGAAAAAAACCAACTGCTCCAAA-3' (SEQ.ID.NO.: 45)

and the 3' primer contained a BamHI site with the sequence:

5'-TAGGATCCATTTGAATGTGGATTTGGTGAAA-3' (SEQ.ID.NO.: 46).

The 1.38 kb PCR fragment was digested with BamHI and cloned into EcoRV-BamHI site of pCMV expression vector. Nucleic acid (SEQ.ID.NO.: 47) and amino acid (SEQ.ID.NO.: 48) sequences for human GPR22 were thereafter determined and verified.

15. GPR24 (GenBank Accession Number: U71092)

The cDNA for human GPR24 was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each 4 nucleotides. The cycle condition was 30 cycles of: 94° C. for 1 min; 56° C. for 1 min; and 72° C. for 1 min and 20 sec. The 5' PCR primer contains a HindIII site with the sequence:

5'-GTGAAGCTTGCCTCTGGTGCCTGCAGGAGG-3' (SEQ.ID.NO.: 49)

and the 3' primer contains an EcoRI site with the sequence:

5'-GCAGAATTCCCGGTGGCGTGTTGTGGTGCCC-3' (SEQ.ID.NO.: 50).

The 1.3 kb PCR fragment was digested with HindIII and EcoRI and cloned into HindIII-EcoRI site of pCMV expression vector. The nucleic acid (SEQ.ID.NO.: 51) and amino acid sequence (SEQ.ID.NO.: 52) for human GPR24 were thereafter determined and verified.

16. GPR30 (GenBank Accession Number: U63917)

The cDNA for human GPR30 was generated and cloned as follows: the coding sequence of GPR30 (1128 bp in length) was amplified from genomic DNA using the primers:

5'-GGCGGATCCATGGATGTGACTTCCCAA-3' (SEQ.ID.NO.: 53) and

5'-GGCGGATCCCTACACGGCACTGCTGAA-3' (SEQ.ID.NO.: 54).

The amplified product was then cloned into a commercially available vector, pCR2.1 (Invitrogen), using a "TOPO-TA Cloning Kit" (Invitrogen, #K4500-01), following manufacturer instructions. The full-length GPR30 insert was liberated by digestion with BamH1, separated from the vector by agarose gel electrophoresis, and purified using a Sephaglas Bandprep™ Kit (Pharmacia, #27-9285-01) following manufacturer instructions. The nucleic acid (SEQ.ID.NO.: 55) and amino acid sequence (SEQ.ID.NO.: 56) for human GPR30 were thereafter determined and verified.

17. GPR31 (GenBank Accession Number: U65402)

The cDNA for human GPR31 was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each of the 4 nucleotides. The cycle condition was 30 cycles of: 94° C. for 1 min; 58° C. for 1 min; and 72° C. for 2 min. The 5' PCR primer contained an EcoRI site with the sequence:

5'-AAGGAATTCACGGCCGGGTGATGCCATTCCC-3' (SEQ.ID.NO.: 57)

and the 3' primer contained a BamHI site with the sequence:

5'-GGTGGATCCATAAACACGGGCGTTGAGGAC-3' (SEQ.ID.NO.: 58).

The 1.0 kb PCR fragment was digested with EcoRI and BamHI and cloned into EcoRI-BamHI site of pCMV expression vector. Nucleic acid (SEQ.ID.NO.: 59) and amino acid (SEQ.ID.NO.: 60) sequences for human GPR31 were thereafter determined and verified.

18. GPR32 (GenBank Accession Number: AF045764)

The cDNA for human GPR32 was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each 4 nucleotides. The cycle condition was 30 cycles of: 94° C. for 1 min; 56° C. for 1 min; and 72° C. for 1 min and 20 sec. The 5' primer contained an EcoRI site with the sequence:

5'-TAAGAATTCCATAAAAATTATGGAATGG-3' (SEQ.ID.NO.:243)

and the 3' primer contained a BamHI site with the sequence:

5'-CCAGGATCCAGCTGAAGTCTTCCATCATTC-3' (SEQ.ID.NO.: 244).

The 1.1 kb PCR fragment was digested with EcoRI and BamHI and cloned into EcoRI-BamHI site of pCMV expression vector. Nucleic acid (SEQ.ID.NO.: 245) and amino acid (SEQ.ID.NO.: 246) sequences for human-GPR32 were thereafter determined and verified.

19. GPR40 (GenBank Accession Number: AF024687)

The cDNA for human GPR40 was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each 4 nucleotides. The cycle condition was 30 cycles of: 94° C. for 1 min, 65° C. for 1 min and 72° C. for 1 min and 10 sec. The 5' PCR primer contained an EcoRI site with the sequence

5'-GCAGAATTCGGCGGCCCCATGGACCTGCCCCC-3' (SEQ.ID.NO.: 247)

and the 3' primer contained a BamHI site with the sequence

5'-GCTGGATCCCCCGAGCAGTGGCGTTACTTC-3' (SEQ.ID.NO.: 248).

The 1 kb PCR fragment was digested with EcoRI and BamHI and cloned into EcoRI-BamHI site of pCMV expression vector. Nucleic acid (SEQ.ID.NO.: 249) and amino acid (SEQ.ID.NO.: 250) sequences for human GPR40 were thereafter determined and verified.

20. GPR41 (GenBank Accession Number AF024688)

The cDNA for human GPR41 was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each 4 nucleotides. The cycle condition was 30 cycles of 94° C. for 1 min, 65° C. for 1 min and 72° C. for 1 min and 10 sec. The 5' PCR primer contained an HindIII site with the sequence:

5'-CTCAAGCTTACTCTCTCTCACCAGTGGCCAC-3' (SEQ.ID.NO.: 251)

and the 3' primer was kinased with the sequence

5'-CCCTCCTCCCCCGGAGGACCTAGC-3' (SEQ.ID.NO.: 252).

The 1 kb PCR fragment was digested with HindIII and cloned into HindIII-blunt site of pCMV expression vector. Nucleic acid (SEQ.ID.NO.: 253) and amino acid (SEQ.ID.NO.: 254) sequences for human GPR41 were thereafter determined and verified.

21. GPR43 (GenBank Accession Number AF024690)

The cDNA for human GPR43 was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each 4 nucleotides. The cycle condition was 30 cycles of: 94° C. for 1 min; 65° C. for 1 min; and 72° C. for 1 min and 10 sec. The 5' PCR primer contains an HindIII site with the sequence:

5'-TTTAAGCTTCCCCTCCAGGATGCTGCCGGAC-3' (SEQ.ID.NO.: 255)

and the 3' primer contained an EcoRI site with the sequence:

5'-GGCGAATTCTGAAGGTCCAGGGAAACTGCTA-3' (SEQ.ID.NO. 256).

The 1 kb PCR fragment was digested with HindIII and EcoRI and cloned into HindIII-EcoRI site of pCMV expression vector. Nucleic acid (SEQ.ID.NO.: 257) and amino acid (SEQ.ID.NO.: 258) sequences for human GPR43 were thereafter determined and verified.

22. APJ (GenBank Accession Number: U03642)

Human APJ cDNA (in pRcCMV vector) was provided by Brian O'Dowd (University of Toronto). The human APJ cDNA was excised from the pRcCMV vector as an EcoRI-XbaI (blunted) fragment and was subcloned into EcoRI-SmaI site of pCMV vector. Nucleic acid (SEQ.ID.NO.: 61) and amino acid (SEQ.ID.NO.: 62) sequences for human APJ were thereafter determined and verified.

23. BLR1 (GenBank Accession Number: X68149)

The cDNA for human BLR1 was generated and cloned into pCMV expression vector as follows: PCR was performed using thymus cDNA as template and rTth polymerase (Perkin Elmer) with the buffer system provided by the manufacturer, 0.25 μM of each primer, and 0.2 mM of each of the 4 nucleotides. The cycle condition was 30 cycles of: 94° C. for 1 min; 62° C. for 1 min; and 72° C. for 1 min and 20 sec.The 5' PCR primer contained an EcoRI site with the sequence:

5'-TGAGAATTCTGGTGACTCACAGCCGGCACAG-3' (SEQ.ID.NO.: 63):

and the 3' primer contained a BamHI site with the sequence:

5'-GCCGGATCCAAGGAAAAGCAGCAATAAAAGG-3' (SEQ.ID.NO.: 64). The 1.2 kb PCR fragment was digested with EcoRI and BamHI and cloned into EcoRI-BamHI site of pCMV expression vector. Nucleic acid (SEQ.ID.NO.: 65) and amino acid (SEQ.ID.NO.: 66) sequences for human BLR1 were thereafter determined and verified.

24. CEPR (GenBank Accession Number: U77827)

The cDNA for human CEPR was generated and cloned into pCMV expression vector as follows: PCR was performed using genomic DNA as template and rTth polymerase (Perkin Elmer) with the buffer system provided by the manufacturer, 0.25 μM of each primer, and 0.2 mM of each of the 4 nucleotides. The cycle condition was 30 cycles of: 94° C. for 1 min; 65° C. for 1 min; and 72° C. for 1 min and 20 sec. The 5' PCR primer was kinased with the sequence:

5'-CAAAGCTTGAAAGCTGCACGGTGCAGAGAC-3' (SEQ.ID.NO.:67)

and the 3' primer contained a BamHI site with the sequence:

5'-GCGGATCCCGAGTCACACCCTGGCTGGGCC-3' (SEQ.ID.NO.: 68).

The 1.2 kb PCR fragment was digested with BamHI and cloned into EcoRV-BamHI site of pCMV expression vector. Nucleic acid (SEQ.ID.NO.: 69) and amino acid (SEQ.ID.NO.: 70) sequences for human CEPR were thereafter determined and verified.

25. EBI1 (GenBank Accession Number: L31581)

The cDNA for human EBI1 was generated and cloned into pCMV expression vector as follows: PCR was performed using thymus cDNA as template and rTth polymerase (Perkin Elmer) with the buffer system provided by the manufacturer, 0.25 μM of each primer, and 0.2 mM of each of the 4 nucleotides. The cycle condition was 30 cycles of: 94° C. for 1 min; 62° C. for 1 min; and 72° C. for 1 min and 20 sec. The 5' PCR primer contained an EcoRI site with the sequence:

5'-ACAGAATTCCTGTGTGGTTTTACCGCCCAG-3' (SEQ.ID.NO.: 71)

and the 3' primer contained a BamHI site with the sequence:

5'-CTCGGATCCAGGCAGAAGAGTCGCCTATGG-3' (SEQ.ID.NO.: 72).

The 1.2 kb PCR fragment was digested with EcoRI and BamHI and cloned into EcoRI-BamHI site of PCMV expression vector. Nucleic acid (SEQ.ID.NO.: 73) and amino acid (SEQ.ID.NO.: 74) sequences for human EBI1 were thereafter determined and verified.

26. EBI2 (GenBank Accession Number: L08177)

The cDNA for human EB2 was generated and cloned into pCMV expression vector as follows: PCR was performed using cDNA clone (graciously provided by Kevin Lynch, University of Virginia Health Sciences Center; the vector utilized was not identified by the source) as template and pfu polymerase (Stratagene) with the buffer system provided by the manufacturer supplemented with 10% DMSO, 0.25 μM of each primer, and 0.5 mM of each of the 4 nucleotides. The cycle condition was 30 cycles of: 94° C. for 1 min; 60° C. for 1 min; and 72° C. for 1 min and 20 sec. The 5' PCR primer contained an EcoRI site with the sequence:

5'-CTGGAATTCACCTGGACCACCACCAATGGATA-3' (SEQ.ID.NO.: 75)

and the 3' primer contained a BamHI site with the sequence

5'-CTCGGATCCTGCAAAGTTTGTCATACAGTT-3' (SEQ.ID.NO.: 76).

The 1.2 kb PCR fragment was digested with EcoRI and BamHI and cloned into EcoRI-BamHI site of pCMV expression vector. Nucleic acid (SEQ.ID.NO.: 77) and amino acid (SEQ.ID.NO.: 78) sequences for human EBI2 were thereafter determined and verified.

27. ETBR-LP2 (GenBank Accession Number: D38449)

The cDNA for human ETBR-LP2 was generated and cloned into pCMV expression vector as follows: PCR was performed using brain cDNA as template and rTth polymerase (Perkin Elmer) with the buffer system provided by the manufacturer, 0.25 μM of each primer, and 0.2 mM of each of the 4 nucleotides. The cycle condition was 30 cycles of: 94° C. for 1 min; 65° C. for 1 min; and 72° C. for 1.5 min. The 5' PCR contained an EcoRI site with the sequence:

5'-CTGGAATTCTCCTGCTCATCCAGCCATGCGG-3' (SEQ.ID.NO.: 79)

and the 3' primer contained a BamHI site with the sequence:

5'-CCTGGATCCCCACCCCTACTGGGGCCTCAG-3' (SEQ.ID.NO.: 80).

The 1.5 kb PCR fragment was digested with EcoRI and BamHI and cloned into EcoRI-BamHI site of pCMV expression vector. Nucleic acid (SEQ.ID.NO.: 81) and amino acid (SEQ.ID.NO.: 82) sequences for human ETBR-LP2 were thereafter determined and verified.

28. GHSR (GenBank Accession Number: U60179)

The cDNA for human GHSR was generated and cloned into pCMV expression vector as follows: PCR was performed using hippocampus cDNA as template and TaqPlus Precision polymerase (Stratagene) with the buffer system provided by the manufacturer, 0.25 μM of each primer, and 0.2 mM of each of the 4 nucleotides. The cycle condition was 30 cycles of: 94° C. for 1 min; 68° C. for 1 min; and 72° C. for 1 min and 10 sec. For first round PCR, the 5' PCR primer sequence was:

5'-ATGTGGAACGCGACGCCCAGCG-3' (SEQ.ID.NO.: 83)

and the 3' primer sequence was:

5'-TCATGTATTAATACTAGATTCT-3' (SEQ.ID.NO.: 84).

Two microliters of the first round PCR was used as template for the second round PCR where the 5' primer was kinased with sequence:

5'-TACCATGTGGAACGCGACGCCCAGCGAA-GAGCCGGGGT-3' (SEQ.ID.NO.:85)

and the 3' primer contained an EcoRI site with the sequence:

5'-CGGAATTCATGTATTAATACTAGATTCT-GTCCAGGCCCG-3' (SEQ.ID.NO.:86).

The 1.1 kb PCR fragment was digested with EcoRI and cloned into blunt-EcoRI site of pCMV expression vector. Nucleic acid (SEQ.ID.NO.: 87) and amino acid (SEQ.ID.NO.: 88) sequences for human GHSR were thereafter determined and verified.

29. GPCR-CNS (GenBank Accession Number: AFO17262)

The cDNA for human GPCR-CNS was generated and cloned into pCMV expression vector as follows: PCR was performed using brain cDNA as template and rTth polymerase (Perkin Elmer) with the buffer system provided by the manufacturer, 0.25 μM of each primer, and 0.2 mM of each of the 4 nucleotides. The cycle condition was 30 cycles of: 94° C. for 1 min; 65° C. for 1 min; and 72° C. for 2 min. The 5' PCR primer contained a HindIII site with the sequence:

5'-GCAAGCTTGTGCCCTCACCAAGCCATGCGAGCC-3' (SEQ.ID.NO.: 89)

and the 3' primer contained an EcoRI site with the sequence:

5'-CGGAATTCAGCAATGAGTTCCGACAGAAGC-3' (SEQ.ID.NO.: 90).

The 1.9 kb PCR fragment was digested with HindIII and EcoRI and cloned into HindIII-EcoRI site of pCMV expression vector. All nine clones sequenced contained a potential polymorphism involving a S284C change. Aside from this difference, nucleic acid (SEQ.ID.NO.: 91) and amino acid (SEQ.ID.NO.: 92) sequences for human GPCR-CNS were thereafter determined and verified.

30. GPR-NGA (GenBank Accession Number: U55312)

The cDNA for human GPR-NGA was generated and cloned into pCMV expression vector as follows: PCR was performed using genomic DNA as template and rTth polymerase (Perkin Elmer) with the buffer system provided by the manufacturer, 0.25 μM of each primer, and 0.2 mM of each of the 4 nucleotides. The cycle condition was 30 cycles of 94° C. for 1 min, 56° C. for 1 min and 72° C. for 1.5 min. The 5' PCR primer contained an EcoRI site with the sequence:

5'-CAGAATTCAGAGAAAAAAAGTGAATATGGTTTTT-3' (SEQ.ID.NO.: 93)

and the 3' primer contained a BamHI site with the sequence:

5'-TTGGATCCCTGGTGCATAACAATTGAAAGAAT-3' (SEQ.ID.NO.: 94).

The 1.3 kb PCR fragment was digested with EcoRI and BamHI and cloned into EcoRI-BamHI site of pCMV expression vector. Nucleic acid (SEQ.ID.NO.: 95) and amino acid (SEQ.ID.NO.: 96) sequences for human GPR-NGA were thereafter determined and verified.

31. H9 (GenBank Accession Number: U52219)

The cDNA for human HB954 was generated and cloned into pCMV expression vector as follows: PCR was performed using pituitary cDNA as template and rTth polymerase (Perkin Elmer) with the buffer system provided by the manufacturer, 0.25 μM of each primer, and 0.2 mM of each 4 nucleotides. The cycle condition was 30 cycles of: 94° C. for 1 min, 62° C. for 1 min and 72° C. for 2 min. The 5' PCR primer contains a HindIII site with the sequence:

5'-GGAAAGCTTAACGATCCCCAGGAGCAACAT-3' (SEQ.ID.NO.: 97)

and the 3' primer contains a BamHI site with the sequence:

5'-CTGGGATCCTACGAGAGCATTTTTCACACAG-3' (SEQ.ID.NO.: 98).

The 1.9 kb PCR fragment was digested with HindIII and BamHI and cloned into HindIII-BamHI site of pCMV expression vector. When compared to the published sequences, a different isoform with 12 bp in frame insertion in the cytoplasmic tail was also identified and designated "H9b." Both isoforms contain two potential polymorphisms involving changes of amino acid P320S and amino acid G448A. Isoform H9a contained another potential polymorphism of amino acid S493N, while isoform H9b contained two additional potential polymorphisms involving changes of amino acid I502T and amino acid A532T (corresponding to amino acid 528 of isoform H9a). Nucleic acid (SEQ.ID.NO.: 99) and amino acid (SEQ.ID.NO.: 100) sequences for human H9 were thereafter determined and verified (in the section below, both isoforms were mutated in accordance with the Human GPCR Proline Marker Algorithm).

32. HB954 (GenBank Accession Number: D38449)

The cDNA for human HB954 was generated and cloned into pCMV expression vector as follows: PCR was performed using brain cDNA as template and rTth polymerase (Perkin Elmer) with the buffer system provided by the manufacturer, 0.25 μM of each primer, and 0.2 mM of each of the 4 nucleotides. The cycle condition was 30 cycles of 94° C. for 1 min, 58° C. for 1 min and 72° C. for 2 min. The 5' PCR contained a HindIII site with the sequence:

5'-TCCAAGCTTCGCCATGGGACATAACGGGAGCT-3' (SEQ.ID.NO.: 101)

and the 3' primer contained an EcoRI site with the sequence:

5'-CGTGAATTCCAAGAATTTACAATCCTTGCT-3' (SEQ.ID.NO.: 102).

The 1.6 kb PCR fragment was digested with HindIII and EcoRI and cloned into HindIII-EcoRI site of pCMV expression vector. Nucleic acid (SEQ.ID.NO.: 103) and amino acid (SEQ.ID.NO.: 104) sequences for human HB954 were thereafter determined and verified.

33. HG38 (GenBank Accession Number: AF062006)

The cDNA for human HG38 was generated and cloned into pCMV expression vector as follows: PCR was performed using brain cDNA as template and rTth polymerase (Perkin Elmer) with the buffer system provided by the manufacturer, 0.25 μM of each primer, and 0.2 mM of each 4 nucleotides. The cycle condition was 30 cycles of 94° C. for 1 min, 56° C. for 1 min and 72° C. for 1 min and 30 sec. Two PCR reactions were performed to separately obtain the 5' and 3' fragment. For the 5' fragment, the 5' PCR primer contained an HindIII site with the sequence:

5'-CCCAAGCTTCGGGCACCATGGACACCTCCC-3' (SEQ.ID.NO.: 259)

and the 3' primer contained a BamHIsite with the sequence:

5'-ACAGGATCCAAATGCACAGCACTGGTAAGC-3' (SEQ.ID.NO.: 260).

This 5' 1.5 kb PCR fragment was digested with HindIII and BamHI and cloned into an HindIII-BamHI site of pCMV. For the 3' fragment, the 5' PCR primer was kinased with the sequence:

5'-CTATAACTGGGTTACATGGTTTAAC-3' (SEQ.ID.NO. 261)

and the 3' primer contained an EcoRI site with the sequence:

5'-TTTGAATTCACATATTAATTAGAGACATGG-3' (SEQ. ID.NO.: 262).

The 1.4 kb 3' PCR fragment was digested with EcoRI and subcloned into a blunt-EcoRI site of pCMV vector. The 5' and 3' fragments were then ligated together through a common EcoRV site to generate the full length cDNA clone. Nucleic acid (SEQ.ID.NO.: 263) and amino acid (SEQ.ID.NO.: 264) sequences for human HG38 were thereafter determined and verified.

34. HM74 (GenBank Accession Number: D10923)

The cDNA for human HM74 was generated and cloned into pCMV expression vector as follows: PCR was performed using either genomic DNA or thymus cDNA (pooled) as template and rTth polymerase (Perkin Elmer) with the buffer system provided by the manufacturer, 0.25 μM of each primer, and 0.2 mM of each of the 4 nucleotides. The cycle condition was 30 cycles of: 94° C. for 1 min; 65° C. for 1 min; and 72° C. for 1 min and 20 sec. The 5' PCR primer contained an EcoRI site with the sequence:

5'-GGAGAATTCACTAGGCGAGGCGCTCCATC-3' (SEQ. ID.NO.: 105)

and the 3' primer was kinased with the sequence:

5'-GGAGGATCCAGGAAACCTTAGGCCGAGTCC-3' (SEQ.ID.NO.:106).

The 1.3 kb PCR fragment was digested with EcoRI and cloned into EcoRI-SmaI site of pCMV expression vector. Clones sequenced revealed a potential polymorphism involving a N94K change. Aside from this difference, nucleic acid (SEQ.ID.NO.: 107) and amino acid (SEQ.ID.NO.: 108) sequences for human HM74 were thereafter determined and verified.

35. MIG (GenBank Accession Numbers: AFO44600 and AFO44601)

The cDNA for human MIG was generated and cloned into pCMV expression vector as follows: PCR was performed using genomic DNA as template and TaqPlus Precision polymerase (Stratagene) for first round PCR or pfu polymerase (Stratagene) for second round PCR with the buffer system provided by the manufacturer, 0.25 μM of each primer, and 0.2 mM (TaqPlus Precision) or 0.5 mM (pfu) of each of the 4 nucleotides. When pfu was used, 10% DMSO was included in the buffer. The cycle condition was 30 cycles of: 94° C. for 1 min; 65° C. for 1 min; and 72° C. for: (a) 1 min for first round PCR; and (b) 2 min for second round PCR. Because there is an intron in the coding region, two sets of primers were separately used to generate overlapping 5' and 3' fragments. The 5' fragment PCR primers were:

5'-ACCATGGCTTGCAATGGCAGTGCGGC-CAGGGGGCACT-3' (external sense) (SEQ.ID.NO.: 109)

and

5'-CGACCAGGACAAACAGCATCTTGGT-CACTTGTCTCCGGC-3' (internal antisense) (SEQ. ID.NO.: 110).

The 3' fragment PCR primers were:

5'-GACCAAGATGCTGTTTGTCCTGGTCGTG-GTGTTTGGCAT-3' (internal sense) (SEQ.ID.NO.: 111) and 5'-CGGAATTCAGGATGGATCGGTCTCT-TGCTGCGCCT-3' (external antisense with an EcoRI site) (SEQ.ID.NO.: 112).

The 5' and 3' fragments were ligated together by using the first round PCR as template and the kinased external sense primer and external antisense primer to perform second round PCR. The 1.2 kb PCR fragment was digested with EcoRI and cloned into the blunt-EcoRI site of pCMV expression vector. Nucleic acid (SEQ.ID.NO.: 113) and amino acid (SEQ. ID.NO.: 114) sequences for human MIG were thereafter determined and verified.

36. OGR1 (GenBank Accession Number: U48405)

The cDNA for human ORG1 was generated and cloned into pCMV expression vector as follows: PCR was performed using genomic DNA as template and rTth polymerase (Perkin Elmer) with the buffer system provided by the manufacturer, 0.25 μM of each primer, and 0.2 mM of each of the 4 nucleotides. The cycle condition was 30 cycles of: 94° C. for 1 min; 65° C. for 1 min; and 72° C. for 1 min and 20 sec. The 5' PCR primer was kinased with the sequence:

5'-GGAAGCTTCAGGCCCAAAGATGGGGAACAT-3' (SEQ.ID.NO.: 115):

and the 3' primer contained a BamHI site with the sequence:

5'-GTGGATCCACCCGCGGAGGACCCAGGCTAG-3' (SEQ.ID.NO.: 116).

The 1.1 kb PCR fragment was digested with BamHI and cloned into the EcoRV-BamHI site of pCMV expression vector. Nucleic acid (SEQ.ID.NO.: 117) and amino acid (SEQ.ID.NO.: 118) sequences for human ORG1 were thereafter determined and verified.

37. Serotonin $5HT_{2A}$

The cDNA encoding endogenous human $5HT_{2A}$ receptor was obtained by RT-PCR using human brain poly-$A^+$ RNA; a 5' primer from the 5' untranslated region with an Xho I restriction site:

5'-GACCTCGAGTCCTTCTACACCTCATC-3' (SEQ. ID.NO: 119)

and a 3' primer from the 3' untranslated region containing an Xba I site:

5'-TGCTCTAGATTCCAGATAGGTGAAAACTTG-3' (SEQ.ID.NO: 120)

PCR was performed using either TaqPlus™ precision polymerase (Stratagene) or rTth™ polymerase (Perkin Elmer) with the buffer system provided by the manufacturers, 0.25 μM of each primer, and 0.2 mM of each of the 4 nucleotides. The cycle condition was 30 cycles of: 94° C. for 1 min; 57° C. for 1 min; and 72° C. for 2 min. The 1.5 kb PCR fragment was digested with Xba I and subcloned into Eco RV-Xba I site of pBluescript. The resulting cDNA clones were fully sequenced and found to encode two amino acid changes from the published sequences. The first one was a T25N mutation in the N-terminal extracellular domain; the second is an H452Y mutation. Because cDNA clones derived from two independent PCR reactions using Taq polymerase from two different commercial sources (TaqPlus™ from Stratagene and rTth™ Perkin Elmer) contained the same two mutations, these mutations are likely to represent sequence polymorphisms rather than PCR errors. With these exceptions, the nucleic acid (SEQ.ID.NO.: 121) and amino acid (SEQ.ID.NO.: 122) sequences for human $5HT_{2A}$ were thereafter determined and verified.

38. Serotonin $5HT_{2C}$

The cDNA encoding endogenous human $5HT_{2C}$ receptor was obtained from human brain poly-$A^+$ RNA by RT-PCR. The 5' and 3' primers were derived from the 5' and 3' untranslated regions and contained the following sequences:

5'-GACCTCGAGGTTGCTTAAGACTGAAGC-3' (SEQ. ID.NO.: 123)

5'-ATTTCTAGACATATGTAGCTTGTACCG-3' (SEQ. ID.NO.: 124)

Nucleic acid (SEQ.ID.NO.: 125) and amino acid (SEQ. ID.NO.: 126) sequences for human $5HT_{2C}$ were thereafter determined and verified.

39. V28 (GenBank Accession Number: U20350)

The cDNA for human V28 was generated and cloned into pCMV expression vector as follows: PCR was performed using brain cDNA as template and rTth polymerase (Perkin Elmer) with the buffer system provided by the manufacturer, 0.25 μM of each primer, and 0.2 mM of each of the 4 nucleotides. The cycle condition was 30 cycles of: 94° C. for 1 min; 65° C. for 1 min; and 72° C. for 1 min and 20 sec. The 5' PCR primer contained a HindIII site with the sequence:

5'-GGTAAGCTTGGCAGTCCACGCCAGGCCTTC-3' (SEQ.ID.NO.: 127)

and the 3' primer contained an EcoRI site with the sequence:

5'-TCCGAATTCTCTGTAGACACAAGGCTTTGG-3' (SEQ.ID.NO.: 128)

The 1.1 kb PCR fragment was digested with HindIII and EcoRI and cloned into HindIII-EcoRI site of pCMV expression vector. Nucleic acid (SEQ.ID.NO.: 129) and amino acid (SEQ.ID.NO.: 130) sequences for human V28 were thereafter determined and verified.

Example 2

Preparation of Non-Endogenous Human GPCRS

1. Site-Directed Mutagenesis

Mutagenesis based upon the Human GPCR Proline Marker approach disclosed herein was performed on the foregoing endogenous human GPCRs using Transformer Site-Directed Mutagenesis Kit (Clontech) according to the manufacturer instructions. For this mutagenesis approach, a Mutation Probe and a Selection Marker Probe (unless otherwise indicated, the probe of SEQ.ID.NO.: 132 was the same throughout) were utilized, and the sequences of these for the specified sequences are listed below in Table B (the parenthetical number is the SEQ. ID.NO.). For convenience, the codon mutation incorporated into the human GPCR is also noted, in standard form:

TABLE B

| Receptor Identifier (Codon Mutation) | Mutation Probe Sequence (5'-3') (SEQ.ID.NO.) | Selection Marker Probe Sequence (5'-3') (SEQ.ID.NO.) |
|---|---|---|
| GPR1 (F245K) | GATCTCCAGTAGGCATAAGT GGACAATTCTGG (131) | CTCCTTCGGTCCTCCTATCG TTGTCAGAAG (132) |
| GPR4 (K223A) | AGAAGGCCAAGATCGCGCG GCTGGCCCTCA (133) | CTCCTTCGGTCCTCCTATCG TTGTCAGAAGT |
| GPR5 (V224K) | CGGCGCCACCGCACGAAAA AGCTCATCTTC (134) | CTCCTTCGGTCCTCCTATCG TTGTCAGAAGT |
| GPR7 (T250K) | GCCAAGAAGCGGGTGAAGT TCCTGGTGGTGGCA (135) | CTCCTTCGGTCCTCCTATCG TTGTCAGAAGT |
| GPR8 (T259K) | CAGGCGGAAGGTGAAAGTC CTGGTCCTCGT (136) | CTCCTTCGGTCCTCCTATCG TTGTCAGAAGT |
| GPR9 (M254K) | CGGCGCCTGCGGGCCAAGC GGCTGGTGGTGGTG (137) | CTCCTTCGGTCCTCCTATCG TTGTCAGAAGT |
| GPR9-6 (L241K) | CCAAGCACAAAGCCAAGAA AGTGACCATCAC (138) | CTCCTTCGGTCCTCCTATCG TTGTCAGAAGT |
| GPR10 (F276K) | GCGCCGGCGCACCAAATGC TTGCTGGTGGT (139) | CTCCTTCGGTCCTCCTATCG TTGTCAGAAGT |
| GPR15 (I240K) | CAAAAAGCTGAAGAAATCT AAGAAGATCATCTTTATTGT CG (140) | CTCCTTCGGTCCTCCTATCG TTGTCAGAAGT |
| GPR17 (V234K) | CAAGACCAAGGCAAAACGC ATGATCGCCAT (141) | CTCCTTCGGTCCTCCTATCG TTGTCAGAAGT |
| GPR18 (I231K) | GTCAAGGAGAAGTCCAAAA GGATCATCATC (142) | CTCCTTCGGTCCTCCTATCG TTGTCAGAAGT |
| GPR20 (M240K) | CGCCGCGTGCGGGCCAAGC AGCTCCTGCTC (143) | CTCCTTCGGTCCTCCTATCG TTGTCAGAAGT |
| GPR21 (A251K) | CCTGATAAGCGCTATAAAAT GGTCCTGTTTCGA (144) | CTCCTTCGGTCCTCCTATCG TTGTCAGAAGT |
| GPR22 (F312K) | GAAAGACAAAAGAGAGTCA AGAGGATGTCTTTATTG (145) | CTCCTTCGGTCCTCCTATCG TTGTCAGAAGT |
| GPR24 (T304K) | CGGAGAAAGAGGGTGAAAC GCACAGCCATCGCC (146) | CTCCTTCGGTCCTCCTATCG TTGTCAGAAGT |

TABLE B-continued

| Receptor Identifier (Codon Mutation) | Mutation Probe Sequence (5'-3') (SEQ.ID.NO.) | Selection Marker Probe Sequence (5'-3') (SEQ.ID.NO.) |
|---|---|---|
| GPR30 (L258K) | alternate approach; below (147) | see alternate approach; see below |
| GPR31 (Q221K) | AAGCTTCAGCGGGCCAAGG CACTGGTCACC (147) | CTCCTTCGGTCCTCCTATCG TTGTCAGAAGT |
| GPR32 (K255A) | CATGCCAACCGGCCCGCGA GGCTGCTGCTGGT (279) | ACCAGCAGCAGCCTCGCGG GCCGGTTGGCATG (280) |
| GPR40 (A223K) | CGGAAGCTGCGGGCCAAAT GGGTGGCCGGC (265) | CTCCTTCGGTCCTCCTATCG TTGTCAGAAGT |
| GPR41 (A223K) | CAGAGGAGGGTGAAGGGGC TGTTGGCG (266) | CTCCTTCGGTCCTCCTATCG TTGTCAGAAGT |
| GPR43 (V221K) | GGCGGCGCCGAGCCAAGGG GCTGGCTGTGG (267) | CTCCTTCGGTCCTCCTATCG TTGTCAGAAGT |
| APJ (L247K) | alternate approach; see below | alternate approach; see below |
| BLR1 (V258K) | CAGCGGCAGAAGGCAAAAA GGGTGGCCATC (148) | CTCCTTCGGTCCTCCTATCG TTGTCAGAAGT |
| CEPR (L258K) | CGGCAGAAGGCGAAGCGCA TGATCCTCGCG (149) | CTCCTTCGGTCCTCCTATCG TTGTCAGAAGT |
| EBI1 (I262K) | GAGCGCAACAAGGCCAAAA AGGTGATCATC (150) | CTCCTTCGGTCCTCCTATCG TTGTCAGAAGT |
| EBI2 (L243K) | GGTGTAAACAAAAAGGCTA AAAACACAATTATTCTTATT (151) | CTCCTTCGGTCCTCCTATCG TTGTCAGAAGT |
| ETBR-LP2 (N358K) | GAGAGCCAGCTCAAGAGCA CCGTGGTG (152) | CTCCTTCGGTCCTCCTATCG TTGTCAGAAGT |
| GHSR (v262K) | CCACAAGCAAACCAAGAAA ATGCTGGCTGT (153) | CTCCTTCGGTCCTCCTATCG TTGTCAGAAGT |
| GPGR-CNS (N491K) | CTAGAGAGTCAGATGAAGT GTACAGTAGTGGCAC (155) | CTCCTTCGGTCCTCCTATCG TTGTCAGAAGT |
| GPR-NGA (I275K) | CGGACAAAAGTGAAAACTA AAAAGATGTTCCTCATT (156) | CTCCTTCGGTCCTCCTATCG TTGTCAGAAGT |
| H9a and H9b (F236K) | GCTGAGGTTCGCAATAAACT AACCATGTTTGTG (157) | CTCCTTCGGTCCTCCTATCG TTGTCAGAAGT |
| HB954 (H265K) | GGGAGGCCGAGCTGAAAGC CACCCTGCTC (158) | CTCCTTCGGTCCTCCTATCG TTGTCAGAAGT |
| HG38 (V765K) | GGGACTGCTCTATGAAAAA ACACATTGCCCTG (268) | CATCAAGTGTATCATGTGCC AAGTACGCCC (154) |
| HM74 (I230K) | CAAGATCAAGAGAGCCAAA ACCTTCATCATG (159) | CTCCTTCGGTCCTCCTATCG TTGTCAGAAGT |
| MIG (T273K) | CCGGAGACAAGTGAAGAAG ATGCTGTTTGTC (160) | CTCCTTCGGTCCTCCTATCG TTGTCAGAAGT |
| OGR1 (Q227K) | GCAAGGACCAGATCAAGCG GCTGGTGCTCA (161) | CTCCTTCGGTCCTCCTATCG TTGTCAGAAGT |
| Serotonin $5HT_{2A}$ (C322K) | alternate approach; see below | alternate approach; see below |
| Serotonin $5HT_{2C}$ (S310K) | alternate approach; see below | alternate approach; see below |
| V28 (I230K) | CAAGAAAGCCAAAGCCAAG AAACTGATCCTTCTG (162) | CTCCTTCGGTCCTCCTATCG TTGTCAGAAGT |

The non-endogenous human GPCRs were then sequenced and the derived and verified nucleic acid and amino acid-sequences are listed in the accompanying "Sequence Listing" appendix to this patent document, as summarized in Table C below:

TABLE C

| Mutated GPCR | Nucleic Acid Sequence Listing | Amino Acid Sequence Listing |
|---|---|---|
| GPR1 (F245K) | SEQ. ID. NO.: 163 | SEQ. ID. NO.: 164 |
| GPR4 (K223A) | SEQ. ID. NO.: 165 | SEQ. ID. NO.: 166 |
| GPR5 (V224K) | SEQ. ID. NO.: 167 | SEQ. ID. NO.: 168 |
| GPR7 (T250K) | SEQ. ID. NO.: 169 | SEQ. ID. NO.: 170 |
| GPR8 (T259K) | SEQ. ID. NO.: 171 | SEQ. ID. NO.: 172 |
| GPR9 (M254K) | SEQ. ID. NO.: 173 | SEQ. ID. NO.: 174 |
| GPR9-6 (L241K) | SEQ. ID. NO.: 175 | SEQ. ID. NO.: 176 |
| GPR10 (F276K) | SEQ. ID. NO.: 177 | SEQ. ID. NO.: 178 |
| GPR15 (I240K) | SEQ. ID. NO.: 179 | SEQ. ID. NO.: 180 |
| GPR17 (V234K) | SEQ. ID. NO.: 181 | SEQ. ID. NO.: 182 |
| GPR18 (I231K) | SEQ. ID. NO.: 183 | SEQ. ID. NO.: 184 |
| GPR20 (M240K) | SEQ. ID. NO.: 185 | SEQ. ID. NO.: 186 |
| GPR21 (A251K) | SEQ. ID. NO.: 187 | SEQ. ID. NO.: 188 |
| GPR22 (F312K) | SEQ. ID. NO.: 189 | SEQ. ID. NO.: 190 |
| GPR24 (T304K) | SEQ. ID. NO.: 191 | SEQ. ID. NO.: 192 |
| GPR30 (L258K) | SEQ. ID. NO.: 193 | SEQ. ID. NO.: 194 |
| GPR31 (Q221K) | SEQ. ID. NO.: 195 | SEQ. ID. NO.: 196 |
| GPR32 (K255A) | SEQ. ID. NO.: 269 | SEQ. ID. NO.: 270 |
| GPR40 (A223K) | SEQ. ID. NO.: 271 | SEQ. ID. NO.: 272 |
| GPR41 (A223K) | SEQ. ID. NO.: 273 | SEQ. ID. NO.: 274 |
| GPR43 (V221K) | SEQ. ID. NO.: 275 | SEQ. ID. NO.: 276 |
| APJ (L247K) | SEQ. ID. NO.: 197 | SEQ. ID. NO.: 198 |
| BLR1 (V258K) | SEQ. ID. NO.: 199 | SEQ. ID. NO.: 200 |
| CEPR (L258K) | SEQ. ID. NO.: 201 | SEQ. ID. NO.: 202 |
| EBI1 (I262K) | SEQ. ID. NO.: 203 | SEQ. ID. NO.: 204 |
| EBI2 (L243K) | SEQ. ID. NO.: 205 | SEQ. ID. NO.: 206 |
| ETBR-LP2 (N358K) | SEQ. ID. NO.: 207 | SEQ. ID. NO.: 208 |
| GHSR (V262K) | SEQ. ID. NO.: 209 | SEQ. ID. NO.: 210 |
| GPCR-CNS (N491K) | SEQ. ID. NO.: 211 | SEQ. ID. NO.: 212 |
| GPR-NGA (I275K) | SEQ. ID. NO.: 213 | SEQ. ID. NO.: 214 |
| H9a (F236K) | SEQ. ID. NO.: 215 | SEQ. ID. NO.: 216 |
| H9b (F236K) | SEQ. ID. NO.: 217 | SEQ. ID. NO.: 218 |
| HB954 (H265K) | SEQ. ID. NO.: 219 | SEQ. ID. NO.: 220 |
| HG38 (V765K) | SEQ. ID. NO.: 277 | SEQ. ID. NO.: 278 |

TABLE C-continued

| Mutated GPCR | Nucleic Acid Sequence Listing | Amino Acid Sequence Listing |
|---|---|---|
| HM74 (I230K) | SEQ. ID. NO.: 221 | SEQ. ID. NO.: 222 |
| MIG (T273K) | SEQ. ID. NO.: 223 | SEQ. ID. NO.: 224 |
| OGR1 (Q227K) | SEQ. ID. NO.: 225 | SEQ. ID. NO.: 226 |
| Serotonin $5HT_{2A}$ (C322K) | SEQ. ID. NO.: 227 | SEQ. ID. NO.: 228 |
| Serotonin $5HT_{2C}$ (S310K) | SEQ. ID. NO.: 229 | SEQ. ID. NO.: 230 |
| V28 (I230K) | SEQ. ID. NO.: 231 | SEQ. ID. NO.: 232 |

2. Alternate Mutation Approaches for Employment of the Proline Marker Algorithm: APJ; Serotonin $5HT_{2A}$; Serotonin $5HT_{2C}$; and GPR30

Although the above site-directed mutagenesis approach is particularly preferred, other approaches can be utilized to create such mutations; those skilled in the art are readily credited with selecting approaches to mutating a GPCR that fits within the particular needs of the artisan.

a. APJ

Preparation of the non-endogenous, human APJ receptor was accomplished by mutating L247K. Two oligonucleotides containing this mutation were synthesized:

5'-GGCTTAAGAGCATCATCGTGGTGCTGGTG-3' (SEQ. ID.NO.: 233)

5'-GTCACCACCAGCACCACGATGATGCTCTTAAGCC-3' (SEQ.ID.NO.: 234)

The two oligonucleotides were annealed and used to replace the NaeI-BstEII fragment of human, endogenous APJ to generate the non-endogenous, version of human APJ.

b. Serotonin $5HT_{2A}$ cDNA containing the point mutation C322K was constructed by utilizing the restriction enzyme site Sph I which encompasses amino acid 322. A primer containing the C322K mutation:

5'-CAAAGAAAGTACTGGGCATCGTCTTCTTCCT-3' (SEQ.ID.NO: 235)

was used along with the primer from the 3' untranslated region of the receptor:

5'-TGCTCTAGATTCCAGATAGGTGAAAACTTG-3' (SEQ.ID.NO.: 236)

to perform PCR (under the conditions described above). The resulting PCR fragment was then used to replace the 3' end of endogenous $5HT_{2A}$ cDNA through the T4 polymerase blunted Sph I site.

c. Serotonin $5HT_{2C}$

The cDNA containing a S310K mutation was constructed by replacing the Sty I restriction fragment containing amino acid 310 with synthetic double stranded oligonucleotides that encode the desired mutation. The sense strand sequence utilized had the following sequence:

5'-CTAGGGGCACCATGCAGGCTATCAA-CAATGAAAGAAAAGCTAAGAAAGTC-3' (SEQ. ID.NO.: 237)

and the antisense strand sequence utilized had the following sequence:

5'-CAAGGACTTTCTTAGCTTTTCTTTCAT-TGTTGATAGCCTGCATGGTGCCC-3' (SEQ. ID. NO.: 238)

d. GPR30

Prior to generating non-endogenous GPR30, several independent pCR2.1/GPR30 isolates were sequenced in their entirety in order to identify clones with no PCR-generated mutations. A clone having no mutations was digested with EcoR1 and the endogenous GPR30 cDNA fragment was transferred into the CMV-driven expression plasmid pCI-neo (Promega), by digesting pCI-Neo with EcoRI and subcloning the EcoRI-liberated GPR30 fragment from pCR2.1/GPR30, to generate pCI/GPR30. Thereafter, the leucine at codon 258 was mutated to a lysine using a Quick-Change™ Site-Directed Mutagenesis Kit (Stratagene, #200518), according to manufacturer's instructions, and the following primers:

5'-CGGCGGCAGAAGGCGAAACGCATGATC-CTCGCGGT-3' (SEQ.ID.NO.: 239)

and

5'-ACCGCGAGGATCATGCGTTTCGCCTTCTGC CGCCG-3' (SEQ.ID.NO.: 240)

Example 3

Receptor (Endogenous and Mutated) Expression

Although a variety of cells are available to the art for the expression of proteins, it is most preferred that mammalian cells be utilized. The primary reason for this is predicated upon practicalities, i.e., utilization of, e.g., yeast cells for the expression of a GPCR, while possible, introduces into the protocol a non-mammalian cell which may not (indeed, in the case of yeast, does not) include the receptor-coupling, genetic-mechanism and secretary pathways that have evolved for mammalian systems—thus, results obtained in non-mammalian cells, while of potential use, are not as preferred as that obtained from mammalian cells. Of the mammalian cells, COS-7, 293 and 293T cells are particularly preferred, although the specific mammalian cell utilized can be predicated upon the particular needs of the artisan.

Unless otherwise noted herein, the following protocol was utilized for the expression of the endogenous and non-endogenous human GPCRs. Table D lists the mammalian cell and number utilized (per 150 mm plate) for GPCR expression.

TABLE D

| Receptor Name (Endogenous or Non-Endogenous) | Mammalian Cell (Number Utilized) |
|---|---|
| GPR17 | 293 ($2 \times 10^4$) |
| GPR30 | 293 ($4 \times 10^4$) |
| APJ | COS-7 ($5 \times 10^6$) |
| ETBR-LP2 | 293 ($1 \times 10^7$) |
| | 293T ($1 \times 10^7$) |
| GHSR | 293 ($1 \times 10^7$) |
| | 293T ($1 \times 10^7$) |
| MIG | 293 ($1 \times 10^7$) |
| Serotonin $5HT_{2A}$ | 293T ($1 \times 10^7$) |
| Serotonin $5HT_{2C}$ | 293T ($1 \times 10^7$) |

On day one, mammalian cells were plated out. On day two, two reaction tubes were prepared (the proportions to follow for each tube are per plate): tube A was prepared by mixing 20 μg DNA (e.g., pCMV vector; pCMV vector with endogenous receptor cDNA, and pCMV vector with non-endogenous receptor cDNA.) in 1.2 ml serum free DMEM (Irvine Scientific, Irvine, Calif.); tube B was prepared by mixing 120 μl lipofectamine (Gibco BRL) in 1.2 ml serum free DMEM. Tubes A and B were then admixed by inversions (several times), followed by incubation at room temperature for 30-45 min. The admixture is referred to as the "transfection mixture". Plated cells were washed with 1XPBS, followed by addition of 10 ml serum free DMEM. 2.4 ml of the transfection mixture was then added to the cells, followed by incubation for 4 hrs at 37° C./5% $CO_2$. The transfection mixture was then removed by aspiration, followed by the addition of 25 ml of DMEM/10% Fetal Bovine Serum. Cells were then incubated at 37° C./5% $CO_2$. After 72 hr incubation, cells were then harvested and utilized for analysis.

1. Gi-Coupled Receptors: Co-Transfection with Gs-Coupled Receptors

In the case of GPR30, it has been determined that this receptor couples the G protein GI. Gi is known to inhibit the enzyme adenylyl cyclase, which is necessary for catalyzing the conversion of ATP to cAMP. Thus, a non-endogenous, constitutively activated form of GPR30 would be expected to be associated with decreased levels of cAMP. Assay confirmation of a non-endogenous, constitutively activated form of GPR30 directly via measurement of decreasing levels of cAMP, while viable, can be preferably measured by cooperative use of a Gs-coupled receptor. For example, a receptor that is Gs-coupled will stimulate adenylyl cyclase, and thus will be associated with an increase in cAMP. The assignee of the present application has discovered that the orphan receptor GPR6 is an endogenous, constitutively activated GPCR. GPR6 couples to the Gs protein. Thus when co-transfected, one can readily verify that a putative GPR30-mutation leads to constitutive activation thereof: i.e., an endogenous, constitutively activated GPR6/endogenous, non-constitutively activated GPR30 cell will evidence an elevated level of cAMP when compared with an endogenous, constitutively active GPR6/non-endogenous, constitutively activated GPR30 (the latter evidencing a comparatively lower level of cAMP). Assays that detect cAMP can be utilized to determine if a candidate compound is e.g., an inverse agonist to a Gs-associated receptor (i.e., such a compound would decrease the levels of cAMP) or a Gi-associated receptor (or a Go-associated receptor) (i.e., such a candidate compound would increase the levels of cAMP). A variety of approaches known in the art for measuring cAMP can be utilized; a preferred approach relies upon the use of anti-cAMP antibodies. Another approach, and most preferred, utilizes a whole cell second messenger reporter system assay. Promoters on genes drive the expression of the proteins that a particular gene encodes. Cyclic AMP drives gene expression by promoting the binding of a cAMP-responsive DNA binding protein or transcription factor (CREB) which then binds to the promoter at specific sites called cAMP response elements and drives the expression of the gene. Reporter systems can be constructed which have a promoter containing multiple cAMP response elements before the reporter gene, e.g., β-galactosidase or luciferase. Thus, an activated receptor such as GPR6 causes the accumulation of cAMP which then activates the gene and expression of the reporter protein. Most preferably, 293 cells are co-transfected with GPR6 (or another Gs-linked receptor) and GPR30 (or another Gi-linked receptor) plasmids, preferably in a 1:1 ratio, most preferably in a 1:4 ratio. Because GPR6 is an endogenous, constitutively active receptor that stimulates the production of cAMP, GPR6 strongly activates the reporter gene and its expression. The reporter protein such as β-galactosidase or luciferase can then be detected using standard biochemical assays (Chen et al. 1995). Co-transfection of endogenous, constitutively active GPR6 with endogenous, non-constitutively active GPR30 evidences an increase in the luciferase reporter protein. Conversely, co-transfection of endogenous, constitutively active GPR6 with non-endogenous, constitutively active GPR30 evidences a drastic decrease in expression of luciferase. Several reporter plasmids are known and available in the art for measuring a second messenger assay. It is considered well within the skilled artisan to determine an appropriate reporter plasmid for a particular gene expression based primarily upon the particular need of the artisan. Although a variety of cells are available for expression, mammalian cells are most preferred, and of these types, 293 cells are most preferred. 293 cells were transfected with the reporter plasmid pCRE-Luc/GPR6 and non-endogenous, constitutively activated GPR30 using a Mammalian Transfection™ Kit (Stratagene, #200285) $CaPO_4$ precipitation protocol according to the manufacturer's instructions (see, 28 Genomics 347 (1995) for the published endogenous GPR6 sequence). The precipitate contained 400 ng reporter, 80 ng CMV-expression plasmid (having a 1:4 GPR6 to endogenous GPR30 or non-endogenous GPR30 ratio) and 20 ng CMV-SEAP (a transfection control plasmid encoding secreted alkaline phosphatase). 50% of the precipitate was split into 3 wells of a 96-well tissue culture dish (containing $4\times10^4$ cells/well); the remaining 50% was discarded. The following morning, the media was changed. 48 hr after the start of the transfection, cells were lysed and examined for luciferase activity using a Luclite™ Kit (Packard, Cat. # 6016911) and Trilux 1450 Microbeta™ liquid scintillation and luminescence counter (Wallac) as per the vendor's instructions. The data were analyzed using GraphPad Prism 2.0a (GraphPad Software Inc.).

With respect to GPR17, which has also been determined to be Gi-linked, a modification of the foregoing approach was utilized, based upon, inter alia, use of another Gs-linked endogenous receptor, GPR3 (see 23 Genomics 609 (1994) and 24 Genomics 391 (1994)). Most preferably, 293 cells are utilized. These cells were plated-out on 96 well plates at a density of $2\times10^4$ cells per well and were transfected using Lipofectamine Reagent (BRL) the following day according to manufacturer instructions. A DNA/lipid mixture was prepared for each 6-well transfection as follows: 260 ng of plasmid DNA in 100 μl of DMEM were gently mixed with 2 μl of lipid in 100 μl of DMEM (the 260 ng of plasmid DNA consisted of 200 ng of a 8×CRE-Luc reporter plasmid (see below), 50 ng of pCMV comprising endogenous receptor or non-endogenous receptor or pCMV alone, and 10 ng of a GPRS expression plasmid (GPRS in pcDNA3 (Invitrogen)). The 8×CRE-Luc reporter plasmid was prepared as follows: vector SRIF-β-gal was obtained by cloning the rat somatostatin promoter (−71/+51) at BglV-HindIII site in the pβgal-Basic Vector (Clontech). Eight (8) copies of cAMP response element were obtained by PCR from an adenovirus template AdpCF126CCRE8 (see 7 Human Gene Therapy 1883 (1996)) and cloned into the SRIF-β-gal vector at the Kpn-BglV site, resulting in the 8×CRE-β-gal reporter vector. The 8×CRE-Luc reporter plasmid was generated by replacing the beta-galactosidase gene in the 8×CRE-β-gal reporter vector with the luciferase gene obtained from the pGL3-basic vector (Promega) at the HindIII-BamHI site. Following 30 min. incubation at room temperature, the DNA/lipid mixture was diluted with 400 μl of DMEM and 100 μl of the diluted mixture was added to each well. 100 μl of DMEM with 10% FCS were added to each well after a 4 hr incubation in a cell culture incubator. The next morning the transfected cells were changed with 200 μl/well of DMEM with 10% FCS. Eight (8) hours later, the wells were changed to 100 μl/well of DMEM without phenol red, after one wash with PBS. Luciferase activity were measured the next day using the LucLite™ reporter gene assay kit (Packard) following manufacturer instructions and read on a 1450 MicroBeta™ scintillation and luminescence counter (Wallac).

FIG. 4 evidences that constitutively active GPR30 inhibits GPR6-mediated activation of CRE-Luc reporter in 293 cells. Luciferase was measured at about 4.1 relative light units in the expression vector pCMV. Endogenous GPR30 expressed luciferase at about 8.5 relative light units, whereas the non-endogenous, constitutively active GPR30 (L258K), expressed luciferase at about 3.8 and 3.1 relative light units, respectively. Co-transfection of endogenous GPR6 with endogenous GPR30, at a 1:4 ratio, drastically increased luciferase expression to about 104.1 relative light units. Co-transfection of endogenous GPR6 with non-endogenous GPR30 (L258K), at the same ratio, drastically decreased the expression, which is evident at about 18.2 and 29.5 relative light units, respectively. Similar results were observed with respect to GPR17 with respect to co-transfection with GPR3, as set forth in FIG. 5.

Example 3

Assays for Determination of Constitutive Activity of Non-Endogenous GPCRS

A. Membrane Binding Assays

1. [$^{35}$S]GTPγS Assay

When a G protein-coupled receptor is in its active state, either as a result of ligand binding or constitutive activation, the receptor couples to a G protein and stimulates the release of GDP and subsequent binding of GTP to the G protein. The alpha subunit of the G protein-receptor complex acts as a GTPase and slowly hydrolyzes the GTP to GDP, at which point the receptor normally is deactivated. Constitutively activated receptors continue to exchange GDP for GTP. The non-hydrolyzable GTP analog, [$^{35}$S]GTPγS, can be utilized to demonstrate enhanced binding of [$^{35}$S]GTPγS to membranes expressing constitutively activated receptors. The advantage of using [$^{35}$S]GTPγS binding to measure constitutive activation is that: (a) it is generically applicable to all G protein-coupled receptors; (b) it is proximal at the membrane surface making it less likely to pick-up molecules which affect the intracellular cascade.

The assay utilizes the ability of G protein coupled receptors to stimulate [$^{35}$S]GTPγS binding to membranes expressing the relevant receptors. The assay can, therefore, be used in the direct identification method to screen candidate compounds to known, orphan and constitutively activated G protein-coupled receptors. The assay is generic and has application to drug discovery at all G protein-coupled receptors. The [$^{35}$S]GTPγS assay was incubated in 20 mM HEPES and between 1 and about 20 mM $MgCl_2$ (this amount can be adjusted for optimization of results, although 20 mM is preferred) pH 7.4, binding buffer with between about 0.3 and about 1.2 nM [$^{35}$S]GTPγS (this amount can be adjusted for optimization of results, although 1.2 is preferred ) and 12.5 to 75 μg membrane protein (e.g, COS-7 cells expressing the receptor; this amount can be adjusted for optimization, although 75 μg is preferred) and 1 μM GDP (this amount can be changed for optimization) for 1 hour. Wheatgerm agglutinin beads (25 μl; Amersham) were then added and the mixture was incubated for another 30 minutes at room temperature. The tubes were then centrifuged at 1500×g for 5 minutes at room temperature and then counted in a scintillation counter.

A less costly but equally applicable alternative has been identified which also meets the needs of large scale screening. Flash plates™ and Wallac™ scintistrips may be utilized to format a high throughput [$^{35}$S]GTPγS binding assay. Further-more, using this technique, the assay can be utilized for known GPCRs to simultaneously monitor tritiated ligand binding to the receptor at the same time as monitoring the efficacy via [$^{35}$S]GTPγS binding. This is possible because the Wallac beta counter can switch energy windows to look at both tritium and $^{35}$S-labeled probes. This assay may also be used to detect other types of membrane activation events resulting in receptor activation. For example, the assay may be used to monitor $^{32}$P phosphorylation of a variety of receptors (both G protein coupled and tyrosine kinase receptors). When the membranes are centrifuged to the bottom of the well, the bound [$^{35}$S]GTPγS or the $^{32}$P-phosphorylated receptor will activate the scintillant which is coated of the wells. Scinti® strips (Wallac) have been used to demonstrate this principle. In addition, the assay also has utility for measuring ligand binding to receptors using radioactively labeled ligands. In a similar manner, when the radiolabeled bound ligand is centrifuged to the bottom of the well, the scintistrip label comes into proximity with the radiolabeled ligand resulting in activation and detection.

Representative results of graph comparing Control (pCMV), Endogenous APJ and Non-Endogenous APJ, based upon the foregoing protocol, are set forth in FIG. 6.

2. Adenylyl Cyclase

A Flash Plate™ Adenylyl Cyclase kit (New England Nuclear; Cat. No. SMP004A) designed for cell-based assays was modified for use with crude plasma membranes. The Flash Plate wells contain a scintillant coating which also contains a specific antibody recognizing cAMP. The cAMP generated in the wells was quantitated by a direct competition for binding of radioactive cAMP tracer to the cAMP antibody. The following serves as a brief protocol for the measurement of changes in cAMP levels in membranes that express the receptors.

Transfected cells were harvested approximately three days after transfection. Membranes were prepared by homogenization of suspended cells in buffer containing 20 mM HEPES, pH 7.4 and 10 mM $MgCl_2$. Homogenization was performed on ice using a Brinkman Polytron™ for approximately 10 seconds. The resulting homogenate was centrifuged at 49,000×g for 15 minutes at 4° C. The resulting pellet was then resuspended in buffer containing 20 mM HEPES, pH 7.4 and 0.1 mM EDTA, homogenized for 10 seconds, followed by centrifugation at 49,000×g for 15 minutes at 4° C. The resulting pellet can be stored at −80° C. until utilized. On the day of measurement, the membrane pellet was slowly thawed at room temperature, resuspended in buffer containing 20 mM HEPES, pH 7.4 and 10 mM $MgCL_2$ (these amounts can be optimized, although the values listed herein are prefereed), to yield a final protein concentration of 0.60 mg/ml (the resuspended membranes were placed on ice until use).

cAMP standards and Detection Buffer (comprising 2 μCi of tracer [$^{125}$I cAMP (100 μl] to 11 ml Detection Buffer) were prepared and maintained in accordance with the manufacturer's instructions. Assay Buffer was prepared fresh for screening and contained 20 mM HEPES, pH 7.4, 10 mM $MgCl_2$, 20mM (Sigma), 0.1 units/ml creatine phosphokinase (Sigma), 50 μM GTP (Sigma), and 0.2 mM ATP (Sigma); Assay Buffer can be stored on ice until utilized. The assay was initiated by addition of 50 ul of assay buffer followed by addition of 50 ul of membrane suspension to the NEN Flash Plate. The resultant assay mixture is incubated for 60 minutes at room temperature followed by addition of 100 ul of detection buffer. Plates are then incubated an additional 2-4 hours followed by counting in a Wallac MicroBeta scintillation counter. Values of cAMP/well are extrapolated from a standard cAMP curve which is contained within each assay plate. The foregoing assay was utilized with respect to analysis of MIG.

B. Reporter-Based Assays

1. CREB Reporter Assay (Gs-associated receptors)

A method to detect Gs stimulation depends on the known property of the transcription factor CREB, which is activated in a cAMP-dependent manner. A PathDetect CREB trans-Reporting System (Stratagene, Catalogue # 219010) was utilized to assay for Gs coupled activity in 293 or 293T cells. Cells were transfected with the plasmids components of this above system and the indicated expression plasmid encoding endogenous or mutant receptor using a Mammalian Transfection Kit (Stratagene, Catalogue #200285) according to the manufacturer's instructions. Briefly, 400 ng pFR-Luc (luciferase reporter plasmid containing Gal4 recognition sequences), 40 ng pFA2-CREB (Gal4-CREB fusion protein containing the Gal4 DNA-binding domain), 80 ng CMV-receptor expression plasmid (comprising the receptor) and 20 ng CMV-SEAP (secreted alkaline phosphatase expression plasmid; alkaline phosphatase activity is measured in the media of transfected cells to control for variations in transfection efficiency between samples) were combined in a calcium phosphate precipitate as per the Kit's instructions. Half of the precipitate was equally distributed over 3 wells in a 96-well plate, kept on the cells overnight, and replaced with fresh medium the following morning. Forty-eight (48) hr after the start of the transfection, cells were treated and assayed for luciferase activity as set forth with resepct to the GPR30 system, above. This assay was used with respect to GHSR.

2. AP1 Reporter Assay (Gq-associated receptors)

Ae method to detect Gq stimulation depends on the known property of Gq-dependent phospholipase C to cause the activation of genes containing AP1 elements in their promoter. A Pathdetect AP-1 cis-Reporting System (Stratagene, Catalogue # 219073) was utilized following the protocl set forth above with respect to the CREB reporter assay, except that the components of the calcium phosphate precipitate were 410 ng pAP1-Luc, 80 ng receptor expression plasmid, and 20 ng CMV-SEAP. This assay was used with respect to ETBR-LP2

C. Intracellular IP3 Accumulation Assay

On day 1, cells comprising the serotonin receptors (endogenous and mutated) were plated onto 24 well plates, usually $1\times10^5$ cells/well. On day 2 cells were transfected by firstly mixing 0.25 ug DNA in 50 ul serumfree DMEM/well and 2 ul lipofectamine in 50 μl serumfree DMEM/well. The solutions were gently mixed and incubated for 15-30 min at room temperature. Cells were washed with 0.5 ml PBS and 400 μl of serum free media was mixed with the transfection media and added to the cells. The cells were then incubated for 3-4 hrs at 37° C./5% $CO_2$ and then the transfection media was removed and replaced with 1 ml/well of regular growth media. On day 3 the cells were labeled with $^3$H-myo-inositol. Briefly, the media was removed the cells were washed with 0.5 ml PBS. Then 0.5 ml inositol-free/serumfree media (GIBCO BRL) was added/well with 0.25 μCi of $^3$H-myo-inositol/well and the cells were incubated for 16-18 hrs o/n at 37° C./5% $CO_2$. On Day 4 the cells were washed with 0.5 ml PBS and 0.45 ml of assay medium was added containing inositol-free/serum free media 10 μM pargyline 10 mM lithium chloride or 0.4 ml of assay medium and 50 ul of 10× ketanserin (ket) to final concentration of 10 μM. The cells were then incubated for 30 min at 37° C. The cells were then washed with 0.5 ml PBS and 200 ul of fresh/icecold stop solution (1M KOH; 18 mM Na-borate; 3.8 mM EDTA) was added/well. The solution was kept on ice for 5-10 min or until cells were lysed and then neutralized by 200 μl of fresh/ice cold neutralization sol. (7.5% HCL). The lysate was then transferred into 1.5 ml eppendorf tubes and 1 ml of chloroform/methanol (1:2) was added/tube. The solution was vortexed for 15 sec and the upper phase was applied to a Biorad AG1-X8 anion exchange resin (100-200 mesh). Firstly, the resin was washed with water at 1:1.25 W/V and 0.9 ml of upper phase was loaded onto the column. The column was washed with 10 mls of 5 mM myo-inositol and 10 ml of 5 mM Na-borate/60 mM Na-formate. The inositol tris phosphates were eluted into scintillation vials containing 10 ml of scintillation cocktail with 2 ml of 0.1 M formic acid/1 M ammonium formate. The columns were regenerated by washing with 10 ml of 0.1 M formic acid/3M ammonium formate and rinsed twice with dd $H_2O$ and stored at 4° C. in water.

FIG. 7 provides an illustration of IP3 production from the human 5-$HT_{2A}$ receptor that incorporates the C322K mutation. While these results evidence that the Proline Mutation Algorithm approach constitutively activates this receptor, for purposes of using such a receptor for screening for identification of potential therapeutics, a more robust difference would be preferred. However, because the activated receptor can be utilized for understanding and elucidating the role of constitutive activation and for the identification of compounds that can be further examined, we believe that this difference is itself useful in differentiating between the endogenous and non-endogenous versions of the human $5HT_{2A}$ receptor.

D. Result Summary

The results for the GPCRs tested are set forth in Table E where the Per-Cent Increase indicates the percentage difference in results observed for the non-endogenous GPCR as compared to the endogenous GPCR; these values are followed by parenthetical indications as to the type of assay utilized. Additionally, the assay sytem utilized is parenthetically listed (and, in cases where different Host Cells were used, both are listed). As these results indicate, a variety of assays can be utilized to determine constitutive activity of the non-endogenous versions of the human GPCRs. Those skilled in the art, based upon the foregoing and with reference to information available to the art, are creditied with theability to selelect and/ot maximize a particular assay approach that suites the particualr needs of theinvestigator.

TABLE E

| Receptor Identifier (Codon Mutation) | Per-Cent Difference |
|---|---|
| GPR17 | 74.5 |
| (V234K) | (CRE-Luc) |
| GPR30 | 71.6 |
| (L258K) | (CREB) |
| APJ | 49.0 |
| (L247K) | (GTPγS) |
| ETBR-LP2 | 48.4(AP1-Luc - 293) |
| (N358K) | 61.1(AP1-Luc - 293T) |
| GHSR | 58.9(CREB - 293) |
| (V262K) | 35.6(CREB - 293T) |
| MIG | 39(cAMP) |
| (I230K) | |
| Serotonin $5HT_{2A}$ | 33.2($IP_3$) |
| (C322K) | |
| Serotonin $5HT_{2C}$ | 39.1($IP_3$) |
| (S310K) | |

Example 6

Tissue Distribution of Endogenous Orphan GPCRs

Using a commercially available human-tissue dot-blot format, endogenous orphan GPCRs were probed for a determination of the areas where such receptors are localized. Except as indicate below, the entire receptor cDNA (radiolabelled) was used as the probe: radiolabeled probe was generated using the complete receptor cDNA (excised from the vector) using a Prime-It II™ Random Primer Labeling Kit (Stratagene, #300385), according to manufacturer's instructions. A human RNA Master Blot™ (Clontech, #7770-1) was hybridized with the GPCR radiolabeled probe and washed under stringent conditions according manufacturer's instructions. The blot was exposed to Kodak BioMax Autoradiography film overnight at −80° C.

Figure 8A:
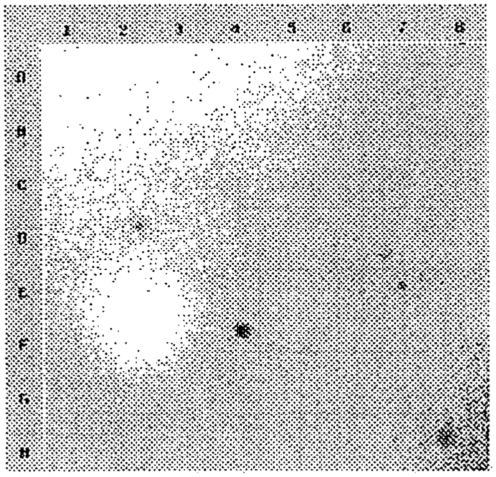
FIG. 8A is a dot-blot format result for GPR1
Figure 8B:
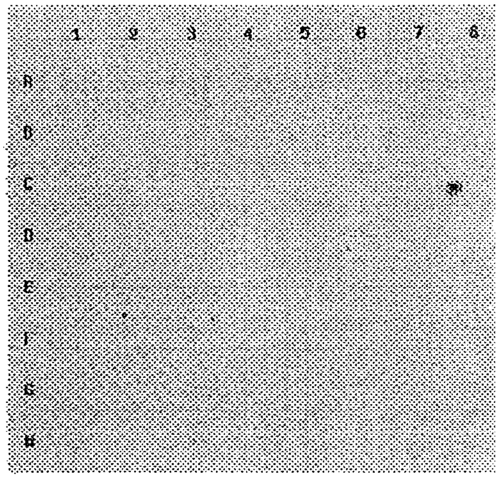
FIG. 8B is a dot-blot format result for GPR30.
Figure 8C:
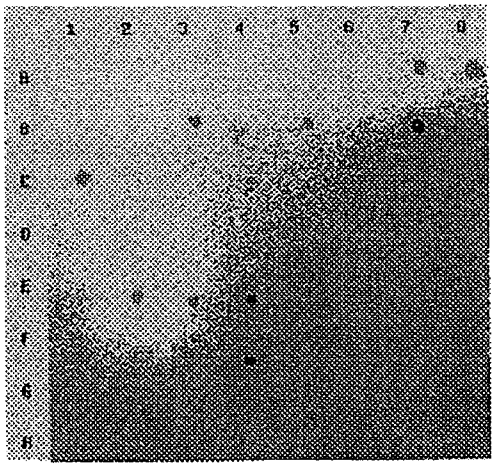
FIG. 8C is a dot-blot format result for APJ.

Representative dot-blot format results are presented in FIG. 8 for GPR1 (8A), GPR30 (8B), and APJ (8C), with results being summarized for all receptors in Table F

TABLE F

| GPCR | Tissue Distribution (highest levels, relative to other tissues in the dot-blot) |
|---|---|
| GPR1 | Placenta, Ovary, Adrenal |
| GPR4 | Broad; highest in Heart, Lung, Adrenal, Thyroid, Spinal Cord |
| GPR5 | Placenta, Thymus, Fetal Thymus<br>Lesser levels in spleen, fetal spleen |
| GPR7 | Liver, Spleen, Spinal Cord, Placenta |
| GPR8 | No expression detected |
| GPR9-6 | Thymus, Fetal Thymus<br>Lesser levels in Small Intestine |
| GPR18 | Spleen, Lymph Node, Fetal Spleen, Testis |
| GPR20 | Broad |
| GPR21 | Broad; very low abundance |
| GPR22 | Heart, Fetal Heart<br>Lesser levels in Brain |
| GPR30 | Stomach |
| GPR31 | Broad |
| BLR1 | Spleen |
| CEPR | Stomach, Liver, Thyroid, Putamen |
| EBI1 | Pancreas<br>Lesser levels in Lymphoid Tissues |
| EBI2 | Lymphoid Tissues, Aorta, Lung, Spinal Cord |
| ETBR-LP2 | Broad; Brain Tissue |
| GPCR-CNS | Brain<br>Lesser levels in Testis, Placenta |
| GPR-NGA | Pituitary<br>Lesser levels in Brain |
| H9 | Pituitary |
| HB954 | Aorta, Cerebellum<br>Lesser levels in most other tissues |
| HM74 | Spleen, Leukocytes, Bone marrow, Mammary Glands, Lung, Trachea |
| MIG | Low levels in Kidney, Liver, Pancreas, Lung, Spleen |
| ORG1 | Pituitary, Stomach, Placenta |
| V28 | Brain, Spleen, Peripheral Leukocytes |

Based upon the foregoing information, it is noted that human GPCRs can also be assessed for distribution in diseased tissue; comparative assessments between "normal" and diseased tissue can then be utilized to determine the potential for over-expression or under-expression of a particular receptor in a diseased state. In those circumstances where it is desirable to utilize the non-endogenous versions of the human GPCRs for the purpose of screening to directly identify candidate compounds of potential therapeutic relevance, it is noted that inverse agonists are useful in the treatment of diseases and disorders where a particular human GPCR is over-expressed, whereas agonists or partial agonists are useful in the treatment of diseases and disorders where a particular human GPCR is under-expressed.

As desired, more detailed, cellular localization of the recepotrs, using techniques well-known to those in the art (e.g., in-situ hybridization) can be utilized to identify particualr cells within these tissues where the receptor of interest is expressed.

References cited throughout this patent document, unless otherwise indicated, are incorporated herein by reference. Modifications and extension of the disclosed inventions that are within the purview of the skilled artisan are encompassed within the above disclosure and the claims that follow.

Although a variety of expression vectors are available to those in the art, for purposes of utilization for both the endogenous and non-endogenous human GPCRs, it is most preferred that the vector utilized be pCMV. This vector has been deposited with the American Type Culture Collection (ATCC) on Oct. 13, 1998 (10801 University Blvd., Manassas, Va. 20110-2209 USA) under the provsions of the Budapest Treaty for the International Recognition of the Deposit of Microorganisms for the Purpose of patent Procedure. The vector was tested by the ATCC on Oct. 13, 1998 and determined to be viable. The ATCC has assigned the following deposit number to pCMV: 203351.

What is claimed is:

1. A method for creating a non-endogenous, constitutively active version of an endogenous human G protein coupled receptor (GPCR), said endogenous GPCR comprising a transmembrane 6 region and an intracellular loop 3 region, the method comprising:

(a) selecting an endogenous human GPCR comprising a proline residue in the transmembrane-6 region, wherein the GPCR is not the β2-adrenergic receptor or the $\alpha_{1B}$-adrenergic receptor;

(b) identifying the endogenous $16^{th}$ amino acid residue from the proline residue of step (a), in a carboxy-terminus to amino-terminus direction;

(c) altering the identified amino acid residue of step (b) to a non-endogenous amino acid residue to create a non-endogenous version of the endogenous human GPCR; and (d) determining if the non-endogenous version of the endogenous human GPCR of step (c) is constitutively active by measuring a difference in an intracellular signal measured for the non-endogenous version as compared with a signal induced by the endogenous human GPCR.

2. The method of claim 1 wherein the amino acid residue that is two residues from said proline residue in the transmembrane 6 region, in a carboxy-terminus to amino-terminus direction, is tryptophan.

3. The method of claim 1 or claim 2 wherein the endogenous $16^{th}$ amino acid residue from said proline residue in a carboxy-terminus to amino-terminus direction has been altered to an alanine residue.

4. The method of claim 1 or claim 2 wherein the endogenous 16th amino acid residue from said proline residue in a carboxy-terminus to aminoterminus direction has been altered to an arginine residue.

5. The method of claim 1 or claim 2 wherein the endogenous $16^{th}$ amino acid residue from said proline residue in a carboxy-terminus to amino-terminus direction has been altered to an histidine residue.

6. A method for creating a non-endogenous, constitutively active version of an endogenous human G protein coupled receptor (GPCR), said endogenous GPCR comprising a transmembrane 6 region and an intracellular loop 3 region, the method comprising:

(a) providing a polynucleotide; said polynucleotide encoding an endogenous human GPCR, said endogenous GPCR comprising a transmembrane 6 region and an intracellular loop 3 region, said transmembrane 6 region comprisin a roline residue, wherein the GPCR is not the β2-adrenergic receptor or the $\alpha_{1B}$-adernergic receptor;

(b) identifying the codon of said polynucleotide corresponding to the endogenous $16^{th}$ amino acid residue from said proline residue of said GPCR of step (a), in a carboxy-terminus to amino-terminus direction;

(c) altering said identified codon of step (b) to encode a non-endogenous amino acid residue, to provide a non-endogenous polynucleotide;

(d) expressing said non-endogenous polynucleotide in a host cell, thereby providing a non-endogenous version of the endogenous human GPCR; and (e) determining if the non-endogenous version of the endogenous human GPCR of step (d) is constitutively active by measuring a difference in an intracellular signal measured for the non-endogenous version as compared with a signal induced by the endogenous human GPCR.

7. The method of claim 6 wherein the amino acid residue that is two residues from said proline residue in the transmembrane 6 region, in a carboxy-terminus to amino-terminus direction, is tryptophan.

8. The method of claim 6 or claim 7 wherein said identified codon of step (b) has been altered to be a codon encoding alanine.

9. The method of claim 6 or claim 7 wherein said identified codon of step (b) has been altered to be a codon encoding arginine.

10. The method of claim 6 or claim 7 wherein said identified codon of step (b) has been altered to be a codon encoding histidine.

* * * * *

UNITED STATES PATENT AND TRADEMARK OFFICE

CERTIFICATE OF CORRECTION

PATENT NO. : 7,410,777 B2
APPLICATION NO. : 10/251385
DATED : August 12, 2008
INVENTOR(S) : Chen W. Liaw It is certified that error appears in the above-identified patent and that said Letters Patent is hereby corrected as shown below:

In Claim 6, Col. 396, line 34, please delete "comprisin" and replace with --comprising--; and In Claim 6, Col. 396, line 34, please delete "roline" and replace with --proline--; and In Claim 6, Col. 396, line 35, after the words $\alpha_{1B}$, please delete "adernergic" and replace with --adrenergic--.

Signed and Sealed this

Twenty-fifth Day of November, 2008

JON W. DUDAS
*Director of the United States Patent and Trademark Office*

SEQUENCE LISTING

```
<160> NUMBER OF SEQ ID NOS: 294

<210> SEQ ID NO 1
<211> LENGTH: 1068
<212> TYPE: DNA
<213> ORGANISM: Homo sapiens

<400> SEQUENCE: 1

atggaagatt tggaggaaac attatttgaa gaatttgaaa actattccta tgacctagac     60

tattactctc tggagtctga tttggaggag aaagtccagc tgggagttgt tcactgggtc    120

tccctggtgt tatattgttt ggcttttgtt ctgggaattc caggaaatgc catcgtcatt    180

tggttcacgg ggctcaagtg gaagaagaca gtcaccactc tgtggttcct caatctagcc    240

attgcggatt tcatttttct tctctttctg cccctgtaca tctcctatgt ggccatgaat    300

ttccactggc cctttggcat ctggctgtgc aaagccaatt ccttcactgc ccagttgaac    360

atgtttgcca gtgttttttt cctgacagtg atcagcctgg accactatat ccacttgatc    420

catcctgtct tatctcatcg gcatcgaacc ctcaagaact ctctgattgt cattatattc    480

atctggcttt tggcttctct aattggcggt cctgccctgt acttccggga cactgtggag    540

ttcaataatc atactctttg ctataacaat tttcagaagc atgatcctga cctcactttg    600

atcaggcacc atgttctgac ttgggtgaaa tttatcattg gctatctctt ccctttgcta    660

acaatgagta tttgctactt gtgtctcatc ttcaaggtga agaagcgaac agtcctgatc    720

tccagtaggc atttctggac aattctggtt gtggttgtgg cctttgtggt ttgctggact    780

ccttatcacc tgtttagcat ttgggagctc accattcacc acaatagcta ttcccaccat    840

gtgatgcagg ctggaatccc cctctccact ggtttggcat tcctcaatag ttgcttgaac    900

cccatccttt atgtcctaat tagtaagaag ttccaagctc gcttccggtc ctcagttgct    960

gagatactca agtacacact gtgggaagtc agctgttctg gcacagtgag tgaacagctc   1020

aggaactcag aaaccaagaa tctgtgtctc ctggaaacag ctcaataa                1068


<210> SEQ ID NO 2
<211> LENGTH: 355
<212> TYPE: PRT
<213> ORGANISM: Homo sapiens

<400> SEQUENCE: 2

Met Glu Asp Leu Glu Glu Thr Leu Phe Glu Glu Phe Glu Asn Tyr Ser
1               5                   10                  15

Tyr Asp Leu Asp Tyr Tyr Ser Leu Glu Ser Asp Leu Glu Glu Lys Val
            20                  25                  30

Gln Leu Gly Val Val His Trp Val Ser Leu Val Leu Tyr Cys Leu Ala
        35                  40                  45
```

-continued

```
Phe Val Leu Gly Ile Pro Gly Asn Ala Ile Val Ile Trp Phe Thr Gly
    50                  55                  60

Leu Lys Trp Lys Lys Thr Val Thr Thr Leu Trp Phe Leu Asn Leu Ala
65                  70                  75                  80

Ile Ala Asp Phe Ile Phe Leu Leu Phe Leu Pro Leu Tyr Ile Ser Tyr
                85                  90                  95

Val Ala Met Asn Phe His Trp Pro Phe Gly Ile Trp Leu Cys Lys Ala
            100                 105                 110

Asn Ser Phe Thr Ala Gln Leu Asn Met Phe Ala Ser Val Phe Phe Leu
        115                 120                 125

Thr Val Ile Ser Leu Asp His Tyr Ile His Leu Ile His Pro Val Leu
    130                 135                 140

Ser His Arg His Arg Thr Leu Lys Asn Ser Leu Ile Val Ile Ile Phe
145                 150                 155                 160

Ile Trp Leu Leu Ala Ser Leu Ile Gly Gly Pro Ala Leu Tyr Phe Arg
                165                 170                 175

Asp Thr Val Glu Phe Asn Asn His Thr Leu Cys Tyr Asn Asn Phe Gln
            180                 185                 190

Lys His Asp Pro Asp Leu Thr Leu Ile Arg His His Val Leu Thr Trp
        195                 200                 205

Val Lys Phe Ile Ile Gly Tyr Leu Phe Pro Leu Leu Thr Met Ser Ile
    210                 215                 220

Cys Tyr Leu Cys Leu Ile Phe Lys Val Lys Lys Arg Thr Val Leu Ile
225                 230                 235                 240

Ser Ser Arg His Phe Trp Thr Ile Leu Val Val Val Val Ala Phe Val
                245                 250                 255

Val Cys Trp Thr Pro Tyr His Leu Phe Ser Ile Trp Glu Leu Thr Ile
            260                 265                 270

His His Asn Ser Tyr Ser His His Val Met Gln Ala Gly Ile Pro Leu
        275                 280                 285

Ser Thr Gly Leu Ala Phe Leu Asn Ser Cys Leu Asn Pro Ile Leu Tyr
    290                 295                 300

Val Leu Ile Ser Lys Lys Phe Gln Ala Arg Phe Arg Ser Ser Val Ala
305                 310                 315                 320

Glu Ile Leu Lys Tyr Thr Leu Trp Glu Val Ser Cys Ser Gly Thr Val
                325                 330                 335

Ser Glu Gln Leu Arg Asn Ser Glu Thr Lys Asn Leu Cys Leu Leu Glu
            340                 345                 350

Thr Ala Gln
        355


<210> SEQ ID NO 3
<211> LENGTH: 1089
<212> TYPE: DNA
<213> ORGANISM: Homo sapiens

<400> SEQUENCE: 3

atgggcaacc acacgtggga gggctgccac gtggactcgc gcgtggacca cctctttccg      60

ccatccctct acatctttgt catcggcgtg ggctgcccca ccaactgcct ggctctgtgg     120

gcggcctacc gccaggtgca acagcgcaac gagctgggcg tctacctgat gaacctcagc     180

atcgccgacc tgctgtacat ctgcacgctg ccgctgtggg tggactactt cctgcaccac     240

gacaactgga tccacggccc cgggtcctgc aagctctttg ggttcatctt ctacaccaat     300

atctacatca gcatcgcctt cctgtgctgc atctcggtgg accgctacct ggctgtggcc     360
```

-continued

```
cacccactcc gcttcgcccg cctgcgccgc gtcaagaccg ccgtggccgt gagctccgtg    420

gtctgggcca cggagctggg cgccaactcg gcgcccctgt tccatgacga gctcttccga    480

gaccgctaca accacacctt ctgctttgag aagttcccca tggaaggctg ggtggcctgg    540

atgaacctct atcgggtgtt cgtgggcttc ctcttcccgt gggcgctcat gctgctgtcg    600

taccggggca tcctgcgggc cgtgcggggc agcgtgtcca ccgagcgcca ggagaaggcc    660

aagatcaagc ggctggccct cagcctcatc gccatcgtgc tggtctgctt tgcgccctat    720

cacgtgctct tgctgtcccg cagcgccatc tacctgggcc gcccctggga ctgcggcttc    780

gaggagcgcg tcttttctgc ataccacagc tcactggctt tcaccagcct caactgtgtg    840

gcggacccca tcctctactg cctggtcaac gagggcgccc gcagcgatgt ggccaaggcc    900

ctgcacaacc tgctccgctt tctggccagc gacaagcccc aggagatggc caatgcctcg    960

ctcaccctgg agaccccact cacctccaag aggaacagca cagccaaagc catgactggc   1020

agctgggcgg ccactccgcc ttcccagggg gaccaggtgc agctgaagat gctgccgcca   1080

gcacaatga                                                           1089
```

```
<210> SEQ ID NO 4
<211> LENGTH: 362
<212> TYPE: PRT
<213> ORGANISM: Homo sapiens

<400> SEQUENCE: 4

Met Gly Asn His Thr Trp Glu Gly Cys His Val Asp Ser Arg Val Asp
1               5                   10                  15

His Leu Phe Pro Pro Ser Leu Tyr Ile Phe Val Ile Gly Val Gly Leu
            20                  25                  30

Pro Thr Asn Cys Leu Ala Leu Trp Ala Ala Tyr Arg Gln Val Gln Gln
        35                  40                  45

Arg Asn Glu Leu Gly Val Tyr Leu Met Asn Leu Ser Ile Ala Asp Leu
    50                  55                  60

Leu Tyr Ile Cys Thr Leu Pro Leu Trp Val Asp Tyr Phe Leu His His
65                  70                  75                  80

Asp Asn Trp Ile His Gly Pro Gly Ser Cys Lys Leu Phe Gly Phe Ile
                85                  90                  95

Phe Tyr Thr Asn Ile Tyr Ile Ser Ile Ala Phe Leu Cys Cys Ile Ser
            100                 105                 110

Val Asp Arg Tyr Leu Ala Val Ala His Pro Leu Arg Phe Ala Arg Leu
        115                 120                 125

Arg Arg Val Lys Thr Ala Val Ala Val Ser Ser Val Val Trp Ala Thr
    130                 135                 140

Glu Leu Gly Ala Asn Ser Ala Pro Leu Phe His Asp Glu Leu Phe Arg
145                 150                 155                 160

Asp Arg Tyr Asn His Thr Phe Cys Phe Glu Lys Phe Pro Met Glu Gly
                165                 170                 175

Trp Val Ala Trp Met Asn Leu Tyr Arg Val Phe Val Gly Phe Leu Phe
            180                 185                 190

Pro Trp Ala Leu Met Leu Leu Ser Tyr Arg Gly Ile Leu Arg Ala Val
        195                 200                 205

Arg Gly Ser Val Ser Thr Glu Arg Gln Glu Lys Ala Lys Ile Lys Arg
    210                 215                 220

Leu Ala Leu Ser Leu Ile Ala Ile Val Leu Val Cys Phe Ala Pro Tyr
225                 230                 235                 240
```

-continued

```
His Val Leu Leu Leu Ser Arg Ser Ala Ile Tyr Leu Gly Arg Pro Trp
                245                 250                 255

Asp Cys Gly Phe Glu Glu Arg Val Phe Ser Ala Tyr His Ser Ser Leu
            260                 265                 270

Ala Phe Thr Ser Leu Asn Cys Val Ala Asp Pro Ile Leu Tyr Cys Leu
        275                 280                 285

Val Asn Glu Gly Ala Arg Ser Asp Val Ala Lys Ala Leu His Asn Leu
    290                 295                 300

Leu Arg Phe Leu Ala Ser Asp Lys Pro Gln Glu Met Ala Asn Ala Ser
305                 310                 315                 320

Leu Thr Leu Glu Thr Pro Leu Thr Ser Lys Arg Asn Ser Thr Ala Lys
                325                 330                 335

Ala Met Thr Gly Ser Trp Ala Ala Thr Pro Pro Ser Gln Gly Asp Gln
            340                 345                 350

Val Gln Leu Lys Met Leu Pro Pro Ala Gln
        355                 360


<210> SEQ ID NO 5
<211> LENGTH: 30
<212> TYPE: DNA
<213> ORGANISM: Artificial Sequence
<220> FEATURE:
<223> OTHER INFORMATION: Novel Sequence
<220> FEATURE:
<221> NAME/KEY: misc_feature
<223> OTHER INFORMATION: Novel Sequence

<400> SEQUENCE: 5

tatgaattca gatgctctaa acgtccctgc                                        30


<210> SEQ ID NO 6
<211> LENGTH: 30
<212> TYPE: DNA
<213> ORGANISM: Artificial Sequence
<220> FEATURE:
<223> OTHER INFORMATION: Novel Sequence
<220> FEATURE:
<221> NAME/KEY: misc_feature
<223> OTHER INFORMATION: Novel Sequence

<400> SEQUENCE: 6

tccggatcca cctgcacctg cgcctgcacc                                        30


<210> SEQ ID NO 7
<211> LENGTH: 1002
<212> TYPE: DNA
<213> ORGANISM: Homo sapiens

<400> SEQUENCE: 7

atggagtcct caggcaaccc agagagcacc accttttttt actatgacct tcagagccag      60

ccgtgtgaga accaggcctg ggtctttgct accctcgcca ccactgtcct gtactgcctg     120

gtgtttctcc tcagcctagt gggcaacagc ctggtcctgt gggtcctggt gaagtatgag     180

agcctggagt ccctcaccaa catcttcatc ctcaacctgt gcctctcaga cctggtgttc     240

gcctgcttgt tgcctgtgtg gatctcccca taccactggg gctgggtgct gggagacttc     300

ctctgcaaac tcctcaatat gatcttctcc atcagcctct acagcagcat cttcttcctg     360

accatcatga ccatccaccg ctacctgtcg gtagtgagcc ccctctccac cctgcgcgtc     420

cccaccctcc gctgccgggt gctggtgacc atggctgtgt gggtagccag catcctgtcc     480
```

-continued

```
tccatcctcg acaccatctt ccacaaggtg ctttcttcgg gctgtgatta ttccgaactc    540

acgtggtacc tcacctccgt ctaccagcac aacctcttct tcctgctgtc cctggggatt    600

atcctgttct gctacgtgga gatcctcagg accctgttcc gctcacgctc caagcggcgc    660

caccgcacgg tcaagctcat cttcgccatc gtggtggcct acttcctcag ctggggtccc    720

tacaacttca ccctgtttct gcagacgctg tttcggaccc agatcatccg gagctgcgag    780

gccaaacagc agctagaata cgccctgctc atctgccgca acctcgcctt ctcccactgc    840

tgctttaacc cggtgctcta tgtcttcgtg ggggtcaagt tccgcacaca cctgaaacat    900

gttctccggc agttctggtt ctgccggctg caggcaccca gcccagcctc gatcccccac    960

tcccctggtg ccttcgccta tgagggcgcc tccttctact ga                      1002
```

<210> SEQ ID NO 8
<211> LENGTH: 333
<212> TYPE: PRT
<213> ORGANISM: Homo sapiens

<400> SEQUENCE: 8

```
Met Glu Ser Ser Gly Asn Pro Glu Ser Thr Thr Phe Phe Tyr Tyr Asp
1               5                   10                  15

Leu Gln Ser Gln Pro Cys Glu Asn Gln Ala Trp Val Phe Ala Thr Leu
            20                  25                  30

Ala Thr Thr Val Leu Tyr Cys Leu Val Phe Leu Leu Ser Leu Val Gly
        35                  40                  45

Asn Ser Leu Val Leu Trp Val Leu Val Lys Tyr Glu Ser Leu Glu Ser
    50                  55                  60

Leu Thr Asn Ile Phe Ile Leu Asn Leu Cys Leu Ser Asp Leu Val Phe
65                  70                  75                  80

Ala Cys Leu Leu Pro Val Trp Ile Ser Pro Tyr His Trp Gly Trp Val
                85                  90                  95

Leu Gly Asp Phe Leu Cys Lys Leu Leu Asn Met Ile Phe Ser Ile Ser
            100                 105                 110

Leu Tyr Ser Ser Ile Phe Phe Leu Thr Ile Met Thr Ile His Arg Tyr
        115                 120                 125

Leu Ser Val Val Ser Pro Leu Ser Thr Leu Arg Val Pro Thr Leu Arg
    130                 135                 140

Cys Arg Val Leu Val Thr Met Ala Val Trp Val Ala Ser Ile Leu Ser
145                 150                 155                 160

Ser Ile Leu Asp Thr Ile Phe His Lys Val Leu Ser Ser Gly Cys Asp
                165                 170                 175

Tyr Ser Glu Leu Thr Trp Tyr Leu Thr Ser Val Tyr Gln His Asn Leu
            180                 185                 190

Phe Phe Leu Leu Ser Leu Gly Ile Ile Leu Phe Cys Tyr Val Glu Ile
        195                 200                 205

Leu Arg Thr Leu Phe Arg Ser Arg Ser Lys Arg Arg His Arg Thr Val
    210                 215                 220

Lys Leu Ile Phe Ala Ile Val Val Ala Tyr Phe Leu Ser Trp Gly Pro
225                 230                 235                 240

Tyr Asn Phe Thr Leu Phe Leu Gln Thr Leu Phe Arg Thr Gln Ile Ile
                245                 250                 255

Arg Ser Cys Glu Ala Lys Gln Gln Leu Glu Tyr Ala Leu Leu Ile Cys
            260                 265                 270

Arg Asn Leu Ala Phe Ser His Cys Cys Phe Asn Pro Val Leu Tyr Val
        275                 280                 285
```

-continued

```
Phe Val Gly Val Lys Phe Arg Thr His Leu Lys His Val Leu Arg Gln
    290                 295                 300

Phe Trp Phe Cys Arg Leu Gln Ala Pro Ser Pro Ala Ser Ile Pro His
305                 310                 315                 320

Ser Pro Gly Ala Phe Ala Tyr Glu Gly Ala Ser Phe Tyr
                325                 330
```

<210> SEQ ID NO 9
<211> LENGTH: 30
<212> TYPE: DNA
<213> ORGANISM: Artificial Sequence
<220> FEATURE:
<223> OTHER INFORMATION: Novel Sequence

<400> SEQUENCE: 9

```
gcaagcttgg gggacgccag gtcgccggct                                    30
```

<210> SEQ ID NO 10
<211> LENGTH: 31
<212> TYPE: DNA
<213> ORGANISM: Artificial Sequence
<220> FEATURE:
<223> OTHER INFORMATION: Novel Sequence

<400> SEQUENCE: 10

```
gcggatccgg acgctggggg agtcaggctg c                                  31
```

<210> SEQ ID NO 11
<211> LENGTH: 987
<212> TYPE: DNA
<213> ORGANISM: Homo sapiens

<400> SEQUENCE: 11

```
atggacaacg cctcgttctc ggagccctgg cccgccaacg catcgggccc ggacccggcg     60

ctgagctgct ccaacgcgtc gactctggcg ccgctgccgg cgccgctggc ggtggctgta    120

ccagttgtct acgcggtgat ctgcgccgtg ggtctggcgg gcaactccgc cgtgctgtac    180

gtgttgctgc gggcgccccg catgaagacc gtcaccaacc tgttcatcct caacctggcc    240

atcgccgacg agctcttcac gctggtgctg cccatcaaca tcgccgactt cctgctgcgg    300

cagtggccct tcggggagct catgtgcaag ctcatcgtgg ctatcgacca gtacaacacc    360

ttctccagcc tctacttcct caccgtcatg agcgccgacc gctacctggt ggtgttggcc    420

actgcggagt cgcgccgggt ggccggccgc acctacagcg ccgcgcgcgc ggtgagcctg    480

gccgtgtggg ggatcgtcac actcgtcgtg ctgcccttcg cagtcttcgc ccggctagac    540

gacgagcagg gccggcgcca gtgcgtgcta gtctttccgc agcccgaggc cttctggtgg    600

cgcgcgagcc gcctctacac gctcgtgctg ggcttcgcca tccccgtgtc caccatctgt    660

gtcctctata ccaccctgct gtgccggctg catgccatgc ggctggacag ccacgccaag    720

gccctggagc gcgccaagaa gcgggtgacc ttcctggtgg tggcaatcct ggcggtgtgc    780

ctcctctgct ggacgcccta ccacctgagc accgtggtgg cgctcaccac cgacctcccg    840

cagacgccgc tggtcatcgc tatctcctac ttcatcacca gcctgacgta cgccaacagc    900

tgcctcaacc ccttcctcta cgccttcctg gacgccagct tccgcaggaa cctccgccag    960

ctgataactt gccgcgcggc agcctga                                       987
```

<210> SEQ ID NO 12
<211> LENGTH: 328

-continued

```
<212> TYPE: PRT
<213> ORGANISM: Homo sapiens

<400> SEQUENCE: 12

Met Asp Asn Ala Ser Phe Ser Glu Pro Trp Pro Ala Asn Ala Ser Gly
1               5                   10                  15

Pro Asp Pro Ala Leu Ser Cys Ser Asn Ala Ser Thr Leu Ala Pro Leu
            20                  25                  30

Pro Ala Pro Leu Ala Val Ala Val Pro Val Val Tyr Ala Val Ile Cys
        35                  40                  45

Ala Val Gly Leu Ala Gly Asn Ser Ala Val Leu Tyr Val Leu Leu Arg
    50                  55                  60

Ala Pro Arg Met Lys Thr Val Thr Asn Leu Phe Ile Leu Asn Leu Ala
65                  70                  75                  80

Ile Ala Asp Glu Leu Phe Thr Leu Val Leu Pro Ile Asn Ile Ala Asp
                85                  90                  95

Phe Leu Leu Arg Gln Trp Pro Phe Gly Glu Leu Met Cys Lys Leu Ile
            100                 105                 110

Val Ala Ile Asp Gln Tyr Asn Thr Phe Ser Ser Leu Tyr Phe Leu Thr
        115                 120                 125

Val Met Ser Ala Asp Arg Tyr Leu Val Val Leu Ala Thr Ala Glu Ser
    130                 135                 140

Arg Arg Val Ala Gly Arg Thr Tyr Ser Ala Ala Arg Ala Val Ser Leu
145                 150                 155                 160

Ala Val Trp Gly Ile Val Thr Leu Val Val Leu Pro Phe Ala Val Phe
                165                 170                 175

Ala Arg Leu Asp Asp Glu Gln Gly Arg Arg Gln Cys Val Leu Val Phe
            180                 185                 190

Pro Gln Pro Glu Ala Phe Trp Trp Arg Ala Ser Arg Leu Tyr Thr Leu
        195                 200                 205

Val Leu Gly Phe Ala Ile Pro Val Ser Thr Ile Cys Val Leu Tyr Thr
    210                 215                 220

Thr Leu Leu Cys Arg Leu His Ala Met Arg Leu Asp Ser His Ala Lys
225                 230                 235                 240

Ala Leu Glu Arg Ala Lys Lys Arg Val Thr Phe Leu Val Val Ala Ile
                245                 250                 255

Leu Ala Val Cys Leu Leu Cys Trp Thr Pro Tyr His Leu Ser Thr Val
            260                 265                 270

Val Ala Leu Thr Thr Asp Leu Pro Gln Thr Pro Leu Val Ile Ala Ile
        275                 280                 285

Ser Tyr Phe Ile Thr Ser Leu Thr Tyr Ala Asn Ser Cys Leu Asn Pro
    290                 295                 300

Phe Leu Tyr Ala Phe Leu Asp Ala Ser Phe Arg Arg Asn Leu Arg Gln
305                 310                 315                 320

Leu Ile Thr Cys Arg Ala Ala Ala
                325


<210> SEQ ID NO 13
<211> LENGTH: 30
<212> TYPE: DNA
<213> ORGANISM: Artificial Sequence
<220> FEATURE:
<223> OTHER INFORMATION: Novel Sequence

<400> SEQUENCE: 13

cggaattcgt caacggtccc agctacaatg                                      30
```

-continued

<210> SEQ ID NO 14
<211> LENGTH: 31
<212> TYPE: DNA
<213> ORGANISM: Artificial Sequence
<220> FEATURE:
<223> OTHER INFORMATION: Novel Sequence

<400> SEQUENCE: 14
atggatccca ggcccttcag caccgcaata t 31

<210> SEQ ID NO 15
<211> LENGTH: 1002
<212> TYPE: DNA
<213> ORGANISM: Homo sapiens

<400> SEQUENCE: 15
atgcaggccg ctgggcaccc agagcccctt gacagcaggg gctccttctc cctccccacg 60
atgggtgcca acgtctctca ggacaatggc actggccaca atgccacctt ctccgagcca 120
ctgccgttcc tctatgtgct cctgcccgcc gtgtactccg ggatctgtgc tgtggggctg 180
actggcaaca cggccgtcat ccttgtaatc ctaagggcgc ccaagatgaa gacggtgacc 240
aacgtgttca tcctgaacct ggccgtcgcc gacgggctct tcacgctggt actgcccgtc 300
aacatcgcgg agcacctgct gcagtactgg cccttcgggg agctgctctg caagctggtg 360
ctggccgtcg accactacaa catcttctcc agcatctact tcctagccgt gatgagcgtg 420
gaccgatacc tggtggtgct ggccaccgtg aggtcccgcc acatgccctg gcgcacctac 480 cgggggcga aggtcgccag cctgtgtgtc tggctgggcg tcacggtcct ggttctgccc 540
ttcttctctt tcgctggcgt ctacagcaac gagctgcagg tcccaagctg tgggctgagc 600
ttcccgtggc ccgagcgggt ctggttcaag gccagccgtg tctacacttt ggtcctgggc 660
ttcgtgctgc ccgtgtgcac catctgtgtg ctctacacag acctcctgcg caggctgcgg 720
gccgtgcggc tccgctctgg agccaaggct ctaggcaagg ccaggcggaa ggtgaccgtc 780
ctggtcctcg tcgtgctggc cgtgtgcctc ctctgctgga cgcccttcca cctggcctct 840
gtcgtggccc tgaccacgga cctgccccag accccactgg tcatcagtat gtcctacgtc 900
atcaccagcc tcacgtacgc caactcgtgc ctgaacccct tcctctacgc ctttctagat 960
gacaacttcc ggaagaactt ccgcagcata ttgcggtgct ga 1002

<210> SEQ ID NO 16
<211> LENGTH: 333
<212> TYPE: PRT
<213> ORGANISM: Homo sapiens

<400> SEQUENCE: 16

Met Gln Ala Ala Gly His Pro Glu Pro Leu Asp Ser Arg Gly Ser Phe
1 5 10 15

Ser Leu Pro Thr Met Gly Ala Asn Val Ser Gln Asp Asn Gly Thr Gly
20 25 30

His Asn Ala Thr Phe Ser Glu Pro Leu Pro Phe Leu Tyr Val Leu Leu
35 40 45

Pro Ala Val Tyr Ser Gly Ile Cys Ala Val Gly Leu Thr Gly Asn Thr
50 55 60

Ala Val Ile Leu Val Ile Leu Arg Ala Pro Lys Met Lys Thr Val Thr
65 70 75 80

Asn Val Phe Ile Leu Asn Leu Ala Val Ala Asp Gly Leu Phe Thr Leu

-continued

```
                85                  90                  95

Val Leu Pro Val Asn Ile Ala Glu His Leu Leu Gln Tyr Trp Pro Phe
            100                 105                 110

Gly Glu Leu Leu Cys Lys Leu Val Leu Ala Val Asp His Tyr Asn Ile
        115                 120                 125

Phe Ser Ser Ile Tyr Phe Leu Ala Val Met Ser Val Asp Arg Tyr Leu
    130                 135                 140

Val Val Leu Ala Thr Val Arg Ser Arg His Met Pro Trp Arg Thr Tyr
145                 150                 155                 160

Arg Gly Ala Lys Val Ala Ser Leu Cys Val Trp Leu Gly Val Thr Val
                165                 170                 175

Leu Val Leu Pro Phe Phe Ser Phe Ala Gly Val Tyr Ser Asn Glu Leu
            180                 185                 190

Gln Val Pro Ser Cys Gly Leu Ser Phe Pro Trp Pro Glu Arg Val Trp
        195                 200                 205

Phe Lys Ala Ser Arg Val Tyr Thr Leu Val Leu Gly Phe Val Leu Pro
    210                 215                 220

Val Cys Thr Ile Cys Val Leu Tyr Thr Asp Leu Leu Arg Arg Leu Arg
225                 230                 235                 240

Ala Val Arg Leu Arg Ser Gly Ala Lys Ala Leu Gly Lys Ala Arg Arg
                245                 250                 255

Lys Val Thr Val Leu Val Leu Val Val Leu Ala Val Cys Leu Leu Cys
            260                 265                 270

Trp Thr Pro Phe His Leu Ala Ser Val Val Ala Leu Thr Thr Asp Leu
        275                 280                 285

Pro Gln Thr Pro Leu Val Ile Ser Met Ser Tyr Val Ile Thr Ser Leu
    290                 295                 300

Thr Tyr Ala Asn Ser Cys Leu Asn Pro Phe Leu Tyr Ala Phe Leu Asp
305                 310                 315                 320

Asp Asn Phe Arg Lys Asn Phe Arg Ser Ile Leu Arg Cys
                325                 330


<210> SEQ ID NO 17
<211> LENGTH: 48
<212> TYPE: DNA
<213> ORGANISM: Artificial Sequence
<220> FEATURE:
<223> OTHER INFORMATION: Novel Sequence

<400> SEQUENCE: 17

acgaattcag ccatggtcct tgaggtgagt gaccaccaag tgctaaat                  48


<210> SEQ ID NO 18
<211> LENGTH: 27
<212> TYPE: DNA
<213> ORGANISM: Artificial Sequence
<220> FEATURE:
<223> OTHER INFORMATION: Novel Sequence

<400> SEQUENCE: 18

gaggatcctg gaatgcgggg aagtcag                                         27


<210> SEQ ID NO 19
<211> LENGTH: 1107
<212> TYPE: DNA
<213> ORGANISM: Homo sapiens

<400> SEQUENCE: 19
```

-continued

```
atggtccttg aggtgagtga ccaccaagtg ctaaatgacg ccgaggttgc cgccctcctg     60

gagaacttca gctcttccta tgactatgga gaaaacgaga gtgactcgtg ctgtacctcc    120

ccgccctgcc cacaggactt cagcctgaac ttcgaccggg ccttcctgcc agccctctac    180

agcctcctct ttctgctggg gctgctgggc aacggcgcgg tggcagccgt gctgctgagc    240

cggcggacag ccctgagcag caccgacacc ttcctgctcc acctagctgt agcagacacg    300

ctgctggtgc tgacactgcc gctctgggca gtggacgctg ccgtccagtg ggtctttggc    360

tctggcctct gcaaagtggc aggtgccctc ttcaacatca acttctacgc aggagccctc    420

ctgctggcct gcatcagctt tgaccgctac ctgaacatag ttcatgccac ccagctctac    480

cgccgggggc ccccggcccg cgtgaccctc acctgcctgg ctgtctgggg gctctgcctg    540

cttttcgccc tcccagactt catcttcctg tcggcccacc acgacgagcg cctcaacgcc    600

acccactgcc aatacaactt cccacaggtg ggccgcacgg ctctgcgggt gctgcagctg    660

gtggctggct ttctgctgcc cctgctggtc atggcctact gctatgccca catcctggcc    720

gtgctgctgg tttccagggg ccagcggcgc ctgcgggcca tgcggctggt ggtggtggtc    780

gtggtggcct ttgccctctg ctggaccccc tatcacctgg tggtgctggt ggacatcctc    840

atggacctgg gcgctttggc ccgcaactgt ggccgagaaa gcagggtaga cgtggccaag    900

tcggtcacct caggcctggg ctacatgcac tgctgcctca acccgctgct ctatgccttt    960

gtaggggtca agttccggga gcggatgtgg atgctgctct tgcgcctggg ctgccccaac   1020

cagagagggc tccagaggca gccatcgtct tcccgccggg attcatcctg gtctgagacc   1080

tcagaggcct cctactcggg cttgtga                                        1107
```

<210> SEQ ID NO 20
<211> LENGTH: 368
<212> TYPE: PRT
<213> ORGANISM: Homo sapiens

<400> SEQUENCE: 20

```
Met Val Leu Glu Val Ser Asp His Gln Val Leu Asn Asp Ala Glu Val
1               5                   10                  15

Ala Ala Leu Leu Glu Asn Phe Ser Ser Ser Tyr Asp Tyr Gly Glu Asn
            20                  25                  30

Glu Ser Asp Ser Cys Cys Thr Ser Pro Pro Cys Pro Gln Asp Phe Ser
        35                  40                  45

Leu Asn Phe Asp Arg Ala Phe Leu Pro Ala Leu Tyr Ser Leu Leu Phe
    50                  55                  60

Leu Leu Gly Leu Leu Gly Asn Gly Ala Val Ala Ala Val Leu Leu Ser
65                  70                  75                  80

Arg Arg Thr Ala Leu Ser Ser Thr Asp Thr Phe Leu Leu His Leu Ala
                85                  90                  95

Val Ala Asp Thr Leu Leu Val Leu Thr Leu Pro Leu Trp Ala Val Asp
            100                 105                 110

Ala Ala Val Gln Trp Val Phe Gly Ser Gly Leu Cys Lys Val Ala Gly
        115                 120                 125

Ala Leu Phe Asn Ile Asn Phe Tyr Ala Gly Ala Leu Leu Leu Ala Cys
    130                 135                 140

Ile Ser Phe Asp Arg Tyr Leu Asn Ile Val His Ala Thr Gln Leu Tyr
145                 150                 155                 160

Arg Arg Gly Pro Pro Ala Arg Val Thr Leu Thr Cys Leu Ala Val Trp
                165                 170                 175
```

-continued

```
Gly Leu Cys Leu Leu Phe Ala Leu Pro Asp Phe Ile Phe Leu Ser Ala
            180                 185                 190

His His Asp Glu Arg Leu Asn Ala Thr His Cys Gln Tyr Asn Phe Pro
        195                 200                 205

Gln Val Gly Arg Thr Ala Leu Arg Val Leu Gln Leu Val Ala Gly Phe
    210                 215                 220

Leu Leu Pro Leu Leu Val Met Ala Tyr Cys Tyr Ala His Ile Leu Ala
225                 230                 235                 240

Val Leu Leu Val Ser Arg Gly Gln Arg Arg Leu Arg Ala Met Arg Leu
                245                 250                 255

Val Val Val Val Val Val Ala Phe Ala Leu Cys Trp Thr Pro Tyr His
            260                 265                 270

Leu Val Val Leu Val Asp Ile Leu Met Asp Leu Gly Ala Leu Ala Arg
        275                 280                 285

Asn Cys Gly Arg Glu Ser Arg Val Asp Val Ala Lys Ser Val Thr Ser
    290                 295                 300

Gly Leu Gly Tyr Met His Cys Cys Leu Asn Pro Leu Leu Tyr Ala Phe
305                 310                 315                 320

Val Gly Val Lys Phe Arg Glu Arg Met Trp Met Leu Leu Leu Arg Leu
                325                 330                 335

Gly Cys Pro Asn Gln Arg Gly Leu Gln Arg Gln Pro Ser Ser Ser Arg
            340                 345                 350

Arg Asp Ser Ser Trp Ser Glu Thr Ser Glu Ala Ser Tyr Ser Gly Leu
        355                 360                 365


<210> SEQ ID NO 21
<211> LENGTH: 30
<212> TYPE: DNA
<213> ORGANISM: Artificial Sequence
<220> FEATURE:
<223> OTHER INFORMATION: Novel Sequence

<400> SEQUENCE: 21

ttaagcttga cctaatgcca tcttgtgtcc                                      30


<210> SEQ ID NO 22
<211> LENGTH: 30
<212> TYPE: DNA
<213> ORGANISM: Artificial Sequence
<220> FEATURE:
<223> OTHER INFORMATION: Novel Sequence

<400> SEQUENCE: 22

ttggatccaa aagaaccatg cacctcagag                                      30


<210> SEQ ID NO 23
<211> LENGTH: 1074
<212> TYPE: DNA
<213> ORGANISM: Homo sapiens

<400> SEQUENCE: 23

atggctgatg actatggctc tgaatccaca tcttccatgg aagactacgt taacttcaac      60

ttcactgact tctactgtga gaaaaacaat gtcaggcagt ttgcgagcca tttcctccca     120

cccttgtact ggctcgtgtt catcgtgggt gccttgggca acagtcttgt tatccttgtc     180

tactggtact gcacaagagt gaagaccatg accgacatgt tcctttttgaa tttggcaatt    240

gctgacctcc tctttcttgt cactcttccc ttctgggcca ttgctgctgc tgaccagtgg     300

aagttccaga ccttcatgtg caaggtggtc aacagcatgt acaagatgaa cttctacagc     360
```

-continued

```
tgtgtgttgc tgatcatgtg catcagcgtg gacaggtaca ttgccattgc ccaggccatg    420

agagcacata cttggaggga gaaaaggctt ttgtacagca aaatggtttg ctttaccatc    480

tgggtattgg cagctgctct ctgcatccca gaaatcttat acagccaaat caaggaggaa    540

tccggcattg ctatctgcac catggtttac cctagcgatg agagcaccaa actgaagtca    600

gctgtcttga ccctgaaggt cattctgggg ttcttccttc ccttcgtggt catggcttgc    660

tgctatacca tcatcattca caccctgata caagccaaga agtcttccaa gcacaaagcc    720

ctaaaagtga ccatcactgt cctgaccgtc tttgtcttgt ctcagtttcc ctacaactgc    780

attttgttgg tgcagaccat tgacgcctat gccatgttca tctccaactg tgccgtttcc    840

accaacattg acatctgctt ccaggtcacc cagaccatcg ccttcttcca cagttgcctg    900

aaccctgttc tctatgtttt tgtgggtgag agattccgcc gggatctcgt gaaaaccctg    960

aagaacttgg gttgcatcag ccaggcccag tgggtttcat ttacaaggag agagggaagc   1020

ttgaagctgt cgtctatgtt gctggagaca acctcaggag cactctccct ctga         1074
```

```
<210> SEQ ID NO 24
<211> LENGTH: 357
<212> TYPE: PRT
<213> ORGANISM: Homo sapiens

<400> SEQUENCE: 24

Met Ala Asp Asp Tyr Gly Ser Glu Ser Thr Ser Ser Met Glu Asp Tyr
1               5                   10                  15

Val Asn Phe Asn Phe Thr Asp Phe Tyr Cys Glu Lys Asn Asn Val Arg
            20                  25                  30

Gln Phe Ala Ser His Phe Leu Pro Pro Leu Tyr Trp Leu Val Phe Ile
        35                  40                  45

Val Gly Ala Leu Gly Asn Ser Leu Val Ile Leu Val Tyr Trp Tyr Cys
    50                  55                  60

Thr Arg Val Lys Thr Met Thr Asp Met Phe Leu Leu Asn Leu Ala Ile
65                  70                  75                  80

Ala Asp Leu Leu Phe Leu Val Thr Leu Pro Phe Trp Ala Ile Ala Ala
                85                  90                  95

Ala Asp Gln Trp Lys Phe Gln Thr Phe Met Cys Lys Val Val Asn Ser
            100                 105                 110

Met Tyr Lys Met Asn Phe Tyr Ser Cys Val Leu Leu Ile Met Cys Ile
        115                 120                 125

Ser Val Asp Arg Tyr Ile Ala Ile Ala Gln Ala Met Arg Ala His Thr
    130                 135                 140

Trp Arg Glu Lys Arg Leu Leu Tyr Ser Lys Met Val Cys Phe Thr Ile
145                 150                 155                 160

Trp Val Leu Ala Ala Ala Leu Cys Ile Pro Glu Ile Leu Tyr Ser Gln
                165                 170                 175

Ile Lys Glu Glu Ser Gly Ile Ala Ile Cys Thr Met Val Tyr Pro Ser
            180                 185                 190

Asp Glu Ser Thr Lys Leu Lys Ser Ala Val Leu Thr Leu Lys Val Ile
        195                 200                 205

Leu Gly Phe Phe Leu Pro Phe Val Val Met Ala Cys Cys Tyr Thr Ile
    210                 215                 220

Ile Ile His Thr Leu Ile Gln Ala Lys Lys Ser Ser Lys His Lys Ala
225                 230                 235                 240

Leu Lys Val Thr Ile Thr Val Leu Thr Val Phe Val Leu Ser Gln Phe
```

-continued

```
                245                 250                 255

Pro Tyr Asn Cys Ile Leu Leu Val Gln Thr Ile Asp Ala Tyr Ala Met
            260                 265                 270

Phe Ile Ser Asn Cys Ala Val Ser Thr Asn Ile Asp Ile Cys Phe Gln
        275                 280                 285

Val Thr Gln Thr Ile Ala Phe Phe His Ser Cys Leu Asn Pro Val Leu
    290                 295                 300

Tyr Val Phe Val Gly Glu Arg Phe Arg Arg Asp Leu Val Lys Thr Leu
305                 310                 315                 320

Lys Asn Leu Gly Cys Ile Ser Gln Ala Gln Trp Val Ser Phe Thr Arg
                325                 330                 335

Arg Glu Gly Ser Leu Lys Leu Ser Ser Met Leu Leu Glu Thr Thr Ser
            340                 345                 350

Gly Ala Leu Ser Leu
        355
```

<210> SEQ ID NO 25
<211> LENGTH: 1110
<212> TYPE: DNA
<213> ORGANISM: Homo sapiens

<400> SEQUENCE: 25

```
atggcctcat cgaccactcg gggccccagg gtttctgact tattttctgg gctgccgccg     60

gcggtcacaa ctcccgccaa ccagagcgca gaggcctcgg cgggcaacgg gtcggtggct    120

ggcgcggacg ctccagccgt cacgcccttc cagagcctgc agctggtgca tcagctgaag    180

gggctgatcg tgctgctcta cagcgtcgtg gtggtcgtgg ggctggtggg caactgcctg    240

ctggtgctgg tgatcgcgcg ggtgccgcgg ctgcacaacg tgacgaactt cctcatcggc    300

aacctggcct tgtccgacgt gctcatgtgc accgcctgcg tgccgctcac gctggcctat    360

gccttcgagc cacgcggctg ggtgttcggc ggcggcctgt gccacctggt cttcttcctg    420

cagccggtca ccgtctatgt gtcggtgttc acgctcacca ccatcgcagt ggaccgctac    480

gtcgtgctgg tgcacccgct gaggcgcgca tctcgctgcg cctcagccta cgctgtgctg    540

gccatctggg cgctgtccgc ggtgctggcg ctgccgcccg ccgtgcacac ctatcacgtg    600

gagctcaagc cgcacgacgt gcgcctctgc gaggagttct ggggctccca ggagcgccag    660

cgccagctct acgcctgggg gctgctgctg gtcacctacc tgctccctct gctggtcatc    720

ctcctgtctt acgtccgggt gtcagtgaag ctccgcaacc gcgtggtgcc gggctgcgtg    780

acccagagcc aggccgactg ggaccgcgct cggcgccggc gcaccttctg cttgctggtg    840

gtggtcgtgg tggtgttcgc cgtctgctgg ctgccgctgc acgtcttcaa cctgctgcgg    900

gacctcgacc cccacgccat cgacccttac gcctttgggc tggtgcagct gctctgccac    960

tggctcgcca tgagttcggc ctgctacaac cccttcatct acgcctggct gcacgacagc   1020

ttccgcgagg agctgcgcaa actgttggtc gcttggcccc gcaagatagc cccccatggc   1080

cagaatatga ccgtcagcgt ggtcatctga                                    1110
```

<210> SEQ ID NO 26
<211> LENGTH: 369
<212> TYPE: PRT
<213> ORGANISM: Homo sapiens

<400> SEQUENCE: 26

```
Met Ala Ser Ser Thr Thr Arg Gly Pro Arg Val Ser Asp Leu Phe Ser
1               5                   10                  15
```

-continued

```
Gly Leu Pro Pro Ala Val Thr Thr Pro Ala Asn Gln Ser Ala Glu Ala
            20                  25                  30

Ser Ala Gly Asn Gly Ser Val Ala Gly Ala Asp Ala Pro Ala Val Thr
        35                  40                  45

Pro Phe Gln Ser Leu Gln Leu Val His Gln Leu Lys Gly Leu Ile Val
    50                  55                  60

Leu Leu Tyr Ser Val Val Val Val Val Gly Leu Val Gly Asn Cys Leu
65                  70                  75                  80

Leu Val Leu Val Ile Ala Arg Val Pro Arg Leu His Asn Val Thr Asn
                85                  90                  95

Phe Leu Ile Gly Asn Leu Ala Leu Ser Asp Val Leu Met Cys Thr Ala
            100                 105                 110

Cys Val Pro Leu Thr Leu Ala Tyr Ala Phe Glu Pro Arg Gly Trp Val
        115                 120                 125

Phe Gly Gly Gly Leu Cys His Leu Val Phe Phe Leu Gln Pro Val Thr
    130                 135                 140

Val Tyr Val Ser Val Phe Thr Leu Thr Thr Ile Ala Val Asp Arg Tyr
145                 150                 155                 160

Val Val Leu Val His Pro Leu Arg Arg Ala Ser Arg Cys Ala Ser Ala
                165                 170                 175

Tyr Ala Val Leu Ala Ile Trp Ala Leu Ser Ala Val Leu Ala Leu Pro
            180                 185                 190

Pro Ala Val His Thr Tyr His Val Glu Leu Lys Pro His Asp Val Arg
        195                 200                 205

Leu Cys Glu Glu Phe Trp Gly Ser Gln Glu Arg Gln Arg Gln Leu Tyr
    210                 215                 220

Ala Trp Gly Leu Leu Leu Val Thr Tyr Leu Leu Pro Leu Leu Val Ile
225                 230                 235                 240

Leu Leu Ser Tyr Val Arg Val Ser Val Lys Leu Arg Asn Arg Val Val
                245                 250                 255

Pro Gly Cys Val Thr Gln Ser Gln Ala Asp Trp Asp Arg Ala Arg Arg
            260                 265                 270

Arg Arg Thr Phe Cys Leu Leu Val Val Val Val Val Val Phe Ala Val
        275                 280                 285

Cys Trp Leu Pro Leu His Val Phe Asn Leu Leu Arg Asp Leu Asp Pro
    290                 295                 300

His Ala Ile Asp Pro Tyr Ala Phe Gly Leu Val Gln Leu Leu Cys His
305                 310                 315                 320

Trp Leu Ala Met Ser Ser Ala Cys Tyr Asn Pro Phe Ile Tyr Ala Trp
                325                 330                 335

Leu His Asp Ser Phe Arg Glu Glu Leu Arg Lys Leu Leu Val Ala Trp
            340                 345                 350

Pro Arg Lys Ile Ala Pro His Gly Gln Asn Met Thr Val Ser Val Val
        355                 360                 365

Ile


<210> SEQ ID NO 27
<211> LENGTH: 1083
<212> TYPE: DNA
<213> ORGANISM: Homo sapiens

<400> SEQUENCE: 27

atggacccag aagaaacttc agtttatttg gattattact atgctacgag cccaaactct      60
```

-continued

```
gacatcaggg agacccactc ccatgttcct tacacctctg tcttccttcc agtcttttac    120

acagctgtgt tcctgactgg agtgctgggg aaccttgttc tcatgggagc gttgcatttc    180

aaacccggca gccgaagact gatcgacatc tttatcatca atctggctgc ctctgacttc    240

atttttcttg tcacattgcc tctctgggtg gataaagaag catctctagg actgtggagg    300

acgggctcct tcctgtgcaa agggagctcc tacatgatct ccgtcaatat gcactgcagt    360

gtcctcctgc tcacttgcat gagtgttgac cgctacctgg ccattgtgtg gccagtcgta    420

tccaggaaat tcagaaggac agactgtgca tatgtagtct gtgccagcat ctggtttatc    480

tcctgcctgc tggggttgcc tactcttctg tccagggagc tcacgctgat tgatgataag    540

ccatactgtg cagagaaaaa ggcaactcca attaaactca tatggtccct ggtggcctta    600

attttcacct tttttgtccc tttgttgagc attgtgacct gctactgttg cattgcaagg    660

aagctgtgtg cccattacca gcaatcagga aagcacaaca aaaagctgaa gaaatctata    720

aagatcatct ttattgtcgt ggcagccttt cttgtctcct ggctgccctt caatactttc    780

aagttcctgg ccattgtctc tgggttgcgg caagaacact atttaccctc agctattctt    840

cagcttggta tggaggtgag tggacccttg gcatttgcca acagctgtgt caaccctttc    900

atttactata tcttcgacag ctacatccgc cgggccattg tccactgctt gtgcccttgc    960

ctgaaaaact atgactttgg gagtagcact gagacatcag atagtcacct cactaaggct   1020

ctctccacct tcattcatgc agaagatttt gccaggagga ggaagaggtc tgtgtcactc   1080

taa                                                                 1083


<210> SEQ ID NO 28
<211> LENGTH: 360
<212> TYPE: PRT
<213> ORGANISM: Homo sapiens

<400> SEQUENCE: 28

Met Asp Pro Glu Glu Thr Ser Val Tyr Leu Asp Tyr Tyr Tyr Ala Thr
1               5                   10                  15

Ser Pro Asn Ser Asp Ile Arg Glu Thr His Ser His Val Pro Tyr Thr
            20                  25                  30

Ser Val Phe Leu Pro Val Phe Tyr Thr Ala Val Phe Leu Thr Gly Val
        35                  40                  45

Leu Gly Asn Leu Val Leu Met Gly Ala Leu His Phe Lys Pro Gly Ser
    50                  55                  60

Arg Arg Leu Ile Asp Ile Phe Ile Ile Asn Leu Ala Ala Ser Asp Phe
65                  70                  75                  80

Ile Phe Leu Val Thr Leu Pro Leu Trp Val Asp Lys Glu Ala Ser Leu
                85                  90                  95

Gly Leu Trp Arg Thr Gly Ser Phe Leu Cys Lys Gly Ser Ser Tyr Met
            100                 105                 110

Ile Ser Val Asn Met His Cys Ser Val Leu Leu Leu Thr Cys Met Ser
        115                 120                 125

Val Asp Arg Tyr Leu Ala Ile Val Trp Pro Val Val Ser Arg Lys Phe
    130                 135                 140

Arg Arg Thr Asp Cys Ala Tyr Val Val Cys Ala Ser Ile Trp Phe Ile
145                 150                 155                 160

Ser Cys Leu Leu Gly Leu Pro Thr Leu Leu Ser Arg Glu Leu Thr Leu
                165                 170                 175

Ile Asp Asp Lys Pro Tyr Cys Ala Glu Lys Lys Ala Thr Pro Ile Lys
            180                 185                 190
```

-continued

```
Leu Ile Trp Ser Leu Val Ala Leu Ile Phe Thr Phe Phe Val Pro Leu
        195                 200                 205

Leu Ser Ile Val Thr Cys Tyr Cys Cys Ile Ala Arg Lys Leu Cys Ala
    210                 215                 220

His Tyr Gln Gln Ser Gly Lys His Asn Lys Lys Leu Lys Lys Ser Ile
225                 230                 235                 240

Lys Ile Ile Phe Ile Val Val Ala Ala Phe Leu Val Ser Trp Leu Pro
                245                 250                 255

Phe Asn Thr Phe Lys Phe Leu Ala Ile Val Ser Gly Leu Arg Gln Glu
            260                 265                 270

His Tyr Leu Pro Ser Ala Ile Leu Gln Leu Gly Met Glu Val Ser Gly
        275                 280                 285

Pro Leu Ala Phe Ala Asn Ser Cys Val Asn Pro Phe Ile Tyr Tyr Ile
    290                 295                 300

Phe Asp Ser Tyr Ile Arg Arg Ala Ile Val His Cys Leu Cys Pro Cys
305                 310                 315                 320

Leu Lys Asn Tyr Asp Phe Gly Ser Ser Thr Glu Thr Ser Asp Ser His
                325                 330                 335

Leu Thr Lys Ala Leu Ser Thr Phe Ile His Ala Glu Asp Phe Ala Arg
            340                 345                 350

Arg Arg Lys Arg Ser Val Ser Leu
        355                 360


<210> SEQ ID NO 29
<211> LENGTH: 31
<212> TYPE: DNA
<213> ORGANISM: Artificial Sequence
<220> FEATURE:
<223> OTHER INFORMATION: Novel Sequence
<220> FEATURE:
<221> NAME/KEY: misc_feature
<223> OTHER INFORMATION: Novel Sequence

<400> SEQUENCE: 29

ctagaattct gactccagcc aaagcatgaa t                                  31


<210> SEQ ID NO 30
<211> LENGTH: 30
<212> TYPE: DNA
<213> ORGANISM: Artificial Sequence
<220> FEATURE:
<223> OTHER INFORMATION: Novel Sequence

<400> SEQUENCE: 30

gctggatcct aaacagtctg cgctcggcct                                    30


<210> SEQ ID NO 31
<211> LENGTH: 1020
<212> TYPE: DNA
<213> ORGANISM: Homo sapiens

<400> SEQUENCE: 31

atgaatggcc ttgaagtggc tcccccaggt ctgatcacca acttctccct ggccacggca     60

gagcaatgtg gccaggagac gccactggag aacatgctgt tcgcctcctt ctaccttctg    120

gattttatcc tggctttagt tggcaatacc ctggctctgt ggcttttcat ccgagaccac    180

aagtccggga ccccggccaa cgtgttcctg atgcatctgg ccgtggccga cttgtcgtgc    240

gtgctggtcc tgcccacccg cctggtctac cacttctctg ggaaccactg gccatttggg    300
```

-continued

```
gaaatcgcat gccgtctcac cggcttcctc ttctacctca acatgtacgc cagcatctac    360

ttcctcacct gcatcagcgc cgaccgtttc ctggccattg tgcacccggt caagtccctc    420

aagctccgca ggcccctcta cgcacacctg gcctgtgcct tcctgtgggt ggtggtggct    480

gtggccatgg ccccgctgct ggtgagccca cagaccgtgc agaccaacca cacggtggtc    540

tgcctgcagc tgtaccggga gaaggcctcc caccatgccc tggtgtccct ggcagtggcc    600

ttcaccttcc cgttcatcac cacggtcacc tgctacctgc tgatcatccg cagcctgcgg    660

cagggcctgc gtgtggagaa gcgcctcaag accaaggcag tgcgcatgat cgccatagtg    720

ctggccatct tcctggtctg cttcgtgccc taccacgtca accgctccgt ctacgtgctg    780

cactaccgca gccatggggc ctcctgcgcc acccagcgca tcctggccct ggcaaaccgc    840

atcacctcct gcctcaccag cctcaacggg gcactcgacc ccatcatgta tttcttcgtg    900

gctgagaagt tccgccacgc cctgtgcaac ttgctctgtg gcaaaaggct caagggcccg    960

ccccccagct tcgaagggaa aaccaacgag agctcgctga gtgccaagtc agagctgtga   1020
```

```
<210> SEQ ID NO 32
<211> LENGTH: 339
<212> TYPE: PRT
<213> ORGANISM: Homo sapiens

<400> SEQUENCE: 32

Met Asn Gly Leu Glu Val Ala Pro Pro Gly Leu Ile Thr Asn Phe Ser
1               5                   10                  15

Leu Ala Thr Ala Glu Gln Cys Gly Gln Glu Thr Pro Leu Glu Asn Met
            20                  25                  30

Leu Phe Ala Ser Phe Tyr Leu Leu Asp Phe Ile Leu Ala Leu Val Gly
        35                  40                  45

Asn Thr Leu Ala Leu Trp Leu Phe Ile Arg Asp His Lys Ser Gly Thr
    50                  55                  60

Pro Ala Asn Val Phe Leu Met His Leu Ala Val Ala Asp Leu Ser Cys
65                  70                  75                  80

Val Leu Val Leu Pro Thr Arg Leu Val Tyr His Phe Ser Gly Asn His
                85                  90                  95

Trp Pro Phe Gly Glu Ile Ala Cys Arg Leu Thr Gly Phe Leu Phe Tyr
            100                 105                 110

Leu Asn Met Tyr Ala Ser Ile Tyr Phe Leu Thr Cys Ile Ser Ala Asp
        115                 120                 125

Arg Phe Leu Ala Ile Val His Pro Val Lys Ser Leu Lys Leu Arg Arg
    130                 135                 140

Pro Leu Tyr Ala His Leu Ala Cys Ala Phe Leu Trp Val Val Val Ala
145                 150                 155                 160

Val Ala Met Ala Pro Leu Leu Val Ser Pro Gln Thr Val Gln Thr Asn
                165                 170                 175

His Thr Val Val Cys Leu Gln Leu Tyr Arg Glu Lys Ala Ser His His
            180                 185                 190

Ala Leu Val Ser Leu Ala Val Ala Phe Thr Phe Pro Phe Ile Thr Thr
        195                 200                 205

Val Thr Cys Tyr Leu Leu Ile Ile Arg Ser Leu Arg Gln Gly Leu Arg
    210                 215                 220

Val Glu Lys Arg Leu Lys Thr Lys Ala Val Arg Met Ile Ala Ile Val
225                 230                 235                 240

Leu Ala Ile Phe Leu Val Cys Phe Val Pro Tyr His Val Asn Arg Ser
                245                 250                 255
```

-continued

Val Tyr Val Leu His Tyr Arg Ser His Gly Ala Ser Cys Ala Thr Gln
260 265 270

Arg Ile Leu Ala Leu Ala Asn Arg Ile Thr Ser Cys Leu Thr Ser Leu
275 280 285

Asn Gly Ala Leu Asp Pro Ile Met Tyr Phe Phe Val Ala Glu Lys Phe
290 295 300

Arg His Ala Leu Cys Asn Leu Leu Cys Gly Lys Arg Leu Lys Gly Pro
305 310 315 320

Pro Pro Ser Phe Glu Gly Lys Thr Asn Glu Ser Ser Leu Ser Ala Lys
325 330 335

Ser Glu Leu

<210> SEQ ID NO 33
<211> LENGTH: 29
<212> TYPE: DNA
<213> ORGANISM: Artificial Sequence
<220> FEATURE:
<223> OTHER INFORMATION: Novel Sequence

<400> SEQUENCE: 33
ataagatgat caccctgaac aatcaagat 29

<210> SEQ ID NO 34
<211> LENGTH: 33
<212> TYPE: DNA
<213> ORGANISM: Artificial Sequence
<220> FEATURE:
<223> OTHER INFORMATION: Novel Sequence

<400> SEQUENCE: 34
tccgaattca taacatttca ctgtttatat tgc 33

<210> SEQ ID NO 35
<211> LENGTH: 996
<212> TYPE: DNA
<213> ORGANISM: Homo sapiens

<400> SEQUENCE: 35
atgatcaccc tgaacaatca agatcaacct gtcactttta acagctcaca tccagatgaa 60
tacaaaattg cagcccttgt cttctatagc tgtatcttca taattggatt atttgttaac 120
atcactgcat tatgggtttt cagttgtacc accaagaaga gaaccacggt aaccatctat 180
atgatgaatg tggcattagt ggacttgata tttataatga ctttaccctt tcgaatgttt 240
tattatgcaa aagatgcatg gccatttgga gagtacttct gccagattat tggagctctc 300
acagtgtttt acccaagcat tgctttatgg cttcttgcct ttattagtgc tgacagatac 360
atggccattg tacagccgaa gtacgccaaa gaacttaaaa acacgtgcaa agccgtgctg 420
gcgtgtgtgg gagtctggat aatgaccctg accacgacca cccctctgct actgctctat 480
aaagacccag ataaagactc cactcccgcc acctgcctca agatttctga catcatctat 540
ctaaaagctg tgaacgtgct gaacctcact cgactgacat ttttttttctt gattcctttg 600 ttcatcatga ttgggtgcta cttggtcatt attcataatc tccttcacgg caggacgtct 660
aagctgaaac ccaaagtcaa ggagaagtcc ataaggatca tcatcacgct gctggtgcag 720
gtgctcgtct gctttatgcc cttccacatc tgtttcgctt tcctgatgct gggaacgggg 780
gagaacagtt acaatccctg ggagcctttt accaccttcc tcatgaacct cagcacgtgt 840
ctggatgtga ttctctacta catcgtttca aaacaatttc aggctcgagt cattagtgtc 900

-continued

```
atgctatacc gtaattacct tcgaagcctg cgcagaaaaa gtttccgatc tggtagtcta    960

aggtcactaa gcaatataaa cagtgaaatg ttatga                              996


<210> SEQ ID NO 36
<211> LENGTH: 331
<212> TYPE: PRT
<213> ORGANISM: Homo sapiens

<400> SEQUENCE: 36

Met Ile Thr Leu Asn Asn Gln Asp Gln Pro Val Thr Phe Asn Ser Ser
1               5                   10                  15

His Pro Asp Glu Tyr Lys Ile Ala Ala Leu Val Phe Tyr Ser Cys Ile
            20                  25                  30

Phe Ile Ile Gly Leu Phe Val Asn Ile Thr Ala Leu Trp Val Phe Ser
        35                  40                  45

Cys Thr Thr Lys Lys Arg Thr Thr Val Thr Ile Tyr Met Met Asn Val
    50                  55                  60

Ala Leu Val Asp Leu Ile Phe Ile Met Thr Leu Pro Phe Arg Met Phe
65                  70                  75                  80

Tyr Tyr Ala Lys Asp Ala Trp Pro Phe Gly Glu Tyr Phe Cys Gln Ile
                85                  90                  95

Ile Gly Ala Leu Thr Val Phe Tyr Pro Ser Ile Ala Leu Trp Leu Leu
            100                 105                 110

Ala Phe Ile Ser Ala Asp Arg Tyr Met Ala Ile Val Gln Pro Lys Tyr
        115                 120                 125

Ala Lys Glu Leu Lys Asn Thr Cys Lys Ala Val Leu Ala Cys Val Gly
    130                 135                 140

Val Trp Ile Met Thr Leu Thr Thr Thr Thr Pro Leu Leu Leu Leu Tyr
145                 150                 155                 160

Lys Asp Pro Asp Lys Asp Ser Thr Pro Ala Thr Cys Leu Lys Ile Ser
                165                 170                 175

Asp Ile Ile Tyr Leu Lys Ala Val Asn Val Leu Asn Leu Thr Arg Leu
            180                 185                 190

Thr Phe Phe Phe Leu Ile Pro Leu Phe Ile Met Ile Gly Cys Tyr Leu
        195                 200                 205

Val Ile Ile His Asn Leu Leu His Gly Arg Thr Ser Lys Leu Lys Pro
    210                 215                 220

Lys Val Lys Glu Lys Ser Ile Arg Ile Ile Ile Thr Leu Leu Val Gln
225                 230                 235                 240

Val Leu Val Cys Phe Met Pro Phe His Ile Cys Phe Ala Phe Leu Met
                245                 250                 255

Leu Gly Thr Gly Glu Asn Ser Tyr Asn Pro Trp Gly Ala Phe Thr Thr
            260                 265                 270

Phe Leu Met Asn Leu Ser Thr Cys Leu Asp Val Ile Leu Tyr Tyr Ile
        275                 280                 285

Val Ser Lys Gln Phe Gln Ala Arg Val Ile Ser Val Met Leu Tyr Arg
    290                 295                 300

Asn Tyr Leu Arg Ser Leu Arg Arg Lys Ser Phe Arg Ser Gly Ser Leu
305                 310                 315                 320

Arg Ser Leu Ser Asn Ile Asn Ser Glu Met Leu
                325                 330


<210> SEQ ID NO 37
<211> LENGTH: 28
```

-continued

<212> TYPE: DNA
<213> ORGANISM: Artificial Sequence
<220> FEATURE:
<223> OTHER INFORMATION: Novel Sequence

<400> SEQUENCE: 37
ccaagcttcc aggcctgggg tgtgctgg 28

<210> SEQ ID NO 38
<211> LENGTH: 29
<212> TYPE: DNA
<213> ORGANISM: Artificial Sequence
<220> FEATURE:
<223> OTHER INFORMATION: Novel Sequence

<400> SEQUENCE: 38
atggatcctg accttcggcc cctggcaga 29

<210> SEQ ID NO 39
<211> LENGTH: 1077
<212> TYPE: DNA
<213> ORGANISM: Homo sapiens

<400> SEQUENCE: 39
atgccctctg tgtctccagc ggggccctcg gccggggcag tccccaatgc caccgcagtg 60
acaacagtgc ggaccaatgc cagcgggctg gaggtgcccc tgttccacct gtttgcccgg 120
ctggacgagg agctgcatgg caccttccca ggcctgtgcg tggcgctgat ggcggtgcac 180
ggagccatct tcctggcagg gctggtgctc aacgggctgg cgctgtacgt cttctgctgc 240
cgcacccggg ccaagacacc ctcagtcatc tacaccatca acctggtggt gaccgatcta 300
ctggtagggc tgtccctgcc cacgcgcttc gctgtgtact acggcgccag ggctgcctg 360 cgctgtgcct tcccgcacgt cctcggttac ttcctcaaca tgcactgctc catcctcttc 420
ctcacctgca tctgcgtgga ccgctacctg gccatcgtgc ggcccgaagg ctcccgccgc 480
tgccgccagc ctgcctgtgc cagggccgtg tgcgccttcg tgtggctggc cgccggtgcc 540
gtcaccctgt cggtgctggg cgtgacaggc agccggccct gctgccgtgt ctttgcgctg 600
actgtcctgg agttcctgct gcccctgctg gtcatcagcg tgtttaccgg ccgcatcatg 660
tgtgcactgt cgcggccggg tctgctccac cagggtcgcc agcgccgcgt gcgggccatg 720
cagctcctgc tcacggtgct catcatcttt ctcgtctgct tcacgccctt ccacgcccgc 780
caagtggccg tggcgctgtg gcccgacatg ccacaccaca cgagcctcgt ggtctaccac 840
gtggccgtga ccctcagcag cctcaacagc tgcatggacc ccatcgtcta ctgcttcgtc 900
accagtggct tccaggccac cgtccgaggc ctcttcggcc agcacggaga gcgtgagccc 960
agcagcggtg acgtggtcag catgcacagg agctccaagg gctcaggccg tcatcacatc 1020
ctcagtgccg gccctcacgc cctcacccag gccctggcta atgggcccga ggcttag 1077

<210> SEQ ID NO 40
<211> LENGTH: 358
<212> TYPE: PRT
<213> ORGANISM: Homo sapiens

<400> SEQUENCE: 40

Met Pro Ser Val Ser Pro Ala Gly Pro Ser Ala Gly Ala Val Pro Asn
1 5 10 15

Ala Thr Ala Val Thr Thr Val Arg Thr Asn Ala Ser Gly Leu Glu Val
20 25 30

-continued

```
Pro Leu Phe His Leu Phe Ala Arg Leu Asp Glu Glu Leu His Gly Thr
        35                  40                  45

Phe Pro Gly Leu Cys Val Ala Leu Met Ala Val His Gly Ala Ile Phe
    50                  55                  60

Leu Ala Gly Leu Val Leu Asn Gly Leu Ala Leu Tyr Val Phe Cys Cys
65                  70                  75                  80

Arg Thr Arg Ala Lys Thr Pro Ser Val Ile Tyr Thr Ile Asn Leu Val
                85                  90                  95

Val Thr Asp Leu Leu Val Gly Leu Ser Leu Pro Thr Arg Phe Ala Val
            100                 105                 110

Tyr Tyr Gly Ala Arg Gly Cys Leu Arg Cys Ala Phe Pro His Val Leu
        115                 120                 125

Gly Tyr Phe Leu Asn Met His Cys Ser Ile Leu Phe Leu Thr Cys Ile
    130                 135                 140

Cys Val Asp Arg Tyr Leu Ala Ile Val Arg Pro Glu Ala Pro Ala Ala
145                 150                 155                 160

Cys Arg Gln Pro Ala Cys Ala Arg Ala Val Cys Ala Phe Val Trp Leu
                165                 170                 175

Ala Ala Gly Ala Val Thr Leu Ser Val Leu Gly Val Thr Gly Ser Arg
            180                 185                 190

Pro Cys Cys Arg Val Phe Ala Leu Thr Val Leu Glu Phe Leu Leu Pro
        195                 200                 205

Leu Leu Val Ile Ser Val Phe Thr Gly Arg Ile Met Cys Ala Leu Ser
    210                 215                 220

Arg Pro Gly Leu Leu His Gln Gly Arg Gln Arg Arg Val Arg Ala Met
225                 230                 235                 240

Gln Leu Leu Leu Thr Val Leu Ile Ile Phe Leu Val Cys Phe Thr Pro
                245                 250                 255

Phe His Ala Arg Gln Val Ala Val Ala Leu Trp Pro Asp Met Pro His
            260                 265                 270

His Thr Ser Leu Val Val Tyr His Val Ala Val Thr Leu Ser Ser Leu
        275                 280                 285

Asn Ser Cys Met Asp Pro Ile Val Tyr Cys Phe Val Thr Ser Gly Phe
    290                 295                 300

Gln Ala Thr Val Arg Gly Leu Phe Gly Gln His Gly Glu Arg Glu Pro
305                 310                 315                 320

Ser Ser Gly Asp Val Val Ser Met His Arg Ser Ser Lys Gly Ser Gly
                325                 330                 335

Arg His His Ile Leu Ser Ala Gly Pro His Ala Leu Thr Gln Ala Leu
            340                 345                 350

Ala Asn Gly Pro Glu Ala
        355


<210> SEQ ID NO 41
<211> LENGTH: 30
<212> TYPE: DNA
<213> ORGANISM: Artificial Sequence
<220> FEATURE:
<223> OTHER INFORMATION: Novel Sequence

<400> SEQUENCE: 41

gagaattcac tcctgagctc aagatgaact                                   30


<210> SEQ ID NO 42
<211> LENGTH: 30
<212> TYPE: DNA
```

-continued

<213> ORGANISM: Artificial Sequence
<220> FEATURE:
<223> OTHER INFORMATION: Novel Sequence

<400> SEQUENCE: 42
cgggatcccc gtaactgagc cacttcagat 30

<210> SEQ ID NO 43
<211> LENGTH: 1050
<212> TYPE: DNA
<213> ORGANISM: Homo sapiens

<400> SEQUENCE: 43
atgaactcca ccttggatgg taatcagagc agccaccctt tttgcctctt ggcatttggc 60
tatttggaaa ctgtcaattt ttgccttttg gaagtattga ttattgtctt tctaactgta 120
ttgattattt ctggcaacat cattgtgatt tttgtatttc actgtgcacc tttgttgaac 180
catcacacta caagttattt tatccagact atggcatatg ctgacctttt tgttggggtg 240
agctgcgtgg tcccttcttt atcactcctc catcaccccc ttccagtaga ggagtccttg 300
acttgccaga tatttggttt tgtagtatca gttctgaaga gcgtctccat ggcttctctg 360
gcctgtatca gcattgatag atacattgcc attactaaac ctttaaccta taatactctg 420
gttacaccct ggagactacg cctgtgtatt ttcctgattt ggctatactc gaccctggtc 480
ttcctgcctt cctttttcca ctggggcaaa cctggatatc atggagatgt gtttcagtgg 540
tgtgcggagt cctggcacac cgactcctac ttcaccctgt tcatcgtgat gatgttatat 600
gccccagcag cccttattgt ctgcttcacc tatttcaaca tcttccgcat ctgccaacag 660
cacacaaagg atatcagcga aaggcaagcc cgcttcagca gccagagtgg ggagactggg 720
gaagtgcagg cctgtcctga taagcgctat gccatggtcc tgtttcgaat cactagtgta 780
ttttacatcc tctggttgcc atatatcatc tacttcttgt tggaaagctc cactggccac 840
agcaaccgct tcgcatcctt cttgaccacc tggcttgcta ttagtaacag tttctgcaac 900
tgtgtaattt atagtctctc caacagtgta ttccaaagag gactaaagcg cctctcaggg 960
gctatgtgta cttcttgtgc aagtcagact acagccaacg acccttacac agttagaagc 1020
aaaggccctc ttaatggatg tcatatctga 1050

<210> SEQ ID NO 44
<211> LENGTH: 349
<212> TYPE: PRT
<213> ORGANISM: Homo sapiens

<400> SEQUENCE: 44

Met Asn Ser Thr Leu Asp Gly Asn Gln Ser Ser His Pro Phe Cys Leu
1 5 10 15

Leu Ala Phe Gly Tyr Leu Glu Thr Val Asn Phe Cys Leu Leu Glu Val
20 25 30

Leu Ile Ile Val Phe Leu Thr Val Leu Ile Ile Ser Gly Asn Ile Ile
35 40 45

Val Ile Phe Val Phe His Cys Ala Pro Leu Leu Asn His His Thr Thr
50 55 60

Ser Tyr Phe Ile Gln Thr Met Ala Tyr Ala Asp Leu Phe Val Gly Val
65 70 75 80

Ser Cys Val Val Pro Ser Leu Ser Leu Leu His His Pro Leu Pro Val
85 90 95

Glu Glu Ser Leu Thr Cys Gln Ile Phe Gly Phe Val Val Ser Val Leu

-continued

```
            100                 105                 110

Lys Ser Val Ser Met Ala Ser Leu Ala Cys Ile Ser Ile Asp Arg Tyr
        115                 120                 125

Ile Ala Ile Thr Lys Pro Leu Thr Tyr Asn Thr Leu Val Thr Pro Trp
    130                 135                 140

Arg Leu Arg Leu Cys Ile Phe Leu Ile Trp Leu Tyr Ser Thr Leu Val
145                 150                 155                 160

Phe Leu Pro Ser Phe Phe His Trp Gly Lys Pro Gly Tyr His Gly Asp
                165                 170                 175

Val Phe Gln Trp Cys Ala Glu Ser Trp His Thr Asp Ser Tyr Phe Thr
            180                 185                 190

Leu Phe Ile Val Met Met Leu Tyr Ala Pro Ala Ala Leu Ile Val Cys
        195                 200                 205

Phe Thr Tyr Phe Asn Ile Phe Arg Ile Cys Gln Gln His Thr Lys Asp
    210                 215                 220

Ile Ser Glu Arg Gln Ala Arg Phe Ser Ser Gln Ser Gly Glu Thr Gly
225                 230                 235                 240

Glu Val Gln Ala Cys Pro Asp Lys Arg Tyr Ala Met Val Leu Phe Arg
                245                 250                 255

Ile Thr Ser Val Phe Tyr Ile Leu Trp Leu Pro Tyr Ile Ile Tyr Phe
            260                 265                 270

Leu Leu Glu Ser Ser Thr Gly His Ser Asn Arg Phe Ala Ser Phe Leu
        275                 280                 285

Thr Thr Trp Leu Ala Ile Ser Asn Ser Phe Cys Asn Cys Val Ile Tyr
    290                 295                 300

Ser Leu Ser Asn Ser Val Phe Gln Arg Gly Leu Lys Arg Leu Ser Gly
305                 310                 315                 320

Ala Met Cys Thr Ser Cys Ala Ser Gln Thr Thr Ala Asn Asp Pro Tyr
                325                 330                 335

Thr Val Arg Ser Lys Gly Pro Leu Asn Gly Cys His Ile
            340                 345
```

<210> SEQ ID NO 45
<211> LENGTH: 30
<212> TYPE: DNA
<213> ORGANISM: Artificial Sequence
<220> FEATURE:
<223> OTHER INFORMATION: Novel Sequence

<400> SEQUENCE: 45
tcccccggga aaaaaaccaa ctgctccaaa 30

<210> SEQ ID NO 46
<211> LENGTH: 31
<212> TYPE: DNA
<213> ORGANISM: Artificial Sequence
<220> FEATURE:
<223> OTHER INFORMATION: Novel Sequence

<400> SEQUENCE: 46
taggatccat ttgaatgtgg atttggtgaa a 31

<210> SEQ ID NO 47
<211> LENGTH: 1302
<212> TYPE: DNA
<213> ORGANISM: Homo sapiens

<400> SEQUENCE: 47

-continued

```
atgtgttttt ctcccattct ggaaatcaac atgcagtctg aatctaacat tacagtgcga     60

gatgacattg atgacatcaa caccaatatg taccaaccac tatcatatcc gttaagcttt    120

caagtgtctc tcaccggatt tcttatgtta gaaattgtgt tgggacttgg cagcaacctc    180

actgtattgg tactttactg catgaaatcc aacttaatca actctgtcag taacattatt    240

acaatgaatc ttcatgtact tgatgtaata atttgtgtgg gatgtattcc tctaactata    300

gttatccttc tgctttcact ggagagtaac actgctctca tttgctgttt ccatgaggct    360

tgtgtatctt ttgcaagtgt ctcaacagca atcaacgttt ttgctatcac tttggacaga    420

tatgacatct ctgtaaaacc tgcaaaccga attctgacaa tgggcagagc tgtaatgtta    480

atgatatcca tttggatttt ttcttttttc tctttcctga ttccttttat tgaggtaaat    540

tttttcagtc ttcaaagtgg aaatacctgg gaaaacaaga cacttttatg tgtcagtaca    600

aatgaatact acactgaact gggaatgtat tatcacctgt tagtacagat cccaatattc    660

tttttcactg ttgtagtaat gttaatcaca tacaccaaaa tacttcaggc tcttaatatt    720

cgaataggca caagattttc aacagggcag aagaagaaag caagaaagaa aaagacaatt    780

tctctaacca cacaacatga ggctacagac atgtcacaaa gcagtggtgg gagaaatgta    840

gtctttggtg taagaacttc agtttctgta ataattgccc tccggcgagc tgtgaaacga    900

caccgtgaac gacgagaaag acaaaagaga gtcttcagga tgtctttatt gattatttct    960

acatttcttc tctgctggac accaatttct gttttaaata ccaccatttt atgtttaggc   1020

ccaagtgacc ttttagtaaa attaagattg tgttttttag tcatggctta tggaacaact   1080

atatttcacc ctctattata tgcattcact agacaaaaat ttcaaaaggt cttgaaaagt   1140

aaaatgaaaa agcgagttgt ttctatagta gaagctgatc ccctgcctaa taatgctgta   1200

atacacaact cttggataga tcccaaaaga aacaaaaaaa ttacctttga agatagtgaa   1260

ataagagaaa aacgtttagt gcctcaggtt gtcacagact ag                      1302


<210> SEQ ID NO 48
<211> LENGTH: 433
<212> TYPE: PRT
<213> ORGANISM: Homo sapiens

<400> SEQUENCE: 48

Met Cys Phe Ser Pro Ile Leu Glu Ile Asn Met Gln Ser Glu Ser Asn
1               5                   10                  15

Ile Thr Val Arg Asp Asp Ile Asp Asp Ile Asn Thr Asn Met Tyr Gln
            20                  25                  30

Pro Leu Ser Tyr Pro Leu Ser Phe Gln Val Ser Leu Thr Gly Phe Leu
        35                  40                  45

Met Leu Glu Ile Val Leu Gly Leu Gly Ser Asn Leu Thr Val Leu Val
    50                  55                  60

Leu Tyr Cys Met Lys Ser Asn Leu Ile Asn Ser Val Ser Asn Ile Ile
65                  70                  75                  80

Thr Met Asn Leu His Val Leu Asp Val Ile Ile Cys Val Gly Cys Ile
                85                  90                  95

Pro Leu Thr Ile Val Ile Leu Leu Leu Ser Leu Glu Ser Asn Thr Ala
            100                 105                 110

Leu Ile Cys Cys Phe His Glu Ala Cys Val Ser Phe Ala Ser Val Ser
        115                 120                 125

Thr Ala Ile Asn Val Phe Ala Ile Thr Leu Asp Arg Tyr Asp Ile Ser
    130                 135                 140
```

-continued

```
Val Lys Pro Ala Asn Arg Ile Leu Thr Met Gly Arg Ala Val Met Leu
145                 150                 155                 160

Met Ile Ser Ile Trp Ile Phe Ser Phe Phe Ser Phe Leu Ile Pro Phe
                165                 170                 175

Ile Glu Val Asn Phe Phe Ser Leu Gln Ser Gly Asn Thr Trp Glu Asn
            180                 185                 190

Lys Thr Leu Leu Cys Val Ser Thr Asn Glu Tyr Tyr Thr Glu Leu Gly
        195                 200                 205

Met Tyr Tyr His Leu Leu Val Gln Ile Pro Ile Phe Phe Phe Thr Val
    210                 215                 220

Val Val Met Leu Ile Thr Tyr Thr Lys Ile Leu Gln Ala Leu Asn Ile
225                 230                 235                 240

Arg Ile Gly Thr Arg Phe Ser Thr Gly Gln Lys Lys Lys Ala Arg Lys
                245                 250                 255

Lys Lys Thr Ile Ser Leu Thr Thr Gln His Glu Ala Thr Asp Met Ser
            260                 265                 270

Gln Ser Ser Gly Gly Arg Asn Val Val Phe Gly Val Arg Thr Ser Val
        275                 280                 285

Ser Val Ile Ile Ala Leu Arg Arg Ala Val Lys Arg His Arg Glu Arg
    290                 295                 300

Arg Glu Arg Gln Lys Arg Val Phe Arg Met Ser Leu Leu Ile Ile Ser
305                 310                 315                 320

Thr Phe Leu Leu Cys Trp Thr Pro Ile Ser Val Leu Asn Thr Thr Ile
                325                 330                 335

Leu Cys Leu Gly Pro Ser Asp Leu Leu Val Lys Leu Arg Leu Cys Phe
            340                 345                 350

Leu Val Met Ala Tyr Gly Thr Thr Ile Phe His Pro Leu Leu Tyr Ala
        355                 360                 365

Phe Thr Arg Gln Lys Phe Gln Lys Val Leu Lys Ser Lys Met Lys Lys
    370                 375                 380

Arg Val Val Ser Ile Val Glu Ala Asp Pro Leu Pro Asn Asn Ala Val
385                 390                 395                 400

Ile His Asn Ser Trp Ile Asp Pro Lys Arg Asn Lys Lys Ile Thr Phe
                405                 410                 415

Glu Asp Ser Glu Ile Arg Glu Lys Arg Leu Val Pro Gln Val Val Thr
            420                 425                 430

Asp
```

<210> SEQ ID NO 49
<211> LENGTH: 30
<212> TYPE: DNA
<213> ORGANISM: Artificial Sequence
<220> FEATURE:
<223> OTHER INFORMATION: Novel Sequence

<400> SEQUENCE: 49
gtgaagcttg cctctggtgc ctgcaggagg 30

<210> SEQ ID NO 50
<211> LENGTH: 31
<212> TYPE: DNA
<213> ORGANISM: Artificial Sequence
<220> FEATURE:
<223> OTHER INFORMATION: Novel Sequence

<400> SEQUENCE: 50
gcagaattcc cggtggcgtg ttgtggtgcc c 31

-continued

<210> SEQ ID NO 51
<211> LENGTH: 1209
<212> TYPE: DNA
<213> ORGANISM: Homo sapiens

<400> SEQUENCE: 51

```
atgttgtgtc cttccaagac agatggctca gggcactctg gtaggattca ccaggaaact     60

catggagaag ggaaaaggga caagattagc aacagtgaag ggagggagaa tggtgggaga    120

ggattccaga tgaacggtgg gtcgctggag gctgagcatg ccagcaggat gtcagttctc    180

agagcaaagc ccatgtcaaa cagccaacgc ttgctccttc tgtccccagg atcacctcct    240

cgcacgggga gcatctccta catcaacatc atcatgcctt cggtgttcgg caccatctgc    300

ctcctgggca tcatcgggaa ctccacggtc atcttcgcgg tcgtgaagaa gtccaagctg    360

cactggtgca acaacgtccc cgacatcttc atcatcaacc tctcggtagt agatctcctc    420

tttctcctgg gcatgccctt catgatccac cagctcatgg gcaatggggt gtggcacttt    480

ggggagacca tgtgcaccct catcacggcc atggatgcca atagtcagtt caccagcacc    540

tacatcctga ccgccatggc cattgaccgc tacctggcca ctgtccaccc catctcttcc    600

acgaagttcc ggaagccctc tgtggccacc ctggtgatct gcctcctgtg ggccctctcc    660

ttcatcagca tcacccctgt gtggctgtat gccagactca tcccccttccc aggaggtgca    720

gtgggctgcg gcatacgcct gcccaaccca gacactgacc tctactggtt caccctgtac    780

cagtttttcc tggcctttgc cctgcctttt gtggtcatca cagccgcata cgtgaggatc    840

ctgcagcgca tgacgtcctc agtggccccc gcctcccagc gcagcatccg gctgcggaca    900

aagagggtga cccgcacagc catcgccatc tgtctggtct tctttgtgtg ctgggcaccc    960

tactatgtgc tacagctgac ccagttgtcc atcagccgcc cgaccctcac ctttgtctac   1020

ttatacaatg cggccatcag cttgggctat gccaacagct gcctcaaccc ctttgtgtac   1080

atcgtgctct gtgagacgtt ccgcaaacgc ttggtcctgt cggtgaagcc tgcagcccag   1140

gggcagcttc gcgctgtcag caacgctcag acggctgacg aggagaggac agaaagcaaa   1200

ggcacctga                                                           1209
```

<210> SEQ ID NO 52
<211> LENGTH: 402
<212> TYPE: PRT
<213> ORGANISM: Homo sapiens

<400> SEQUENCE: 52

```
Met Leu Cys Pro Ser Lys Thr Asp Gly Ser Gly His Ser Gly Arg Ile
1               5                   10                  15

His Gln Glu Thr His Gly Glu Gly Lys Arg Asp Lys Ile Ser Asn Ser
            20                  25                  30

Glu Gly Arg Glu Asn Gly Gly Arg Gly Phe Gln Met Asn Gly Gly Ser
        35                  40                  45

Leu Glu Ala Glu His Ala Ser Arg Met Ser Val Leu Arg Ala Lys Pro
    50                  55                  60

Met Ser Asn Ser Gln Arg Leu Leu Leu Leu Ser Pro Gly Ser Pro Pro
65                  70                  75                  80

Arg Thr Gly Ser Ile Ser Tyr Ile Asn Ile Ile Met Pro Ser Val Phe
                85                  90                  95

Gly Thr Ile Cys Leu Leu Gly Ile Ile Gly Asn Ser Thr Val Ile Phe
            100                 105                 110
```

-continued

```
Ala Val Val Lys Lys Ser Lys Leu His Trp Cys Asn Asn Val Pro Asp
        115                 120                 125

Ile Phe Ile Ile Asn Leu Ser Val Val Asp Leu Leu Phe Leu Leu Gly
    130                 135                 140

Met Pro Phe Met Ile His Gln Leu Met Gly Asn Gly Val Trp His Phe
145                 150                 155                 160

Gly Glu Thr Met Cys Thr Leu Ile Thr Ala Met Asp Ala Asn Ser Gln
                165                 170                 175

Phe Thr Ser Thr Tyr Ile Leu Thr Ala Met Ala Ile Asp Arg Tyr Leu
            180                 185                 190

Ala Thr Val His Pro Ile Ser Ser Thr Lys Phe Arg Lys Pro Ser Val
        195                 200                 205

Ala Thr Leu Val Ile Cys Leu Leu Trp Ala Leu Ser Phe Ile Ser Ile
    210                 215                 220

Thr Pro Val Trp Leu Tyr Ala Arg Leu Ile Pro Phe Pro Gly Gly Ala
225                 230                 235                 240

Val Gly Cys Gly Ile Arg Leu Pro Asn Pro Asp Thr Asp Leu Tyr Trp
                245                 250                 255

Phe Thr Leu Tyr Gln Phe Phe Leu Ala Phe Ala Leu Pro Phe Val Val
            260                 265                 270

Ile Thr Ala Ala Tyr Val Arg Ile Leu Gln Arg Met Thr Ser Ser Val
        275                 280                 285

Ala Pro Ala Ser Gln Arg Ser Ile Arg Leu Arg Thr Lys Arg Val Thr
    290                 295                 300

Arg Thr Ala Ile Ala Ile Cys Leu Val Phe Phe Val Cys Trp Ala Pro
305                 310                 315                 320

Tyr Tyr Val Leu Gln Leu Thr Gln Leu Ser Ile Ser Arg Pro Thr Leu
                325                 330                 335

Thr Phe Val Tyr Leu Tyr Asn Ala Ala Ile Ser Leu Gly Tyr Ala Asn
            340                 345                 350

Ser Cys Leu Asn Pro Phe Val Tyr Ile Val Leu Cys Glu Thr Phe Arg
        355                 360                 365

Lys Arg Leu Val Leu Ser Val Lys Pro Ala Ala Gln Gly Gln Leu Arg
    370                 375                 380

Ala Val Ser Asn Ala Gln Thr Ala Asp Glu Glu Arg Thr Glu Ser Lys
385                 390                 395                 400

Gly Thr


<210> SEQ ID NO 53
<211> LENGTH: 27
<212> TYPE: DNA
<213> ORGANISM: Artificial Sequence
<220> FEATURE:
<223> OTHER INFORMATION: Novel Sequence

<400> SEQUENCE: 53

ggcggatcca tggatgtgac ttcccaa                                          27


<210> SEQ ID NO 54
<211> LENGTH: 27
<212> TYPE: DNA
<213> ORGANISM: Artificial Sequence
<220> FEATURE:
<223> OTHER INFORMATION: Novel Sequence

<400> SEQUENCE: 54
```

-continued ggcggatccc tacacggcac tgctgaa 27

<210> SEQ ID NO 55
<211> LENGTH: 1128
<212> TYPE: DNA
<213> ORGANISM: Homo sapiens

<400> SEQUENCE: 55
atggatgtga cttcccaagc ccggggcgtg ggcctggaga tgtacccagg caccgcgcac 60
gctgcggccc ccaacaccac ctcccccgag ctcaacctgt cccacccgct cctgggcacc 120
gccctggcca atgggacagg tgagctctcg gagcaccagc agtacgtgat cggcctgttc 180
ctctcgtgcc tctacaccat cttcctcttc cccatcggct ttgtgggcaa catcctgatc 240
ctggtggtga acatcagctt ccgcgagaag atgaccatcc ccgacctgta cttcatcaac 300
ctggcggtgg cggacctcat cctggtggcc gactccctca ttgaggtgtt caacctgcac 360
gagcggtact acgacatcgc cgtcctgtgc accttcatgt cgctcttcct gcaggtcaac 420
atgtacagca gcgtcttctt cctcacctgg atgagcttcg accgctacat cgccctggcc 480
agggccatgc gctgcagcct gttccgcacc aagcaccacg cccggctgag ctgtggcctc 540
atctggatgg catccgtgtc agccacgctg gtgcccttca ccgccgtgca cctgcagcac 600
accgacgagg cctgcttctg tttcgcggat gtccgggagg tgcagtggct cgaggtcacg 660
ctgggcttca tcgtgccctt cgccatcatc ggcctgtgct actccctcat tgtccgggtg 720
ctggtcaggg cgcaccggca ccgtgggctg cggccccggc ggcagaaggc gctccgcatg 780
atcctcgcgg tggtgctggt cttcttcgtc tgctggctgc cggagaacgt cttcatcagc 840
gtgcacctcc tgcagcggac gcagcctggg gccgctccct gcaagcagtc tttccgccat 900
gcccaccccc tcacgggcca cattgtcaac ctcgccgcct tctccaacag ctgcctaaac 960
cccctcatct acagctttct cggggagacc ttcagggaca agctgaggct gtacattgag 1020
cagaaaacaa atttgccggc cctgaaccgc ttctgtcacg ctgccctgaa ggccgtcatt 1080
ccagacagca ccgagcagtc ggatgtgagg ttcagcagtg ccgtgtga 1128

<210> SEQ ID NO 56
<211> LENGTH: 375
<212> TYPE: PRT
<213> ORGANISM: Homo sapiens

<400> SEQUENCE: 56

Met Asp Val Thr Ser Gln Ala Arg Gly Val Gly Leu Glu Met Tyr Pro
1 5 10 15

Gly Thr Ala His Ala Ala Ala Pro Asn Thr Thr Ser Pro Glu Leu Asn
20 25 30

Leu Ser His Pro Leu Leu Gly Thr Ala Leu Ala Asn Gly Thr Gly Glu
35 40 45

Leu Ser Glu His Gln Gln Tyr Val Ile Gly Leu Phe Leu Ser Cys Leu
50 55 60

Tyr Thr Ile Phe Leu Phe Pro Ile Gly Phe Val Gly Asn Ile Leu Ile
65 70 75 80

Leu Val Val Asn Ile Ser Phe Arg Glu Lys Met Thr Ile Pro Asp Leu
85 90 95

Tyr Phe Ile Asn Leu Ala Val Ala Asp Leu Ile Leu Val Ala Asp Ser
100 105 110

Leu Ile Glu Val Phe Asn Leu His Glu Arg Tyr Tyr Asp Ile Ala Val
115 120 125

-continued

```
Leu Cys Thr Phe Met Ser Leu Phe Leu Gln Val Asn Met Tyr Ser Ser
    130                 135                 140

Val Phe Phe Leu Thr Trp Met Ser Phe Asp Arg Tyr Ile Ala Leu Ala
145                 150                 155                 160

Arg Ala Met Arg Cys Ser Leu Phe Arg Thr Lys His His Ala Arg Leu
                165                 170                 175

Ser Cys Gly Leu Ile Trp Met Ala Ser Val Ser Ala Thr Leu Val Pro
            180                 185                 190

Phe Thr Ala Val His Leu Gln His Thr Asp Glu Ala Cys Phe Cys Phe
        195                 200                 205

Ala Asp Val Arg Glu Val Gln Trp Leu Glu Val Thr Leu Gly Phe Ile
    210                 215                 220

Val Pro Phe Ala Ile Ile Gly Leu Cys Tyr Ser Leu Ile Val Arg Val
225                 230                 235                 240

Leu Val Arg Ala His Arg His Arg Gly Leu Arg Pro Arg Arg Gln Lys
                245                 250                 255

Ala Leu Arg Met Ile Leu Ala Val Val Leu Val Phe Phe Val Cys Trp
            260                 265                 270

Leu Pro Glu Asn Val Phe Ile Ser Val His Leu Leu Gln Arg Thr Gln
        275                 280                 285

Pro Gly Ala Ala Pro Cys Lys Gln Ser Phe Arg His Ala His Pro Leu
    290                 295                 300

Thr Gly His Ile Val Asn Leu Ala Ala Phe Ser Asn Ser Cys Leu Asn
305                 310                 315                 320

Pro Leu Ile Tyr Ser Phe Leu Gly Glu Thr Phe Arg Asp Lys Leu Arg
                325                 330                 335

Leu Tyr Ile Glu Gln Lys Thr Asn Leu Pro Ala Leu Asn Arg Phe Cys
            340                 345                 350

His Ala Ala Leu Lys Ala Val Ile Pro Asp Ser Thr Glu Gln Ser Asp
        355                 360                 365

Val Arg Phe Ser Ser Ala Val
    370                 375


<210> SEQ ID NO 57
<211> LENGTH: 31
<212> TYPE: DNA
<213> ORGANISM: Artificial Sequence
<220> FEATURE:
<223> OTHER INFORMATION: Novel Sequence

<400> SEQUENCE: 57

aaggaattca cggccgggtg atgccattcc c                                    31


<210> SEQ ID NO 58
<211> LENGTH: 30
<212> TYPE: DNA
<213> ORGANISM: Artificial Sequence
<220> FEATURE:
<223> OTHER INFORMATION: Novel Sequence

<400> SEQUENCE: 58

ggtggatcca taaacacggg cgttgaggac                                      30


<210> SEQ ID NO 59
<211> LENGTH: 960
<212> TYPE: DNA
<213> ORGANISM: Homo sapiens
```

-continued

<400> SEQUENCE: 59

```
atgccattcc caaactgctc agcccccagc actgtggtgg ccacagctgt gggtgtcttg     60
ctggggctgg agtgtgggct gggtctgctg ggcaacgcgg tggcgctgtg gaccttcctg    120
ttccgggtca gggtgtggaa gccgtacgct gtctacctgc tcaacctggc cctggctgac    180
ctgctgttgg ctgcgtgcct gcctttcctg gccgccttct acctgagcct ccaggcttgg    240
catctgggcc gtgtgggctg ctgggccctg cgcttcctgc tggacctcag ccgcagcgtg    300
gggatggcct tcctggccgc cgtggctttg gaccggtacc tccgtgtggt ccaccctcgg    360
cttaaggtca acctgctgtc tcctcaggcg gccctggggg tctcgggcct cgtctggctc    420
ctgatggtcg ccctcacctg cccgggcttg ctcatctctg aggccgccca gaactccacc    480
aggtgccaca gtttctactc cagggcagac ggctccttca gcatcatctg gcaggaagca    540
ctctcctgcc ttcagtttgt cctccccttt ggcctcatcg tgttctgcaa tgcaggcatc    600
atcagggctc tccagaaaag actccgggag cctgagaaac agcccaagct tcagcgggcc    660
caggcactgg tcaccttggt ggtggtgctg tttgctctgt gctttctgcc ctgcttcctg    720
gccagagtcc tgatgcacat cttccagaat ctggggagct gcagggccct ttgtgcagtg    780
gctcatacct cggatgtcac gggcagcctc acctacctgc acagtgtcgt caaccccgtg    840
gtatactgct tctccagccc caccttcagg agctcctatc ggagggtctt ccacaccctc    900
cgaggcaaag ggcaggcagc agagcccccca gatttcaacc ccagagactc ctattcctga    960
```

<210> SEQ ID NO 60
<211> LENGTH: 319
<212> TYPE: PRT
<213> ORGANISM: Homo sapiens

<400> SEQUENCE: 60

```
Met Pro Phe Pro Asn Cys Ser Ala Pro Ser Thr Val Val Ala Thr Ala
1               5                   10                  15

Val Gly Val Leu Leu Gly Leu Glu Cys Gly Leu Gly Leu Leu Gly Asn
            20                  25                  30

Ala Val Ala Leu Trp Thr Phe Leu Phe Arg Val Arg Val Trp Lys Pro
        35                  40                  45

Tyr Ala Val Tyr Leu Leu Asn Leu Ala Leu Ala Asp Leu Leu Leu Ala
    50                  55                  60

Ala Cys Leu Pro Phe Leu Ala Ala Phe Tyr Leu Ser Leu Gln Ala Trp
65                  70                  75                  80

His Leu Gly Arg Val Gly Cys Trp Ala Leu Arg Phe Leu Leu Asp Leu
                85                  90                  95

Ser Arg Ser Val Gly Met Ala Phe Leu Ala Ala Val Ala Leu Asp Arg
            100                 105                 110

Tyr Leu Arg Val Val His Pro Arg Leu Lys Val Asn Leu Leu Ser Pro
        115                 120                 125

Gln Ala Ala Leu Gly Val Ser Gly Leu Val Trp Leu Leu Met Val Ala
    130                 135                 140

Leu Thr Cys Pro Gly Leu Leu Ile Ser Glu Ala Ala Gln Asn Ser Thr
145                 150                 155                 160

Arg Cys His Ser Phe Tyr Ser Arg Ala Asp Gly Ser Phe Ser Ile Ile
                165                 170                 175

Trp Gln Glu Ala Leu Ser Cys Leu Gln Phe Val Leu Pro Phe Gly Leu
            180                 185                 190

Ile Val Phe Cys Asn Ala Gly Ile Ile Arg Ala Leu Gln Lys Arg Leu
```

-continued

```
        195                 200                 205

Arg Glu Pro Glu Lys Gln Pro Lys Leu Gln Arg Ala Gln Ala Leu Val
    210                 215                 220

Thr Leu Val Val Val Leu Phe Ala Leu Cys Phe Leu Pro Cys Phe Leu
225                 230                 235                 240

Ala Arg Val Leu Met His Ile Phe Gln Asn Leu Gly Ser Cys Arg Ala
                245                 250                 255

Leu Cys Ala Val Ala His Thr Ser Asp Val Thr Gly Ser Leu Thr Tyr
            260                 265                 270

Leu His Ser Val Val Asn Pro Val Val Tyr Cys Phe Ser Ser Pro Thr
        275                 280                 285

Phe Arg Ser Ser Tyr Arg Arg Val Phe His Thr Leu Arg Gly Lys Gly
    290                 295                 300

Gln Ala Ala Glu Pro Pro Asp Phe Asn Pro Arg Asp Ser Tyr Ser
305                 310                 315


<210> SEQ ID NO 61
<211> LENGTH: 1143
<212> TYPE: DNA
<213> ORGANISM: Homo sapiens

<400> SEQUENCE: 61

atggaggaag gtggtgattt tgacaactac tatggggcag acaaccagtc tgagtgtgag      60

tacacagact ggaaatcctc gggggccctc atccctgcca tctacatgtt ggtcttcctc     120

ctgggcacca cgggaaacgg tctggtgctc tggaccgtgt ttcggagcag ccgggagaag     180

aggcgctcag ctgatatctt cattgctagc ctggcggtgg ctgacctgac cttcgtggtg     240

acgctgcccc tgtgggctac ctacacgtac cgggactatg actggccctt tgggaccttc     300

ttctgcaagc tcagcagcta cctcatcttc gtcaacatgt acgccagcgt cttctgcctc     360

accggcctca gcttcgaccg ctacctggcc atcgtgaggc cagtggccaa tgctcggctg     420

aggctgcggg tcagcggggc cgtggccacg gcagttcttt gggtgctggc cgccctcctg     480

gccatgcctg tcatggtgtt acgcaccacc ggggacttgg agaacaccac taaggtgcag     540

tgctacatgg actactccat ggtggccact gtgagctcag agtgggcctg ggaggtgggc     600

cttggggtct cgtccaccac cgtgggcttt gtggtgccct tcaccatcat gctgacctgt     660

tacttcttca tcgcccaaac catcgctggc cacttccgca aggaacgcat cgagggcctg     720

cggaagcggc gccggctgct cagcatcatc gtggtgctgg tggtgacctt tgccctgtgc     780

tggatgccct accacctggt gaagacgctg tacatgctgg gcagcctgct gcactggccc     840

tgtgactttg acctcttcct catgaacatc ttcccctact gcacctgcat cagctacgtc     900

aacagctgcc tcaacccctt cctctatgcc tttttcgacc cccgcttccg ccaggcctgc     960

acctccatgc tctgctgtgg ccagagcagg tgcgcaggca cctcccacag cagcagtggg    1020

gagaagtcag ccagctactc ttcggggcac agccaggggc ccggccccaa catgggcaag    1080

ggtggagaac agatgcacga gaaatccatc ccctacagcc aggagaccct tgtggttgac    1140

tag                                                                  1143


<210> SEQ ID NO 62
<211> LENGTH: 380
<212> TYPE: PRT
<213> ORGANISM: Homo sapiens

<400> SEQUENCE: 62
```

-continued

```
Met Glu Glu Gly Gly Asp Phe Asp Asn Tyr Tyr Gly Ala Asp Asn Gln
1               5                   10                  15

Ser Glu Cys Glu Tyr Thr Asp Trp Lys Ser Ser Gly Ala Leu Ile Pro
            20                  25                  30

Ala Ile Tyr Met Leu Val Phe Leu Leu Gly Thr Thr Gly Asn Gly Leu
        35                  40                  45

Val Leu Trp Thr Val Phe Arg Ser Ser Arg Glu Lys Arg Arg Ser Ala
    50                  55                  60

Asp Ile Phe Ile Ala Ser Leu Ala Val Ala Asp Leu Thr Phe Val Val
65                  70                  75                  80

Thr Leu Pro Leu Trp Ala Thr Tyr Thr Tyr Arg Asp Tyr Asp Trp Pro
                85                  90                  95

Phe Gly Thr Phe Phe Cys Lys Leu Ser Ser Tyr Leu Ile Phe Val Asn
            100                 105                 110

Met Tyr Ala Ser Val Phe Cys Leu Thr Gly Leu Ser Phe Asp Arg Tyr
        115                 120                 125

Leu Ala Ile Val Arg Pro Val Ala Asn Ala Arg Leu Arg Leu Arg Val
    130                 135                 140

Ser Gly Ala Val Ala Thr Ala Val Leu Trp Val Leu Ala Ala Leu Leu
145                 150                 155                 160

Ala Met Pro Val Met Val Leu Arg Thr Thr Gly Asp Leu Glu Asn Thr
                165                 170                 175

Thr Lys Val Gln Cys Tyr Met Asp Tyr Ser Met Val Ala Thr Val Ser
            180                 185                 190

Ser Glu Trp Ala Trp Glu Val Gly Leu Gly Val Ser Ser Thr Thr Val
        195                 200                 205

Gly Phe Val Val Pro Phe Thr Ile Met Leu Thr Cys Tyr Phe Phe Ile
    210                 215                 220

Ala Gln Thr Ile Ala Gly His Phe Arg Lys Glu Arg Ile Glu Gly Leu
225                 230                 235                 240

Arg Lys Arg Arg Arg Leu Leu Ser Ile Ile Val Val Leu Val Val Thr
                245                 250                 255

Phe Ala Leu Cys Trp Met Pro Tyr His Leu Val Lys Thr Leu Tyr Met
            260                 265                 270

Leu Gly Ser Leu Leu His Trp Pro Cys Asp Phe Asp Leu Phe Leu Met
        275                 280                 285

Asn Ile Phe Pro Tyr Cys Thr Cys Ile Ser Tyr Val Asn Ser Cys Leu
    290                 295                 300

Asn Pro Phe Leu Tyr Ala Phe Phe Asp Pro Arg Phe Arg Gln Ala Cys
305                 310                 315                 320

Thr Ser Met Leu Cys Cys Gly Gln Ser Arg Cys Ala Gly Thr Ser His
                325                 330                 335

Ser Ser Ser Gly Glu Lys Ser Ala Ser Tyr Ser Ser Gly His Ser Gln
            340                 345                 350

Gly Pro Gly Pro Asn Met Gly Lys Gly Gly Glu Gln Met His Glu Lys
        355                 360                 365

Ser Ile Pro Tyr Ser Gln Glu Thr Leu Val Val Asp
    370                 375                 380
```

<210> SEQ ID NO 63
<211> LENGTH: 31
<212> TYPE: DNA
<213> ORGANISM: Artificial Sequence
<220> FEATURE:
<223> OTHER INFORMATION: Novel Sequence -continued

<400> SEQUENCE: 63
tgagaattct ggtgactcac agccggcaca g 31

<210> SEQ ID NO 64
<211> LENGTH: 31
<212> TYPE: DNA
<213> ORGANISM: Artificial Sequence
<220> FEATURE:
<223> OTHER INFORMATION: Novel Sequence

<400> SEQUENCE: 64
gccggatcca aggaaaagca gcaataaaag g 31

<210> SEQ ID NO 65
<211> LENGTH: 1119
<212> TYPE: DNA
<213> ORGANISM: Homo sapiens

<400> SEQUENCE: 65
atgaactacc cgctaacgct ggaaatggac ctcgagaacc tggaggacct gttctgggaa 60
ctggacagat tggacaacta taacgacacc tccctggtgg aaaatcatct ctgccctgcc 120
acagagggtc ccctcatggc ctccttcaag gccgtgttcg tgcccgtggc ctacagcctc 180
atcttcctcc tgggcgtgat cggcaacgtc ctggtgctgg tgatcctgga gcggcaccgg 240
cagacacgca gttccacgga gaccttcctg ttccacctgg ccgtggccga cctcctgctg 300
gtcttcatct tgccctttgc cgtggccgag ggctctgtgg gctgggtcct ggggaccttc 360
ctctgcaaaa ctgtgattgc cctgcacaaa gtcaacttct actgcagcag cctgctcctg 420
gcctgcatcg ccgtggaccg ctacctggcc attgtccacg ccgtccatgc ctaccgccac 480
cgccgcctcc tctccatcca catcacctgt gggaccatct ggctggtggg cttcctcctt 540
gccttgccag agattctctt cgccaaagtc agccaaggcc atcacaacaa ctccctgcca 600
cgttgcacct tctcccaaga gaaccaagca gaaacgcatg cctggttcac ctcccgattc 660
ctctaccatg tggcgggatt cctgctgccc atgctggtga tgggctggtg ctacgtgggg 720
gtagtgcaca ggttgcgcca ggcccagcgg cgccctcagc ggcagaaggc agtcagggtg 780
gccatcctgg tgacaagcat cttcttcctc tgctggtcac cctaccacat cgtcatcttc 840
ctggacaccc tggcgaggct gaaggccgtg gacaatacct gcaagctgaa tggctctctc 900
cccgtggcca tcaccatgtg tgagttcctg ggcctggccc actgctgcct caaccccatg 960
ctctacactt tcgccggcgt gaagttccgc agtgacctgt cgcggctcct gaccaagctg 1020
ggctgtaccg gccctgcctc cctgtgccag ctcttcccta gctggcgcag gagcagtctc 1080
tctgagtcag agaatgccac ctctctcacc acgttctag 1119

<210> SEQ ID NO 66
<211> LENGTH: 372
<212> TYPE: PRT
<213> ORGANISM: Homo sapiens

<400> SEQUENCE: 66

Met Asn Tyr Pro Leu Thr Leu Glu Met Asp Leu Glu Asn Leu Glu Asp
1 5 10 15

Leu Phe Trp Glu Leu Asp Arg Leu Asp Asn Tyr Asn Asp Thr Ser Leu
20 25 30

Val Glu Asn His Leu Cys Pro Ala Thr Glu Gly Pro Leu Met Ala Ser
35 40 45

-continued

```
Phe Lys Ala Val Phe Val Pro Val Ala Tyr Ser Leu Ile Phe Leu Leu
    50                  55                  60

Gly Val Ile Gly Asn Val Leu Val Leu Val Ile Leu Glu Arg His Arg
65                  70                  75                  80

Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
            100                 105                 110

Val Gly Trp Val Leu Gly Thr Phe Leu Cys Lys Thr Val Ile Ala Leu
        115                 120                 125

His Lys Val Asn Phe Tyr Cys Ser Ser Leu Leu Leu Ala Cys Ile Ala
    130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175

Gly Phe Leu Leu Ala Leu Pro Glu Ile Leu Phe Ala Lys Val Ser Gln
            180                 185                 190

Gly His His Asn Asn Ser Leu Pro Arg Cys Thr Phe Ser Gln Glu Asn
        195                 200                 205

Gln Ala Glu Thr His Ala Trp Phe Thr Ser Arg Phe Leu Tyr His Val
    210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Arg Pro Gln Arg Gln Lys
                245                 250                 255

Ala Val Arg Val Ala Ile Leu Val Thr Ser Ile Phe Phe Leu Cys Trp
            260                 265                 270

Ser Pro Tyr His Ile Val Ile Phe Leu Asp Thr Leu Ala Arg Leu Lys
        275                 280                 285

Ala Val Asp Asn Thr Cys Lys Leu Asn Gly Ser Leu Pro Val Ala Ile
    290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
                325                 330                 335

Leu Thr Lys Leu Gly Cys Thr Gly Pro Ala Ser Leu Cys Gln Leu Phe
            340                 345                 350

Pro Ser Trp Arg Arg Ser Ser Leu Ser Glu Ser Glu Asn Ala Thr Ser
        355                 360                 365

Leu Thr Thr Phe
    370
```

<210> SEQ ID NO 67
<211> LENGTH: 30
<212> TYPE: DNA
<213> ORGANISM: Artificial Sequence
<220> FEATURE:
<223> OTHER INFORMATION: Novel Sequence

<400> SEQUENCE: 67
caaagcttga aagctgcacg gtgcagagac 30

<210> SEQ ID NO 68
<211> LENGTH: 30

-continued

<212> TYPE: DNA
<213> ORGANISM: Artificial Sequence
<220> FEATURE:
<223> OTHER INFORMATION: Novel Sequence

<400> SEQUENCE: 68
gcggatcccg agtcacaccc tggctgggcc 30

<210> SEQ ID NO 69
<211> LENGTH: 1128
<212> TYPE: DNA
<213> ORGANISM: Homo sapiens

<400> SEQUENCE: 69
atggatgtga cttcccaagc ccggggcgtg ggcctggaga tgtacccagg caccgcgcag 60
cctgcggccc ccaacaccac ctcccccgag ctcaacctgt cccacccgct cctgggcacc 120
gccctggcca atgggacagg tgagctctcg gagcaccagc agtacgtgat cggcctgttc 180
ctctcgtgcc tctacaccat cttcctcttc cccatcggct ttgtgggcaa catcctgatc 240
ctggtggtga acatcagctt ccgcgagaag atgaccatcc ccgacctgta cttcatcaac 300
ctggcggtgg cggacctcat cctggtggcc gactccctca ttgaggtgtt caacctgcac 360
gagcggtact acgacatcgc cgtcctgtgc accttcatgt cgctcttcct gcaggtcaac 420
atgtacagca gcgtcttctt cctcacctgg atgagcttcg accgctacat cgccctggcc 480
agggccatgc gctgcagcct gttccgcacc aagcaccacg cccggctgag ctgtggcctc 540
atctggatgg catccgtgtc agccacgctg gtgcccttca ccgccgtgca cctgcagcac 600
accgacgagg cctgcttctg tttcgcggat gtccgggagg tgcagtggct cgaggtcacg 660
ctgggcttca tcgtgccctt cgccatcatc ggcctgtgct actccctcat tgtccgggtg 720
ctggtcaggg cgcaccggca ccgtgggctg cggccccggc ggcagaaggc gctccgcatg 780
atcctcgcgg tggtgctggt cttcttcgtc tgctggctgc cggagaacgt cttcatcagc 840
gtgcacctcc tgcagcggac gcagcctggg gccgctccct gcaagcagtc tttccgccat 900
gcccaccccc tcacgggcca cattgtcaac ctcaccgcct tctccaacag ctgcctaaac 960
cccctcatct acagctttct cggggagacc ttcagggaca agctgaggct gtacattgag 1020
cagaaaacaa atttgccggc cctgaaccgc ttctgtcacg ctgccctgaa ggccgtcatt 1080
ccagacagca ccgagcagtc ggatgtgagg ttcagcagtg ccgtgtag 1128

<210> SEQ ID NO 70
<211> LENGTH: 375
<212> TYPE: PRT
<213> ORGANISM: Homo sapiens

<400> SEQUENCE: 70

Met Asp Val Thr Ser Gln Ala Arg Gly Val Gly Leu Glu Met Tyr Pro
1 5 10 15

Gly Thr Ala Gln Pro Ala Ala Pro Asn Thr Thr Ser Pro Glu Leu Asn
20 25 30

Leu Ser His Pro Leu Leu Gly Thr Ala Leu Ala Asn Gly Thr Gly Glu
35 40 45

Leu Ser Glu His Gln Gln Tyr Val Ile Gly Leu Phe Leu Ser Cys Leu
50 55 60

Tyr Thr Ile Phe Leu Phe Pro Ile Gly Phe Val Gly Asn Ile Leu Ile
65 70 75 80

Leu Val Val Asn Ile Ser Phe Arg Glu Lys Met Thr Ile Pro Asp Leu

-continued

```
                85                  90                  95

Tyr Phe Ile Asn Leu Ala Val Ala Asp Leu Ile Leu Val Ala Asp Ser
            100                 105                 110

Leu Ile Glu Val Phe Asn Leu His Glu Arg Tyr Tyr Asp Ile Ala Val
        115                 120                 125

Leu Cys Thr Phe Met Ser Leu Phe Leu Gln Val Asn Met Tyr Ser Ser
    130                 135                 140

Val Phe Phe Leu Thr Trp Met Ser Phe Asp Arg Tyr Ile Ala Leu Ala
145                 150                 155                 160

Arg Ala Met Arg Cys Ser Leu Phe Arg Thr Lys His His Ala Arg Leu
                165                 170                 175

Ser Cys Gly Leu Ile Trp Met Ala Ser Val Ser Ala Thr Leu Val Pro
            180                 185                 190

Phe Thr Ala Val His Leu Gln His Thr Asp Glu Ala Cys Phe Cys Phe
        195                 200                 205

Ala Asp Val Arg Glu Val Gln Trp Leu Glu Val Thr Leu Gly Phe Ile
    210                 215                 220

Val Pro Phe Ala Ile Ile Gly Leu Cys Tyr Ser Leu Ile Val Arg Val
225                 230                 235                 240

Leu Val Arg Ala His Arg His Arg Gly Leu Arg Pro Arg Arg Gln Lys
                245                 250                 255

Ala Leu Arg Met Ile Leu Ala Val Val Leu Val Phe Phe Val Cys Trp
            260                 265                 270

Leu Pro Glu Asn Val Phe Ile Ser Val His Leu Leu Gln Arg Thr Gln
        275                 280                 285

Pro Gly Ala Ala Pro Cys Lys Gln Ser Phe Arg His Ala His Pro Leu
    290                 295                 300

Thr Gly His Ile Val Asn Leu Thr Ala Phe Ser Asn Ser Cys Leu Asn
305                 310                 315                 320

Pro Leu Ile Tyr Ser Phe Leu Gly Glu Thr Phe Arg Asp Lys Leu Arg
                325                 330                 335

Leu Tyr Ile Glu Gln Lys Thr Asn Leu Pro Ala Leu Asn Arg Phe Cys
            340                 345                 350

His Ala Ala Leu Lys Ala Val Ile Pro Asp Ser Thr Glu Gln Ser Asp
        355                 360                 365

Val Arg Phe Ser Ser Ala Val
    370                 375


<210> SEQ ID NO 71
<211> LENGTH: 30
<212> TYPE: DNA
<213> ORGANISM: Artificial Sequence
<220> FEATURE:
<223> OTHER INFORMATION: Novel Sequence

<400> SEQUENCE: 71

acagaattcc tgtgtggttt taccgcccag                                       30


<210> SEQ ID NO 72
<211> LENGTH: 30
<212> TYPE: DNA
<213> ORGANISM: Artificial Sequence
<220> FEATURE:
<223> OTHER INFORMATION: Novel Sequence

<400> SEQUENCE: 72

ctcggatcca ggcagaagag tcgcctatgg                                       30
```

-continued

<210> SEQ ID NO 73
<211> LENGTH: 1137
<212> TYPE: DNA
<213> ORGANISM: Homo sapiens

<400> SEQUENCE: 73
atggacctgg ggaaaccaat gaaaagcgtg ctggtggtgg ctctccttgt cattttccag 60
gtatgcctgt gtcaagatga ggtcacggac gattacatcg gagacaacac cacagtggac 120
tacactttgt tcgagtcttt gtgctccaag aaggacgtgc ggaactttaa agcctggttc 180
ctccctatca tgtactccat catttgtttc gtgggcctac tgggcaatgg gctggtcgtg 240
ttgacctata tctatttcaa gaggctcaag accatgaccg atacctacct gctcaacctg 300
gcggtggcag acatcctctt cctcctgacc cttcccttct gggcctacag cgcggccaag 360
tcctgggtct tcggtgtcca cttttgcaag ctcatctttg ccatctacaa gatgagcttc 420
ttcagtggca tgctcctact tctttgcatc agcattgacc gctacgtggc catcgtccag 480
gctgtctcag ctcaccgcca ccgtgcccgc gtccttctca tcagcaagct gtcctgtgtg 540
ggcatctgga tactagccac agtgctctcc atcccagagc tcctgtacag tgacctccag 600
aggagcagca gtgagcaagc gatgcgatgc tctctcatca cagagcatgt ggaggccttt 660
atcaccatcc aggtggccca gatggtgatc ggctttctgg tcccctgct ggccatgagc 720 ttctgttacc ttgtcatcat ccgcaccctg ctccaggcac gcaactttga gcgcaacaag 780
gccatcaagg tgatcatcgc tgtggtcgtg gtcttcatag tcttccagct gccctacaat 840
ggggtggtcc tggcccagac ggtggccaac ttcaacatca ccagtagcac ctgtgagctc 900
agtaagcaac tcaacatcgc ctacgacgtc acctacagcc tggcctgcgt ccgctgctgc 960
gtcaaccctt tcttgtacgc cttcatcggc gtcaagttcc gcaacgatct cttcaagctc 1020
ttcaaggacc tgggctgcct cagccaggag cagctccggc agtggtcttc ctgtcggcac 1080
atccggcgct cctccatgag tgtggaggcc gagaccacca ccaccttctc cccatag 1137

<210> SEQ ID NO 74
<211> LENGTH: 378
<212> TYPE: PRT
<213> ORGANISM: Homo sapiens

<400> SEQUENCE: 74

Met Asp Leu Gly Lys Pro Met Lys Ser Val Leu Val Val Ala Leu Leu
1 5 10 15

Val Ile Phe Gln Val Cys Leu Cys Gln Asp Glu Val Thr Asp Asp Tyr
20 25 30

Ile Gly Asp Asn Thr Thr Val Asp Tyr Thr Leu Phe Glu Ser Leu Cys
35 40 45

Ser Lys Lys Asp Val Arg Asn Phe Lys Ala Trp Phe Leu Pro Ile Met
50 55 60

Tyr Ser Ile Ile Cys Phe Val Gly Leu Leu Gly Asn Gly Leu Val Val
65 70 75 80

Leu Thr Tyr Ile Tyr Phe Lys Arg Leu Lys Thr Met Thr Asp Thr Tyr
85 90 95

Leu Leu Asn Leu Ala Val Ala Asp Ile Leu Phe Leu Leu Thr Leu Pro
100 105 110

Phe Trp Ala Tyr Ser Ala Ala Lys Ser Trp Val Phe Gly Val His Phe
115 120 125

-continued

```
Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Ser Glu Gln Ala Met
        195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ile Ala Val Val Val Val Phe
            260                 265                 270

Ile Val Phe Gln Leu Pro Tyr Asn Gly Val Val Leu Ala Gln Thr Val
        275                 280                 285

Ala Asn Phe Asn Ile Thr Ser Ser Thr Cys Glu Leu Ser Lys Gln Leu
    290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
        355                 360                 365

Glu Ala Glu Thr Thr Thr Thr Phe Ser Pro
    370                 375


<210> SEQ ID NO 75
<211> LENGTH: 32
<212> TYPE: DNA
<213> ORGANISM: Artificial Sequence
<220> FEATURE:
<223> OTHER INFORMATION: Novel Sequence

<400> SEQUENCE: 75

ctggaattca cctggaccac caccaatgga ta                                 32


<210> SEQ ID NO 76
<211> LENGTH: 30
<212> TYPE: DNA
<213> ORGANISM: Artificial Sequence
<220> FEATURE:
<223> OTHER INFORMATION: Novel Sequence

<400> SEQUENCE: 76

ctcggatcct gcaaagtttg tcatacagtt                                    30


<210> SEQ ID NO 77
<211> LENGTH: 1086
<212> TYPE: DNA
<213> ORGANISM: Homo sapiens

<400> SEQUENCE: 77
```

-continued

```
atggatatac aaatggcaaa caattttact ccgccctctg caactcctca gggaaatgac     60
tgtgacctct atgcacatca cagcacggcc aggatagtaa tgcctctgca ttacagcctc    120
gtcttcatca ttgggctcgt gggaaactta ctagccttgg tcgtcattgt tcaaaacagg    180
aaaaaaatca actctaccac cctctattca acaaatttgg tgatttctga tatacttttt    240
accacggctt tgcctacacg aatagcctac tatgcaatgg gctttgactg gagaatcgga    300
gatgccttgt gtaggataac tgcgctagtg ttttacatca acacatatgc aggtgtgaac    360
tttatgacct gcctgagtat tgaccgcttc attgctgtgg tgcaccctct acgctacaac    420
aagataaaaa ggattgaaca tgcaaaaggc gtgtgcatat ttgtctggat tctagtattt    480
gctcagacac tcccactcct catcaaccct atgtcaaagc aggaggctga aaggattaca    540
tgcatggagt atccaaactt tgaagaaact aaatctcttc cctggattct gcttggggca    600
tgtttcatag gatatgtact tccacttata atcattctca tctgctattc tcagatctgc    660
tgcaaactct tcagaactgc caaacaaaac ccactcactg agaaatctgg tgtaaacaaa    720
aaggctctca acacaattat tcttattatt gttgtgtttg ttctctgttt cacaccttac    780
catgttgcaa ttattcaaca tatgattaag aagcttcgtt tctctaattt cctggaatgt    840
agccaaagac attcgttcca gatttctctg cactttacag tatgcctgat gaacttcaat    900
tgctgcatgg accctttttat ctacttcttt gcatgtaaag ggtataagag aaaggttatg    960
aggatgctga aacggcaagt cagtgtatcg atttctagtg ctgtgaagtc agcccctgaa   1020
gaaaattcac gtgaaatgac agaaacgcag atgatgatac attccaagtc ttcaaatgga   1080
aagtga                                                              1086
```

<210> SEQ ID NO 78
<211> LENGTH: 361
<212> TYPE: PRT
<213> ORGANISM: Homo sapiens

<400> SEQUENCE: 78

```
Met Asp Ile Gln Met Ala Asn Asn Phe Thr Pro Pro Ser Ala Thr Pro
1               5                   10                  15

Gln Gly Asn Asp Cys Asp Leu Tyr Ala His His Ser Thr Ala Arg Ile
            20                  25                  30

Val Met Pro Leu His Tyr Ser Leu Val Phe Ile Ile Gly Leu Val Gly
        35                  40                  45

Asn Leu Leu Ala Leu Val Val Ile Val Gln Asn Arg Lys Lys Ile Asn
    50                  55                  60

Ser Thr Thr Leu Tyr Ser Thr Asn Leu Val Ile Ser Asp Ile Leu Phe
65                  70                  75                  80

Thr Thr Ala Leu Pro Thr Arg Ile Ala Tyr Tyr Ala Met Gly Phe Asp
                85                  90                  95

Trp Arg Ile Gly Asp Ala Leu Cys Arg Ile Thr Ala Leu Val Phe Tyr
            100                 105                 110

Ile Asn Thr Tyr Ala Gly Val Asn Phe Met Thr Cys Leu Ser Ile Asp
        115                 120                 125

Arg Phe Ile Ala Val Val His Pro Leu Arg Tyr Asn Lys Ile Lys Arg
    130                 135                 140

Ile Glu His Ala Lys Gly Val Cys Ile Phe Val Trp Ile Leu Val Phe
145                 150                 155                 160

Ala Gln Thr Leu Pro Leu Leu Ile Asn Pro Met Ser Lys Gln Glu Ala
                165                 170                 175
```

-continued

```
Glu Arg Ile Thr Cys Met Glu Tyr Pro Asn Phe Glu Glu Thr Lys Ser
            180                 185                 190

Leu Pro Trp Ile Leu Leu Gly Ala Cys Phe Ile Gly Tyr Val Leu Pro
        195                 200                 205

Leu Ile Ile Ile Leu Ile Cys Tyr Ser Gln Ile Cys Cys Lys Leu Phe
    210                 215                 220

Arg Thr Ala Lys Gln Asn Pro Leu Thr Glu Lys Ser Gly Val Asn Lys
225                 230                 235                 240

Lys Ala Leu Asn Thr Ile Ile Leu Ile Ile Val Val Phe Val Leu Cys
                245                 250                 255

Phe Thr Pro Tyr His Val Ala Ile Ile Gln His Met Ile Lys Lys Leu
            260                 265                 270

Arg Phe Ser Asn Phe Leu Glu Cys Ser Gln Arg His Ser Phe Gln Ile
        275                 280                 285

Ser Leu His Phe Thr Val Cys Leu Met Asn Phe Asn Cys Cys Met Asp
    290                 295                 300

Pro Phe Ile Tyr Phe Phe Ala Cys Lys Gly Tyr Lys Arg Lys Val Met
305                 310                 315                 320

Arg Met Leu Lys Arg Gln Val Ser Val Ser Ile Ser Ser Ala Val Lys
                325                 330                 335

Ser Ala Pro Glu Glu Asn Ser Arg Glu Met Thr Glu Thr Gln Met Met
            340                 345                 350

Ile His Ser Lys Ser Ser Asn Gly Lys
        355                 360


<210> SEQ ID NO 79
<211> LENGTH: 31
<212> TYPE: DNA
<213> ORGANISM: Artificial Sequence
<220> FEATURE:
<223> OTHER INFORMATION: Novel Sequence

<400> SEQUENCE: 79

ctggaattct cctgctcatc cagccatgcg g                                 31


<210> SEQ ID NO 80
<211> LENGTH: 30
<212> TYPE: DNA
<213> ORGANISM: Artificial Sequence
<220> FEATURE:
<223> OTHER INFORMATION: Novel Sequence

<400> SEQUENCE: 80

cctggatccc cacccctact ggggcctcag                                   30


<210> SEQ ID NO 81
<211> LENGTH: 1446
<212> TYPE: DNA
<213> ORGANISM: Homo sapiens

<400> SEQUENCE: 81

atgcggtggc tgtggcccct ggctgtctct cttgctgtga ttttggctgt ggggctaagc      60

agggtctctg gggtgcccc cctgcacctg ggcaggcaca gagccgagac ccaggagcag     120

cagagccgat ccaagagggg caccgaggat gaggaggcca agggcgtgca gcagtatgtg    180

cctgaggagt gggcggagta cccccggccc attcaccctg ctggcctgca gccaaccaag    240

cccttggtgg ccaccagccc taaccccgac aaggatgggg gcaccccaga cagtgggcag    300
```

-continued

```
gaactgaggg gcaatctgac aggggcacca gggcagaggc tacagatcca gaaccccctg    360
tatccggtga ccgagagctc ctacagtgcc tatgccatca tgcttctggc gctggtggtg    420
tttgcggtgg gcattgtggg caacctgtcg gtcatgtgca tcgtgtggca cagctactac    480
ctgaagagcg cctggaactc catccttgcc agcctggccc tctgggattt tctggtcctc    540
tttttctgcc tccctattgt catcttcaac gagatcacca agcagaggct actgggtgac    600
gtttcttgtc gtgccgtgcc cttcatggag gtctcctctc tgggagtcac gactttcagc    660
ctctgtgccc tgggcattga ccgcttccac gtggccacca gcaccctgcc caaggtgagg    720
cccatcgagc ggtgccaatc catcctggcc aagttggctg tcatctgggt gggctccatg    780
acgctggctg tgcctgagct cctgctgtgg cagctggcac aggagcctgc cccccaccatg    840
ggcaccctgg actcatgcat catgaaaccc tcagccagcc tgcccgagtc cctgtattca    900
ctggtgatga cctaccagaa cgcccgcatg tggtggtact ttggctgcta cttctgcctg    960
cccatcctct tcacagtcac ctgccagctg gtgacatggc gggtgcgagg ccctccaggg   1020
aggaagtcag agtgcagggc cagcaagcac gagcagtgtg agagccagct caacagcacc   1080
gtggtgggcc tgaccgtggt ctacgccttc tgcaccctcc cagagaacgt ctgcaacatc   1140
gtggtggcct acctctccac cgagctgacc cgccagaccc tggacctcct gggcctcatc   1200
aaccagttct ccaccttctt caagggcgcc atcaccccag tgctgctcct ttgcatctgc   1260
aggccgctgg gccaggcctt cctggactgc tgctgctgct gctgctgtga ggagtgcggc   1320
ggggcttcgg aggcctctgc tgccaatggg tcggacaaca agctcaagac cgaggtgtcc   1380
tcttccatct acttccacaa gcccagggag tcacccccac tcctgcccct gggcacacct   1440
tgctga                                                               1446
```

<210> SEQ ID NO 82
<211> LENGTH: 481
<212> TYPE: PRT
<213> ORGANISM: Homo sapiens

<400> SEQUENCE: 82

```
Met Arg Trp Leu Trp Pro Leu Ala Val Ser Leu Ala Val Ile Leu Ala
1               5                   10                  15

Val Gly Leu Ser Arg Val Ser Gly Gly Ala Pro Leu His Leu Gly Arg
            20                  25                  30

His Arg Ala Glu Thr Gln Glu Gln Gln Ser Arg Ser Lys Arg Gly Thr
        35                  40                  45

Glu Asp Glu Glu Ala Lys Gly Val Gln Gln Tyr Val Pro Glu Glu Trp
    50                  55                  60

Ala Glu Tyr Pro Arg Pro Ile His Pro Ala Gly Leu Gln Pro Thr Lys
65                  70                  75                  80

Pro Leu Val Ala Thr Ser Pro Asn Pro Asp Lys Asp Gly Gly Thr Pro
                85                  90                  95

Asp Ser Gly Gln Glu Leu Arg Gly Asn Leu Thr Gly Ala Pro Gly Gln
            100                 105                 110

Arg Leu Gln Ile Gln Asn Pro Leu Tyr Pro Val Thr Glu Ser Ser Tyr
        115                 120                 125

Ser Ala Tyr Ala Ile Met Leu Leu Ala Leu Val Val Phe Ala Val Gly
    130                 135                 140

Ile Val Gly Asn Leu Ser Val Met Cys Ile Val Trp His Ser Tyr Tyr
145                 150                 155                 160

Leu Lys Ser Ala Trp Asn Ser Ile Leu Ala Ser Leu Ala Leu Trp Asp
```

-continued

```
                165                 170                 175

Phe Leu Val Leu Phe Phe Cys Leu Pro Ile Val Ile Phe Asn Glu Ile
            180                 185                 190

Thr Lys Gln Arg Leu Leu Gly Asp Val Ser Cys Arg Ala Val Pro Phe
        195                 200                 205

Met Glu Val Ser Ser Leu Gly Val Thr Thr Phe Ser Leu Cys Ala Leu
    210                 215                 220

Gly Ile Asp Arg Phe His Val Ala Thr Ser Thr Leu Pro Lys Val Arg
225                 230                 235                 240

Pro Ile Glu Arg Cys Gln Ser Ile Leu Ala Lys Leu Ala Val Ile Trp
                245                 250                 255

Val Gly Ser Met Thr Leu Ala Val Pro Glu Leu Leu Leu Trp Gln Leu
            260                 265                 270

Ala Gln Glu Pro Ala Pro Thr Met Gly Thr Leu Asp Ser Cys Ile Met
        275                 280                 285

Lys Pro Ser Ala Ser Leu Pro Glu Ser Leu Tyr Ser Leu Val Met Thr
    290                 295                 300

Tyr Gln Asn Ala Arg Met Trp Trp Tyr Phe Gly Cys Tyr Phe Cys Leu
305                 310                 315                 320

Pro Ile Leu Phe Thr Val Thr Cys Gln Leu Val Thr Trp Arg Val Arg
                325                 330                 335

Gly Pro Pro Gly Arg Lys Ser Glu Cys Arg Ala Ser Lys His Glu Gln
            340                 345                 350

Cys Glu Ser Gln Leu Asn Ser Thr Val Val Gly Leu Thr Val Val Tyr
        355                 360                 365

Ala Phe Cys Thr Leu Pro Glu Asn Val Cys Asn Ile Val Val Ala Tyr
    370                 375                 380

Leu Ser Thr Glu Leu Thr Arg Gln Thr Leu Asp Leu Leu Gly Leu Ile
385                 390                 395                 400

Asn Gln Phe Ser Thr Phe Phe Lys Gly Ala Ile Thr Pro Val Leu Leu
                405                 410                 415

Leu Cys Ile Cys Arg Pro Leu Gly Gln Ala Phe Leu Asp Cys Cys Cys
            420                 425                 430

Cys Cys Cys Cys Glu Glu Cys Gly Gly Ala Ser Glu Ala Ser Ala Ala
        435                 440                 445

Asn Gly Ser Asp Asn Lys Leu Lys Thr Glu Val Ser Ser Ser Ile Tyr
    450                 455                 460

Phe His Lys Pro Arg Glu Ser Pro Pro Leu Leu Pro Leu Gly Thr Pro
465                 470                 475                 480

Cys


<210> SEQ ID NO 83
<211> LENGTH: 22
<212> TYPE: DNA
<213> ORGANISM: Artificial Sequence
<220> FEATURE:
<223> OTHER INFORMATION: Novel Sequence
<220> FEATURE:
<221> NAME/KEY: misc_feature
<223> OTHER INFORMATION: Novel Sequence

<400> SEQUENCE: 83

atgtggaacg cgacgcccag cg                                            22


<210> SEQ ID NO 84
<211> LENGTH: 22
```

-continued

<212> TYPE: DNA
<213> ORGANISM: Artificial Sequence
<220> FEATURE:
<223> OTHER INFORMATION: Novel Sequence

<400> SEQUENCE: 84
tcatgtatta atactagatt ct 22

<210> SEQ ID NO 85
<211> LENGTH: 38
<212> TYPE: DNA
<213> ORGANISM: Artificial Sequence
<220> FEATURE:
<223> OTHER INFORMATION: Novel Sequence

<400> SEQUENCE: 85
taccatgtgg aacgcgacgc ccagcgaaga gccggggt 38

<210> SEQ ID NO 86
<211> LENGTH: 39
<212> TYPE: DNA
<213> ORGANISM: Artificial Sequence
<220> FEATURE:
<223> OTHER INFORMATION: Novel Sequence

<400> SEQUENCE: 86
cggaattcat gtattaatac tagattctgt ccaggcccg 39

<210> SEQ ID NO 87
<211> LENGTH: 1101
<212> TYPE: DNA
<213> ORGANISM: Homo sapiens

<400> SEQUENCE: 87
atgtggaacg cgacgcccag cgaagagccg gggttcaacc tcacactggc cgacctggac 60
tgggatgctt cccccggcaa cgactcgctg ggcgacgagc tgctgcagct cttccccgcg 120
ccgctgctgg cgggcgtcac agccacctgc gtggcactct tcgtggtggg tatcgctggc 180
aacctgctca ccatgctggt ggtgtcgcgc ttccgcgagc tgcgcaccac caccaacctc 240
tacctgtcca gcatggcctt ctccgatctg ctcatcttcc tctgcatgcc cctggacctc 300
gttcgcctct ggcagtaccg gccctggaac ttcggcgacc tcctctgcaa actcttccaa 360
ttcgtcagtg agagctgcac ctacgccacg gtgctcacca tcacagcgct gagcgtcgag 420
cgctacttcg ccatctgctt cccactccgg gccaaggtgg tggtcaccaa ggggcgggtg 480
aagctggtca tcttcgtcat ctgggccgtg gccttctgca gcgccgggcc catcttcgtg 540
ctagtcgggg tggagcacga gaacggcacc gacccttggg acaccaacga gtgccgcccc 600
accgagtttg cggtgcgctc tggactgctc acggtcatgg tgtgggtgtc cagcatcttc 660
ttcttccttc ctgtcttctg tctcacggtc ctctacagtc tcatcggcag gaagctgtgg 720
cggaggaggc gcggcgatgc tgtcgtgggt gcctcgctca gggaccagaa ccacaagcaa 780
accgtgaaaa tgctggctgt agtggtgttt gccttcatcc tctgctggct ccccttccac 840
gtagggcgat atttattttc caaatccttt gagcctggct ccttggagat tgctcagatc 900
agccagtact gcaacctcgt gtcctttgtc ctcttctacc tcagtgctgc catcaacccc 960
attctgtaca acatcatgtc caagaagtac cgggtggcag tgttcagact tctgggattc 1020
gaacccttct cccagagaaa gctctccact ctgaaagatg aaagttctcg ggcctggaca 1080
gaatctagta ttaatacatg a 1101

-continued

<210> SEQ ID NO 88
<211> LENGTH: 366
<212> TYPE: PRT
<213> ORGANISM: Homo sapiens

<400> SEQUENCE: 88

Met Trp Asn Ala Thr Pro Ser Glu Glu Pro Gly Phe Asn Leu Thr Leu
1 5 10 15

Ala Asp Leu Asp Trp Asp Ala Ser Pro Gly Asn Asp Ser Leu Gly Asp
20 25 30

Glu Leu Leu Gln Leu Phe Pro Ala Pro Leu Leu Ala Gly Val Thr Ala
35 40 45

Thr Cys Val Ala Leu Phe Val Val Gly Ile Ala Gly Asn Leu Leu Thr
50 55 60

Met Leu Val Val Ser Arg Phe Arg Glu Leu Arg Thr Thr Thr Asn Leu
65 70 75 80

Tyr Leu Ser Ser Met Ala Phe Ser Asp Leu Leu Ile Phe Leu Cys Met
85 90 95

Pro Leu Asp Leu Val Arg Leu Trp Gln Tyr Arg Pro Trp Asn Phe Gly
100 105 110

Asp Leu Leu Cys Lys Leu Phe Gln Phe Val Ser Glu Ser Cys Thr Tyr
115 120 125

Ala Thr Val Leu Thr Ile Thr Ala Leu Ser Val Glu Arg Tyr Phe Ala
130 135 140

Ile Cys Phe Pro Leu Arg Ala Lys Val Val Val Thr Lys Gly Arg Val
145 150 155 160

Lys Leu Val Ile Phe Val Ile Trp Ala Val Ala Phe Cys Ser Ala Gly
165 170 175

Pro Ile Phe Val Leu Val Gly Val Glu His Glu Asn Gly Thr Asp Pro
180 185 190

Trp Asp Thr Asn Glu Cys Arg Pro Thr Glu Phe Ala Val Arg Ser Gly
195 200 205

Leu Leu Thr Val Met Val Trp Val Ser Ser Ile Phe Phe Phe Leu Pro
210 215 220

Val Phe Cys Leu Thr Val Leu Tyr Ser Leu Ile Gly Arg Lys Leu Trp
225 230 235 240

Arg Arg Arg Arg Gly Asp Ala Val Val Gly Ala Ser Leu Arg Asp Gln
245 250 255

Asn His Lys Gln Thr Val Lys Met Leu Ala Val Val Val Phe Ala Phe
260 265 270

Ile Leu Cys Trp Leu Pro Phe His Val Gly Arg Tyr Leu Phe Ser Lys
275 280 285

Ser Phe Glu Pro Gly Ser Leu Glu Ile Ala Gln Ile Ser Gln Tyr Cys
290 295 300

Asn Leu Val Ser Phe Val Leu Phe Tyr Leu Ser Ala Ala Ile Asn Pro
305 310 315 320

Ile Leu Tyr Asn Ile Met Ser Lys Lys Tyr Arg Val Ala Val Phe Arg
325 330 335

Leu Leu Gly Phe Glu Pro Phe Ser Gln Arg Lys Leu Ser Thr Leu Lys
340 345 350

Asp Glu Ser Ser Arg Ala Trp Thr Glu Ser Ser Ile Asn Thr
355 360 365

<210> SEQ ID NO 89

-continued

<211> LENGTH: 33
<212> TYPE: DNA
<213> ORGANISM: Artificial Sequence
<220> FEATURE:
<223> OTHER INFORMATION: Novel Sequence

<400> SEQUENCE: 89
gcaagcttgt gccctcacca agccatgcga gcc 33

<210> SEQ ID NO 90
<211> LENGTH: 30
<212> TYPE: DNA
<213> ORGANISM: Artificial Sequence
<220> FEATURE:
<223> OTHER INFORMATION: Novel Sequence

<400> SEQUENCE: 90
cggaattcag caatgagttc cgacagaagc 30

<210> SEQ ID NO 91
<211> LENGTH: 1842
<212> TYPE: DNA
<213> ORGANISM: Homo sapiens

<400> SEQUENCE: 91
atgcgagccc cgggcgcgct tctcgcccgc atgtcgcggc tactgcttct gctactgctc 60
aaggtgtctg cctcttctgc cctcggggtc gcccctgcgt ccagaaacga aacttgtctg 120
ggggagagct gtgcacctac agtgatccag cgccgcggca gggacgcctg gggaccggga 180
aattctgcaa gagacgttct gcgagcccga gcacccaggg aggagcaggg ggcagcgttt 240
cttgcgggac cctcctggga cctgccggcg gccccgggcc gtgacccggc tgcaggcaga 300
ggggcggagg cgtcggcagc cggacccccg ggacctccaa ccaggccacc tggcccctgg 360
aggtggaaag gtgctcgggg tcaggagcct tctgaaactt tggggagagg gaaccccacg 420
gccctccagc tcttccttca gatctcagag gaggaagaga agggtcccag aggcgctggc 480
atttccgggc gtagccagga gcagagtgtg aagacagtcc ccggagccag cgatcttttt 540
tactggccaa ggagagccgg gaaactccag ggttcccacc acaagcccct gtccaagacg 600
gccaatggac tggcggggca cgaagggtgg acaattgcac tcccgggccg ggcgctggcc 660
cagaatggat ccttgggtga aggaatccat gagcctgggg gtccccgccg gggaaacagc 720
acgaaccggc gtgtgagact gaagaacccc ttctacccgc tgacccagga gtcctatgga 780
gcctacgcgg tcatgtgtct gtccgtggtg atcttcggga ccggcatcat tggcaacctg 840
gcggtgatga gcatcgtgtg ccacaactac tacatgcgga gcatctccaa ctccctcttg 900
gccaacctgg ccttctggga ctttctcatc atcttcttct gccttccgct ggtcatcttc 960
cacgagctga ccaagaagtg gctgctggag gacttctcct gcaagatcgt gccctatata 1020
gaggtcgctt ctctgggagt caccactttc accttatgtg ctctgtgcat agaccgcttc 1080
cgtgctgcca ccaacgtaca gatgtactac gaaatgatcg aaaactgttc ctcaacaact 1140
gccaaacttg ctgttatatg ggtgggagct ctattgttag cacttccaga agttgttctc 1200
cgccagctga gcaaggagga tttggggttt agtggccgag ctccggcaga aaggtgcatt 1260
attaagatct ctcctgattt accagacacc atctatgttc tagccctcac ctacgacagt 1320
gcgagactgt ggtggtattt tggctgttac ttttgtttgc ccacgctttt caccatcacc 1380
tgctctctag tgactgcgag gaaaatccgc aaagcagaga aagcctgtac ccgagggaat 1440
aaacggcaga ttcaactaga gagtcagatg aactgtacag tagtggcact gaccatttta 1500

-continued

```
tatggatttt gcattattcc tgaaaatatc tgcaacattg ttactgccta catggctaca   1560

ggggtttcac agcagacaat ggacctcctt aatatcatca gccagttcct tttgttcttt   1620

aagtcctgtg tcaccccagt cctccttttc tgtctctgca aacccttcag tcgggccttc   1680

atggagtgct gctgctgttg ctgtgaggaa tgcattcaga agtcttcaac ggtgaccagt   1740

gatgacaatg acaacgagta caccacggaa ctcgaactct cgcctttcag taccatacgc   1800

cgtgaaatgt ccacttttgc ttctgtcgga actcattgct ga                      1842


<210> SEQ ID NO 92
<211> LENGTH: 613
<212> TYPE: PRT
<213> ORGANISM: Homo sapiens

<400> SEQUENCE: 92

Met Arg Ala Pro Gly Ala Leu Leu Ala Arg Met Ser Arg Leu Leu Leu
1               5                   10                  15

Leu Leu Leu Leu Lys Val Ser Ala Ser Ser Ala Leu Gly Val Ala Pro
            20                  25                  30

Ala Ser Arg Asn Glu Thr Cys Leu Gly Glu Ser Cys Ala Pro Thr Val
        35                  40                  45

Ile Gln Arg Arg Gly Arg Asp Ala Trp Gly Pro Gly Asn Ser Ala Arg
    50                  55                  60

Asp Val Leu Arg Ala Arg Ala Pro Arg Glu Glu Gln Gly Ala Ala Phe
65                  70                  75                  80

Leu Ala Gly Pro Ser Trp Asp Leu Pro Ala Ala Pro Gly Arg Asp Pro
                85                  90                  95

Ala Ala Gly Arg Gly Ala Glu Ala Ser Ala Ala Gly Pro Pro Gly Pro
            100                 105                 110

Pro Thr Arg Pro Pro Gly Pro Trp Arg Trp Lys Gly Ala Arg Gly Gln
        115                 120                 125

Glu Pro Ser Glu Thr Leu Gly Arg Gly Asn Pro Thr Ala Leu Gln Leu
    130                 135                 140

Phe Leu Gln Ile Ser Glu Glu Glu Lys Gly Pro Arg Gly Ala Gly
145                 150                 155                 160

Ile Ser Gly Arg Ser Gln Glu Gln Ser Val Lys Thr Val Pro Gly Ala
                165                 170                 175

Ser Asp Leu Phe Tyr Trp Pro Arg Arg Ala Gly Lys Leu Gln Gly Ser
            180                 185                 190

His His Lys Pro Leu Ser Lys Thr Ala Asn Gly Leu Ala Gly His Glu
        195                 200                 205

Gly Trp Thr Ile Ala Leu Pro Gly Arg Ala Leu Ala Gln Asn Gly Ser
    210                 215                 220

Leu Gly Glu Gly Ile His Glu Pro Gly Gly Pro Arg Arg Gly Asn Ser
225                 230                 235                 240

Thr Asn Arg Arg Val Arg Leu Lys Asn Pro Phe Tyr Pro Leu Thr Gln
                245                 250                 255

Glu Ser Tyr Gly Ala Tyr Ala Val Met Cys Leu Ser Val Val Ile Phe
            260                 265                 270

Gly Thr Gly Ile Ile Gly Asn Leu Ala Val Met Ser Ile Val Cys His
        275                 280                 285

Asn Tyr Tyr Met Arg Ser Ile Ser Asn Ser Leu Leu Ala Asn Leu Ala
    290                 295                 300

Phe Trp Asp Phe Leu Ile Ile Phe Phe Cys Leu Pro Leu Val Ile Phe
```

-continued

```
305                 310                 315                 320

His Glu Leu Thr Lys Lys Trp Leu Leu Glu Asp Phe Ser Cys Lys Ile
                325                 330                 335

Val Pro Tyr Ile Glu Val Ala Ser Leu Gly Val Thr Thr Phe Thr Leu
            340                 345                 350

Cys Ala Leu Cys Ile Asp Arg Phe Arg Ala Ala Thr Asn Val Gln Met
        355                 360                 365

Tyr Tyr Glu Met Ile Glu Asn Cys Ser Ser Thr Thr Ala Lys Leu Ala
    370                 375                 380

Val Ile Trp Val Gly Ala Leu Leu Leu Ala Leu Pro Glu Val Val Leu
385                 390                 395                 400

Arg Gln Leu Ser Lys Glu Asp Leu Gly Phe Ser Gly Arg Ala Pro Ala
                405                 410                 415

Glu Arg Cys Ile Ile Lys Ile Ser Pro Asp Leu Pro Asp Thr Ile Tyr
            420                 425                 430

Val Leu Ala Leu Thr Tyr Asp Ser Ala Arg Leu Trp Trp Tyr Phe Gly
        435                 440                 445

Cys Tyr Phe Cys Leu Pro Thr Leu Phe Thr Ile Thr Cys Ser Leu Val
    450                 455                 460

Thr Ala Arg Lys Ile Arg Lys Ala Glu Lys Ala Cys Thr Arg Gly Asn
465                 470                 475                 480

Lys Arg Gln Ile Gln Leu Glu Ser Gln Met Asn Cys Thr Val Val Ala
                485                 490                 495

Leu Thr Ile Leu Tyr Gly Phe Cys Ile Ile Pro Glu Asn Ile Cys Asn
            500                 505                 510

Ile Val Thr Ala Tyr Met Ala Thr Gly Val Ser Gln Gln Thr Met Asp
        515                 520                 525

Leu Leu Asn Ile Ile Ser Gln Phe Leu Leu Phe Phe Lys Ser Cys Val
    530                 535                 540

Thr Pro Val Leu Leu Phe Cys Leu Cys Lys Pro Phe Ser Arg Ala Phe
545                 550                 555                 560

Met Glu Cys Cys Cys Cys Cys Cys Glu Glu Cys Ile Gln Lys Ser Ser
                565                 570                 575

Thr Val Thr Ser Asp Asp Asn Asp Asn Glu Tyr Thr Thr Glu Leu Glu
            580                 585                 590

Leu Ser Pro Phe Ser Thr Ile Arg Arg Glu Met Ser Thr Phe Ala Ser
        595                 600                 605

Val Gly Thr His Cys
    610
```

<210> SEQ ID NO 93
<211> LENGTH: 34
<212> TYPE: DNA
<213> ORGANISM: Artificial Sequence
<220> FEATURE:
<223> OTHER INFORMATION: Novel Sequence

<400> SEQUENCE: 93
cagaattcag agaaaaaaag tgaatatggt tttt 34

<210> SEQ ID NO 94
<211> LENGTH: 32
<212> TYPE: DNA
<213> ORGANISM: Artificial Sequence
<220> FEATURE:
<223> OTHER INFORMATION: Novel Sequence -continued

<400> SEQUENCE: 94
ttggatccct ggtgcataac aattgaaaga at 32

<210> SEQ ID NO 95
<211> LENGTH: 1248
<212> TYPE: DNA
<213> ORGANISM: Homo sapiens

<400> SEQUENCE: 95
atggtttttg ctcacagaat ggataacagc aagccacatt tgattattcc tacacttctg 60
gtgcccctcc aaaaccgcag ctgcactgaa acagccacac ctctgccaag ccaatacctg 120
atggaattaa gtgaggagca cagttggatg agcaaccaaa cagaccttca ctatgtgctg 180
aaacccgggg aagtggccac agccagcatc ttctttggga ttctgtggtt gttttctatc 240
ttcggcaatt ccctggtttg tttggtcatc cataggagta ggaggactca gtctaccacc 300
aactactttg tggtctccat ggcatgtgct gaccttctca tcagcgttgc cagcacgcct 360
ttcgtcctgc tccagttcac cactggaagg tggacgctgg gtagtgcaac gtgcaaggtt 420
gtgcgatatt ttcaatatct cactccaggt gtccagatct acgttctcct ctccatctgc 480
atagaccggt tctacaccat cgtctatcct ctgagcttca aggtgtccag agaaaaagcc 540
aagaaaatga ttgcggcatc gtggatcttt gatgcaggct ttgtgacccc tgtgctcttt 600
ttctatggct ccaactggga cagtcattgt aactatttcc tcccctcctc ttgggaaggc 660
actgcctaca ctgtcatcca cttcttggtg ggctttgtga ttccatctgt cctcataatt 720
ttattttacc aaaaggtcat aaaatatatt tggagaatag gcacagatgg ccgaacggtg 780
aggaggacaa tgaacattgt ccctcggaca aaagtgaaaa ctatcaagat gttcctcatt 840
ttaaatctgt tgtttttgct ctcctggctg cctttttcatg tagctcagct atggcacccc 900
catgaacaag actataagaa aagttccctt gttttcacag ctatcacatg gatatccttt 960
agttcttcag cctctaaacc tactctgtat tcaatttata atgccaattt tcggagaggg 1020
atgaaagaga ctttttgcat gtcctctatg aaatgttacc gaagcaatgc ctatactatc 1080
acaacaagtt caaggatggc caaaaaaaac tacgttggca tttcagaaat cccttccatg 1140
gccaaaacta ttaccaaaga ctcgatctat gactcatttg acagagaagc caaggaaaaa 1200
aagcttgctt ggcccattaa ctcaaatcca ccaaatactt ttgtctaa 1248

<210> SEQ ID NO 96
<211> LENGTH: 415
<212> TYPE: PRT
<213> ORGANISM: Homo sapiens

<400> SEQUENCE: 96

```
Met Val Phe Ala His Arg Met Asp Asn Ser Lys Pro His Leu Ile Ile
1               5                   10                  15

Pro Thr Leu Leu Val Pro Leu Gln Asn Arg Ser Cys Thr Glu Thr Ala
            20                  25                  30

Thr Pro Leu Pro Ser Gln Tyr Leu Met Glu Leu Ser Glu Glu His Ser
        35                  40                  45

Trp Met Ser Asn Gln Thr Asp Leu His Tyr Val Leu Lys Pro Gly Glu
    50                  55                  60

Val Ala Thr Ala Ser Ile Phe Phe Gly Ile Leu Trp Leu Phe Ser Ile
65                  70                  75                  80

Phe Gly Asn Ser Leu Val Cys Leu Val Ile His Arg Ser Arg Arg Thr
                85                  90                  95
```

-continued

```
Gln Ser Thr Thr Asn Tyr Phe Val Val Ser Met Ala Cys Ala Asp Leu
            100                 105                 110

Leu Ile Ser Val Ala Ser Thr Pro Phe Val Leu Leu Gln Phe Thr Thr
        115                 120                 125

Gly Arg Trp Thr Leu Gly Ser Ala Thr Cys Lys Val Val Arg Tyr Phe
    130                 135                 140

Gln Tyr Leu Thr Pro Gly Val Gln Ile Tyr Val Leu Leu Ser Ile Cys
145                 150                 155                 160

Ile Asp Arg Phe Tyr Thr Ile Val Tyr Pro Leu Ser Phe Lys Val Ser
                165                 170                 175

Arg Glu Lys Ala Lys Lys Met Ile Ala Ala Ser Trp Ile Phe Asp Ala
            180                 185                 190

Gly Phe Val Thr Pro Val Leu Phe Phe Tyr Gly Ser Asn Trp Asp Ser
        195                 200                 205

His Cys Asn Tyr Phe Leu Pro Ser Ser Trp Glu Gly Thr Ala Tyr Thr
    210                 215                 220

Val Ile His Phe Leu Val Gly Phe Val Ile Pro Ser Val Leu Ile Ile
225                 230                 235                 240

Leu Phe Tyr Gln Lys Val Ile Lys Tyr Ile Trp Arg Ile Gly Thr Asp
                245                 250                 255

Gly Arg Thr Val Arg Arg Thr Met Asn Ile Val Pro Arg Thr Lys Val
            260                 265                 270

Lys Thr Ile Lys Met Phe Leu Ile Leu Asn Leu Leu Phe Leu Leu Ser
        275                 280                 285

Trp Leu Pro Phe His Val Ala Gln Leu Trp His Pro His Glu Gln Asp
    290                 295                 300

Tyr Lys Lys Ser Ser Leu Val Phe Thr Ala Ile Thr Trp Ile Ser Phe
305                 310                 315                 320

Ser Ser Ser Ala Ser Lys Pro Thr Leu Tyr Ser Ile Tyr Asn Ala Asn
                325                 330                 335

Phe Arg Arg Gly Met Lys Glu Thr Phe Cys Met Ser Ser Met Lys Cys
            340                 345                 350

Tyr Arg Ser Asn Ala Tyr Thr Ile Thr Thr Ser Ser Arg Met Ala Lys
        355                 360                 365

Lys Asn Tyr Val Gly Ile Ser Glu Ile Pro Ser Met Ala Lys Thr Ile
    370                 375                 380

Thr Lys Asp Ser Ile Tyr Asp Ser Phe Asp Arg Glu Ala Lys Glu Lys
385                 390                 395                 400

Lys Leu Ala Trp Pro Ile Asn Ser Asn Pro Pro Asn Thr Phe Val
                405                 410                 415
```

<210> SEQ ID NO 97
<211> LENGTH: 30
<212> TYPE: DNA
<213> ORGANISM: Artificial Sequence
<220> FEATURE:
<223> OTHER INFORMATION: Novel Sequence

<400> SEQUENCE: 97
ggaaagctta acgatcccca ggagcaacat 30

<210> SEQ ID NO 98
<211> LENGTH: 31
<212> TYPE: DNA
<213> ORGANISM: Artificial Sequence
<220> FEATURE:

-continued

<223> OTHER INFORMATION: Novel Sequence

<400> SEQUENCE: 98
ctgggatcct acgagagcat ttttcacaca g 31

<210> SEQ ID NO 99
<211> LENGTH: 1842
<212> TYPE: DNA
<213> ORGANISM: Homo sapiens

<400> SEQUENCE: 99
atggggccca ccctagcggt tcccaccccc tatggctgta ttggctgtaa gctaccccag 60
ccagaatacc caccggctct aatcatcttt atgttctgcg cgatggttat caccatcgtt 120
gtagacctaa tcggcaactc catggtcatt ttggctgtga cgaagaacaa gaagctccgg 180
aattctggca acatcttcgt ggtcagtctc tctgtggccg atatgctggt ggccatctac 240
ccataccctt tgatgctgca tgccatgtcc attgggggct gggatctgag ccagttacag 300
tgccagatgg tcgggttcat cacagggctg agtgtggtcg gctccatctt caacatcgtg 360
gcaatcgcta tcaaccgtta ctgctacatc tgccacagcc tccagtacga acggatcttc 420
agtgtgcgca atacctgcat ctacctggtc atcacctgga tcatgaccgt cctggctgtc 480
ctgcccaaca tgtacattgg caccatcgag tacgatcctc gcacctacac ctgcatcttc 540
aactatctga acaaccctgt cttcactgtt accatcgtct gcatccactt cgtcctccct 600
ctcctcatcg tgggtttctg ctacgtgagg atctggacca aagtgctggc ggcccgtgac 660
cctgcagggc agaatcctga caaccaactt gctgaggttc gcaattttct aaccatgttt 720
gtgatcttcc tcctctttgc agtgtgctgg tgccctatca acgtgctcac tgtcttggtg 780
gctgtcagtc cgaaggagat ggcaggcaag atccccaact ggctttatct tgcagcctac 840
ttcatagcct acttcaacag ctgcctcaac gctgtgatct acgggctcct caatgagaat 900
ttccgaagag aatactggac catcttccat gctatgcggc accctatcat attcttccct 960
ggcctcatca gtgatattcg tgagatgcag gaggcccgta ccctggcccg cgcccgtgcc 1020
catgctcgcg accaagctcg tgaacaagac cgtgcccatg cctgtcctgc tgtggaggaa 1080
accccgatga atgtccggaa tgttccatta cctggtgatg ctgcagctgg ccaccccgac 1140
cgtgcctctg gccaccctaa gccccattcc agatcctcct ctgcctatcg caaatctgcc 1200
tctacccacc acaagtctgt ctttagccac tccaaggctg cctctggtca cctcaagcct 1260
gtctctggcc actccaagcc tgcctctggt caccccaagt ctgccactgt ctaccctaag 1320
cctgcctctg tccatttcaa gggtgactct gtccatttca agggtgactc tgtccatttc 1380
aagcctgact ctgttcattt caagcctgct tccagcaacc ccaagcccat cactggccac 1440
catgtctctg ctggcagcca ctccaagtct gccttcagtg ctgccaccag ccaccctaaa 1500
cccatcaagc cagctaccag ccatgctgag cccaccactg ctgactatcc caagcctgcc 1560
actaccagcc accctaagcc cgctgctgct gacaaccctg agctctctgc ctcccattgc 1620
cccgagatcc ctgccattgc ccaccctgtg tctgacgaca gtgacctccc tgagtcggcc 1680
tctagccctg ccgctgggcc caccaagcct gctgccagcc agctggagtc tgacaccatc 1740
gctgaccttc ctgaccctac tgtagtcact accagtacca atgattacca tgatgtcgtg 1800
gttgttgatg ttgaagatga tcctgatgaa atggctgtgt ga 1842

<210> SEQ ID NO 100
<211> LENGTH: 613

<212> TYPE: PRT
<213> ORGANISM: Homo sapiens

<400> SEQUENCE: 100

```
Met Gly Pro Thr Leu Ala Val Pro Thr Pro Tyr Gly Cys Ile Gly Cys
1               5                   10                  15

Lys Leu Pro Gln Pro Glu Tyr Pro Pro Ala Leu Ile Ile Phe Met Phe
            20                  25                  30

Cys Ala Met Val Ile Thr Ile Val Val Asp Leu Ile Gly Asn Ser Met
        35                  40                  45

Val Ile Leu Ala Val Thr Lys Asn Lys Lys Leu Arg Asn Ser Gly Asn
    50                  55                  60

Ile Phe Val Val Ser Leu Ser Val Ala Asp Met Leu Val Ala Ile Tyr
65                  70                  75                  80

Pro Tyr Pro Leu Met Leu His Ala Met Ser Ile Gly Gly Trp Asp Leu
                85                  90                  95

Ser Gln Leu Gln Cys Gln Met Val Gly Phe Ile Thr Gly Leu Ser Val
            100                 105                 110

Val Gly Ser Ile Phe Asn Ile Val Ala Ile Ala Ile Asn Arg Tyr Cys
        115                 120                 125

Tyr Ile Cys His Ser Leu Gln Tyr Glu Arg Ile Phe Ser Val Arg Asn
    130                 135                 140

Thr Cys Ile Tyr Leu Val Ile Thr Trp Ile Met Thr Val Leu Ala Val
145                 150                 155                 160

Leu Pro Asn Met Tyr Ile Gly Thr Ile Glu Tyr Asp Pro Arg Thr Tyr
                165                 170                 175

Thr Cys Ile Phe Asn Tyr Leu Asn Asn Pro Val Phe Thr Val Thr Ile
            180                 185                 190

Val Cys Ile His Phe Val Leu Pro Leu Leu Ile Val Gly Phe Cys Tyr
        195                 200                 205

Val Arg Ile Trp Thr Lys Val Leu Ala Ala Arg Asp Pro Ala Gly Gln
    210                 215                 220

Asn Pro Asp Asn Gln Leu Ala Glu Val Arg Asn Phe Leu Thr Met Phe
225                 230                 235                 240

Val Ile Phe Leu Leu Phe Ala Val Cys Trp Cys Pro Ile Asn Val Leu
                245                 250                 255

Thr Val Leu Val Ala Val Ser Pro Lys Glu Met Ala Gly Lys Ile Pro
            260                 265                 270

Asn Trp Leu Tyr Leu Ala Ala Tyr Phe Ile Ala Tyr Phe Asn Ser Cys
        275                 280                 285

Leu Asn Ala Val Ile Tyr Gly Leu Leu Asn Glu Asn Phe Arg Arg Glu
    290                 295                 300

Tyr Trp Thr Ile Phe His Ala Met Arg His Pro Ile Ile Phe Phe Pro
305                 310                 315                 320

Gly Leu Ile Ser Asp Ile Arg Glu Met Gln Glu Ala Arg Thr Leu Ala
                325                 330                 335

Arg Ala Arg Ala His Ala Arg Asp Gln Ala Arg Glu Gln Asp Arg Ala
            340                 345                 350

His Ala Cys Pro Ala Val Glu Glu Thr Pro Met Asn Val Arg Asn Val
        355                 360                 365

Pro Leu Pro Gly Asp Ala Ala Ala Gly His Pro Asp Arg Ala Ser Gly
    370                 375                 380

His Pro Lys Pro His Ser Arg Ser Ser Ser Ala Tyr Arg Lys Ser Ala
385                 390                 395                 400
```

-continued

```
Ser Thr His His Lys Ser Val Phe Ser His Ser Lys Ala Ala Ser Gly
                405                 410                 415

His Leu Lys Pro Val Ser Gly His Ser Lys Pro Ala Ser Gly His Pro
            420                 425                 430

Lys Ser Ala Thr Val Tyr Pro Lys Pro Ala Ser Val His Phe Lys Gly
        435                 440                 445

Asp Ser Val His Phe Lys Gly Asp Ser Val His Phe Lys Pro Asp Ser
    450                 455                 460

Val His Phe Lys Pro Ala Ser Ser Asn Pro Lys Pro Ile Thr Gly His
465                 470                 475                 480

His Val Ser Ala Gly Ser His Ser Lys Ser Ala Phe Ser Ala Ala Thr
                485                 490                 495

Ser His Pro Lys Pro Ile Lys Pro Ala Thr Ser His Ala Glu Pro Thr
            500                 505                 510

Thr Ala Asp Tyr Pro Lys Pro Ala Thr Thr Ser His Pro Lys Pro Ala
        515                 520                 525

Ala Ala Asp Asn Pro Glu Leu Ser Ala Ser His Cys Pro Glu Ile Pro
    530                 535                 540

Ala Ile Ala His Pro Val Ser Asp Asp Ser Asp Leu Pro Glu Ser Ala
545                 550                 555                 560

Ser Ser Pro Ala Ala Gly Pro Thr Lys Pro Ala Ala Ser Gln Leu Glu
                565                 570                 575

Ser Asp Thr Ile Ala Asp Leu Pro Asp Pro Thr Val Val Thr Thr Ser
            580                 585                 590

Thr Asn Asp Tyr His Asp Val Val Val Val Asp Val Glu Asp Asp Pro
        595                 600                 605

Asp Glu Met Ala Val
    610
```

<210> SEQ ID NO 101
<211> LENGTH: 32
<212> TYPE: DNA
<213> ORGANISM: Artificial Sequence
<220> FEATURE:
<223> OTHER INFORMATION: Novel Sequence

<400> SEQUENCE: 101
tccaagcttc gccatgggac ataacgggag ct 32

<210> SEQ ID NO 102
<211> LENGTH: 30
<212> TYPE: DNA
<213> ORGANISM: Artificial Sequence
<220> FEATURE:
<223> OTHER INFORMATION: Novel Sequence

<400> SEQUENCE: 102
cgtgaattcc aagaatttac aatccttgct 30

<210> SEQ ID NO 103
<211> LENGTH: 1548
<212> TYPE: DNA
<213> ORGANISM: Homo sapiens

<400> SEQUENCE: 103
atgggacata acgggagctg gatctctcca aatgccagcg agccgcacaa cgcgtccggc 60
gccgaggctg cgggtgtgaa ccgcagcgcg ctcggggagt tcggcgaggc gcagctgtac 120

-continued

```
cgccagttca ccaccaccgt gcaggtcgtc atcttcatag gctcgctgct cggaaacttc    180

atggtgttat ggtcaacttg ccgcacaacc gtgttcaaat ctgtcaccaa caggttcatt    240

aaaaacctgg cctgctcggg gatttgtgcc agcctggtct gtgtgccctt cgacatcatc    300

ctcagcacca gtcctcactg ttgctggtgg atctacacca tgctcttctg caaggtcgtc    360

aaatttttgc acaaagtatt ctgctctgtg accatcctca gcttccctgc tattgctttg    420

gacaggtact actcagtcct ctatccactg gagaggaaaa tatctgatgc caagtcccgt    480

gaactggtga tgtacatctg ggcccatgca gtggtggcca gtgtccctgt gtttgcagta    540

accaatgtgg ctgacatcta tgccacgtcc acctgcacgg aagtctggag caactccttg    600

ggccacctgg tgtacgttct ggtgtataac atcaccacgg tcattgtgcc tgtggtggtg    660

gtgttcctct tcttgatact gatccgacgg gccctgagtg ccagccagaa gaagaaggtc    720

atcatagcag cgctccggac cccacagaac accatctcta ttccctatgc ctcccagcgg    780

gaggccgagc tgcacgccac cctgctctcc atggtgatgg tcttcatctt gtgtagcgtg    840

ccctatgcca ccctggtcgt ctaccagact gtgctcaatg tccctgacac ttccgtcttc    900

ttgctgctca ctgctgtttg gctgcccaaa gtctccctgc tggcaaaccc tgttctcttt    960

cttactgtga acaaatctgt ccgcaagtgc ttgataggga ccctggtgca actacaccac   1020

cggtacagtc gccgtaatgt ggtcagtaca gggagtggca tggctgaggc cagcctggaa   1080

cccagcatac gctcgggtag ccagctcctg gagatgttcc acattgggca gcagcagatc   1140

tttaagccca cagaggatga ggaagagagt gaggccaagt acattggctc agctgacttc   1200

caggccaagg agatatttag cacctgcctg gagggagagc aggggccaca gtttgcgccc   1260

tctgccccac ccctgagcac agtggactct gtatcccagg tggcaccggc agcccctgtg   1320

gaacctgaaa cattccctga taagtattcc ctgcagtttg gctttgggcc ttttgagttg   1380

cctcctcagt ggctctcaga gacccgaaac agcaagaagc ggctgcttcc ccccttgggc   1440

aacaccccag aagagctgat ccagacaaag gtgcccaagg taggcagggt ggagcggaag   1500

atgagcagaa acaataaagt gagcattttt ccaaaggtgg attcctag                1548
```

<210> SEQ ID NO 104
<211> LENGTH: 515
<212> TYPE: PRT
<213> ORGANISM: Homo sapiens

<400> SEQUENCE: 104

```
Met Gly His Asn Gly Ser Trp Ile Ser Pro Asn Ala Ser Glu Pro His
1               5                   10                  15

Asn Ala Ser Gly Ala Glu Ala Ala Gly Val Asn Arg Ser Ala Leu Gly
            20                  25                  30

Glu Phe Gly Glu Ala Gln Leu Tyr Arg Gln Phe Thr Thr Thr Val Gln
        35                  40                  45

Val Val Ile Phe Ile Gly Ser Leu Leu Gly Asn Phe Met Val Leu Trp
    50                  55                  60

Ser Thr Cys Arg Thr Thr Val Phe Lys Ser Val Thr Asn Arg Phe Ile
65                  70                  75                  80

Lys Asn Leu Ala Cys Ser Gly Ile Cys Ala Ser Leu Val Cys Val Pro
                85                  90                  95

Phe Asp Ile Ile Leu Ser Thr Ser Pro His Cys Cys Trp Trp Ile Tyr
            100                 105                 110

Thr Met Leu Phe Cys Lys Val Val Lys Phe Leu His Lys Val Phe Cys
        115                 120                 125
```

-continued

```
Ser Val Thr Ile Leu Ser Phe Pro Ala Ile Ala Leu Asp Arg Tyr Tyr
    130                 135                 140

Ser Val Leu Tyr Pro Leu Glu Arg Lys Ile Ser Asp Ala Lys Ser Arg
145                 150                 155                 160

Glu Leu Val Met Tyr Ile Trp Ala His Ala Val Val Ala Ser Val Pro
                165                 170                 175

Val Phe Ala Val Thr Asn Val Ala Asp Ile Tyr Ala Thr Ser Thr Cys
            180                 185                 190

Thr Glu Val Trp Ser Asn Ser Leu Gly His Leu Val Tyr Val Leu Val
        195                 200                 205

Tyr Asn Ile Thr Thr Val Ile Val Pro Val Val Val Val Phe Leu Phe
    210                 215                 220

Leu Ile Leu Ile Arg Arg Ala Leu Ser Ala Ser Gln Lys Lys Lys Val
225                 230                 235                 240

Ile Ile Ala Ala Leu Arg Thr Pro Gln Asn Thr Ile Ser Ile Pro Tyr
                245                 250                 255

Ala Ser Gln Arg Glu Ala Glu Leu His Ala Thr Leu Leu Ser Met Val
            260                 265                 270

Met Val Phe Ile Leu Cys Ser Val Pro Tyr Ala Thr Leu Val Val Tyr
        275                 280                 285

Gln Thr Val Leu Asn Val Pro Asp Thr Ser Val Phe Leu Leu Leu Thr
    290                 295                 300

Ala Val Trp Leu Pro Lys Val Ser Leu Leu Ala Asn Pro Val Leu Phe
305                 310                 315                 320

Leu Thr Val Asn Lys Ser Val Arg Lys Cys Leu Ile Gly Thr Leu Val
                325                 330                 335

Gln Leu His His Arg Tyr Ser Arg Arg Asn Val Val Ser Thr Gly Ser
            340                 345                 350

Gly Met Ala Glu Ala Ser Leu Glu Pro Ser Ile Arg Ser Gly Ser Gln
        355                 360                 365

Leu Leu Glu Met Phe His Ile Gly Gln Gln Gln Ile Phe Lys Pro Thr
    370                 375                 380

Glu Asp Glu Glu Glu Ser Glu Ala Lys Tyr Ile Gly Ser Ala Asp Phe
385                 390                 395                 400

Gln Ala Lys Glu Ile Phe Ser Thr Cys Leu Glu Gly Glu Gln Gly Pro
                405                 410                 415

Gln Phe Ala Pro Ser Ala Pro Pro Leu Ser Thr Val Asp Ser Val Ser
            420                 425                 430

Gln Val Ala Pro Ala Ala Pro Val Glu Pro Glu Thr Phe Pro Asp Lys
        435                 440                 445

Tyr Ser Leu Gln Phe Gly Phe Gly Pro Phe Glu Leu Pro Pro Gln Trp
    450                 455                 460

Leu Ser Glu Thr Arg Asn Ser Lys Lys Arg Leu Leu Pro Pro Leu Gly
465                 470                 475                 480

Asn Thr Pro Glu Glu Leu Ile Gln Thr Lys Val Pro Lys Val Gly Arg
                485                 490                 495

Val Glu Arg Lys Met Ser Arg Asn Asn Lys Val Ser Ile Phe Pro Lys
            500                 505                 510

Val Asp Ser
        515
```

<210> SEQ ID NO 105
<211> LENGTH: 29

-continued

<212> TYPE: DNA
<213> ORGANISM: Artificial Sequence
<220> FEATURE:
<223> OTHER INFORMATION: Novel Sequence

<400> SEQUENCE: 105
ggagaattca ctaggcgagg cgctccatc 29

<210> SEQ ID NO 106
<211> LENGTH: 30
<212> TYPE: DNA
<213> ORGANISM: Artificial Sequence
<220> FEATURE:
<223> OTHER INFORMATION: Novel Sequence

<400> SEQUENCE: 106
ggaggatcca ggaaacctta ggccgagtcc 30

<210> SEQ ID NO 107
<211> LENGTH: 1164
<212> TYPE: DNA
<213> ORGANISM: Homo sapiens

<400> SEQUENCE: 107
atgaatcggc accatctgca ggatcacttt ctggaaatag acaagaagaa ctgctgtgtg 60
ttccgagatg acttcattgc caaggtgttg ccgccggtgt tggggctgga gtttatcttt 120
gggcttctgg gcaatggcct tgccctgtgg attttctgtt tccacctcaa gtcctggaaa 180
tccagccgga ttttcctgtt caacctggca gtagctgact ttctactgat catctgcctg 240
ccgttcgtga tggactacta tgtgcggcgt tcagactgga actttgggga catcccttgc 300
cggctggtgc tcttcatgtt tgccatgaac cgccagggca gcatcatctt cctcacggtg 360
gtggcggtag acaggtattt ccgggtggtc catccccacc acgccctgaa caagatctcc 420
aattggacag cagccatcat ctcttgcctt ctgtggggca tcactgttgg cctaacagtc 480
cacctcctga agaagaagtt gctgatccag aatggccctg caaatgtgtg catcagcttc 540
agcatctgcc ataccttccg gtggcacgaa gctatgttcc tcctggagtt cctcctgccc 600
ctgggcatca tcctgttctg ctcagccaga attatctgga gcctgcggca gagacaaatg 660
gaccggcatg ccaagatcaa gagagccatc accttcatca tggtggtggc catcgtcttt 720
gtcatctgct tccttcccag cgtggttgtg cggatccgca tcttctggct cctgcacact 780
tcgggcacgc agaattgtga agtgtaccgc tcggtggacc tggcgttctt tatcactctc 840
agcttcacct acatgaacag catgctggac cccgtggtgt actacttctc cagcccatcc 900
tttcccaact tcttctccac tttgatcaac cgctgcctcc agaggaagat gacaggtgag 960
ccagataata accgcagcac gagcgtcgag ctcacagggg accccaacaa aaccagaggc 1020
gctccagagg cgttaatggc caactccggt gagccatgga gcccctctta tctgggccca 1080
acctcaaata accattccaa gaagggacat tgtcaccaag aaccagcatc tctggagaaa 1140
cagttgggct gttgcatcga gtaa 1164

<210> SEQ ID NO 108
<211> LENGTH: 387
<212> TYPE: PRT
<213> ORGANISM: Homo sapiens

<400> SEQUENCE: 108

Met Asn Arg His His Leu Gln Asp His Phe Leu Glu Ile Asp Lys Lys
1 5 10 15

-continued

```
Asn Cys Cys Val Phe Arg Asp Asp Phe Ile Ala Lys Val Leu Pro Pro
            20                  25                  30

Val Leu Gly Leu Glu Phe Ile Phe Gly Leu Leu Gly Asn Gly Leu Ala
        35                  40                  45

Leu Trp Ile Phe Cys Phe His Leu Lys Ser Trp Lys Ser Ser Arg Ile
    50                  55                  60

Phe Leu Phe Asn Leu Ala Val Ala Asp Phe Leu Leu Ile Ile Cys Leu
65                  70                  75                  80

Pro Phe Val Met Asp Tyr Tyr Val Arg Arg Ser Asp Trp Asn Phe Gly
                85                  90                  95

Asp Ile Pro Cys Arg Leu Val Leu Phe Met Phe Ala Met Asn Arg Gln
            100                 105                 110

Gly Ser Ile Ile Phe Leu Thr Val Val Ala Val Asp Arg Tyr Phe Arg
        115                 120                 125

Val Val His Pro His His Ala Leu Asn Lys Ile Ser Asn Trp Thr Ala
    130                 135                 140

Ala Ile Ile Ser Cys Leu Leu Trp Gly Ile Thr Val Gly Leu Thr Val
145                 150                 155                 160

His Leu Leu Lys Lys Lys Leu Leu Ile Gln Asn Gly Pro Ala Asn Val
                165                 170                 175

Cys Ile Ser Phe Ser Ile Cys His Thr Phe Arg Trp His Glu Ala Met
            180                 185                 190

Phe Leu Leu Glu Phe Leu Leu Pro Leu Gly Ile Ile Leu Phe Cys Ser
        195                 200                 205

Ala Arg Ile Ile Trp Ser Leu Arg Gln Arg Gln Met Asp Arg His Ala
    210                 215                 220

Lys Ile Lys Arg Ala Ile Thr Phe Ile Met Val Val Ala Ile Val Phe
225                 230                 235                 240

Val Ile Cys Phe Leu Pro Ser Val Val Val Arg Ile Arg Ile Phe Trp
                245                 250                 255

Leu Leu His Thr Ser Gly Thr Gln Asn Cys Glu Val Tyr Arg Ser Val
            260                 265                 270

Asp Leu Ala Phe Phe Ile Thr Leu Ser Phe Thr Tyr Met Asn Ser Met
        275                 280                 285

Leu Asp Pro Val Val Tyr Tyr Phe Ser Ser Pro Ser Phe Pro Asn Phe
    290                 295                 300

Phe Ser Thr Leu Ile Asn Arg Cys Leu Gln Arg Lys Met Thr Gly Glu
305                 310                 315                 320

Pro Asp Asn Asn Arg Ser Thr Ser Val Glu Leu Thr Gly Asp Pro Asn
                325                 330                 335

Lys Thr Arg Gly Ala Pro Glu Ala Leu Met Ala Asn Ser Gly Glu Pro
            340                 345                 350

Trp Ser Pro Ser Tyr Leu Gly Pro Thr Ser Asn Asn His Ser Lys Lys
        355                 360                 365

Gly His Cys His Gln Glu Pro Ala Ser Leu Glu Lys Gln Leu Gly Cys
    370                 375                 380

Cys Ile Glu
385
```

<210> SEQ ID NO 109
<211> LENGTH: 37
<212> TYPE: DNA
<213> ORGANISM: Artificial Sequence
<220> FEATURE:

-continued

<223> OTHER INFORMATION: Novel Sequence

<400> SEQUENCE: 109
accatggctt gcaatggcag tgcggccagg gggcact 37

<210> SEQ ID NO 110
<211> LENGTH: 39
<212> TYPE: DNA
<213> ORGANISM: Artificial Sequence
<220> FEATURE:
<223> OTHER INFORMATION: Novel Sequence

<400> SEQUENCE: 110
cgaccaggac aaacagcatc ttggtcactt gtctccggc 39

<210> SEQ ID NO 111
<211> LENGTH: 39
<212> TYPE: DNA
<213> ORGANISM: Artificial Sequence
<220> FEATURE:
<223> OTHER INFORMATION: Novel Sequence

<400> SEQUENCE: 111
gaccaagatg ctgtttgtcc tggtcgtggt gtttggcat 39

<210> SEQ ID NO 112
<211> LENGTH: 35
<212> TYPE: DNA
<213> ORGANISM: Artificial Sequence
<220> FEATURE:
<223> OTHER INFORMATION: Novel Sequence

<400> SEQUENCE: 112
cggaattcag gatggatcgg tctcttgctg cgcct 35

<210> SEQ ID NO 113
<211> LENGTH: 1212
<212> TYPE: DNA
<213> ORGANISM: Homo sapiens

<400> SEQUENCE: 113
atggcttgca atggcagtgc ggccaggggg cactttgacc ctgaggactt gaacctgact 60
gacgaggcac tgagactcaa gtacctgggg ccccagcaga cagagctgtt catgcccatc 120
tgtgccacat acctgctgat cttcgtggtg ggcgctgtgg gcaatgggct gacctgtctg 180
gtcatcctgc gccacaaggc catgcgcacg cctaccaact actacctctt cagcctggcc 240
gtgtcggacc tgctggtgct gctggtgggc ctgcccctgg agctctatga gatgtggcac 300
aactacccct tcctgctggg cgttggtggc tgctatttcc gcacgctact gtttgagatg 360
gtctgcctgg cctcagtgct caacgtcact gccctgagcg tggaacgcta tgtggccgtg 420
gtgcacccac tccaggccag gtccatggtg acgcgggccc atgtgcgccg agtgcttggg 480
gccgtctggg gtcttgccat gctctgctcc ctgcccaaca ccagcctgca cggcatccgg 540
cagctgcacg tgccctgccg gggcccagtg ccagactcag ctgtttgcat gctggtccgc 600
ccacgggccc tctacaacat ggtagtgcag accaccgcgc tgctcttctt ctgcctgccc 660
atggccatca tgagcgtgct ctacctgctc attgggctgc gactgcggcg ggagaggctg 720
ctgctcatgc aggaggccaa gggcaggggc tctgcagcag ccaggtccag atacacctgc 780
aggctccagc agcacgatcg gggccggaga caagtgacca agatgctgtt tgtcctggtc 840
gtggtgtttg gcatctgctg ggccccgttc cacgccgacc gcgtcatgtg gagcgtcgtg 900

-continued

```
tcacagtgga cagatggcct gcacctggcc ttccagcacg tgcacgtcat ctccggcatc    960

ttcttctacc tgggctcggc ggccaacccc gtgctctata gcctcatgtc cagccgcttc   1020

cgagagacct tccaggaggc cctgtgcctc ggggcctgct gccatcgcct cagaccccgc   1080

cacagctccc acagcctcag caggatgacc acaggcagca ccctgtgtga tgtgggctcc   1140

ctgggcagct gggtccaccc cctggctggg aacgatggcc cagaggcgca gcaagagacc   1200

gatccatcct ga                                                       1212
```

<210> SEQ ID NO 114
<211> LENGTH: 403
<212> TYPE: PRT
<213> ORGANISM: Homo sapiens

<400> SEQUENCE: 114

```
Met Ala Cys Asn Gly Ser Ala Ala Arg Gly His Phe Asp Pro Glu Asp
1               5                   10                  15

Leu Asn Leu Thr Asp Glu Ala Leu Arg Leu Lys Tyr Leu Gly Pro Gln
            20                  25                  30

Gln Thr Glu Leu Phe Met Pro Ile Cys Ala Thr Tyr Leu Leu Ile Phe
        35                  40                  45

Val Val Gly Ala Val Gly Asn Gly Leu Thr Cys Leu Val Ile Leu Arg
    50                  55                  60

His Lys Ala Met Arg Thr Pro Thr Asn Tyr Tyr Leu Phe Ser Leu Ala
65                  70                  75                  80

Val Ser Asp Leu Leu Val Leu Leu Val Gly Leu Pro Leu Glu Leu Tyr
                85                  90                  95

Glu Met Trp His Asn Tyr Pro Phe Leu Leu Gly Val Gly Gly Cys Tyr
            100                 105                 110

Phe Arg Thr Leu Leu Phe Glu Met Val Cys Leu Ala Ser Val Leu Asn
        115                 120                 125

Val Thr Ala Leu Ser Val Glu Arg Tyr Val Ala Val Val His Pro Leu
    130                 135                 140

Gln Ala Arg Ser Met Val Thr Arg Ala His Val Arg Arg Val Leu Gly
145                 150                 155                 160

Ala Val Trp Gly Leu Ala Met Leu Cys Ser Leu Pro Asn Thr Ser Leu
                165                 170                 175

His Gly Ile Arg Gln Leu His Val Pro Cys Arg Gly Pro Val Pro Asp
            180                 185                 190

Ser Ala Val Cys Met Leu Val Arg Pro Arg Ala Leu Tyr Asn Met Val
        195                 200                 205

Val Gln Thr Thr Ala Leu Leu Phe Phe Cys Leu Pro Met Ala Ile Met
    210                 215                 220

Ser Val Leu Tyr Leu Leu Ile Gly Leu Arg Leu Arg Arg Glu Arg Leu
225                 230                 235                 240

Leu Leu Met Gln Glu Ala Lys Gly Arg Gly Ser Ala Ala Ala Arg Ser
                245                 250                 255

Arg Tyr Thr Cys Arg Leu Gln Gln His Asp Arg Gly Arg Arg Gln Val
            260                 265                 270

Thr Lys Met Leu Phe Val Leu Val Val Val Phe Gly Ile Cys Trp Ala
        275                 280                 285

Pro Phe His Ala Asp Arg Val Met Trp Ser Val Val Ser Gln Trp Thr
    290                 295                 300

Asp Gly Leu His Leu Ala Phe Gln His Val His Val Ile Ser Gly Ile
```

-continued

```
305                 310                 315                 320

Phe Phe Tyr Leu Gly Ser Ala Ala Asn Pro Val Leu Tyr Ser Leu Met
                325                 330                 335

Ser Ser Arg Phe Arg Glu Thr Phe Gln Glu Ala Leu Cys Leu Gly Ala
            340                 345                 350

Cys Cys His Arg Leu Arg Pro Arg His Ser Ser His Ser Leu Ser Arg
        355                 360                 365

Met Thr Thr Gly Ser Thr Leu Cys Asp Val Gly Ser Leu Gly Ser Trp
    370                 375                 380

Val His Pro Leu Ala Gly Asn Asp Gly Pro Glu Ala Gln Gln Glu Thr
385                 390                 395                 400

Asp Pro Ser


<210> SEQ ID NO 115
<211> LENGTH: 30
<212> TYPE: DNA
<213> ORGANISM: Artificial Sequence
<220> FEATURE:
<223> OTHER INFORMATION: Novel Sequence

<400> SEQUENCE: 115

ggaagcttca ggcccaaaga tggggaacat                                        30


<210> SEQ ID NO 116
<211> LENGTH: 30
<212> TYPE: DNA
<213> ORGANISM: Artificial Sequence
<220> FEATURE:
<223> OTHER INFORMATION: Novel Sequence

<400> SEQUENCE: 116

gtggatccac ccgcggagga cccaggctag                                        30


<210> SEQ ID NO 117
<211> LENGTH: 1098
<212> TYPE: DNA
<213> ORGANISM: Homo sapiens

<400> SEQUENCE: 117

atggggaaca tcactgcaga caactcctcg atgagctgta ccatcgacca taccatccac     60

cagacgctgg ccccggtggt ctatgttacc gtgctggtgg tgggcttccc ggccaactgc    120

ctgtccctct acttcggcta cctgcagatc aaggcccgga acgagctggg cgtgtacctg    180

tgcaacctga cggtggccga cctcttctac atctgctcgc tgcccttctg gctgcagtac    240

gtgctgcagc acgacaactg gtctcacggc gacctgtcct gccaggtgtg cggcatcctc    300

ctgtacgaga acatctacat cagcgtgggc ttcctctgct gcatctccgt ggaccgctac    360

ctggctgtgg cccatccctt ccgcttccac cagttccgga ccctgaaggc ggccgtcggc    420

gtcagcgtgg tcatctgggc caaggagctg ctgaccagca tctacttcct gatgcacgag    480

gaggtcatcg aggacgagaa ccagcaccgc gtgtgctttg agcactaccc catccaggca    540

tggcagcgcg ccatcaacta ctaccgcttc ctggtgggct tcctcttccc catctgcctg    600

ctgctggcgt cctaccaggg catcctgcgc gccgtgcgcc ggagccacgg cacccagaag    660

agccgcaagg accagatcca gcggctggtg ctcagcaccg tggtcatctt cctggcctgc    720

ttcctgccct accacgtgtt gctgctggtg cgcagcgtct gggaggccag ctgcgacttc    780

gccaagggcg ttttcaacgc ctaccacttc tccctcctgc tcaccagctt caactgcgtc    840
```

-continued

```
gccgaccccg tgctctactg cttcgtcagc gagaccaccc accgggacct ggcccgcctc    900

cgcggggcct gcctggcctt cctcacctgc tccaggaccg gccgggccag ggaggcctac    960

ccgctgggtg cccccgaggc ctccgggaaa agcggggccc agggtgagga gcccgagctg   1020

ttgaccaagc tccacccggc cttccagacc cctaactcgc cagggtcggg cgggttcccc   1080

acgggcaggt tggcctag                                                 1098
```

<210> SEQ ID NO 118
<211> LENGTH: 365
<212> TYPE: PRT
<213> ORGANISM: Homo sapiens

<400> SEQUENCE: 118

```
Met Gly Asn Ile Thr Ala Asp Asn Ser Ser Met Ser Cys Thr Ile Asp
1               5                   10                  15

His Thr Ile His Gln Thr Leu Ala Pro Val Val Tyr Val Thr Val Leu
            20                  25                  30

Val Val Gly Phe Pro Ala Asn Cys Leu Ser Leu Tyr Phe Gly Tyr Leu
        35                  40                  45

Gln Ile Lys Ala Arg Asn Glu Leu Gly Val Tyr Leu Cys Asn Leu Thr
    50                  55                  60

Val Ala Asp Leu Phe Tyr Ile Cys Ser Leu Pro Phe Trp Leu Gln Tyr
65                  70                  75                  80

Val Leu Gln His Asp Asn Trp Ser His Gly Asp Leu Ser Cys Gln Val
                85                  90                  95

Cys Gly Ile Leu Leu Tyr Glu Asn Ile Tyr Ile Ser Val Gly Phe Leu
            100                 105                 110

Cys Cys Ile Ser Val Asp Arg Tyr Leu Ala Val Ala His Pro Phe Arg
        115                 120                 125

Phe His Gln Phe Arg Thr Leu Lys Ala Ala Val Gly Val Ser Val Val
    130                 135                 140

Ile Trp Ala Lys Glu Leu Leu Thr Ser Ile Tyr Phe Leu Met His Glu
145                 150                 155                 160

Glu Val Ile Glu Asp Glu Asn Gln His Arg Val Cys Phe Glu His Tyr
                165                 170                 175

Pro Ile Gln Ala Trp Gln Arg Ala Ile Asn Tyr Tyr Arg Phe Leu Val
            180                 185                 190

Gly Phe Leu Phe Pro Ile Cys Leu Leu Leu Ala Ser Tyr Gln Gly Ile
        195                 200                 205

Leu Arg Ala Val Arg Arg Ser His Gly Thr Gln Lys Ser Arg Lys Asp
    210                 215                 220

Gln Ile Gln Arg Leu Val Leu Ser Thr Val Val Ile Phe Leu Ala Cys
225                 230                 235                 240

Phe Leu Pro Tyr His Val Leu Leu Leu Val Arg Ser Val Trp Glu Ala
                245                 250                 255

Ser Cys Asp Phe Ala Lys Gly Val Phe Asn Ala Tyr His Phe Ser Leu
            260                 265                 270

Leu Leu Thr Ser Phe Asn Cys Val Ala Asp Pro Val Leu Tyr Cys Phe
        275                 280                 285

Val Ser Glu Thr Thr His Arg Asp Leu Ala Arg Leu Arg Gly Ala Cys
    290                 295                 300

Leu Ala Phe Leu Thr Cys Ser Arg Thr Gly Arg Ala Arg Glu Ala Tyr
305                 310                 315                 320

Pro Leu Gly Ala Pro Glu Ala Ser Gly Lys Ser Gly Ala Gln Gly Glu
```

-continued

```
                325                 330                 335

Glu Pro Glu Leu Leu Thr Lys Leu His Pro Ala Phe Gln Thr Pro Asn
            340                 345                 350

Ser Pro Gly Ser Gly Gly Phe Pro Thr Gly Arg Leu Ala
        355                 360                 365


<210> SEQ ID NO 119
<211> LENGTH: 26
<212> TYPE: DNA
<213> ORGANISM: Artificial Sequence
<220> FEATURE:
<223> OTHER INFORMATION: Novel Sequence

<400> SEQUENCE: 119

gacctcgagt ccttctacac ctcatc                                            26


<210> SEQ ID NO 120
<211> LENGTH: 30
<212> TYPE: DNA
<213> ORGANISM: Artificial Sequence
<220> FEATURE:
<223> OTHER INFORMATION: Novel Sequence

<400> SEQUENCE: 120

tgctctagat tccagatagg tgaaaacttg                                        30


<210> SEQ ID NO 121
<211> LENGTH: 1416
<212> TYPE: DNA
<213> ORGANISM: Homo sapiens

<400> SEQUENCE: 121

atggatattc tttgtgaaga aaatacttct ttgagctcaa ctacgaactc cctaatgcaa      60

ttaaatgatg acaacaggct ctacagtaat gactttaact ccggagaagc taacacttct     120

gatgcattta actggacagt cgactctgaa aatcgaacca acctttcctg tgaagggtgc     180

ctctcaccgt cgtgtctctc cttacttcat ctccaggaaa aaaactggtc tgctttactg     240

acagccgtag tgattattct aactattgct ggaaacatac tcgtcatcat ggcagtgtcc     300

ctagagaaaa agctgcagaa tgccaccaac tatttcctga tgtcacttgc catagctgat     360

atgctgctgg gtttccttgt catgcccgtg tccatgttaa ccatcctgta tgggtaccgg     420

tggcctctgc cgagcaagct ttgtgcagtc tggatttacc tggacgtgct cttctccacg     480

gcctccatca tgcacctctg cgccatctcg ctggaccgct acgtcgccat ccagaatccc     540

atccaccaca gccgcttcaa ctccagaact aaggcatttc tgaaaatcat tgctgtttgg     600

accatatcag taggtatatc catgccaata ccagtctttg ggctacagga cgattcgaag     660

gtctttaagg aggggagttg cttactcgcc gatgataact ttgtcctgat cggctctttt     720

gtgtcatttt tcattccctt aaccatcatg gtgatcacct actttctaac tatcaagtca     780

ctccagaaag aagctacttt gtgtgtaagt gatcttggca cacgggccaa attagcttct     840

ttcagcttcc tccctcagag ttctttgtct tcagaaaagc tcttccagcg gtcgatccat     900

agggagccag ggtcctacac aggcaggagg actatgcagt ccatcagcaa tgagcaaaag     960

gcatgcaagg tgctgggcat cgtcttcttc ctgtttgtgg tgatgtggtg ccctttcttc    1020

atcacaaaca tcatggccgt catctgcaaa gagtcctgca atgaggatgt cattggggcc    1080

ctgctcaatg tgtttgtttg gatcggttat ctctcttcag cagtcaaccc actagtctac    1140

acactgttca acaagaccta taggtcagcc ttttcacggt atattcagtg tcagtacaag    1200
```

-continued

```
gaaaacaaaa aaccattgca gttaatttta gtgaacacaa taccggcttt ggcctacaag   1260

tctagccaac ttcaaatggg acaaaaaaag aattcaaagc aagatgccaa gacaacagat   1320

aatgactgct caatggttgc tctaggaaag cagtattctg aagaggcttc taaagacaat   1380

agcgacggag tgaatgaaaa ggtgagctgt gtgtga                              1416


<210> SEQ ID NO 122
<211> LENGTH: 471
<212> TYPE: PRT
<213> ORGANISM: Homo sapiens

<400> SEQUENCE: 122

Met Asp Ile Leu Cys Glu Glu Asn Thr Ser Leu Ser Ser Thr Thr Asn
1               5                   10                  15

Ser Leu Met Gln Leu Asn Asp Asp Asn Arg Leu Tyr Ser Asn Asp Phe
            20                  25                  30

Asn Ser Gly Glu Ala Asn Thr Ser Asp Ala Phe Asn Trp Thr Val Asp
        35                  40                  45

Ser Glu Asn Arg Thr Asn Leu Ser Cys Glu Gly Cys Leu Ser Pro Ser
    50                  55                  60

Cys Leu Ser Leu Leu His Leu Gln Glu Lys Asn Trp Ser Ala Leu Leu
65                  70                  75                  80

Thr Ala Val Val Ile Ile Leu Thr Ile Ala Gly Asn Ile Leu Val Ile
                85                  90                  95

Met Ala Val Ser Leu Glu Lys Lys Leu Gln Asn Ala Thr Asn Tyr Phe
            100                 105                 110

Leu Met Ser Leu Ala Ile Ala Asp Met Leu Leu Gly Phe Leu Val Met
        115                 120                 125

Pro Val Ser Met Leu Thr Ile Leu Tyr Gly Tyr Arg Trp Pro Leu Pro
    130                 135                 140

Ser Lys Leu Cys Ala Val Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
            180                 185                 190

Phe Leu Lys Ile Ile Ala Val Trp Thr Ile Ser Val Gly Ile Ser Met
        195                 200                 205

Pro Ile Pro Val Phe Gly Leu Gln Asp Asp Ser Lys Val Phe Lys Glu
    210                 215                 220

Gly Ser Cys Leu Leu Ala Asp Asp Asn Phe Val Leu Ile Gly Ser Phe
225                 230                 235                 240

Val Ser Phe Phe Ile Pro Leu Thr Ile Met Val Ile Thr Tyr Phe Leu
                245                 250                 255

Thr Ile Lys Ser Leu Gln Lys Glu Ala Thr Leu Cys Val Ser Asp Leu
            260                 265                 270

Gly Thr Arg Ala Lys Leu Ala Ser Phe Ser Phe Leu Pro Gln Ser Ser
        275                 280                 285

Leu Ser Ser Glu Lys Leu Phe Gln Arg Ser Ile His Arg Glu Pro Gly
    290                 295                 300

Ser Tyr Thr Gly Arg Arg Thr Met Gln Ser Ile Ser Asn Glu Gln Lys
305                 310                 315                 320

Ala Cys Lys Val Leu Gly Ile Val Phe Phe Leu Phe Val Val Met Trp
                325                 330                 335
```

-continued

```
Cys Pro Phe Phe Ile Thr Asn Ile Met Ala Val Ile Cys Lys Glu Ser
            340                 345                 350

Cys Asn Glu Asp Val Ile Gly Ala Leu Leu Asn Val Phe Val Trp Ile
        355                 360                 365

Gly Tyr Leu Ser Ser Ala Val Asn Pro Leu Val Tyr Thr Leu Phe Asn
    370                 375                 380

Lys Thr Tyr Arg Ser Ala Phe Ser Arg Tyr Ile Gln Cys Gln Tyr Lys
385                 390                 395                 400

Glu Asn Lys Lys Pro Leu Gln Leu Ile Leu Val Asn Thr Ile Pro Ala
                405                 410                 415

Leu Ala Tyr Lys Ser Ser Gln Leu Gln Met Gly Gln Lys Lys Asn Ser
            420                 425                 430

Lys Gln Asp Ala Lys Thr Thr Asp Asn Asp Cys Ser Met Val Ala Leu
        435                 440                 445

Gly Lys Gln Tyr Ser Glu Glu Ala Ser Lys Asp Asn Ser Asp Gly Val
    450                 455                 460

Asn Glu Lys Val Ser Cys Val
465                 470
```

<210> SEQ ID NO 123
<211> LENGTH: 27
<212> TYPE: DNA
<213> ORGANISM: Artificial Sequence
<220> FEATURE:
<223> OTHER INFORMATION: Novel Sequence

<400> SEQUENCE: 123

```
gacctcgagg ttgcttaaga ctgaagc                                          27
```

<210> SEQ ID NO 124
<211> LENGTH: 27
<212> TYPE: DNA
<213> ORGANISM: Artificial Sequence
<220> FEATURE:
<223> OTHER INFORMATION: Novel Sequence

<400> SEQUENCE: 124

```
atttctagac atatgtagct tgtaccg                                          27
```

<210> SEQ ID NO 125
<211> LENGTH: 1377
<212> TYPE: DNA
<213> ORGANISM: Homo sapiens

<400> SEQUENCE: 125

```
atggtgaacc tgaggaatgc ggtgcattca ttccttgtgc acctaattgg cctattggtt      60

tggcaatgtg atatttctgt gagcccagta gcagctatag taactgacat tttcaatacc     120

tccgatggtg gacgcttcaa attcccagac ggggtacaaa actggccagc actttcaatc     180

gtcatcataa taatcatgac aataggtggc aacatccttg tgatcatggc agtaagcatg     240

gaaaagaaac tgcacaatgc caccaattac ttcttaatgt ccctagccat tgctgatatg     300

ctagtgggac tacttgtcat gcccctgtct ctcctggcaa tcctttatga ttatgtctgg     360

ccactaccta gatatttgtg ccccgtctgg atttctttag atgttttatt ttcaacagcg     420

tccatcatgc acctctgcgc tatatcgctg gatcggtatg tagcaatacg taatcctatt     480

gagcatagcc gtttcaattc gcggactaag gccatcatga agattgctat tgtttgggca     540

atttctatag gtgtatcagt tcctatccct gtgattggac tgagggacga agaaaaggtg     600
```

-continued

```
ttcgtgaaca acacgacgtg cgtgctcaac gacccaaatt tcgttcttat tgggtccttc    660

gtagctttct tcataccgct gacgattatg gtgattacgt attgcctgac catctacgtt    720

ctgcgccgac aagctttgat gttactgcac ggccacaccg aggaaccgcc tggactaagt    780

ctggatttcc tgaagtgctg caagaggaat acggccgagg aagagaactc tgcaaaccct    840

aaccaagacc agaacgcacg ccgaagaaag aagaaggaga gacgtcctag gggcaccatg    900

caggctatca acaatgaaag aaaagcttcg aaagtccttg ggattgtttt ctttgtgttt    960

ctgatcatgt ggtgcccatt tttcattacc aatattctgt ctgttctttg tgagaagtcc   1020

tgtaaccaaa agctcatgga aaagcttctg aatgtgtttg tttggattgg ctatgtttgt   1080

tcaggaatca atcctctggt gtatactctg ttcaacaaaa tttaccgaag ggcattctcc   1140

aactatttgc gttgcaatta taaggtagag aaaaagcctc ctgtcaggca gattccaaga   1200

gttgccgcca ctgctttgtc tgggagggag cttaatgtta acatttatcg gcataccaat   1260

gaaccggtga tcgagaaagc cagtgacaat gagcccggta tagagatgca agttgagaat   1320

ttagagttac cagtaaatcc ctccagtgtg gttagcgaaa ggattagcag tgtgtga      1377


<210> SEQ ID NO 126
<211> LENGTH: 458
<212> TYPE: PRT
<213> ORGANISM: Homo sapiens

<400> SEQUENCE: 126

Met Val Asn Leu Arg Asn Ala Val His Ser Phe Leu Val His Leu Ile
1               5                   10                  15

Gly Leu Leu Val Trp Gln Cys Asp Ile Ser Val Ser Pro Val Ala Ala
            20                  25                  30

Ile Val Thr Asp Ile Phe Asn Thr Ser Asp Gly Gly Arg Phe Lys Phe
        35                  40                  45

Pro Asp Gly Val Gln Asn Trp Pro Ala Leu Ser Ile Val Ile Ile Ile
    50                  55                  60

Ile Met Thr Ile Gly Gly Asn Ile Leu Val Ile Met Ala Val Ser Met
65                  70                  75                  80

Glu Lys Lys Leu His Asn Ala Thr Asn Tyr Phe Leu Met Ser Leu Ala
                85                  90                  95

Ile Ala Asp Met Leu Val Gly Leu Leu Val Met Pro Leu Ser Leu Leu
            100                 105                 110

Ala Ile Leu Tyr Asp Tyr Val Trp Pro Leu Pro Arg Tyr Leu Cys Pro
        115                 120                 125

Val Trp Ile Ser Leu Asp Val Leu Phe Ser Thr Ala Ser Ile Met His
    130                 135                 140

Leu Cys Ala Ile Ser Leu Asp Arg Tyr Val Ala Ile Arg Asn Pro Ile
145                 150                 155                 160

Glu His Ser Arg Phe Asn Ser Arg Thr Lys Ala Ile Met Lys Ile Ala
                165                 170                 175

Ile Val Trp Ala Ile Ser Ile Gly Val Ser Val Pro Ile Pro Val Ile
            180                 185                 190

Gly Leu Arg Asp Glu Glu Lys Val Phe Val Asn Asn Thr Thr Cys Val
        195                 200                 205

Leu Asn Asp Pro Asn Phe Val Leu Ile Gly Ser Phe Val Ala Phe Phe
    210                 215                 220

Ile Pro Leu Thr Ile Met Val Ile Thr Tyr Cys Leu Thr Ile Tyr Val
225                 230                 235                 240
```

-continued

```
Leu Arg Arg Gln Ala Leu Met Leu Leu His Gly His Thr Glu Glu Pro
                245                 250                 255

Pro Gly Leu Ser Leu Asp Phe Leu Lys Cys Cys Lys Arg Asn Thr Ala
            260                 265                 270

Glu Glu Glu Asn Ser Ala Asn Pro Asn Gln Asp Gln Asn Ala Arg Arg
        275                 280                 285

Arg Lys Lys Lys Glu Arg Arg Pro Arg Gly Thr Met Gln Ala Ile Asn
    290                 295                 300

Asn Glu Arg Lys Ala Ser Lys Val Leu Gly Ile Val Phe Phe Val Phe
305                 310                 315                 320

Leu Ile Met Trp Cys Pro Phe Phe Ile Thr Asn Ile Leu Ser Val Leu
                325                 330                 335

Cys Glu Lys Ser Cys Asn Gln Lys Leu Met Glu Lys Leu Leu Asn Val
            340                 345                 350

Phe Val Trp Ile Gly Tyr Val Cys Ser Gly Ile Asn Pro Leu Val Tyr
        355                 360                 365

Thr Leu Phe Asn Lys Ile Tyr Arg Arg Ala Phe Ser Asn Tyr Leu Arg
    370                 375                 380

Cys Asn Tyr Lys Val Glu Lys Lys Pro Pro Val Arg Gln Ile Pro Arg
385                 390                 395                 400

Val Ala Ala Thr Ala Leu Ser Gly Arg Glu Leu Asn Val Asn Ile Tyr
                405                 410                 415

Arg His Thr Asn Glu Pro Val Ile Glu Lys Ala Ser Asp Asn Glu Pro
            420                 425                 430

Gly Ile Glu Met Gln Val Glu Asn Leu Glu Leu Pro Val Asn Pro Ser
        435                 440                 445

Ser Val Val Ser Glu Arg Ile Ser Ser Val
    450                 455
```

<210> SEQ ID NO 127
<211> LENGTH: 30
<212> TYPE: DNA
<213> ORGANISM: Artificial Sequence
<220> FEATURE:
<223> OTHER INFORMATION: Novel Sequence

<400> SEQUENCE: 127

```
ggtaagcttg gcagtccacg ccaggccttc                                    30
```

<210> SEQ ID NO 128
<211> LENGTH: 30
<212> TYPE: DNA
<213> ORGANISM: Artificial Sequence
<220> FEATURE:
<223> OTHER INFORMATION: Novel Sequence

<400> SEQUENCE: 128

```
tccgaattct ctgtagacac aaggctttgg                                    30
```

<210> SEQ ID NO 129
<211> LENGTH: 1068
<212> TYPE: DNA
<213> ORGANISM: Homo sapiens

<400> SEQUENCE: 129

```
atggatcagt tccctgaatc agtgacagaa aactttgagt acgatgattt ggctgaggcc     60

tgttatattg ggacatcgt ggtctttggg actgtgttcc tgtccatatt ctactccgtc    120
```

-continued

```
atctttgcca ttggcctggt gggaaatttg ttggtagtgt ttgccctcac caacagcaag    180

aagcccaaga gtgtcaccga catttacctc ctgaacctgg ccttgtctga tctgctgttt    240

gtagccactt tgcccttctg gactcactat ttgataaatg aaaagggcct ccacaatgcc    300

atgtgcaaat tcactaccgc cttcttcttc atcggctttt ttggaagcat attcttcatc    360

accgtcatca gcattgatag gtacctggcc atcgtcctgg ccgccaactc catgaacaac    420

cggaccgtgc agcatggcgt caccatcagc ctaggcgtct gggcagcagc cattttggtg    480

gcagcacccc agttcatgtt cacaaagcag aaagaaaatg aatgccttgg tgactacccc    540

gaggtcctcc aggaaatctg gcccgtgctc cgcaatgtgg aaacaaattt tcttggcttc    600

ctactccccc tgctcattat gagttattgc tacttcagaa tcatccagac gctgttttcc    660

tgcaagaacc acaagaaagc caaagccatt aaactgatcc ttctggtggt catcgtgttt    720

ttcctcttct ggacacccta caacgttatg attttcctgg agacgcttaa gctctatgac    780

ttctttccca gttgtgacat gaggaaggat ctgaggctgg ccctcagtgt gactgagacg    840

gttgcattta gccattgttg cctgaatcct ctcatctatg catttgctgg ggagaagttc    900

agaagatacc tttaccacct gtatgggaaa tgcctggctg tcctgtgtgg gcgctcagtc    960

cacgttgatt tctcctcatc tgaatcacaa aggagcaggc atggaagtgt tctgagcagc   1020

aattttactt accacacgag tgatggagat gcattgctcc ttctctga                1068
```

```
<210> SEQ ID NO 130
<211> LENGTH: 355
<212> TYPE: PRT
<213> ORGANISM: Homo sapiens

<400> SEQUENCE: 130

Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Val Phe Gly Thr Val
            20                  25                  30

Phe Leu Ser Ile Phe Tyr Ser Val Ile Phe Ala Ile Gly Leu Val Gly
        35                  40                  45

Asn Leu Leu Val Val Phe Ala Leu Thr Asn Ser Lys Lys Pro Lys Ser
    50                  55                  60

Val Thr Asp Ile Tyr Leu Leu Asn Leu Ala Leu Ser Asp Leu Leu Phe
65                  70                  75                  80

Val Ala Thr Leu Pro Phe Trp Thr His Tyr Leu Ile Asn Glu Lys Gly
                85                  90                  95

Leu His Asn Ala Met Cys Lys Phe Thr Thr Ala Phe Phe Phe Ile Gly
            100                 105                 110

Phe Phe Gly Ser Ile Phe Phe Ile Thr Val Ile Ser Ile Asp Arg Tyr
        115                 120                 125

Leu Ala Ile Val Leu Ala Ala Asn Ser Met Asn Asn Arg Thr Val Gln
    130                 135                 140

His Gly Val Thr Ile Ser Leu Gly Val Trp Ala Ala Ala Ile Leu Val
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Phe Leu Gly Phe Leu Leu Pro Leu Leu Ile Met Ser
        195                 200                 205
```

-continued

```
Tyr Cys Tyr Phe Arg Ile Ile Gln Thr Leu Phe Ser Cys Lys Asn His
    210                 215                 220

Lys Lys Ala Lys Ala Ile Lys Leu Ile Leu Leu Val Val Ile Val Phe
225                 230                 235                 240

Phe Leu Phe Trp Thr Pro Tyr Asn Val Met Ile Phe Leu Glu Thr Leu
                245                 250                 255

Lys Leu Tyr Asp Phe Phe Pro Ser Cys Asp Met Arg Lys Asp Leu Arg
            260                 265                 270

Leu Ala Leu Ser Val Thr Glu Thr Val Ala Phe Ser His Cys Cys Leu
        275                 280                 285

Asn Pro Leu Ile Tyr Ala Phe Ala Gly Glu Lys Phe Arg Arg Tyr Leu
    290                 295                 300

Tyr His Leu Tyr Gly Lys Cys Leu Ala Val Leu Cys Gly Arg Ser Val
305                 310                 315                 320

His Val Asp Phe Ser Ser Ser Glu Ser Gln Arg Ser Arg His Gly Ser
                325                 330                 335

Val Leu Ser Ser Asn Phe Thr Tyr His Thr Ser Asp Gly Asp Ala Leu
            340                 345                 350

Leu Leu Leu
        355


<210> SEQ ID NO 131
<211> LENGTH: 32
<212> TYPE: DNA
<213> ORGANISM: Artificial Sequence
<220> FEATURE:
<223> OTHER INFORMATION: Novel Sequence

<400> SEQUENCE: 131

gatctccagt aggcataagt ggacaattct gg                                32


<210> SEQ ID NO 132
<211> LENGTH: 30
<212> TYPE: DNA
<213> ORGANISM: Artificial Sequence
<220> FEATURE:
<223> OTHER INFORMATION: Novel Sequence

<400> SEQUENCE: 132

ctccttcggt cctcctatcg ttgtcagaag                                   30


<210> SEQ ID NO 133
<211> LENGTH: 30
<212> TYPE: DNA
<213> ORGANISM: Artificial Sequence
<220> FEATURE:
<223> OTHER INFORMATION: Novel Sequence

<400> SEQUENCE: 133

agaaggccaa gatcgcgcgg ctggccctca                                   30


<210> SEQ ID NO 134
<211> LENGTH: 30
<212> TYPE: DNA
<213> ORGANISM: Artificial Sequence
<220> FEATURE:
<223> OTHER INFORMATION: Novel Sequence

<400> SEQUENCE: 134

cggcgccacc gcacgaaaaa gctcatcttc                                   30
```

-continued

<210> SEQ ID NO 135
<211> LENGTH: 33
<212> TYPE: DNA
<213> ORGANISM: Artificial Sequence
<220> FEATURE:
<223> OTHER INFORMATION: Novel Sequence

<400> SEQUENCE: 135
gccaagaagc gggtgaagtt cctggtggtg gca 33

<210> SEQ ID NO 136
<211> LENGTH: 30
<212> TYPE: DNA
<213> ORGANISM: Artificial Sequence
<220> FEATURE:
<223> OTHER INFORMATION: Novel Sequence

<400> SEQUENCE: 136
caggcggaag gtgaaagtcc tggtcctcgt 30

<210> SEQ ID NO 137
<211> LENGTH: 33
<212> TYPE: DNA
<213> ORGANISM: Artificial Sequence
<220> FEATURE:
<223> OTHER INFORMATION: Novel Sequence

<400> SEQUENCE: 137
cggcgcctgc gggccaagcg gctggtggtg gtg 33

<210> SEQ ID NO 138
<211> LENGTH: 31
<212> TYPE: DNA
<213> ORGANISM: Artificial Sequence
<220> FEATURE:
<223> OTHER INFORMATION: Novel Sequence

<400> SEQUENCE: 138
ccaagcacaa agccaagaaa gtgaccatca c 31

<210> SEQ ID NO 139
<211> LENGTH: 30
<212> TYPE: DNA
<213> ORGANISM: Artificial Sequence
<220> FEATURE:
<223> OTHER INFORMATION: Novel Sequence

<400> SEQUENCE: 139
gcgccggcgc accaaatgct tgctggtggt 30

<210> SEQ ID NO 140
<211> LENGTH: 41
<212> TYPE: DNA
<213> ORGANISM: Artificial Sequence
<220> FEATURE:
<223> OTHER INFORMATION: Novel Sequence

<400> SEQUENCE: 140
caaaaagctg aagaaatcta agaagatcat ctttattgtc g 41

<210> SEQ ID NO 141
<211> LENGTH: 30
<212> TYPE: DNA
<213> ORGANISM: Artificial Sequence
<220> FEATURE:
<223> OTHER INFORMATION: Novel Sequence -continued

<400> SEQUENCE: 141
caagaccaag gcaaaacgca tgatcgccat 30

<210> SEQ ID NO 142
<211> LENGTH: 30
<212> TYPE: DNA
<213> ORGANISM: Artificial Sequence
<220> FEATURE:
<223> OTHER INFORMATION: Novel Sequence

<400> SEQUENCE: 142
gtcaaggaga agtccaaaag gatcatcatc 30

<210> SEQ ID NO 143
<211> LENGTH: 30
<212> TYPE: DNA
<213> ORGANISM: Artificial Sequence
<220> FEATURE:
<223> OTHER INFORMATION: Novel Sequence

<400> SEQUENCE: 143
cgccgcgtgc gggccaagca gctcctgctc 30

<210> SEQ ID NO 144
<211> LENGTH: 33
<212> TYPE: DNA
<213> ORGANISM: Artificial Sequence
<220> FEATURE:
<223> OTHER INFORMATION: Novel Sequence

<400> SEQUENCE: 144
cctgataagc gctataaaat ggtcctgttt cga 33

<210> SEQ ID NO 145
<211> LENGTH: 36
<212> TYPE: DNA
<213> ORGANISM: Artificial Sequence
<220> FEATURE:
<223> OTHER INFORMATION: Novel Sequence

<400> SEQUENCE: 145
gaaagacaaa agagagtcaa gaggatgtct ttattg 36

<210> SEQ ID NO 146
<211> LENGTH: 33
<212> TYPE: DNA
<213> ORGANISM: Artificial Sequence
<220> FEATURE:
<223> OTHER INFORMATION: Novel Sequence

<400> SEQUENCE: 146
cggagaaaga gggtgaaacg cacagccatc gcc 33

<210> SEQ ID NO 147
<211> LENGTH: 30
<212> TYPE: DNA
<213> ORGANISM: Artificial Sequence
<220> FEATURE:
<223> OTHER INFORMATION: Novel Sequence

<400> SEQUENCE: 147
aagcttcagc gggccaaggc actggtcacc 30

<210> SEQ ID NO 148
<211> LENGTH: 30

-continued

<212> TYPE: DNA
<213> ORGANISM: Artificial Sequence
<220> FEATURE:
<223> OTHER INFORMATION: Novel Sequence

<400> SEQUENCE: 148
cagcggcaga aggcaaaaag ggtggccatc 30

<210> SEQ ID NO 149
<211> LENGTH: 30
<212> TYPE: DNA
<213> ORGANISM: Artificial Sequence
<220> FEATURE:
<223> OTHER INFORMATION: Novel Sequence

<400> SEQUENCE: 149
cggcagaagg cgaagcgcat gatcctcgcg 30

<210> SEQ ID NO 150
<211> LENGTH: 30
<212> TYPE: DNA
<213> ORGANISM: Artificial Sequence
<220> FEATURE:
<223> OTHER INFORMATION: Novel Sequence

<400> SEQUENCE: 150
gagcgcaaca aggccaaaaa ggtgatcatc 30

<210> SEQ ID NO 151
<211> LENGTH: 39
<212> TYPE: DNA
<213> ORGANISM: Artificial Sequence
<220> FEATURE:
<223> OTHER INFORMATION: Novel Sequence

<400> SEQUENCE: 151
ggtgtaaaca aaaaggctaa aaacacaatt attcttatt 39

<210> SEQ ID NO 152
<211> LENGTH: 27
<212> TYPE: DNA
<213> ORGANISM: Artificial Sequence
<220> FEATURE:
<223> OTHER INFORMATION: Novel Sequence

<400> SEQUENCE: 152
gagagccagc tcaagagcac cgtggtg 27

<210> SEQ ID NO 153
<211> LENGTH: 30
<212> TYPE: DNA
<213> ORGANISM: Artificial Sequence
<220> FEATURE:
<223> OTHER INFORMATION: Novel Sequence

<400> SEQUENCE: 153
ccacaagcaa accaagaaaa tgctggctgt 30

<210> SEQ ID NO 154
<211> LENGTH: 30
<212> TYPE: DNA
<213> ORGANISM: Artificial Sequence
<220> FEATURE:
<223> OTHER INFORMATION: Novel Sequence

<400> SEQUENCE: 154

-continued catcaagtgt atcatgtgcc aagtacgccc 30

<210> SEQ ID NO 155
<211> LENGTH: 34
<212> TYPE: DNA
<213> ORGANISM: Artificial Sequence
<220> FEATURE:
<223> OTHER INFORMATION: Novel Sequence

<400> SEQUENCE: 155
ctagagagtc agatgaagtg tacagtagtg gcac 34

<210> SEQ ID NO 156
<211> LENGTH: 36
<212> TYPE: DNA
<213> ORGANISM: Artificial Sequence
<220> FEATURE:
<223> OTHER INFORMATION: Novel Sequence

<400> SEQUENCE: 156
cggacaaaag tgaaaactaa aaagatgttc ctcatt 36

<210> SEQ ID NO 157
<211> LENGTH: 33
<212> TYPE: DNA
<213> ORGANISM: Artificial Sequence
<220> FEATURE:
<223> OTHER INFORMATION: Novel Sequence

<400> SEQUENCE: 157
gctgaggttc gcaataaact aaccatgttt gtg 33

<210> SEQ ID NO 158
<211> LENGTH: 29
<212> TYPE: DNA
<213> ORGANISM: Artificial Sequence
<220> FEATURE:
<223> OTHER INFORMATION: Novel Sequence

<400> SEQUENCE: 158
gggaggccga gctgaaagcc accctgctc 29

<210> SEQ ID NO 159
<211> LENGTH: 31
<212> TYPE: DNA
<213> ORGANISM: Artificial Sequence
<220> FEATURE:
<223> OTHER INFORMATION: Novel Sequence

<400> SEQUENCE: 159
caagatcaag agagccaaaa ccttcatcat g 31

<210> SEQ ID NO 160
<211> LENGTH: 31
<212> TYPE: DNA
<213> ORGANISM: Artificial Sequence
<220> FEATURE:
<223> OTHER INFORMATION: Novel Sequence

<400> SEQUENCE: 160
ccggagacaa gtgaagaaga tgctgtttgt c 31

<210> SEQ ID NO 161
<211> LENGTH: 30
<212> TYPE: DNA
<213> ORGANISM: Artificial Sequence -continued
<220> FEATURE:
<223> OTHER INFORMATION: Novel Sequence

<400> SEQUENCE: 161
gcaaggacca gatcaagcgg ctggtgctca 30

<210> SEQ ID NO 162
<211> LENGTH: 34
<212> TYPE: DNA
<213> ORGANISM: Artificial Sequence
<220> FEATURE:
<223> OTHER INFORMATION: Novel Sequence

<400> SEQUENCE: 162
caagaaagcc aaagccaaga aactgatcct tctg 34

<210> SEQ ID NO 163
<211> LENGTH: 1068
<212> TYPE: DNA
<213> ORGANISM: Homo sapiens

<400> SEQUENCE: 163
atggaagatt tggaggaaac attatttgaa gaatttgaaa actattccta tgacctagac 60
tattactctc tggagtctga tttggaggag aaagtccagc tgggagttgt tcactgggtc 120
tccctggtgt tatattgttt ggcttttgtt ctgggaattc caggaaatgc catcgtcatt 180
tggttcacgg ggctcaagtg gaagaagaca gtcaccactc tgtggttcct caatctagcc 240
attgcggatt tcattttttct tctctttctg ccctgtaca tctcctatgt ggccatgaat 300
ttccactggc cctttggcat ctggctgtgc aaagccaatt ccttcactgc ccagttgaac 360
atgtttgcca gtgtttttt cctgacagtg atcagcctgg accactatat ccacttgatc 420
catcctgtct tatctcatcg gcatcgaacc ctcaagaact ctctgattgt cattatattc 480
atctggcttt tggcttctct aattggcggt cctgccctgt acttccggga cactgtggag 540
ttcaataatc atactctttg ctataacaat tttcagaagc atgatcctga cctcactttg 600
atcaggcacc atgttctgac ttgggtgaaa tttatcattg gctatctctt ccctttgcta 660
acaatgagta tttgctactt gtgtctcatc ttcaaggtga agaagcgaac agtcctgatc 720
tccagtaggc ataagtggac aattctggtt gtggttgtgg cctttgtggt ttgctggact 780
ccttatcacc tgtttagcat ttgggagctc accattcacc acaatagcta ttcccaccat 840
gtgatgcagg ctggaatccc cctctccact ggtttggcat tcctcaatag ttgcttgaac 900
cccatccttt atgtcctaat tagtaagaag ttccaagctc gcttccggtc ctcagttgct 960
gagatactca agtacacact gtgggaagtc agctgttctg gcacagtgag tgaacagctc 1020
aggaactcag aaaccaagaa tctgtgtctc ctggaaacag ctcaataa 1068

<210> SEQ ID NO 164
<211> LENGTH: 355
<212> TYPE: PRT
<213> ORGANISM: Homo sapiens

<400> SEQUENCE: 164

Met Glu Asp Leu Glu Glu Thr Leu Phe Glu Glu Phe Glu Asn Tyr Ser
1               5                   10                  15

Tyr Asp Leu Asp Tyr Tyr Ser Leu Glu Ser Asp Leu Glu Glu Lys Val
            20                  25                  30

Gln Leu Gly Val Val His Trp Val Ser Leu Val Leu Tyr Cys Leu Ala
        35                  40                  45

-continued

```
Phe Val Leu Gly Ile Pro Gly Asn Ala Ile Val Ile Trp Phe Thr Gly
    50                  55                  60

Leu Lys Trp Lys Lys Thr Val Thr Thr Leu Trp Phe Leu Asn Leu Ala
65                  70                  75                  80

Ile Ala Asp Phe Ile Phe Leu Leu Phe Leu Pro Leu Tyr Ile Ser Tyr
                85                  90                  95

Val Ala Met Asn Phe His Trp Pro Phe Gly Ile Trp Leu Cys Lys Ala
            100                 105                 110

Asn Ser Phe Thr Ala Gln Leu Asn Met Phe Ala Ser Val Phe Phe Leu
        115                 120                 125

Thr Val Ile Ser Leu Asp His Tyr Ile His Leu Ile His Pro Val Leu
    130                 135                 140

Ser His Arg His Arg Thr Leu Lys Asn Ser Leu Ile Val Ile Ile Phe
145                 150                 155                 160

Ile Trp Leu Leu Ala Ser Leu Ile Gly Gly Pro Ala Leu Tyr Phe Arg
                165                 170                 175

Asp Thr Val Glu Phe Asn Asn His Thr Leu Cys Tyr Asn Asn Phe Gln
            180                 185                 190

Lys His Asp Pro Asp Leu Thr Leu Ile Arg His His Val Leu Thr Trp
        195                 200                 205

Val Lys Phe Ile Ile Gly Tyr Leu Phe Pro Leu Leu Thr Met Ser Ile
    210                 215                 220

Cys Tyr Leu Cys Leu Ile Phe Lys Val Lys Lys Arg Thr Val Leu Ile
225                 230                 235                 240

Ser Ser Arg His Lys Trp Thr Ile Leu Val Val Val Val Ala Phe Val
                245                 250                 255

Val Cys Trp Thr Pro Tyr His Leu Phe Ser Ile Trp Glu Leu Thr Ile
            260                 265                 270

His His Asn Ser Tyr Ser His His Val Met Gln Ala Gly Ile Pro Leu
        275                 280                 285

Ser Thr Gly Leu Ala Phe Leu Asn Ser Cys Leu Asn Pro Ile Leu Tyr
    290                 295                 300

Val Leu Ile Ser Lys Lys Phe Gln Ala Arg Phe Arg Ser Ser Val Ala
305                 310                 315                 320

Glu Ile Leu Lys Tyr Thr Leu Trp Glu Val Ser Cys Ser Gly Thr Val
                325                 330                 335

Ser Glu Gln Leu Arg Asn Ser Glu Thr Lys Asn Leu Cys Leu Leu Glu
            340                 345                 350

Thr Ala Gln
        355
```

<210> SEQ ID NO 165
<211> LENGTH: 1089
<212> TYPE: DNA
<213> ORGANISM: Homo sapiens

<400> SEQUENCE: 165

```
atgggcaacc acacgtggga gggctgccac gtggactcgc gcgtggacca cctctttccg      60

ccatccctct acatctttgt catcggcgtg gggctgccca ccaactgcct ggctctgtgg     120

gcggcctacc gccaggtgca acagcgcaac gagctgggcg tctacctgat gaacctcagc     180

atcgccgacc tgctgtacat ctgcacgctg ccgctgtggg tggactactt cctgcaccac     240

gacaactgga tccacggccc cgggtcctgc aagctctttg ggttcatctt ctacaccaat     300
```

-continued

```
atctacatca gcatcgcctt cctgtgctgc atctcggtgg accgctacct ggctgtggcc    360

cacccactcc gcttcgcccg cctgcgccgc gtcaagaccg ccgtggccgt gagctccgtg    420

gtctgggcca cggagctggg cgccaactcg gcgcccctgt tccatgacga gctcttccga    480

gaccgctaca accacacctt ctgctttgag aagttcccca tggaaggctg ggtggcctgg    540

atgaacctct atcgggtgtt cgtgggcttc ctcttcccgt gggcgctcat gctgctgtcg    600

taccggggca tcctgcgggc cgtgcggggc agcgtgtcca ccgagcgcca ggagaaggcc    660

aagatcgcgc ggctggccct cagcctcatc gccatcgtgc tggtctgctt tgcgccctat    720

cacgtgctct tgctgtcccg cagcgccatc tacctgggcc gcccctggga ctgcggcttc    780

gaggagcgcg tcttttctgc ataccacagc tcactggctt tcaccagcct caactgtgtg    840

gcggacccca tcctctactg cctggtcaac gagggcgccc gcagcgatgt ggccaaggcc    900

ctgcacaacc tgctccgctt tctggccagc gacaagcccc aggagatggc caatgcctcg    960

ctcaccctgg agaccccact cacctccaag aggaacagca cagccaaagc catgactggc   1020

agctgggcgg ccactccgcc ttcccagggg gaccaggtgc agctgaagat gctgccgcca   1080

gcacaatga                                                           1089


<210> SEQ ID NO 166
<211> LENGTH: 362
<212> TYPE: PRT
<213> ORGANISM: Homo sapiens

<400> SEQUENCE: 166

Met Gly Asn His Thr Trp Glu Gly Cys His Val Asp Ser Arg Val Asp
1               5                   10                  15

His Leu Phe Pro Pro Ser Leu Tyr Ile Phe Val Ile Gly Val Gly Leu
            20                  25                  30

Pro Thr Asn Cys Leu Ala Leu Trp Ala Ala Tyr Arg Gln Val Gln Gln
        35                  40                  45

Arg Asn Glu Leu Gly Val Tyr Leu Met Asn Leu Ser Ile Ala Asp Leu
    50                  55                  60

Leu Tyr Ile Cys Thr Leu Pro Leu Trp Val Asp Tyr Phe Leu His His
65                  70                  75                  80

Asp Asn Trp Ile His Gly Pro Gly Ser Cys Lys Leu Phe Gly Phe Ile
                85                  90                  95

Phe Tyr Thr Asn Ile Tyr Ile Ser Ile Ala Phe Leu Cys Cys Ile Ser
            100                 105                 110

Val Asp Arg Tyr Leu Ala Val Ala His Pro Leu Arg Phe Ala Arg Leu
        115                 120                 125

Arg Arg Val Lys Thr Ala Val Ala Val Ser Ser Val Val Trp Ala Thr
    130                 135                 140

Glu Leu Gly Ala Asn Ser Ala Pro Leu Phe His Asp Glu Leu Phe Arg
145                 150                 155                 160

Asp Arg Tyr Asn His Thr Phe Cys Phe Glu Lys Phe Pro Met Glu Gly
                165                 170                 175

Trp Val Ala Trp Met Asn Leu Tyr Arg Val Phe Val Gly Phe Leu Phe
            180                 185                 190

Pro Trp Ala Leu Met Leu Leu Ser Tyr Arg Gly Ile Leu Arg Ala Val
        195                 200                 205

Arg Gly Ser Val Ser Thr Glu Arg Gln Glu Lys Ala Lys Ile Ala Arg
    210                 215                 220

Leu Ala Leu Ser Leu Ile Ala Ile Val Leu Val Cys Phe Ala Pro Tyr
```

-continued

```
225                 230                 235                 240

His Val Leu Leu Leu Ser Arg Ser Ala Ile Tyr Leu Gly Arg Pro Trp
                245                 250                 255

Asp Cys Gly Phe Glu Glu Arg Val Phe Ser Ala Tyr His Ser Ser Leu
            260                 265                 270

Ala Phe Thr Ser Leu Asn Cys Val Ala Asp Pro Ile Leu Tyr Cys Leu
        275                 280                 285

Val Asn Glu Gly Ala Arg Ser Asp Val Ala Lys Ala Leu His Asn Leu
    290                 295                 300

Leu Arg Phe Leu Ala Ser Asp Lys Pro Gln Glu Met Ala Asn Ala Ser
305                 310                 315                 320

Leu Thr Leu Glu Thr Pro Leu Thr Ser Lys Arg Asn Ser Thr Ala Lys
                325                 330                 335

Ala Met Thr Gly Ser Trp Ala Ala Thr Pro Pro Ser Gln Gly Asp Gln
            340                 345                 350

Val Gln Leu Lys Met Leu Pro Pro Ala Gln
        355                 360
```

<210> SEQ ID NO 167
<211> LENGTH: 1002
<212> TYPE: DNA
<213> ORGANISM: Homo sapiens

<400> SEQUENCE: 167

```
atggagtcct caggcaaccc agagagcacc accttttttt actatgacct tcagagccag     60

ccgtgtgaga accaggcctg ggtctttgct accctcgcca ccactgtcct gtactgcctg    120

gtgtttctcc tcagcctagt gggcaacagc ctggtcctgt gggtcctggt gaagtatgag    180

agcctggagt ccctcaccaa catcttcatc ctcaacctgt gcctctcaga cctggtgttc    240

gcctgcttgt tgcctgtgtg gatctcccca taccactggg gctgggtgct gggagacttc    300

ctctgcaaac tcctcaatat gatcttctcc atcagcctct acagcagcat cttcttcctg    360

accatcatga ccatccaccg ctacctgtcg gtagtgagcc ccctctccac cctgcgcgtc    420

cccaccctcc gctgccgggt gctggtgacc atggctgtgt gggtagccag catcctgtcc    480

tccatcctcg acaccatctt ccacaaggtg ctttcttcgg gctgtgatta ttccgaactc    540

acgtggtacc tcacctccgt ctaccagcac aacctcttct tcctgctgtc cctggggatt    600

atcctgttct gctacgtgga gatcctcagg accctgttcc gctcacgctc caagcggcgc    660

caccgcacga aaaagctcat cttcgccatc gtggtggcct acttcctcag ctggggtccc    720

tacaacttca ccctgtttct gcagacgctg tttcggaccc agatcatccg gagctgcgag    780

gccaaacagc agctagaata cgccctgctc atctgccgca acctcgcctt ctcccactgc    840

tgctttaacc cggtgctcta tgtcttcgtg ggggtcaagt tccgcacaca cctgaaacat    900

gttctccggc agttctggtt ctgccggctg caggcaccca gcccagcctc gatcccccac    960

tcccctggtg ccttcgccta tgagggcgcc tccttctact ga                      1002
```

<210> SEQ ID NO 168
<211> LENGTH: 333
<212> TYPE: PRT
<213> ORGANISM: Homo sapiens

<400> SEQUENCE: 168

```
Met Glu Ser Ser Gly Asn Pro Glu Ser Thr Thr Phe Phe Tyr Tyr Asp
1               5                   10                  15
```

-continued

```
Leu Gln Ser Gln Pro Cys Glu Asn Gln Ala Trp Val Phe Ala Thr Leu
            20                  25                  30

Ala Thr Thr Val Leu Tyr Cys Leu Val Phe Leu Leu Ser Leu Val Gly
        35                  40                  45

Asn Ser Leu Val Leu Trp Val Leu Val Lys Tyr Glu Ser Leu Glu Ser
    50                  55                  60

Leu Thr Asn Ile Phe Ile Leu Asn Leu Cys Leu Ser Asp Leu Val Phe
65                  70                  75                  80

Ala Cys Leu Leu Pro Val Trp Ile Ser Pro Tyr His Trp Gly Trp Val
                85                  90                  95

Leu Gly Asp Phe Leu Cys Lys Leu Leu Asn Met Ile Phe Ser Ile Ser
            100                 105                 110

Leu Tyr Ser Ser Ile Phe Phe Leu Thr Ile Met Thr Ile His Arg Tyr
        115                 120                 125

Leu Ser Val Val Ser Pro Leu Ser Thr Leu Arg Val Pro Thr Leu Arg
    130                 135                 140

Cys Arg Val Leu Val Thr Met Ala Val Trp Val Ala Ser Ile Leu Ser
145                 150                 155                 160

Ser Ile Leu Asp Thr Ile Phe His Lys Val Leu Ser Ser Gly Cys Asp
                165                 170                 175

Tyr Ser Glu Leu Thr Trp Tyr Leu Thr Ser Val Tyr Gln His Asn Leu
            180                 185                 190

Phe Phe Leu Leu Ser Leu Gly Ile Ile Leu Phe Cys Tyr Val Glu Ile
        195                 200                 205

Leu Arg Thr Leu Phe Arg Ser Arg Ser Lys Arg Arg His Arg Thr Lys
    210                 215                 220

Lys Leu Ile Phe Ala Ile Val Val Ala Tyr Phe Leu Ser Trp Gly Pro
225                 230                 235                 240

Tyr Asn Phe Thr Leu Phe Leu Gln Thr Leu Phe Arg Thr Gln Ile Ile
                245                 250                 255

Arg Ser Cys Glu Ala Lys Gln Gln Leu Glu Tyr Ala Leu Leu Ile Cys
            260                 265                 270

Arg Asn Leu Ala Phe Ser His Cys Cys Phe Asn Pro Val Leu Tyr Val
        275                 280                 285

Phe Val Gly Val Lys Phe Arg Thr His Leu Lys His Val Leu Arg Gln
    290                 295                 300

Phe Trp Phe Cys Arg Leu Gln Ala Pro Ser Pro Ala Ser Ile Pro His
305                 310                 315                 320

Ser Pro Gly Ala Phe Ala Tyr Glu Gly Ala Ser Phe Tyr
                325                 330
```

<210> SEQ ID NO 169
<211> LENGTH: 987
<212> TYPE: DNA
<213> ORGANISM: Homo sapiens

<400> SEQUENCE: 169

```
atggacaacg cctcgttctc ggagccctgg cccgccaacg catcgggccc ggacccggcg      60

ctgagctgct ccaacgcgtc gactctggcg ccgctgccgg cgccgctggc ggtggctgta     120

ccagttgtct acgcggtgat ctgcgccgtg ggtctggcgg gcaactccgc cgtgctgtac     180

gtgttgctgc gggcgccccg catgaagacc gtcaccaacc tgttcatcct caacctggcc     240

atcgccgacg agctcttcac gctggtgctg cccatcaaca tcgccgactt cctgctgcgg     300

cagtggccct tcggggagct catgtgcaag ctcatcgtgg ctatcgacca gtacaacacc     360
```

-continued ttctccagcc tctacttcct caccgtcatg agcgccgacc gctacctggt ggtgttggcc 420
actgcggagt cgcgccgggt ggccggccgc acctacagcg ccgcgcgcgc ggtgagcctg 480
gccgtgtggg ggatcgtcac actcgtcgtg ctgcccttcg cagtcttcgc ccggctagac 540
gacgagcagg gccggcgcca gtgcgtgcta gtctttccgc agcccgaggc cttctggtgg 600
cgcgcgagcc gcctctacac gctcgtgctg ggcttcgcca tccccgtgtc caccatctgt 660
gtcctctata ccaccctgct gtgccggctg catgccatgc ggctggacag ccacgccaag 720
gccctggagc gcgccaagaa gcgggtgaag ttcctggtgg tggcaatcct ggcggtgtgc 780
ctcctctgct ggacgcccta ccacctgagc accgtggtgg cgctcaccac cgacctcccg 840
cagacgccgc tggtcatcgc tatctcctac ttcatcacca gcctgacgta cgccaacagc 900
tgcctcaacc ccttcctcta cgccttcctg gacgccagct tccgcaggaa cctccgccag 960
ctgataactt gccgcgcggc agcctga 987

<210> SEQ ID NO 170
<211> LENGTH: 328
<212> TYPE: PRT
<213> ORGANISM: Homo sapiens

<400> SEQUENCE: 170

Met Asp Asn Ala Ser Phe Ser Glu Pro Trp Pro Ala Asn Ala Ser Gly
1 5 10 15

Pro Asp Pro Ala Leu Ser Cys Ser Asn Ala Ser Thr Leu Ala Pro Leu
20 25 30

Pro Ala Pro Leu Ala Val Ala Val Pro Val Val Tyr Ala Val Ile Cys
35 40 45

Ala Val Gly Leu Ala Gly Asn Ser Ala Val Leu Tyr Val Leu Leu Arg
50 55 60

Ala Pro Arg Met Lys Thr Val Thr Asn Leu Phe Ile Leu Asn Leu Ala
65 70 75 80

Ile Ala Asp Glu Leu Phe Thr Leu Val Leu Pro Ile Asn Ile Ala Asp
85 90 95

Phe Leu Leu Arg Gln Trp Pro Phe Gly Glu Leu Met Cys Lys Leu Ile
100 105 110

Val Ala Ile Asp Gln Tyr Asn Thr Phe Ser Ser Leu Tyr Phe Leu Thr
115 120 125

Val Met Ser Ala Asp Arg Tyr Leu Val Val Leu Ala Thr Ala Glu Ser
130 135 140

Arg Arg Val Ala Gly Arg Thr Tyr Ser Ala Ala Arg Ala Val Ser Leu
145 150 155 160

Ala Val Trp Gly Ile Val Thr Leu Val Val Leu Pro Phe Ala Val Phe
165 170 175

Ala Arg Leu Asp Asp Glu Gln Gly Arg Arg Gln Cys Val Leu Val Phe
180 185 190

Pro Gln Pro Glu Ala Phe Trp Trp Arg Ala Ser Arg Leu Tyr Thr Leu
195 200 205

Val Leu Gly Phe Ala Ile Pro Val Ser Thr Ile Cys Val Leu Tyr Thr
210 215 220

Thr Leu Leu Cys Arg Leu His Ala Met Arg Leu Asp Ser His Ala Lys
225 230 235 240

Ala Leu Glu Arg Ala Lys Lys Arg Val Lys Phe Leu Val Val Ala Ile
245 250 255

-continued

```
Leu Ala Val Cys Leu Leu Cys Trp Thr Pro Tyr His Leu Ser Thr Val
            260                 265                 270

Val Ala Leu Thr Thr Asp Leu Pro Gln Thr Pro Leu Val Ile Ala Ile
        275                 280                 285

Ser Tyr Phe Ile Thr Ser Leu Thr Tyr Ala Asn Ser Cys Leu Asn Pro
    290                 295                 300

Phe Leu Tyr Ala Phe Leu Asp Ala Ser Phe Arg Arg Asn Leu Arg Gln
305                 310                 315                 320

Leu Ile Thr Cys Arg Ala Ala Ala
                325


<210> SEQ ID NO 171
<211> LENGTH: 1002
<212> TYPE: DNA
<213> ORGANISM: Homo sapiens

<400> SEQUENCE: 171

atgcaggccg ctgggcaccc agagcccctt gacagcaggg gctccttctc cctccccacg     60

atgggtgcca acgtctctca ggacaatggc actggccaca atgccacctt ctccgagcca    120

ctgccgttcc tctatgtgct cctgcccgcc gtgtactccg ggatctgtgc tgtggggctg    180

actggcaaca cggccgtcat ccttgtaatc ctaagggcgc ccaagatgaa gacggtgacc    240

aacgtgttca tcctgaacct ggccgtcgcc gacgggctct tcacgctggt actgcctgtc    300

aacatcgcgg agcacctgct gcagtactgg cccttcgggg agctgctctg caagctggtg    360

ctggccgtcg accactacaa catcttctcc agcatctact tcctagccgt gatgagcgtg    420

gaccgatacc tggtggtgct ggccaccgtg aggtcccgcc acatgccctg gcgcacctac    480

cggggggcga aggtcgccag cctgtgtgtc tggctgggcg tcacggtcct ggttctgccc    540

ttcttctctt tcgctggcgt ctacagcaac gagctgcagg tcccaagctg tgggctgagc    600

ttcccgtggc ccgagcaggt ctggttcaag gccagccgtg tctacacgtt ggtcctgggc    660

ttcgtgctgc ccgtgtgcac catctgtgtg ctctacacag acctcctgcg caggctgcgg    720

gccgtgcggc tccgctctgg agccaaggct ctaggcaagg ccaggcggaa ggtgaaagtc    780

ctggtcctcg tcgtgctggc cgtgtgcctc ctctgctgga cgcccttcca cctggcctct    840

gtcgtggccc tgaccacgga cctgccccag accccactgg tcatcagtat gtcctacgtc    900

atcaccagcc tcacgtacgc caactcgtgc ctgaacccct tcctctacgc ctttctagat    960

gacaacttcc ggaagaactt ccgcagcata ttgcggtgct ga                      1002


<210> SEQ ID NO 172
<211> LENGTH: 333
<212> TYPE: PRT
<213> ORGANISM: Homo sapiens

<400> SEQUENCE: 172

Met Gln Ala Ala Gly His Pro Glu Pro Leu Asp Ser Arg Gly Ser Phe
1               5                   10                  15

Ser Leu Pro Thr Met Gly Ala Asn Val Ser Gln Asp Asn Gly Thr Gly
            20                  25                  30

His Asn Ala Thr Phe Ser Glu Pro Leu Pro Phe Leu Tyr Val Leu Leu
        35                  40                  45

Pro Ala Val Tyr Ser Gly Ile Cys Ala Val Gly Leu Thr Gly Asn Thr
    50                  55                  60

Ala Val Ile Leu Val Ile Leu Arg Ala Pro Lys Met Lys Thr Val Thr
65                  70                  75                  80
```

-continued

```
Asn Val Phe Ile Leu Asn Leu Ala Val Ala Asp Gly Leu Phe Thr Leu
                85                  90                  95

Val Leu Pro Val Asn Ile Ala Glu His Leu Leu Gln Tyr Trp Pro Phe
            100                 105                 110

Gly Glu Leu Leu Cys Lys Leu Val Leu Ala Val Asp His Tyr Asn Ile
        115                 120                 125

Phe Ser Ser Ile Tyr Phe Leu Ala Val Met Ser Val Asp Arg Tyr Leu
    130                 135                 140

Val Val Leu Ala Thr Val Arg Ser Arg His Met Pro Trp Arg Thr Tyr
145                 150                 155                 160

Arg Gly Ala Lys Val Ala Ser Leu Cys Val Trp Leu Gly Val Thr Val
                165                 170                 175

Leu Val Leu Pro Phe Phe Ser Phe Ala Gly Val Tyr Ser Asn Glu Leu
            180                 185                 190

Gln Val Pro Ser Cys Gly Leu Ser Phe Pro Trp Pro Glu Gln Val Trp
        195                 200                 205

Phe Lys Ala Ser Arg Val Tyr Thr Leu Val Leu Gly Phe Val Leu Pro
    210                 215                 220

Val Cys Thr Ile Cys Val Leu Tyr Thr Asp Leu Leu Arg Arg Leu Arg
225                 230                 235                 240

Ala Val Arg Leu Arg Ser Gly Ala Lys Ala Leu Gly Lys Ala Arg Arg
                245                 250                 255

Lys Val Lys Val Leu Val Leu Val Val Leu Ala Val Cys Leu Leu Cys
            260                 265                 270

Trp Thr Pro Phe His Leu Ala Ser Val Val Ala Leu Thr Thr Asp Leu
        275                 280                 285

Pro Gln Thr Pro Leu Val Ile Ser Met Ser Tyr Val Ile Thr Ser Leu
    290                 295                 300

Thr Tyr Ala Asn Ser Cys Leu Asn Pro Phe Leu Tyr Ala Phe Leu Asp
305                 310                 315                 320

Asp Asn Phe Arg Lys Asn Phe Arg Ser Ile Leu Arg Cys
                325                 330


<210> SEQ ID NO 173
<211> LENGTH: 1107
<212> TYPE: DNA
<213> ORGANISM: Homo sapiens

<400> SEQUENCE: 173

atggtccttg aggtgagtga ccaccaagtg ctaaatgacg ccgaggttgc cgccctcctg      60

gagaacttca gctcttccta tgactatgga gaaaacgaga gtgactcgtg ctgtacctcc     120

ccgccctgcc cacaggactt cagcctgaac ttcgaccggg ccttcctgcc agccctctac     180

agcctcctct ttctgctggg gctgctgggc aacggcgcgg tggcagccgt gctgctgagc     240

cggcggacag ccctgagcag caccgacacc ttcctgctcc acctagctgt agcagacacg     300

ctgctggtgc tgacactgcc gctctgggca gtggacgctg ccgtccagtg ggtctttggc     360

tctggcctct gcaaagtggc aggtgccctc ttcaacatca acttctacgc aggagccctc     420

ctgctggcct gcatcagctt tgaccgctac ctgaacatag ttcatgccac ccagctctac     480

cgccgggggc ccccggcccg cgtgaccctc acctgcctgg ctgtctgggg gctctgcctg     540

cttttcgccc tcccagactt catcttcctg tcggcccacc acgacgagcg cctcaacgcc     600

acccactgcc aatacaactt cccacaggtg ggccgcacgg ctctgcgggt gctgcagctg     660
```

-continued

```
gtggctggct ttctgctgcc cctgctggtc atggcctact gctatgccca catcctggcc    720

gtgctgctgg tttccagggg ccagcggcgc ctgcgggcca agcggctggt ggtggtggtc    780

gtggtggcct ttgccctctg ctggaccccc tatcacctgg tggtgctggt ggacatcctc    840

atggacctgg gcgctttggc ccgcaactgt ggccgagaaa gcagggtaga cgtggccaag    900

tcggtcacct caggcctggg ctacatgcac tgctgcctca acccgctgct ctatgccttt    960

gtaggggtca agttccggga gcggatgtgg atgctgctct tgcgcctggg ctgccccaac   1020

cagagagggc tccagaggca gccatcgtct tcccgccggg attcatcctg gtctgagacc   1080

tcagaggcct cctactcggg cttgtga                                        1107
```

```
<210> SEQ ID NO 174
<211> LENGTH: 368
<212> TYPE: PRT
<213> ORGANISM: Homo sapiens

<400> SEQUENCE: 174

Met Val Leu Glu Val Ser Asp His Gln Val Leu Asn Asp Ala Glu Val
1               5                   10                  15

Ala Ala Leu Leu Glu Asn Phe Ser Ser Ser Tyr Asp Tyr Gly Glu Asn
            20                  25                  30

Glu Ser Asp Ser Cys Cys Thr Ser Pro Pro Cys Pro Gln Asp Phe Ser
        35                  40                  45

Leu Asn Phe Asp Arg Ala Phe Leu Pro Ala Leu Tyr Ser Leu Leu Phe
    50                  55                  60

Leu Leu Gly Leu Leu Gly Asn Gly Ala Val Ala Ala Val Leu Leu Ser
65                  70                  75                  80

Arg Arg Thr Ala Leu Ser Ser Thr Asp Thr Phe Leu Leu His Leu Ala
                85                  90                  95

Val Ala Asp Thr Leu Leu Val Leu Thr Leu Pro Leu Trp Ala Val Asp
            100                 105                 110

Ala Ala Val Gln Trp Val Phe Gly Ser Gly Leu Cys Lys Val Ala Gly
        115                 120                 125

Ala Leu Phe Asn Ile Asn Phe Tyr Ala Gly Ala Leu Leu Leu Ala Cys
    130                 135                 140

Ile Ser Phe Asp Arg Tyr Leu Asn Ile Val His Ala Thr Gln Leu Tyr
145                 150                 155                 160

Arg Arg Gly Pro Pro Ala Arg Val Thr Leu Thr Cys Leu Ala Val Trp
                165                 170                 175

Gly Leu Cys Leu Leu Phe Ala Leu Pro Asp Phe Ile Phe Leu Ser Ala
            180                 185                 190

His His Asp Glu Arg Leu Asn Ala Thr His Cys Gln Tyr Asn Phe Pro
        195                 200                 205

Gln Val Gly Arg Thr Ala Leu Arg Val Leu Gln Leu Val Ala Gly Phe
    210                 215                 220

Leu Leu Pro Leu Leu Val Met Ala Tyr Cys Tyr Ala His Ile Leu Ala
225                 230                 235                 240

Val Leu Leu Val Ser Arg Gly Gln Arg Arg Leu Arg Ala Lys Arg Leu
                245                 250                 255

Val Val Val Val Val Val Ala Phe Ala Leu Cys Trp Thr Pro Tyr His
            260                 265                 270

Leu Val Val Leu Val Asp Ile Leu Met Asp Leu Gly Ala Leu Ala Arg
        275                 280                 285

Asn Cys Gly Arg Glu Ser Arg Val Asp Val Ala Lys Ser Val Thr Ser
```

-continued

```
    290                 295                 300

Gly Leu Gly Tyr Met His Cys Cys Leu Asn Pro Leu Leu Tyr Ala Phe
305                 310                 315                 320

Val Gly Val Lys Phe Arg Glu Arg Met Trp Met Leu Leu Leu Arg Leu
                325                 330                 335

Gly Cys Pro Asn Gln Arg Gly Leu Gln Arg Gln Pro Ser Ser Ser Arg
            340                 345                 350

Arg Asp Ser Ser Trp Ser Glu Thr Ser Glu Ala Ser Tyr Ser Gly Leu
        355                 360                 365


<210> SEQ ID NO 175
<211> LENGTH: 1074
<212> TYPE: DNA
<213> ORGANISM: Homo sapiens

<400> SEQUENCE: 175

atggctgatg actatggctc tgaatccaca tcttccatgg aagactacgt taacttcaac      60

ttcactgact tctactgtga gaaaaacaat gtcaggcagt ttgcgagcca tttcctccca     120

cccttgtact ggctcgtgtt catcgtgggt gccttgggca acagtcttgt tatccttgtc     180

tactggtact gcacaagagt gaagaccatg accgacatgt tccttttgaa tttggcaatt     240

gctgacctcc tctttcttgt cactcttccc ttctgggcca ttgctgctgc tgaccagtgg     300

aagttccaga ccttcatgtg caaggtggtc aacagcatgt acaagatgaa cttctacagc     360

tgtgtgttgc tgatcatgtg catcagcgtg gacaggtaca ttgccattgc ccaggccatg     420

agagcacata cttggaggga gaaaaggctt ttgtacagca aaatggtttg ctttaccatc     480

tgggtattgg cagctgctct ctgcatccca gaaatcttat acagccaaat caaggaggaa     540

tccggcattg ctatctgcac catggtttac cctagcgatg agagcaccaa actgaagtca     600

gctgtcttga ccctgaaggt cattctgggg ttcttccttc ccttcgtggt catggcttgc     660

tgctatacca tcatcattca caccctgata caagccaaga agtcttccaa gcacaaagcc     720

aagaaagtga ccatcactgt cctgaccgtc tttgtcttgt ctcagtttcc ctacaactgc     780

attttgttgg tgcagaccat tgacgcctat gccatgttca tctccaactg tgccgtttcc     840

accaacattg acatctgctt ccaggtcacc cagaccatcg ccttcttcca cagttgcctg     900

aaccctgttc tctatgtttt tgtgggtgag agattccgcc gggatctcgt gaaaaccctg     960

aagaacttgg gttgcatcag ccaggcccag tgggtttcat ttacaaggag agagggaagc    1020

ttgaagctgt cgtctatgtt gctggagaca acctcaggag cactctccct ctga          1074


<210> SEQ ID NO 176
<211> LENGTH: 357
<212> TYPE: PRT
<213> ORGANISM: Homo sapiens

<400> SEQUENCE: 176

Met Ala Asp Asp Tyr Gly Ser Glu Ser Thr Ser Ser Met Glu Asp Tyr
1               5                   10                  15

Val Asn Phe Asn Phe Thr Asp Phe Tyr Cys Glu Lys Asn Asn Val Arg
            20                  25                  30

Gln Phe Ala Ser His Phe Leu Pro Pro Leu Tyr Trp Leu Val Phe Ile
        35                  40                  45

Val Gly Ala Leu Gly Asn Ser Leu Val Ile Leu Val Tyr Trp Tyr Cys
    50                  55                  60

Thr Arg Val Lys Thr Met Thr Asp Met Phe Leu Leu Asn Leu Ala Ile
```

-continued 65 70 75 80

Ala Asp Leu Leu Phe Leu Val Thr Leu Pro Phe Trp Ala Ile Ala Ala
85 90 95

Ala Asp Gln Trp Lys Phe Gln Thr Phe Met Cys Lys Val Val Asn Ser
100 105 110

Met Tyr Lys Met Asn Phe Tyr Ser Cys Val Leu Leu Ile Met Cys Ile
115 120 125

Ser Val Asp Arg Tyr Ile Ala Ile Ala Gln Ala Met Arg Ala His Thr
130 135 140

Trp Arg Glu Lys Arg Leu Leu Tyr Ser Lys Met Val Cys Phe Thr Ile
145 150 155 160

Trp Val Leu Ala Ala Ala Leu Cys Ile Pro Glu Ile Leu Tyr Ser Gln
165 170 175

Ile Lys Glu Glu Ser Gly Ile Ala Ile Cys Thr Met Val Tyr Pro Ser
180 185 190

Asp Glu Ser Thr Lys Leu Lys Ser Ala Val Leu Thr Leu Lys Val Ile
195 200 205

Leu Gly Phe Phe Leu Pro Phe Val Val Met Ala Cys Cys Tyr Thr Ile
210 215 220

Ile Ile His Thr Leu Ile Gln Ala Lys Lys Ser Ser Lys His Lys Ala
225 230 235 240

Lys Lys Val Thr Ile Thr Val Leu Thr Val Phe Val Leu Ser Gln Phe
245 250 255

Pro Tyr Asn Cys Ile Leu Leu Val Gln Thr Ile Asp Ala Tyr Ala Met
260 265 270

Phe Ile Ser Asn Cys Ala Val Ser Thr Asn Ile Asp Ile Cys Phe Gln
275 280 285

Val Thr Gln Thr Ile Ala Phe Phe His Ser Cys Leu Asn Pro Val Leu
290 295 300

Tyr Val Phe Val Gly Glu Arg Phe Arg Arg Asp Leu Val Lys Thr Leu
305 310 315 320

Lys Asn Leu Gly Cys Ile Ser Gln Ala Gln Trp Val Ser Phe Thr Arg
325 330 335

Arg Glu Gly Ser Leu Lys Leu Ser Ser Met Leu Leu Glu Thr Thr Ser
340 345 350

Gly Ala Leu Ser Leu
355

<210> SEQ ID NO 177
<211> LENGTH: 1110
<212> TYPE: DNA
<213> ORGANISM: Homo sapiens

<400> SEQUENCE: 177
atggcctcat cgaccactcg gggccccagg gtttctgact tattttctgg gctgccgccg 60
gcggtcacaa ctcccgccaa ccagagcgca gaggcctcgg cgggcaacgg gtcggtggct 120
ggcgcggacg ctccagccgt cacgcccttc cagagcctgc agctggtgca tcagctgaag 180
gggctgatcg tgctgctcta cagcgtcgtg gtggtcgtgg ggctggtggg caactgcctg 240
ctggtgctgg tgatcgcgcg ggtgccgcgg ctgcacaacg tgacgaactt cctcatcggc 300
aacctggcct tgtccgacgt gctcatgtgc accgcctgcg tgccgctcac gctggcctat 360
gccttcgagc cacgcggctg ggtgttcggc ggcggcctgt gccacctggt cttcttcctg 420
cagccggtca ccgtctatgt gtcggtgttc acgctcacca ccatcgcagt ggaccgctac 480

-continued

```
gtcgtgctgg tgcacccgct gaggcgcgca tctcgctgcg cctcagccta cgctgtgctg    540

gccatctggg cgctgtccgc ggtgctggcg ctgccgcccg ccgtgcacac ctatcacgtg    600

gagctcaagc cgcacgacgt gcgcctctgc gaggagttct ggggctccca ggagcgccag    660

cgccagctct acgcctgggg gctgctgctg gtcacctacc tgctccctct gctggtcatc    720

ctcctgtctt acgtccgggt gtcagtgaag ctccgcaacc gcgtggtgcc gggctgcgtg    780

acccagagcc aggccgactg ggaccgcgct cggcgccggc gcaccaaatg cttgctggtg    840

gtggtcgtgg tggtgttcgc cgtctgctgg ctgccgctgc acgtcttcaa cctgctgcgg    900

gacctcgacc cccacgccat cgacccttac gcctttgggc tggtgcagct gctctgccac    960

tggctcgcca tgagttcggc ctgctacaac cccttcatct acgcctggct gcacgacagc   1020

ttccgcgagg agctgcgcaa actgttggtc gcttggcccc gcaagatagc cccccatggc   1080

cagaatatga ccgtcagcgt ggtcatctga                                    1110


<210> SEQ ID NO 178
<211> LENGTH: 369
<212> TYPE: PRT
<213> ORGANISM: Homo sapiens

<400> SEQUENCE: 178

Met Ala Ser Ser Thr Thr Arg Gly Pro Arg Val Ser Asp Leu Phe Ser
1               5                   10                  15

Gly Leu Pro Pro Ala Val Thr Thr Pro Ala Asn Gln Ser Ala Glu Ala
            20                  25                  30

Ser Ala Gly Asn Gly Ser Val Ala Gly Ala Asp Ala Pro Ala Val Thr
        35                  40                  45

Pro Phe Gln Ser Leu Gln Leu Val His Gln Leu Lys Gly Leu Ile Val
    50                  55                  60

Leu Leu Tyr Ser Val Val Val Val Val Gly Leu Val Gly Asn Cys Leu
65                  70                  75                  80

Leu Val Leu Val Ile Ala Arg Val Pro Arg Leu His Asn Val Thr Asn
                85                  90                  95

Phe Leu Ile Gly Asn Leu Ala Leu Ser Asp Val Leu Met Cys Thr Ala
            100                 105                 110

Cys Val Pro Leu Thr Leu Ala Tyr Ala Phe Glu Pro Arg Gly Trp Val
        115                 120                 125

Phe Gly Gly Gly Leu Cys His Leu Val Phe Phe Leu Gln Pro Val Thr
    130                 135                 140

Val Tyr Val Ser Val Phe Thr Leu Thr Thr Ile Ala Val Asp Arg Tyr
145                 150                 155                 160

Val Val Leu Val His Pro Leu Arg Arg Ala Ser Arg Cys Ala Ser Ala
                165                 170                 175

Tyr Ala Val Leu Ala Ile Trp Ala Leu Ser Ala Val Leu Ala Leu Pro
            180                 185                 190

Pro Ala Val His Thr Tyr His Val Glu Leu Lys Pro His Asp Val Arg
        195                 200                 205

Leu Cys Glu Glu Phe Trp Gly Ser Gln Glu Arg Gln Arg Gln Leu Tyr
    210                 215                 220

Ala Trp Gly Leu Leu Leu Val Thr Tyr Leu Leu Pro Leu Leu Val Ile
225                 230                 235                 240

Leu Leu Ser Tyr Val Arg Val Ser Val Lys Leu Arg Asn Arg Val Val
                245                 250                 255
```

-continued

```
Pro Gly Cys Val Thr Gln Ser Gln Ala Asp Trp Asp Arg Ala Arg Arg
            260                 265                 270

Arg Arg Thr Lys Cys Leu Leu Val Val Val Val Val Val Phe Ala Val
        275                 280                 285

Cys Trp Leu Pro Leu His Val Phe Asn Leu Leu Arg Asp Leu Asp Pro
    290                 295                 300

His Ala Ile Asp Pro Tyr Ala Phe Gly Leu Val Gln Leu Leu Cys His
305                 310                 315                 320

Trp Leu Ala Met Ser Ser Ala Cys Tyr Asn Pro Phe Ile Tyr Ala Trp
                325                 330                 335

Leu His Asp Ser Phe Arg Glu Glu Leu Arg Lys Leu Leu Val Ala Trp
            340                 345                 350

Pro Arg Lys Ile Ala Pro His Gly Gln Asn Met Thr Val Ser Val Val
        355                 360                 365

Ile
```

<210> SEQ ID NO 179
<211> LENGTH: 1083
<212> TYPE: DNA
<213> ORGANISM: Homo sapiens

<400> SEQUENCE: 179

```
atggacccag aagaaacttc agtttatttg gattattact atgctacgag cccaaactct      60

gacatcaggg agacccactc ccatgttcct tacacctctg tcttccttcc agtcttttac     120

acagctgtgt tcctgactgg agtgctgggg aaccttgttc tcatgggagc gttgcatttc     180

aaacccggca gccgaagact gatcgacatc tttatcatca atctggctgc ctctgacttc     240

atttttcttg tcacattgcc tctctgggtg gataaagaag catctctagg actgtggagg     300

acgggctcct tcctgtgcaa agggagctcc tacatgatct ccgtcaatat gcactgcagt     360

gtcctcctgc tcacttgcat gagtgttgac cgctacctgg ccattgtgtg gccagtcgta     420

tccaggaaat tcagaaggac agactgtgca tatgtagtct gtgccagcat ctggtttatc     480

tcctgcctgc tggggttgcc tactcttctg tccagggagc tcacgctgat tgatgataag     540

ccatactgtg cagagaaaaa ggcaactcca attaaactca tatggtccct ggtggcctta     600

attttcacct tttttgtccc tttgttgagc attgtgacct gctactgttg cattgcaagg     660

aagctgtgtg cccattacca gcaatcagga aagcacaaca aaaagctgaa gaaatctaag     720

aagatcatct ttattgtcgt ggcagccttt cttgtctcct ggctgccctt caatactttc     780

aagttcctgg ccattgtctc tgggttgcgg caagaacact atttaccctc agctattctt     840

cagcttggta tggaggtgag tggacccttg gcatttgcca acagctgtgt caaccctttc     900

atttactata tcttcgacag ctacatccgc cgggccattg tccactgctt gtgcccttgc     960

ctgaaaaact atgactttgg gagtagcact gagacatcag atagtcacct cactaaggct    1020

ctctccacct tcattcatgc agaagatttt gccaggagga ggaagaggtc tgtgtcactc    1080

taa                                                                  1083
```

<210> SEQ ID NO 180
<211> LENGTH: 360
<212> TYPE: PRT
<213> ORGANISM: Homo sapiens

<400> SEQUENCE: 180

```
Met Asp Pro Glu Glu Thr Ser Val Tyr Leu Asp Tyr Tyr Tyr Ala Thr
1               5                   10                  15
```

-continued

```
Ser Pro Asn Ser Asp Ile Arg Glu Thr His Ser His Val Pro Tyr Thr
            20                  25                  30

Ser Val Phe Leu Pro Val Phe Tyr Thr Ala Val Phe Leu Thr Gly Val
        35                  40                  45

Leu Gly Asn Leu Val Leu Met Gly Ala Leu His Phe Lys Pro Gly Ser
    50                  55                  60

Arg Arg Leu Ile Asp Ile Phe Ile Ile Asn Leu Ala Ala Ser Asp Phe
65                  70                  75                  80

Ile Phe Leu Val Thr Leu Pro Leu Trp Val Asp Lys Glu Ala Ser Leu
                85                  90                  95

Gly Leu Trp Arg Thr Gly Ser Phe Leu Cys Lys Gly Ser Ser Tyr Met
            100                 105                 110

Ile Ser Val Asn Met His Cys Ser Val Leu Leu Leu Thr Cys Met Ser
        115                 120                 125

Val Asp Arg Tyr Leu Ala Ile Val Trp Pro Val Val Ser Arg Lys Phe
    130                 135                 140

Arg Arg Thr Asp Cys Ala Tyr Val Val Cys Ala Ser Ile Trp Phe Ile
145                 150                 155                 160

Ser Cys Leu Leu Gly Leu Pro Thr Leu Leu Ser Arg Glu Leu Thr Leu
                165                 170                 175

Ile Asp Asp Lys Pro Tyr Cys Ala Glu Lys Lys Ala Thr Pro Ile Lys
            180                 185                 190

Leu Ile Trp Ser Leu Val Ala Leu Ile Phe Thr Phe Phe Val Pro Leu
        195                 200                 205

Leu Ser Ile Val Thr Cys Tyr Cys Cys Ile Ala Arg Lys Leu Cys Ala
    210                 215                 220

His Tyr Gln Gln Ser Gly Lys His Asn Lys Lys Leu Lys Lys Ser Lys
225                 230                 235                 240

Lys Ile Ile Phe Ile Val Val Ala Ala Phe Leu Val Ser Trp Leu Pro
                245                 250                 255

Phe Asn Thr Phe Lys Phe Leu Ala Ile Val Ser Gly Leu Arg Gln Glu
            260                 265                 270

His Tyr Leu Pro Ser Ala Ile Leu Gln Leu Gly Met Glu Val Ser Gly
        275                 280                 285

Pro Leu Ala Phe Ala Asn Ser Cys Val Asn Pro Phe Ile Tyr Tyr Ile
    290                 295                 300

Phe Asp Ser Tyr Ile Arg Arg Ala Ile Val His Cys Leu Cys Pro Cys
305                 310                 315                 320

Leu Lys Asn Tyr Asp Phe Gly Ser Ser Thr Glu Thr Ser Asp Ser His
                325                 330                 335

Leu Thr Lys Ala Leu Ser Thr Phe Ile His Ala Glu Asp Phe Ala Arg
            340                 345                 350

Arg Arg Lys Arg Ser Val Ser Leu
        355                 360
```

<210> SEQ ID NO 181
<211> LENGTH: 1020
<212> TYPE: DNA
<213> ORGANISM: Homo sapiens

<400> SEQUENCE: 181

```
atgaatggcc ttgaagtggc tcccccaggt ctgatcacca acttctccct ggccacggca      60

gagcaatgtg gccaggagac gccactggag aacatgctgt tcgcctcctt ctaccttctg     120
```

-continued

```
gattttatcc tggctttagt tggcaatacc ctggctctgt ggcttttcat ccgagaccac    180

aagtccggga ccccggccaa cgtgttcctg atgcatctgg ccgtggccga cttgtcgtgc    240

gtgctggtcc tgcccacccg cctggtctac cacttctctg ggaaccactg gccatttggg    300

gaaatcgcat gccgtctcac cggcttcctc ttctacctca acatgtacgc cagcatctac    360

ttcctcacct gcatcagcgc cgaccgtttc ctggccattg tgcacccggt caagtccctc    420

aagctccgca ggcccctcta cgcacacctg gcctgtgcct tcctgtgggt ggtggtggct    480

gtggccatgg ccccgctgct ggtgagccca cagaccgtgc agaccaacca cacggtggtc    540

tgcctgcagc tgtaccggga gaaggcctcc caccatgccc tggtgtccct ggcagtggcc    600

ttcaccttcc cgttcatcac cacggtcacc tgctacctgc tgatcatccg cagcctgcgg    660

cagggcctgc gtgtggagaa gcgcctcaag accaaggcaa aacgcatgat cgccatagtg    720

ctggccatct tcctggtctg cttcgtgccc taccacgtca accgctccgt ctacgtgctg    780

cactaccgca gccatggggc ctcctgcgcc acccagcgca tcctggccct ggcaaaccgc    840

atcacctcct gcctcaccag cctcaacggg gcactcgacc ccatcatgta tttcttcgtg    900

gctgagaagt tccgccacgc cctgtgcaac ttgctctgtg gcaaaaggct caagggcccg    960

ccccccagct tcgaagggaa aaccaacgag agctcgctga gtgccaagtc agagctgtga   1020
```

<210> SEQ ID NO 182
<211> LENGTH: 339
<212> TYPE: PRT
<213> ORGANISM: Homo sapiens

<400> SEQUENCE: 182

```
Met Asn Gly Leu Glu Val Ala Pro Pro Gly Leu Ile Thr Asn Phe Ser
1               5                   10                  15

Leu Ala Thr Ala Glu Gln Cys Gly Gln Glu Thr Pro Leu Glu Asn Met
            20                  25                  30

Leu Phe Ala Ser Phe Tyr Leu Leu Asp Phe Ile Leu Ala Leu Val Gly
        35                  40                  45

Asn Thr Leu Ala Leu Trp Leu Phe Ile Arg Asp His Lys Ser Gly Thr
    50                  55                  60

Pro Ala Asn Val Phe Leu Met His Leu Ala Val Ala Asp Leu Ser Cys
65                  70                  75                  80

Val Leu Val Leu Pro Thr Arg Leu Val Tyr His Phe Ser Gly Asn His
                85                  90                  95

Trp Pro Phe Gly Glu Ile Ala Cys Arg Leu Thr Gly Phe Leu Phe Tyr
            100                 105                 110

Leu Asn Met Tyr Ala Ser Ile Tyr Phe Leu Thr Cys Ile Ser Ala Asp
        115                 120                 125

Arg Phe Leu Ala Ile Val His Pro Val Lys Ser Leu Lys Leu Arg Arg
    130                 135                 140

Pro Leu Tyr Ala His Leu Ala Cys Ala Phe Leu Trp Val Val Val Ala
145                 150                 155                 160

Val Ala Met Ala Pro Leu Leu Val Ser Pro Gln Thr Val Gln Thr Asn
                165                 170                 175

His Thr Val Val Cys Leu Gln Leu Tyr Arg Glu Lys Ala Ser His His
            180                 185                 190

Ala Leu Val Ser Leu Ala Val Ala Phe Thr Phe Pro Phe Ile Thr Thr
        195                 200                 205

Val Thr Cys Tyr Leu Leu Ile Ile Arg Ser Leu Arg Gln Gly Leu Arg
    210                 215                 220
```

-continued

Val Glu Lys Arg Leu Lys Thr Lys Ala Lys Arg Met Ile Ala Ile Val
225 230 235 240

Leu Ala Ile Phe Leu Val Cys Phe Val Pro Tyr His Val Asn Arg Ser
245 250 255

Val Tyr Val Leu His Tyr Arg Ser His Gly Ala Ser Cys Ala Thr Gln
260 265 270

Arg Ile Leu Ala Leu Ala Asn Arg Ile Thr Ser Cys Leu Thr Ser Leu
275 280 285

Asn Gly Ala Leu Asp Pro Ile Met Tyr Phe Phe Val Ala Glu Lys Phe
290 295 300

Arg His Ala Leu Cys Asn Leu Leu Cys Gly Lys Arg Leu Lys Gly Pro
305 310 315 320

Pro Pro Ser Phe Glu Gly Lys Thr Asn Glu Ser Ser Leu Ser Ala Lys
325 330 335

Ser Glu Leu

<210> SEQ ID NO 183
<211> LENGTH: 996
<212> TYPE: DNA
<213> ORGANISM: Homo sapiens

<400> SEQUENCE: 183
atgatcaccc tgaacaatca agatcaacct gtccctttta acagctcaca tccagatgaa 60
tacaaaattg cagcccttgt cttctatagc tgtatcttca taattggatt atttgttaac 120
atcactgcat tatgggtttt cagttgtacc accaagaaga gaaccacggt aaccatctat 180
atgatgaatg tggcattagt ggacttgata tttataatga ctttaccctt tcgaatgttt 240
tattatgcaa aagatgaatg gccatttgga gagtacttct gccagattct tggagctctc 300
acagtgtttt acccaagcat tgctttatgg cttcttgcct ttattagtgc tgacagatac 360
atggccattg tacagccgaa gtacgccaaa gaacttaaaa acacgtgcaa agccgtgctg 420
gcgtgtgtgg gagtctggat aatgaccctg accacgacca cccctctgct actgctctat 480
aaagacccag ataaagactc cactcccgcc acctgcctca agatttctga catcatctat 540
ctaaaagctg tgaacgtgct gaacctcact cgactgacat ttttttcttt gattcctttg 600
ttcatcatga ttgggtgcta cttggtcatt attcataatc tccttcacgg caggacgtct 660
aagctgaaac ccaaagtcaa ggagaagtcc aaaaggatca tcatcacgct gctggtgcag 720
gtgctcgtct gctttatgcc cttccacatc tgtttcgctt tcctgatgct gggaacgggg 780
gagaatagtt acaatccctg gggagccttt accaccttcc tcatgaacct cagcacgtgt 840
ctggatgtga ttctctacta catcgtttca aaacaatttc aggctcgagt cattagtgtc 900
atgctatacc gtaattacct tcgaagcatg cgcagaaaaa gtttccgatc tggtagtcta 960
aggtcactaa gcaatataaa cagtgaaatg ttatga 996

<210> SEQ ID NO 184
<211> LENGTH: 331
<212> TYPE: PRT
<213> ORGANISM: Homo sapiens

<400> SEQUENCE: 184

Met Ile Thr Leu Asn Asn Gln Asp Gln Pro Val Pro Phe Asn Ser Ser
1 5 10 15

His Pro Asp Glu Tyr Lys Ile Ala Ala Leu Val Phe Tyr Ser Cys Ile
20 25 30

-continued

```
Phe Ile Ile Gly Leu Phe Val Asn Ile Thr Ala Leu Trp Val Phe Ser
        35                  40                  45

Cys Thr Thr Lys Lys Arg Thr Thr Val Thr Ile Tyr Met Met Asn Val
    50                  55                  60

Ala Leu Val Asp Leu Ile Phe Ile Met Thr Leu Pro Phe Arg Met Phe
65                  70                  75                  80

Tyr Tyr Ala Lys Asp Glu Trp Pro Phe Gly Glu Tyr Phe Cys Gln Ile
                85                  90                  95

Leu Gly Ala Leu Thr Val Phe Tyr Pro Ser Ile Ala Leu Trp Leu Leu
            100                 105                 110

Ala Phe Ile Ser Ala Asp Arg Tyr Met Ala Ile Val Gln Pro Lys Tyr
        115                 120                 125

Ala Lys Glu Leu Lys Asn Thr Cys Lys Ala Val Leu Ala Cys Val Gly
    130                 135                 140

Val Trp Ile Met Thr Leu Thr Thr Thr Thr Pro Leu Leu Leu Leu Tyr
145                 150                 155                 160

Lys Asp Pro Asp Lys Asp Ser Thr Pro Ala Thr Cys Leu Lys Ile Ser
                165                 170                 175

Asp Ile Ile Tyr Leu Lys Ala Val Asn Val Leu Asn Leu Thr Arg Leu
            180                 185                 190

Thr Phe Phe Phe Leu Ile Pro Leu Phe Ile Met Ile Gly Cys Tyr Leu
        195                 200                 205

Val Ile Ile His Asn Leu Leu His Gly Arg Thr Ser Lys Leu Lys Pro
    210                 215                 220

Lys Val Lys Glu Lys Ser Lys Arg Ile Ile Ile Thr Leu Leu Val Gln
225                 230                 235                 240

Val Leu Val Cys Phe Met Pro Phe His Ile Cys Phe Ala Phe Leu Met
                245                 250                 255

Leu Gly Thr Gly Glu Asn Ser Tyr Asn Pro Trp Gly Ala Phe Thr Thr
            260                 265                 270

Phe Leu Met Asn Leu Ser Thr Cys Leu Asp Val Ile Leu Tyr Tyr Ile
        275                 280                 285

Val Ser Lys Gln Phe Gln Ala Arg Val Ile Ser Val Met Leu Tyr Arg
    290                 295                 300

Asn Tyr Leu Arg Ser Met Arg Arg Lys Ser Phe Arg Ser Gly Ser Leu
305                 310                 315                 320

Arg Ser Leu Ser Asn Ile Asn Ser Glu Met Leu
                325                 330
```

<210> SEQ ID NO 185
<211> LENGTH: 1077
<212> TYPE: DNA
<213> ORGANISM: Homo sapiens

<400> SEQUENCE: 185

```
atgccctctg tgtctccagc ggggccctcg gccggggcag tccccaatgc caccgcagtg      60

acaacagtgc ggaccaatgc cagcgggctg gaggtgcccc tgttccacct gtttgcccgg     120

ctggacgagg agctgcatgg caccttccca ggcctgtgcg tggcgctgat ggcggtgcac     180

ggagccatct tcctggcagg gctggtgctc aacgggctgg cgctgtacgt cttctgctgc     240

cgcacccggg ccaagacacc ctcagtcatc tacaccatca acctggtggt gaccgatcta     300

ctggtagggc tgtccctgcc cacgcgcttc gctgtgtact acggcgccag ggggctgcctg    360

cgctgtgcct tcccgcacgt cctcggttac ttcctcaaca tgcactgctc catcctcttc     420
```

-continued

```
ctcacctgca tctgcgtgga ccgctacctg gccatcgtgc ggcccgaagg ctcccgccgc    480

tgccgccagc ctgcctgtgc cagggccgtg tgcgccttcg tgtggctggc cgccggtgcc    540

gtcaccctgt cggtgctggg cgtgacaggc agccggccct gctgccgtgt ctttgcgctg    600

actgtcctgg agttcctgct gcccctgctg gtcatcagcg tgtttaccgg ccgcatcatg    660

tgtgcactgt cgcggccggg tctgctccac cagggtcgcc agcgccgcgt gcgggccaag    720

cagctcctgc tcacggtgct catcatcttt ctcgtctgct tcacgccctt ccacgcccgc    780

caagtggccg tggcgctgtg gcccgacatg ccacaccaca cgagcctcgt ggtctaccac    840

gtggccgtga ccctcagcag cctcaacagc tgcatggacc ccatcgtcta ctgcttcgtc    900

accagtggct tccaggccac cgtccgaggc ctcttcggcc agcacggaga gcgtgagccc    960

agcagcggtg acgtggtcag catgcacagg agctccaagg gctcaggccg tcatcacatc   1020

ctcagtgccg gccctcacgc cctcacccag gccctggcta atgggcccga ggcttag      1077


<210> SEQ ID NO 186
<211> LENGTH: 358
<212> TYPE: PRT
<213> ORGANISM: Homo sapiens

<400> SEQUENCE: 186

Met Pro Ser Val Ser Pro Ala Gly Pro Ser Ala Gly Ala Val Pro Asn
1               5                   10                  15

Ala Thr Ala Val Thr Thr Val Arg Thr Asn Ala Ser Gly Leu Glu Val
            20                  25                  30

Pro Leu Phe His Leu Phe Ala Arg Leu Asp Glu Glu Leu His Gly Thr
        35                  40                  45

Phe Pro Gly Leu Cys Val Ala Leu Met Ala Val His Gly Ala Ile Phe
    50                  55                  60

Leu Ala Gly Leu Val Leu Asn Gly Leu Ala Leu Tyr Val Phe Cys Cys
65                  70                  75                  80

Arg Thr Arg Ala Lys Thr Pro Ser Val Ile Tyr Thr Ile Asn Leu Val
                85                  90                  95

Val Thr Asp Leu Leu Val Gly Leu Ser Leu Pro Thr Arg Phe Ala Val
            100                 105                 110

Tyr Tyr Gly Ala Arg Gly Cys Leu Arg Cys Ala Phe Pro His Val Leu
        115                 120                 125

Gly Tyr Phe Leu Asn Met His Cys Ser Ile Leu Phe Leu Thr Cys Ile
    130                 135                 140

Cys Val Asp Arg Tyr Leu Ala Ile Val Arg Pro Glu Gly Ser Arg Ala
145                 150                 155                 160

Cys Arg Gln Pro Ala Cys Ala Arg Ala Val Cys Ala Phe Val Trp Leu
                165                 170                 175

Ala Ala Gly Ala Val Thr Leu Ser Val Leu Gly Val Thr Gly Ser Arg
            180                 185                 190

Pro Cys Cys Arg Val Phe Ala Leu Thr Val Leu Glu Phe Leu Leu Pro
        195                 200                 205

Leu Leu Val Ile Ser Val Phe Thr Gly Arg Ile Met Cys Ala Leu Ser
    210                 215                 220

Arg Pro Gly Leu Leu His Gln Gly Arg Gln Arg Arg Val Arg Ala Lys
225                 230                 235                 240

Gln Leu Leu Leu Thr Val Leu Ile Ile Phe Leu Val Cys Phe Thr Pro
                245                 250                 255
```

-continued

```
Phe His Ala Arg Gln Val Ala Val Ala Leu Trp Pro Asp Met Pro His
            260                 265                 270

His Thr Ser Leu Val Val Tyr His Val Ala Val Thr Leu Ser Ser Leu
        275                 280                 285

Asn Ser Cys Met Asp Pro Ile Val Tyr Cys Phe Val Thr Ser Gly Phe
    290                 295                 300

Gln Ala Thr Val Arg Gly Leu Phe Gly Gln His Gly Glu Arg Glu Pro
305                 310                 315                 320

Ser Ser Gly Asp Val Val Ser Met His Arg Ser Ser Lys Gly Ser Gly
                325                 330                 335

Arg His His Ile Leu Ser Ala Gly Pro His Ala Leu Thr Gln Ala Leu
            340                 345                 350

Ala Asn Gly Pro Glu Ala
        355


<210> SEQ ID NO 187
<211> LENGTH: 1050
<212> TYPE: DNA
<213> ORGANISM: Homo sapiens

<400> SEQUENCE: 187

atgaactcca ccttggatgg taatcagagc agccaccctt tttgcctctt ggcatttggc      60

tatttggaaa ctgtcaattt ttgccttttg gaagtattga ttattgtctt tctaactgta     120

ttgattattt ctggcaacat cattgtgatt tttgtatttc actgtgcacc tttgttgaac     180

catcacacta caagttattt tatccagact atggcatatg ctgacctttt tgttggggtg     240

agctgcgtgg tcccttcttt atcactcctc catcaccccc ttccagtaga ggagtccttg     300

acttgccaga tatttggttt tgtagtatca gttctgaaga gcgtctccat ggcttctctg     360

gcctgtatca gcattgatag atacattgcc attactaaac ctttaaccta taatactctg     420

gttacaccct ggagactacg cctgtgtatt ttcctgattt ggctatactc gaccctggtc     480

ttcctgcctt cctttttcca ctggggcaaa cctggatatc atggagatgt gtttcagtgg     540

tgtgcggagt cctggcacac cgactcctac ttcaccctgt tcatcgtgat gatgttatat     600

gccccagcag cccttattgt ctgcttcacc tatttcaaca tcttccgcat ctgccaacag     660

cacacaaagg atatcagcga aaggcaagcc cgcttcagca gccagagtgg ggagactggg     720

gaagtgcagg cctgtcctga taagcgctat aaaatggtcc tgtttcgaat cactagtgta     780

ttttacatcc tctggttgcc atatatcatc tacttcttgt tggaaagctc cactggccac     840

agcaaccgct tcgcatcctt cttgaccacc tggcttgcta ttagtaacag tttctgcaac     900

tgtgtaattt atagtctctc caacagtgta ttccaaagag gactaaagcg cctctcaggg     960

gctatgtgta cttcttgtgc aagtcagact acagccaacg acccttacac agttagaagc    1020

aaaggccctc ttaatggatg tcatatctga                                     1050


<210> SEQ ID NO 188
<211> LENGTH: 349
<212> TYPE: PRT
<213> ORGANISM: Homo sapiens

<400> SEQUENCE: 188

Met Asn Ser Thr Leu Asp Gly Asn Gln Ser Ser His Pro Phe Cys Leu
1               5                   10                  15

Leu Ala Phe Gly Tyr Leu Glu Thr Val Asn Phe Cys Leu Leu Glu Val
            20                  25                  30
```

-continued

```
Leu Ile Ile Val Phe Leu Thr Val Leu Ile Ile Ser Gly Asn Ile Ile
        35                  40                  45

Val Ile Phe Val Phe His Cys Ala Pro Leu Leu Asn His His Thr Thr
    50                  55                  60

Ser Tyr Phe Ile Gln Thr Met Ala Tyr Ala Asp Leu Phe Val Gly Val
65                  70                  75                  80

Ser Cys Val Val Pro Ser Leu Ser Leu Leu His His Pro Leu Pro Val
                85                  90                  95

Glu Glu Ser Leu Thr Cys Gln Ile Phe Gly Phe Val Val Ser Val Leu
            100                 105                 110

Lys Ser Val Ser Met Ala Ser Leu Ala Cys Ile Ser Ile Asp Arg Tyr
        115                 120                 125

Ile Ala Ile Thr Lys Pro Leu Thr Tyr Asn Thr Leu Val Thr Pro Trp
    130                 135                 140

Arg Leu Arg Leu Cys Ile Phe Leu Ile Trp Leu Tyr Ser Thr Leu Val
145                 150                 155                 160

Phe Leu Pro Ser Phe Phe His Trp Gly Lys Pro Gly Tyr His Gly Asp
                165                 170                 175

Val Phe Gln Trp Cys Ala Glu Ser Trp His Thr Asp Ser Tyr Phe Thr
            180                 185                 190

Leu Phe Ile Val Met Met Leu Tyr Ala Pro Ala Ala Leu Ile Val Cys
        195                 200                 205

Phe Thr Tyr Phe Asn Ile Phe Arg Ile Cys Gln Gln His Thr Lys Asp
    210                 215                 220

Ile Ser Glu Arg Gln Ala Arg Phe Ser Ser Gln Ser Gly Glu Thr Gly
225                 230                 235                 240

Glu Val Gln Ala Cys Pro Asp Lys Arg Tyr Lys Met Val Leu Phe Arg
                245                 250                 255

Ile Thr Ser Val Phe Tyr Ile Leu Trp Leu Pro Tyr Ile Ile Tyr Phe
            260                 265                 270

Leu Leu Glu Ser Ser Thr Gly His Ser Asn Arg Phe Ala Ser Phe Leu
        275                 280                 285

Thr Thr Trp Leu Ala Ile Ser Asn Ser Phe Cys Asn Cys Val Ile Tyr
    290                 295                 300

Ser Leu Ser Asn Ser Val Phe Gln Arg Gly Leu Lys Arg Leu Ser Gly
305                 310                 315                 320

Ala Met Cys Thr Ser Cys Ala Ser Gln Thr Thr Ala Asn Asp Pro Tyr
                325                 330                 335

Thr Val Arg Ser Lys Gly Pro Leu Asn Gly Cys His Ile
            340                 345
```

<210> SEQ ID NO 189
<211> LENGTH: 1302
<212> TYPE: DNA
<213> ORGANISM: Homo sapiens

<400> SEQUENCE: 189

```
atgtgttttt ctcccattct ggaaatcaac atgcagtctg aatctaacat tacagtgcga      60

gatgacattg atgacatcaa caccaatatg taccaaccac tatcatatcc gttaagcttt     120

caagtgtctc tcaccggatt tcttatgtta gaaattgtgt tgggacttgg cagcaacctc     180

actgtattgg tactttactg catgaaatcc aacttaatca actctgtcag taacattatt     240

acaatgaatc ttcatgtact tgatgtaata atttgtgtgg gatgtattcc tctaactata     300

gttatccttc tgctttcact ggagagtaac actgctctca tttgctgttt ccatgaggct     360
```

-continued

```
tgtgtatctt ttgcaagtgt ctcaacagca atcaacgttt ttgctatcac tttggacaga    420

tatgacatct ctgtaaaacc tgcaaaccga attctgacaa tgggcagagc tgtaatgtta    480

atgatatcca tttggatttt ttcttttttc tctttcctga ttccttttat tgaggtaaat    540

tttttcagtc ttcaaagtgg aaatacctgg gaaaacaaga cacttttatg tgtcagtaca    600

aatgaatact acactgaact gggaatgtat tatcacctgt tagtacagat cccaatattc    660

tttttcactg ttgtagtaat gttaatcaca tacaccaaaa tacttcaggc tcttaatatt    720

cgaataggca caagattttc aacagggcag aagaagaaag caagaaagaa aaagacaatt    780

tctctaacca cacaacatga ggctacagac atgtcacaaa gcagtggtgg gagaaatgta    840

gtctttggtg taagaacttc agtttctgta ataattgccc tccggcgagc tgtgaaacga    900

caccgtgaac gacgagaaag acaaaagaga gtcaagagga tgtctttatt gattatttct    960

acatttcttc tctgctggac accaatttct gttttaaata ccaccatttt atgtttaggc   1020

ccaagtgacc ttttagtaaa attaagattg tgttttttag tcatggctta tggaacaact   1080

atatttcacc ctctattata tgcattcact agacaaaaat ttcaaaaggt cttgaaaagt   1140

aaaatgaaaa agcgagttgt ttctatagta gaagctgatc cctgcctaaa taatgctgta   1200

atacacaact cttggataga tcccaaaaga aacaaaaaaa ttacctttga agatagtgaa   1260

ataagagaaa aacgtttagt gcctcaggtt gtcacagact ag                       1302
```

```
<210> SEQ ID NO 190
<211> LENGTH: 433
<212> TYPE: PRT
<213> ORGANISM: Homo sapiens

<400> SEQUENCE: 190

Met Cys Phe Ser Pro Ile Leu Glu Ile Asn Met Gln Ser Glu Ser Asn
1               5                   10                  15

Ile Thr Val Arg Asp Asp Ile Asp Asp Ile Asn Thr Asn Met Tyr Gln
            20                  25                  30

Pro Leu Ser Tyr Pro Leu Ser Phe Gln Val Ser Leu Thr Gly Phe Leu
        35                  40                  45

Met Leu Glu Ile Val Leu Gly Leu Gly Ser Asn Leu Thr Val Leu Val
    50                  55                  60

Leu Tyr Cys Met Lys Ser Asn Leu Ile Asn Ser Val Ser Asn Ile Ile
65                  70                  75                  80

Thr Met Asn Leu His Val Leu Asp Val Ile Ile Cys Val Gly Cys Ile
                85                  90                  95

Pro Leu Thr Ile Val Ile Leu Leu Leu Ser Leu Glu Ser Asn Thr Ala
            100                 105                 110

Leu Ile Cys Cys Phe His Glu Ala Cys Val Ser Phe Ala Ser Val Ser
        115                 120                 125

Thr Ala Ile Asn Val Phe Ala Ile Thr Leu Asp Arg Tyr Asp Ile Ser
    130                 135                 140

Val Lys Pro Ala Asn Arg Ile Leu Thr Met Gly Arg Ala Val Met Leu
145                 150                 155                 160

Met Ile Ser Ile Trp Ile Phe Ser Phe Phe Ser Phe Leu Ile Pro Phe
                165                 170                 175

Ile Glu Val Asn Phe Phe Ser Leu Gln Ser Gly Asn Thr Trp Glu Asn
            180                 185                 190

Lys Thr Leu Leu Cys Val Ser Thr Asn Glu Tyr Tyr Thr Glu Leu Gly
        195                 200                 205
```

-continued

```
Met Tyr Tyr His Leu Leu Val Gln Ile Pro Ile Phe Phe Phe Thr Val
    210                 215                 220

Val Val Met Leu Ile Thr Tyr Thr Lys Ile Leu Gln Ala Leu Asn Ile
225                 230                 235                 240

Arg Ile Gly Thr Arg Phe Ser Thr Gly Gln Lys Lys Lys Ala Arg Lys
                245                 250                 255

Lys Lys Thr Ile Ser Leu Thr Thr Gln His Glu Ala Thr Asp Met Ser
            260                 265                 270

Gln Ser Ser Gly Gly Arg Asn Val Val Phe Gly Val Arg Thr Ser Val
        275                 280                 285

Ser Val Ile Ile Ala Leu Arg Arg Ala Val Lys Arg His Arg Glu Arg
    290                 295                 300

Arg Glu Arg Gln Lys Arg Val Lys Arg Met Ser Leu Leu Ile Ile Ser
305                 310                 315                 320

Thr Phe Leu Leu Cys Trp Thr Pro Ile Ser Val Leu Asn Thr Thr Ile
                325                 330                 335

Leu Cys Leu Gly Pro Ser Asp Leu Leu Val Lys Leu Arg Leu Cys Phe
            340                 345                 350

Leu Val Met Ala Tyr Gly Thr Thr Ile Phe His Pro Leu Leu Tyr Ala
        355                 360                 365

Phe Thr Arg Gln Lys Phe Gln Lys Val Leu Lys Ser Lys Met Lys Lys
    370                 375                 380

Arg Val Val Ser Ile Val Glu Ala Asp Pro Leu Pro Asn Asn Ala Val
385                 390                 395                 400

Ile His Asn Ser Trp Ile Asp Pro Lys Arg Asn Lys Lys Ile Thr Phe
                405                 410                 415

Glu Asp Ser Glu Ile Arg Glu Lys Arg Leu Val Pro Gln Val Val Thr
            420                 425                 430

Asp
```

<210> SEQ ID NO 191
<211> LENGTH: 1209
<212> TYPE: DNA
<213> ORGANISM: Homo sapiens

<400> SEQUENCE: 191

```
atgttgtgtc cttccaagac agatggctca gggcactctg gtaggattca ccaggaaact      60

catggagaag ggaaaaggga caagattagc aacagtgaag ggagggagaa tggtgggaga     120

ggattccaga tgaacggtgg gtcgctggag gctgagcatg ccagcaggat gtcagttctc     180

agagcaaagc ccatgtcaaa cagccaacgc ttgctccttc tgtccccagg atcacctcct     240

cgcacgggga gcatctccta catcaacatc atcatgcctt cggtgttcgg caccatctgc     300

ctcctgggca tcatcgggaa ctccacggtc atcttcgcgg tcgtgaagaa gtccaagctg     360

cactggtgca acaacgtccc cgacatcttc atcatcaacc tctcggtagt agatctcctc     420

tttctcctgg gcatgccctt catgatccac cagctcatgg gcaatggggt gtggcacttt     480

ggggagacca tgtgcaccct catcacggcc atggatgcca atagtcagtt caccagcacc     540

tacatcctga ccgccatggc cattgaccgc tacctggcca ctgtccaccc catctcttcc     600

acgaagttcc ggaagccctc tgtggccacc ctggtgatct gcctcctgtg ggccctctcc     660

ttcatcagca tcacccctgt gtggctgtat gccagactca tccccttccc aggaggtgca     720

gtgggctgcg gcatacgcct gcccaaccca gacactgacc tctactggtt caccctgtac     780
```

-continued

```
cagtttttcc tggcctttgc cctgcctttt gtggtcatca cagccgcata cgtgaggatc    840

ctgcagcgca tgacgtcctc agtggccccc gcctcccagc gcagcatccg gctgcggaca    900

aagagggtga aacgcacagc catcgccatc tgtctggtct tctttgtgtg ctgggcaccc    960

tactatgtgc tacagctgac ccagttgtcc atcagccgcc cgaccctcac ctttgtctac   1020

ttatacaatg cggccatcag cttgggctat gccaacagct gcctcaaccc ctttgtgtac   1080

atcgtgctct gtgagacgtt ccgcaaacgc ttggtcctgt cggtgaagcc tgcagcccag   1140

gggcagcttc gcgctgtcag caacgctcag acggctgacg aggagaggac agaaagcaaa   1200

ggcacctga                                                           1209


<210> SEQ ID NO 192
<211> LENGTH: 402
<212> TYPE: PRT
<213> ORGANISM: Homo sapiens

<400> SEQUENCE: 192

Met Leu Cys Pro Ser Lys Thr Asp Gly Ser Gly His Ser Gly Arg Ile
1               5                   10                  15

His Gln Glu Thr His Gly Glu Gly Lys Arg Asp Lys Ile Ser Asn Ser
            20                  25                  30

Glu Gly Arg Glu Asn Gly Gly Arg Gly Phe Gln Met Asn Gly Gly Ser
        35                  40                  45

Leu Glu Ala Glu His Ala Ser Arg Met Ser Val Leu Arg Ala Lys Pro
    50                  55                  60

Met Ser Asn Ser Gln Arg Leu Leu Leu Leu Ser Pro Gly Ser Pro Pro
65                  70                  75                  80

Arg Thr Gly Ser Ile Ser Tyr Ile Asn Ile Ile Met Pro Ser Val Phe
                85                  90                  95

Gly Thr Ile Cys Leu Leu Gly Ile Ile Gly Asn Ser Thr Val Ile Phe
            100                 105                 110

Ala Val Val Lys Lys Ser Lys Leu His Trp Cys Asn Asn Val Pro Asp
        115                 120                 125

Ile Phe Ile Ile Asn Leu Ser Val Val Asp Leu Leu Phe Leu Leu Gly
    130                 135                 140

Met Pro Phe Met Ile His Gln Leu Met Gly Asn Gly Val Trp His Phe
145                 150                 155                 160

Gly Glu Thr Met Cys Thr Leu Ile Thr Ala Met Asp Ala Asn Ser Gln
                165                 170                 175

Phe Thr Ser Thr Tyr Ile Leu Thr Ala Met Ala Ile Asp Arg Tyr Leu
            180                 185                 190

Ala Thr Val His Pro Ile Ser Ser Thr Lys Phe Arg Lys Pro Ser Val
        195                 200                 205

Ala Thr Leu Val Ile Cys Leu Leu Trp Ala Leu Ser Phe Ile Ser Ile
    210                 215                 220

Thr Pro Val Trp Leu Tyr Ala Arg Leu Ile Pro Phe Pro Gly Gly Ala
225                 230                 235                 240

Val Gly Cys Gly Ile Arg Leu Pro Asn Pro Asp Thr Asp Leu Tyr Trp
                245                 250                 255

Phe Thr Leu Tyr Gln Phe Phe Leu Ala Phe Ala Leu Pro Phe Val Val
            260                 265                 270

Ile Thr Ala Ala Tyr Val Arg Ile Leu Gln Arg Met Thr Ser Ser Val
        275                 280                 285

Ala Pro Ala Ser Gln Arg Ser Ile Arg Leu Arg Thr Lys Arg Val Lys
```

-continued

```
    290                 295                 300

Arg Thr Ala Ile Ala Ile Cys Leu Val Phe Phe Val Cys Trp Ala Pro
305                 310                 315                 320

Tyr Tyr Val Leu Gln Leu Thr Gln Leu Ser Ile Ser Arg Pro Thr Leu
                325                 330                 335

Thr Phe Val Tyr Leu Tyr Asn Ala Ala Ile Ser Leu Gly Tyr Ala Asn
            340                 345                 350

Ser Cys Leu Asn Pro Phe Val Tyr Ile Val Leu Cys Glu Thr Phe Arg
        355                 360                 365

Lys Arg Leu Val Leu Ser Val Lys Pro Ala Ala Gln Gly Gln Leu Arg
    370                 375                 380

Ala Val Ser Asn Ala Gln Thr Ala Asp Glu Glu Arg Thr Glu Ser Lys
385                 390                 395                 400

Gly Thr


<210> SEQ ID NO 193
<211> LENGTH: 1128
<212> TYPE: DNA
<213> ORGANISM: Homo sapiens

<400> SEQUENCE: 193

atggatgtga cttcccaagc ccggggcgtg ggcctggaga tgtacccagg caccgcgcac      60

gctgcggccc ccaacaccac ctcccccgag ctcaacctgt cccacccgct cctgggcacc     120

gccctggcca atgggacagg tgagctctcg gagcaccagc agtacgtgat cggcctgttc     180

ctctcgtgcc tctacaccat cttcctcttc cccatcggct ttgtgggcaa catcctgatc     240

ctggtggtga acatcagctt ccgcgagaag atgaccatcc ccgacctgta cttcatcaac     300

ctggcggtgg cggacctcat cctggtggcc gactccctca ttgaggtgtt caacctgcac     360

gagcggtact acgacatcgc cgtcctgtgc accttcatgt cgctcttcct gcaggtcaac     420

atgtacagca gcgtcttctt cctcacctgg atgagcttcg accgctacat cgccctggcc     480

agggccatgc gctgcagcct gttccgcacc aagcaccacg cccggctgag ctgtggcctc     540

atctggatgg catccgtgtc agccacgctg gtgcccttca ccgccgtgca cctgcagcac     600

accgacgagg cctgcttctg tttcgcggat gtccgggagg tgcagtggct cgaggtcacg     660

ctgggcttca tcgtgccctt cgccatcatc ggcctgtgct actccctcat tgtccgggtg     720

ctggtcaggg cgcaccggca ccgtgggctg cggccccggc ggcagaaggc gaaacgcatg     780

atcctcgcgg tggtgctggt cttcttcgtc tgctggctgc cggagaacgt cttcatcagc     840

gtgcacctcc tgcagcggac gcagcctggg gccgctccct gcaagcagtc tttccgccat     900

gcccaccccc tcacgggcca cattgtcaac ctcgccgcct tctccaacag ctgcctaaac     960

cccctcatct acagctttct cggggagacc ttcagggaca agctgaggct gtacattgag    1020

cagaaaacaa atttgccggc cctgaaccgc ttctgtcacg ctgccctgaa ggccgtcatt    1080

ccagacagca ccgagcagtc ggatgtgagg ttcagcagtg ccgtgtga                 1128


<210> SEQ ID NO 194
<211> LENGTH: 375
<212> TYPE: PRT
<213> ORGANISM: Homo sapiens

<400> SEQUENCE: 194

Met Asp Val Thr Ser Gln Ala Arg Gly Val Gly Leu Glu Met Tyr Pro
1               5                   10                  15
```

-continued

```
Gly Thr Ala His Ala Ala Ala Pro Asn Thr Thr Ser Pro Glu Leu Asn
            20                  25                  30

Leu Ser His Pro Leu Leu Gly Thr Ala Leu Ala Asn Gly Thr Gly Glu
        35                  40                  45

Leu Ser Glu His Gln Gln Tyr Val Ile Gly Leu Phe Leu Ser Cys Leu
    50                  55                  60

Tyr Thr Ile Phe Leu Phe Pro Ile Gly Phe Val Gly Asn Ile Leu Ile
65                  70                  75                  80

Leu Val Val Asn Ile Ser Phe Arg Glu Lys Met Thr Ile Pro Asp Leu
                85                  90                  95

Tyr Phe Ile Asn Leu Ala Val Ala Asp Leu Ile Leu Val Ala Asp Ser
            100                 105                 110

Leu Ile Glu Val Phe Asn Leu His Glu Arg Tyr Tyr Asp Ile Ala Val
        115                 120                 125

Leu Cys Thr Phe Met Ser Leu Phe Leu Gln Val Asn Met Tyr Ser Ser
    130                 135                 140

Val Phe Phe Leu Thr Trp Met Ser Phe Asp Arg Tyr Ile Ala Leu Ala
145                 150                 155                 160

Arg Ala Met Arg Cys Ser Leu Phe Arg Thr Lys His His Ala Arg Leu
                165                 170                 175

Ser Cys Gly Leu Ile Trp Met Ala Ser Val Ser Ala Thr Leu Val Pro
            180                 185                 190

Phe Thr Ala Val His Leu Gln His Thr Asp Glu Ala Cys Phe Cys Phe
        195                 200                 205

Ala Asp Val Arg Glu Val Gln Trp Leu Glu Val Thr Leu Gly Phe Ile
    210                 215                 220

Val Pro Phe Ala Ile Ile Gly Leu Cys Tyr Ser Leu Ile Val Arg Val
225                 230                 235                 240

Leu Val Arg Ala His Arg His Arg Gly Leu Arg Pro Arg Arg Gln Lys
                245                 250                 255

Ala Lys Arg Met Ile Leu Ala Val Val Leu Val Phe Phe Val Cys Trp
            260                 265                 270

Leu Pro Glu Asn Val Phe Ile Ser Val His Leu Leu Gln Arg Thr Gln
        275                 280                 285

Pro Gly Ala Ala Pro Cys Lys Gln Ser Phe Arg His Ala His Pro Leu
    290                 295                 300

Thr Gly His Ile Val Asn Leu Ala Ala Phe Ser Asn Ser Cys Leu Asn
305                 310                 315                 320

Pro Leu Ile Tyr Ser Phe Leu Gly Glu Thr Phe Arg Asp Lys Leu Arg
                325                 330                 335

Leu Tyr Ile Glu Gln Lys Thr Asn Leu Pro Ala Leu Asn Arg Phe Cys
            340                 345                 350

His Ala Ala Leu Lys Ala Val Ile Pro Asp Ser Thr Glu Gln Ser Asp
        355                 360                 365

Val Arg Phe Ser Ser Ala Val
    370                 375
```

<210> SEQ ID NO 195
<211> LENGTH: 960
<212> TYPE: DNA
<213> ORGANISM: Homo sapiens

<400> SEQUENCE: 195
atgccattcc caaactgctc agcccccagc actgtggtgg ccacagctgt gggtgtcttg     60

-continued

```
ctggggctgg agtgtgggct gggtctgctg ggcaacgcgg tggcgctgtg gaccttcctg    120

ttccgggtca gggtgtggaa gccgtacgct gtctacctgc tcaacctggc cctggctgac    180

ctgctgttgg ctgcgtgcct gcctttcctg gccgccttct acctgagcct ccaggcttgg    240

catctgggcc gtgtgggctg ctgggccctg cgcttcctgc tggacctcag ccgcagcgtg    300

gggatggcct tcctggccgc cgtggctttg gaccggtacc tccgtgtggt ccaccctcgg    360

cttaaggtca acctgctgtc tcctcaggcg gccctggggg tctcgggcct cgtctggctc    420

ctgatggtcg ccctcacctg cccgggcttg ctcatctctg aggccgccca gaactccacc    480

aggtgccaca gtttctactc cagggcagac ggctccttca gcatcatctg gcaggaagca    540

ctctcctgcc ttcagtttgt cctccccttt ggcctcatcg tgttctgcaa tgcaggcatc    600

atcagggctc tccagaaaag actccgggag cctgagaaac agcccaagct tcagcgggcc    660

aaggcactgg tcaccttggt ggtggtgctg tttgctctgt gctttctgcc ctgcttcctg    720

gccagagtcc tgatgcacat cttccagaat ctggggagct gcagggccct ttgtgcagtg    780

gctcatacct cggatgtcac gggcagcctc acctacctgc acagtgtcgt caaccccgtg    840

gtatactgct tctccagccc caccttcagg agctcctatc ggagggtctt ccacaccctc    900

cgaggcaaag ggcaggcagc agagcccccca gatttcaacc ccagagactc ctattcctga    960
```

```
<210> SEQ ID NO 196
<211> LENGTH: 319
<212> TYPE: PRT
<213> ORGANISM: Homo sapiens

<400> SEQUENCE: 196

Met Pro Phe Pro Asn Cys Ser Ala Pro Ser Thr Val Val Ala Thr Ala
1               5                   10                  15

Val Gly Val Leu Leu Gly Leu Glu Cys Gly Leu Gly Leu Leu Gly Asn
            20                  25                  30

Ala Val Ala Leu Trp Thr Phe Leu Phe Arg Val Arg Val Trp Lys Pro
        35                  40                  45

Tyr Ala Val Tyr Leu Leu Asn Leu Ala Leu Ala Asp Leu Leu Leu Ala
    50                  55                  60

Ala Cys Leu Pro Phe Leu Ala Ala Phe Tyr Leu Ser Leu Gln Ala Trp
65                  70                  75                  80

His Leu Gly Arg Val Gly Cys Trp Ala Leu Arg Phe Leu Leu Asp Leu
                85                  90                  95

Ser Arg Ser Val Gly Met Ala Phe Leu Ala Ala Val Ala Leu Asp Arg
            100                 105                 110

Tyr Leu Arg Val Val His Pro Arg Leu Lys Val Asn Leu Leu Ser Pro
        115                 120                 125

Gln Ala Ala Leu Gly Val Ser Gly Leu Val Trp Leu Leu Met Val Ala
    130                 135                 140

Leu Thr Cys Pro Gly Leu Leu Ile Ser Glu Ala Ala Gln Asn Ser Thr
145                 150                 155                 160

Arg Cys His Ser Phe Tyr Ser Arg Ala Asp Gly Ser Phe Ser Ile Ile
                165                 170                 175

Trp Gln Glu Ala Leu Ser Cys Leu Gln Phe Val Leu Pro Phe Gly Leu
            180                 185                 190

Ile Val Phe Cys Asn Ala Gly Ile Ile Arg Ala Leu Gln Lys Arg Leu
        195                 200                 205

Arg Glu Pro Glu Lys Gln Pro Lys Leu Gln Arg Ala Lys Ala Leu Val
    210                 215                 220
```

-continued

```
Thr Leu Val Val Val Leu Phe Ala Leu Cys Phe Leu Pro Cys Phe Leu
225                 230                 235                 240

Ala Arg Val Leu Met His Ile Phe Gln Asn Leu Gly Ser Cys Arg Ala
                245                 250                 255

Leu Cys Ala Val Ala His Thr Ser Asp Val Thr Gly Ser Leu Thr Tyr
            260                 265                 270

Leu His Ser Val Val Asn Pro Val Val Tyr Cys Phe Ser Ser Pro Thr
        275                 280                 285

Phe Arg Ser Ser Tyr Arg Arg Val Phe His Thr Leu Arg Gly Lys Gly
    290                 295                 300

Gln Ala Ala Glu Pro Pro Asp Phe Asn Pro Arg Asp Ser Tyr Ser
305                 310                 315
```

<210> SEQ ID NO 197
<211> LENGTH: 1143
<212> TYPE: DNA
<213> ORGANISM: Homo sapiens

<400> SEQUENCE: 197

```
atggaggaag gtggtgattt tgacaactac tatggggcag acaaccagtc tgagtgtgag      60

tacacagact ggaaatcctc gggggccctc atccctgcca tctacatgtt ggtcttcctc     120

ctgggcacca cgggaaacgg tctggtgctc tggaccgtgt ttcggagcag ccgggagaag     180

aggcgctcag ctgatatctt cattgctagc ctggcggtgg ctgacctgac cttcgtggtg     240

acgctgcccc tgtgggctac ctacacgtac cgggactatg actggccctt tgggaccttc     300

ttctgcaagc tcagcagcta cctcatcttc gtcaacatgt acgccagcgt cttctgcctc     360

accggcctca gcttcgaccg ctacctggcc atcgtgaggc cagtggccaa tgctcggctg     420

aggctgcggg tcagcggggc cgtggccacg gcagttcttt gggtgctggc cgccctcctg     480

gccatgcctg tcatggtgtt acgcaccacc ggggacttgg agaacaccac taaggtgcag     540

tgctacatgg actactccat ggtggccact gtgagctcag agtgggcctg ggaggtgggc     600

cttggggtct cgtccaccac cgtgggcttt gtggtgccct tcaccatcat gctgacctgt     660

tacttcttca tcgcccaaac catcgctggc cacttccgca aggaacgcat cgagggcctg     720

cggaagcggc gccggcttaa gagcatcatc gtggtgctgg tggtgacctt tgccctgtgc     780

tggatgccct accacctggt gaagacgctg tacatgctgg gcagcctgct gcactggccc     840

tgtgactttg acctcttcct catgaacatc ttcccctact gcacctgcat cagctacgtc     900

aacagctgcc tcaacccctt cctctatgcc tttttcgacc cccgcttccg ccaggcctgc     960

acctccatgc tctgctgtgg ccagagcagg tgcgcaggca cctcccacag cagcagtggg    1020

gagaagtcag ccagctactc ttcggggcac agccaggggc ccggccccaa catgggcaag    1080

ggtggagaac agatgcacga gaaatccatc ccctacagcc aggagaccct tgtggttgac    1140

tag                                                                  1143
```

<210> SEQ ID NO 198
<211> LENGTH: 380
<212> TYPE: PRT
<213> ORGANISM: Homo sapiens

<400> SEQUENCE: 198

```
Met Glu Glu Gly Gly Asp Phe Asp Asn Tyr Tyr Gly Ala Asp Asn Gln
1               5                   10                  15

Ser Glu Cys Glu Tyr Thr Asp Trp Lys Ser Ser Gly Ala Leu Ile Pro
```

-continued

```
            20                  25                  30

Ala Ile Tyr Met Leu Val Phe Leu Leu Gly Thr Thr Gly Asn Gly Leu
        35                  40                  45

Val Leu Trp Thr Val Phe Arg Ser Ser Arg Glu Lys Arg Arg Ser Ala
    50                  55                  60

Asp Ile Phe Ile Ala Ser Leu Ala Val Ala Asp Leu Thr Phe Val Val
65                  70                  75                  80

Thr Leu Pro Leu Trp Ala Thr Tyr Thr Tyr Arg Asp Tyr Asp Trp Pro
                85                  90                  95

Phe Gly Thr Phe Phe Cys Lys Leu Ser Ser Tyr Leu Ile Phe Val Asn
            100                 105                 110

Met Tyr Ala Ser Val Phe Cys Leu Thr Gly Leu Ser Phe Asp Arg Tyr
        115                 120                 125

Leu Ala Ile Val Arg Pro Val Ala Asn Ala Arg Leu Arg Leu Arg Val
    130                 135                 140

Ser Gly Ala Val Ala Thr Ala Val Leu Trp Val Leu Ala Ala Leu Leu
145                 150                 155                 160

Ala Met Pro Val Met Val Leu Arg Thr Thr Gly Asp Leu Glu Asn Thr
                165                 170                 175

Thr Lys Val Gln Cys Tyr Met Asp Tyr Ser Met Val Ala Thr Val Ser
            180                 185                 190

Ser Glu Trp Ala Trp Glu Val Gly Leu Gly Val Ser Ser Thr Thr Val
        195                 200                 205

Gly Phe Val Val Pro Phe Thr Ile Met Leu Thr Cys Tyr Phe Phe Ile
    210                 215                 220

Ala Gln Thr Ile Ala Gly His Phe Arg Lys Glu Arg Ile Glu Gly Leu
225                 230                 235                 240

Arg Lys Arg Arg Arg Leu Lys Ser Ile Ile Val Val Leu Val Val Thr
                245                 250                 255

Phe Ala Leu Cys Trp Met Pro Tyr His Leu Val Lys Thr Leu Tyr Met
            260                 265                 270

Leu Gly Ser Leu Leu His Trp Pro Cys Asp Phe Asp Leu Phe Leu Met
        275                 280                 285

Asn Ile Phe Pro Tyr Cys Thr Cys Ile Ser Tyr Val Asn Ser Cys Leu
    290                 295                 300

Asn Pro Phe Leu Tyr Ala Phe Phe Asp Pro Arg Phe Arg Gln Ala Cys
305                 310                 315                 320

Thr Ser Met Leu Cys Cys Gly Gln Ser Arg Cys Ala Gly Thr Ser His
                325                 330                 335

Ser Ser Ser Gly Glu Lys Ser Ala Ser Tyr Ser Ser Gly His Ser Gln
            340                 345                 350

Gly Pro Gly Pro Asn Met Gly Lys Gly Gly Glu Gln Met His Glu Lys
        355                 360                 365

Ser Ile Pro Tyr Ser Gln Glu Thr Leu Val Val Asp
    370                 375                 380

<210> SEQ ID NO 199
<211> LENGTH: 1119
<212> TYPE: DNA
<213> ORGANISM: Homo sapiens

<400> SEQUENCE: 199

atgaactacc cgctaacgct ggaaatggac ctcgagaacc tggaggacct gttctgggaa      60

ctggacagat tggacaacta taacgacacc tccctggtgg aaaatcatct ctgccctgcc     120
```

-continued

```
acagagggtc ccctcatggc ctccttcaag gccgtgttcg tgcccgtggc ctacagcctc    180

atcttcctcc tgggcgtgat cggcaacgtc ctggtgctgg tgatcctgga gcggcaccgg    240

cagacacgca gttccacgga gaccttcctg ttccacctgg ccgtggccga cctcctgctg    300

gtcttcatct tgccctttgc cgtggccgag ggctctgtgg gctgggtcct ggggaccttc    360

ctctgcaaaa ctgtgattgc cctgcacaaa gtcaacttct actgcagcag cctgctcctg    420

gcctgcatcg ccgtggaccg ctacctggcc attgtccacg ccgtccatgc ctaccgccac    480

cgccgcctcc tctccatcca catcacctgt gggaccatct ggctggtggg cttcctcctt    540

gccttgccag agattctctt cgccaaagtc agccaaggcc atcacaacaa ctccctgcca    600

cgttgcacct tctcccaaga gaaccaagca gaaacgcatg cctggttcac ctcccgattc    660

ctctaccatg tggcgggatt cctgctgccc atgctggtga tgggctggtg ctacgtgggg    720

gtagtgcaca ggttgcgcca ggcccagcgg cgccctcagc ggcagaaggc aaaaagggtg    780

gccatcctgg tgacaagcat cttcttcctc tgctggtcac cctaccacat cgtcatcttc    840

ctggacaccc tggcgaggct gaaggccgtg gacaatacct gcaagctgaa tggctctctc    900

cccgtggcca tcaccatgtg tgagttcctg ggcctggccc actgctgcct caaccccatg    960

ctctacactt tcgccggcgt gaagttccgc agtgacctgt cgcggctcct gaccaagctg   1020

ggctgtaccg gccctgcctc cctgtgccag ctcttcccta gctggcgcag gagcagtctc   1080

tctgagtcag agaatgccac ctctctcacc acgttctag                          1119
```

<210> SEQ ID NO 200
<211> LENGTH: 372
<212> TYPE: PRT
<213> ORGANISM: Homo sapiens

<400> SEQUENCE: 200

```
Met Asn Tyr Pro Leu Thr Leu Glu Met Asp Leu Glu Asn Leu Glu Asp
1               5                   10                  15

Leu Phe Trp Glu Leu Asp Arg Leu Asp Asn Tyr Asn Asp Thr Ser Leu
            20                  25                  30

Val Glu Asn His Leu Cys Pro Ala Thr Glu Gly Pro Leu Met Ala Ser
        35                  40                  45

Phe Lys Ala Val Phe Val Pro Val Ala Tyr Ser Leu Ile Phe Leu Leu
    50                  55                  60

Gly Val Ile Gly Asn Val Leu Val Leu Val Ile Leu Glu Arg His Arg
65                  70                  75                  80

Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
            100                 105                 110

Val Gly Trp Val Leu Gly Thr Phe Leu Cys Lys Thr Val Ile Ala Leu
        115                 120                 125

His Lys Val Asn Phe Tyr Cys Ser Ser Leu Leu Leu Ala Cys Ile Ala
    130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175

Gly Phe Leu Leu Ala Leu Pro Glu Ile Leu Phe Ala Lys Val Ser Gln
            180                 185                 190
```

-continued

```
Gly His His Asn Asn Ser Leu Pro Arg Cys Thr Phe Ser Gln Glu Asn
        195                 200                 205

Gln Ala Glu Thr His Ala Trp Phe Thr Ser Arg Phe Leu Tyr His Val
    210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Arg Pro Gln Arg Gln Lys
                245                 250                 255

Ala Lys Arg Val Ala Ile Leu Val Thr Ser Ile Phe Phe Leu Cys Trp
            260                 265                 270

Ser Pro Tyr His Ile Val Ile Phe Leu Asp Thr Leu Ala Arg Leu Lys
        275                 280                 285

Ala Val Asp Asn Thr Cys Lys Leu Asn Gly Ser Leu Pro Val Ala Ile
    290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
                325                 330                 335

Leu Thr Lys Leu Gly Cys Thr Gly Pro Ala Ser Leu Cys Gln Leu Phe
            340                 345                 350

Pro Ser Trp Arg Arg Ser Ser Leu Ser Glu Ser Glu Asn Ala Thr Ser
        355                 360                 365

Leu Thr Thr Phe
    370


<210> SEQ ID NO 201
<211> LENGTH: 1128
<212> TYPE: DNA
<213> ORGANISM: Homo sapiens

<400> SEQUENCE: 201

atggatgtga cttcccaagc ccggggcgtg ggcctggaga tgtacccagg caccgcgcag      60

cctgcggccc ccaacaccac ctcccccgag ctcaacctgt cccacccgct cctgggcacc     120

gccctggcca atgggacagg tgagctctcg gagcaccagc agtacgtgat cggcctgttc     180

ctctcgtgcc tctacaccat cttcctcttc cccatcggct ttgtgggcaa catcctgatc     240

ctggtggtga acatcagctt ccgcgagaag atgaccatcc ccgacctgta cttcatcaac     300

ctggcggtgg cggacctcat cctggtggcc gactccctca ttgaggtgtt caacctgcac     360

gagcggtact acgacatcgc cgtcctgtgc accttcatgt cgctcttcct gcaggtcaac     420

atgtacagca gcgtcttctt cctcacctgg atgagcttcg accgctacat cgccctggcc     480

agggccatgc gctgcagcct gttccgcacc aagcaccacg cccggctgag ctgtggcctc     540

atctggatgg catccgtgtc agccacgctg gtgcccttca ccgccgtgca cctgcagcac     600

accgacgagg cctgcttctg tttcgcggat gtccgggagg tgcagtggct cgaggtcacg     660

ctgggcttca tcgtgccctt cgccatcatc ggcctgtgct actccctcat tgtccgggtg     720

ctggtcaggg cgcaccggca ccgtgggctg cggccccggc ggcagaaggc gaagcgcatg     780

atcctcgcgg tggtgctggt cttcttcgtc tgctggctgc cggagaacgt cttcatcagc     840

gtgcacctcc tgcagcggac gcagcctggg gccgctccct gcaagcagtc tttccgccat     900

gcccaccccc tcacgggcca cattgtcaac ctcaccgcct tctccaacag ctgcctaaac     960

cccctcatct acagctttct cggggagacc ttcagggaca agctgaggct gtacattgag    1020

cagaaaacaa atttgccggc cctgaaccgc ttctgtcacg ctgccctgaa ggccgtcatt    1080
```

-continued

```
ccagacagca ccgagcagtc ggatgtgagg ttcagcagtg ccgtgtag                1128


<210> SEQ ID NO 202
<211> LENGTH: 375
<212> TYPE: PRT
<213> ORGANISM: Homo sapiens

<400> SEQUENCE: 202

Met Asp Val Thr Ser Gln Ala Arg Gly Val Gly Leu Glu Met Tyr Pro
1               5                   10                  15

Gly Thr Ala Gln Pro Ala Ala Pro Asn Thr Thr Ser Pro Glu Leu Asn
            20                  25                  30

Leu Ser His Pro Leu Leu Gly Thr Ala Leu Ala Asn Gly Thr Gly Glu
        35                  40                  45

Leu Ser Glu His Gln Gln Tyr Val Ile Gly Leu Phe Leu Ser Cys Leu
    50                  55                  60

Tyr Thr Ile Phe Leu Phe Pro Ile Gly Phe Val Gly Asn Ile Leu Ile
65                  70                  75                  80

Leu Val Val Asn Ile Ser Phe Arg Glu Lys Met Thr Ile Pro Asp Leu
                85                  90                  95

Tyr Phe Ile Asn Leu Ala Val Ala Asp Leu Ile Leu Val Ala Asp Ser
            100                 105                 110

Leu Ile Glu Val Phe Asn Leu His Glu Arg Tyr Tyr Asp Ile Ala Val
        115                 120                 125

Leu Cys Thr Phe Met Ser Leu Phe Leu Gln Val Asn Met Tyr Ser Ser
    130                 135                 140

Val Phe Phe Leu Thr Trp Met Ser Phe Asp Arg Tyr Ile Ala Leu Ala
145                 150                 155                 160

Arg Ala Met Arg Cys Ser Leu Phe Arg Thr Lys His His Ala Arg Leu
                165                 170                 175

Ser Cys Gly Leu Ile Trp Met Ala Ser Val Ser Ala Thr Leu Val Pro
            180                 185                 190

Phe Thr Ala Val His Leu Gln His Thr Asp Glu Ala Cys Phe Cys Phe
        195                 200                 205

Ala Asp Val Arg Glu Val Gln Trp Leu Glu Val Thr Leu Gly Phe Ile
    210                 215                 220

Val Pro Phe Ala Ile Ile Gly Leu Cys Tyr Ser Leu Ile Val Arg Val
225                 230                 235                 240

Leu Val Arg Ala His Arg His Arg Gly Leu Arg Pro Arg Arg Gln Lys
                245                 250                 255

Ala Lys Arg Met Ile Leu Ala Val Val Leu Val Phe Phe Val Cys Trp
            260                 265                 270

Leu Pro Glu Asn Val Phe Ile Ser Val His Leu Leu Gln Arg Thr Gln
        275                 280                 285

Pro Gly Ala Ala Pro Cys Lys Gln Ser Phe Arg His Ala His Pro Leu
    290                 295                 300

Thr Gly His Ile Val Asn Leu Thr Ala Phe Ser Asn Ser Cys Leu Asn
305                 310                 315                 320

Pro Leu Ile Tyr Ser Phe Leu Gly Glu Thr Phe Arg Asp Lys Leu Arg
                325                 330                 335

Leu Tyr Ile Glu Gln Lys Thr Asn Leu Pro Ala Leu Asn Arg Phe Cys
            340                 345                 350

His Ala Ala Leu Lys Ala Val Ile Pro Asp Ser Thr Glu Gln Ser Asp
        355                 360                 365
```

-continued

Val Arg Phe Ser Ser Ala Val
370 375

<210> SEQ ID NO 203
<211> LENGTH: 1137
<212> TYPE: DNA
<213> ORGANISM: Homo sapiens

<400> SEQUENCE: 203
atggacctgg ggaaaccaat gaaaagcgtg ctggtggtgg ctctccttgt cattttccag 60
gtatgcctgt gtcaagatga ggtcacggac gattacatcg gagacaacac cacagtggac 120
tacactttgt tcgagtcttt gtgctccaag aaggacgtgc ggaactttaa agcctggttc 180
ctccctatca tgtactccat catttgtttc gtgggcctac tgggcaatgg gctggtcgtg 240
ttgacctata tctatttcaa gaggctcaag accatgaccg atacctacct gctcaacctg 300
gcggtggcag acatcctctt cctcctgacc cttcccttct gggcctacag cgcggccaag 360
tcctgggtct tcggtgtcca cttttgcaag ctcatctttg ccatctacaa gatgagcttc 420
ttcagtggca tgctcctact tctttgcatc agcattgacc gctacgtggc catcgtccag 480
gctgtctcag ctcaccgcca ccgtgcccgc gtccttctca tcagcaagct gtcctgtgtg 540
ggcatctgga tactagccac agtgctctcc atcccagagc tcctgtacag tgacctccag 600
aggagcagca gtgagcaagc gatgcgatgc tctctcatca cagagcatgt ggaggccttt 660
atcaccatcc aggtggccca gatggtgatc ggctttctgg tcccccctgct ggccatgagc 720 ttctgttacc ttgtcatcat ccgcaccctg ctccaggcac gcaactttga gcgcaacaag 780
gccaaaaagg tgatcatcgc tgtggtcgtg gtcttcatag tcttccagct gccctacaat 840
ggggtggtcc tggcccagac ggtggccaac ttcaacatca ccagtagcac ctgtgagctc 900
agtaagcaac tcaacatcgc ctacgacgtc acctacagcc tggcctgcgt ccgctgctgc 960
gtcaaccctt tcttgtacgc cttcatcggc gtcaagttcc gcaacgatct cttcaagctc 1020
ttcaaggacc tgggctgcct cagccaggag cagctccggc agtggtcttc ctgtcggcac 1080
atccggcgct cctccatgag tgtggaggcc gagaccacca ccaccttctc cccatag 1137

<210> SEQ ID NO 204
<211> LENGTH: 378
<212> TYPE: PRT
<213> ORGANISM: Homo sapiens

<400> SEQUENCE: 204

Met Asp Leu Gly Lys Pro Met Lys Ser Val Leu Val Val Ala Leu Leu
1 5 10 15

Val Ile Phe Gln Val Cys Leu Cys Gln Asp Glu Val Thr Asp Asp Tyr
20 25 30

Ile Gly Asp Asn Thr Thr Val Asp Tyr Thr Leu Phe Glu Ser Leu Cys
35 40 45

Ser Lys Lys Asp Val Arg Asn Phe Lys Ala Trp Phe Leu Pro Ile Met
50 55 60

Tyr Ser Ile Ile Cys Phe Val Gly Leu Leu Gly Asn Gly Leu Val Val
65 70 75 80

Leu Thr Tyr Ile Tyr Phe Lys Arg Leu Lys Thr Met Thr Asp Thr Tyr
85 90 95

Leu Leu Asn Leu Ala Val Ala Asp Ile Leu Phe Leu Leu Thr Leu Pro
100 105 110

-continued

```
Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Ser Glu Gln Ala Met
        195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Lys Lys Val Ile Ile Ala Val Val Val Val Phe
            260                 265                 270

Ile Val Phe Gln Leu Pro Tyr Asn Gly Val Val Leu Ala Gln Thr Val
        275                 280                 285

Ala Asn Phe Asn Ile Thr Ser Ser Thr Cys Glu Leu Ser Lys Gln Leu
    290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
        355                 360                 365

Glu Ala Glu Thr Thr Thr Thr Phe Ser Pro
    370                 375
```

<210> SEQ ID NO 205
<211> LENGTH: 1086
<212> TYPE: DNA
<213> ORGANISM: Homo sapiens

<400> SEQUENCE: 205

```
atggatatac aaatggcaaa caattttact ccgccctctg caactcctca gggaaatgac     60

tgtgacctct atgcacatca cagcacggcc aggatagtaa tgcctctgca ttacagcctc    120

gtcttcatca ttgggctcgt gggaaactta ctagccttgg tcgtcattgt tcaaaacagg    180

aaaaaaatca actctaccac cctctattca acaaatttgg tgatttctga tatacttttt    240

accacggctt tgcctacacg aatagcctac tatgcaatgg gctttgactg gagaatcgga    300

gatgccttgt gtaggataac tgcgctagtg ttttacatca acacatatgc aggtgtgaac    360

tttatgacct gcctgagtat tgaccgcttc attgctgtgg tgcaccctct acgctacaac    420

aagataaaaa ggattgaaca tgcaaaaggc gtgtgcatat ttgtctggat tctagtattt    480

gctcagacac tcccactcct catcaaccct atgtcaaagc aggaggctga aaggattaca    540

tgcatggagt atccaaactt tgaagaaact aaatctcttc cctggattct gcttggggca    600
```

-continued

```
tgtttcatag gatatgtact tccacttata atcattctca tctgctattc tcagatctgc    660

tgcaaactct tcagaactgc caaacaaaac ccactcactg agaaatctgg tgtaaacaaa    720

aaggctaaaa acacaattat tcttattatt gttgtgtttg ttctctgttt cacaccttac    780

catgttgcaa ttattcaaca tatgattaag aagcttcgtt tctctaattt cctggaatgt    840

agccaaagac attcgttcca gatttctctg cactttacag tatgcctgat gaacttcaat    900

tgctgcatgg acccttttat ctacttcttt gcatgtaaag ggtataagag aaaggttatg    960

aggatgctga aacggcaagt cagtgtatcg atttctagtg ctgtgaagtc agcccctgaa   1020

gaaaattcac gtgaaatgac agaaacgcag atgatgatac attccaagtc ttcaaatgga   1080

aagtga                                                              1086
```

```
<210> SEQ ID NO 206
<211> LENGTH: 361
<212> TYPE: PRT
<213> ORGANISM: Homo sapiens

<400> SEQUENCE: 206

Met Asp Ile Gln Met Ala Asn Asn Phe Thr Pro Pro Ser Ala Thr Pro
1               5                   10                  15

Gln Gly Asn Asp Cys Asp Leu Tyr Ala His His Ser Thr Ala Arg Ile
            20                  25                  30

Val Met Pro Leu His Tyr Ser Leu Val Phe Ile Ile Gly Leu Val Gly
        35                  40                  45

Asn Leu Leu Ala Leu Val Val Ile Val Gln Asn Arg Lys Lys Ile Asn
    50                  55                  60

Ser Thr Thr Leu Tyr Ser Thr Asn Leu Val Ile Ser Asp Ile Leu Phe
65                  70                  75                  80

Thr Thr Ala Leu Pro Thr Arg Ile Ala Tyr Tyr Ala Met Gly Phe Asp
                85                  90                  95

Trp Arg Ile Gly Asp Ala Leu Cys Arg Ile Thr Ala Leu Val Phe Tyr
            100                 105                 110

Ile Asn Thr Tyr Ala Gly Val Asn Phe Met Thr Cys Leu Ser Ile Asp
        115                 120                 125

Arg Phe Ile Ala Val Val His Pro Leu Arg Tyr Asn Lys Ile Lys Arg
    130                 135                 140

Ile Glu His Ala Lys Gly Val Cys Ile Phe Val Trp Ile Leu Val Phe
145                 150                 155                 160

Ala Gln Thr Leu Pro Leu Leu Ile Asn Pro Met Ser Lys Gln Glu Ala
                165                 170                 175

Glu Arg Ile Thr Cys Met Glu Tyr Pro Asn Phe Glu Glu Thr Lys Ser
            180                 185                 190

Leu Pro Trp Ile Leu Leu Gly Ala Cys Phe Ile Gly Tyr Val Leu Pro
        195                 200                 205

Leu Ile Ile Ile Leu Ile Cys Tyr Ser Gln Ile Cys Cys Lys Leu Phe
    210                 215                 220

Arg Thr Ala Lys Gln Asn Pro Leu Thr Glu Lys Ser Gly Val Asn Lys
225                 230                 235                 240

Lys Ala Lys Asn Thr Ile Ile Leu Ile Ile Val Val Phe Val Leu Cys
                245                 250                 255

Phe Thr Pro Tyr His Val Ala Ile Ile Gln His Met Ile Lys Lys Leu
            260                 265                 270

Arg Phe Ser Asn Phe Leu Glu Cys Ser Gln Arg His Ser Phe Gln Ile
        275                 280                 285
```

-continued

```
Ser Leu His Phe Thr Val Cys Leu Met Asn Phe Asn Cys Cys Met Asp
    290                 295                 300

Pro Phe Ile Tyr Phe Phe Ala Cys Lys Gly Tyr Lys Arg Lys Val Met
305                 310                 315                 320

Arg Met Leu Lys Arg Gln Val Ser Val Ser Ile Ser Ser Ala Val Lys
                325                 330                 335

Ser Ala Pro Glu Glu Asn Ser Arg Glu Met Thr Glu Thr Gln Met Met
            340                 345                 350

Ile His Ser Lys Ser Ser Asn Gly Lys
        355                 360
```

<210> SEQ ID NO 207
<211> LENGTH: 1446
<212> TYPE: DNA
<213> ORGANISM: Homo sapiens

<400> SEQUENCE: 207

```
atgcggtggc tgtggcccct ggctgtctct cttgctgtga ttttggctgt ggggctaagc     60

agggtctctg ggggtgcccc cctgcacctg ggcaggcaca gagccgagac ccaggagcag    120

cagagccgat ccaagagggg caccgaggat gaggaggcca agggcgtgca gcagtatgtg    180

cctgaggagt gggcggagta cccccggccc attcaccctg ctggcctgca gccaaccaag    240

cccttggtgg ccaccagccc taacccccgac aaggatgggg gcaccccaga cagtgggcag    300

gaactgaggg gcaatctgac aggggcacca gggcagaggc tacagatcca gaaccccctg    360

tatccggtga ccgagagctc ctacagtgcc tatgccatca tgcttctggc gctggtggtg    420

tttgcggtgg gcattgtggg caacctgtcg gtcatgtgca tcgtgtggca cagctactac    480

ctgaagagcg cctggaactc catccttgcc agcctggccc tctgggattt tctggtcctc    540

tttttctgcc tccctattgt catcttcaac gagatcacca agcagaggct actgggtgac    600

gtttcttgtc gtgccgtgcc cttcatggag gtctcctctc tgggagtcac gactttcagc    660

ctctgtgccc tgggcattga ccgcttccac gtggccacca gcaccctgcc caaggtgagg    720

cccatcgagc ggtgccaatc catcctggcc aagttggctg tcatctgggt gggctccatg    780

acgctggctg tgcctgagct cctgctgtgg cagctggcac aggagcctgc ccccaccatg    840

ggcaccctgg actcatgcat catgaaaccc tcagccagcc tgcccgagtc cctgtattca    900

ctggtgatga cctaccagaa cgcccgcatg tggtggtact ttggctgcta cttctgcctg    960

cccatcctct tcacagtcac ctgccagctg gtgacatggc gggtgcgagg ccctccaggg   1020

aggaagtcag agtgcagggc cagcaagcac gagcagtgtg agagccagct caagagcacc   1080

gtggtgggcc tgaccgtggt ctacgccttc tgcaccctcc cagagaacgt ctgcaacatc   1140

gtggtggcct acctctccac cgagctgacc cgccagaccc tggacctcct gggcctcatc   1200

aaccagttct ccaccttctt caagggcgcc atcaccccag tgctgctcct ttgcatctgc   1260

aggccgctgg gccaggcctt cctggactgc tgctgctgct gctgctgtga ggagtgcggc   1320

ggggcttcgg aggcctctgc tgccaatggg tcggacaaca agctcaagac cgaggtgtcc   1380

tcttccatct acttccacaa gcccagggag tcacccccac tcctgcccct gggcacacct   1440

tgctga                                                              1446
```

<210> SEQ ID NO 208
<211> LENGTH: 481
<212> TYPE: PRT
<213> ORGANISM: Homo sapiens

<400> SEQUENCE: 208

Met Arg Trp Leu Trp Pro Leu Ala Val Ser Leu Ala Val Ile Leu Ala
1               5                   10                  15

Val Gly Leu Ser Arg Val Ser Gly Gly Ala Pro Leu His Leu Gly Arg
            20                  25                  30

His Arg Ala Glu Thr Gln Glu Gln Gln Ser Arg Ser Lys Arg Gly Thr
        35                  40                  45

Glu Asp Glu Glu Ala Lys Gly Val Gln Gln Tyr Val Pro Glu Glu Trp
    50                  55                  60

Ala Glu Tyr Pro Arg Pro Ile His Pro Ala Gly Leu Gln Pro Thr Lys
65                  70                  75                  80

Pro Leu Val Ala Thr Ser Pro Asn Pro Asp Lys Asp Gly Gly Thr Pro
                85                  90                  95

Asp Ser Gly Gln Glu Leu Arg Gly Asn Leu Thr Gly Ala Pro Gly Gln
            100                 105                 110

Arg Leu Gln Ile Gln Asn Pro Leu Tyr Pro Val Thr Glu Ser Ser Tyr
        115                 120                 125

Ser Ala Tyr Ala Ile Met Leu Leu Ala Leu Val Val Phe Ala Val Gly
    130                 135                 140

Ile Val Gly Asn Leu Ser Val Met Cys Ile Val Trp His Ser Tyr Tyr
145                 150                 155                 160

Leu Lys Ser Ala Trp Asn Ser Ile Leu Ala Ser Leu Ala Leu Trp Asp
                165                 170                 175

Phe Leu Val Leu Phe Phe Cys Leu Pro Ile Val Ile Phe Asn Glu Ile
            180                 185                 190

Thr Lys Gln Arg Leu Leu Gly Asp Val Ser Cys Arg Ala Val Pro Phe
        195                 200                 205

Met Glu Val Ser Ser Leu Gly Val Thr Thr Phe Ser Leu Cys Ala Leu
    210                 215                 220

Gly Ile Asp Arg Phe His Val Ala Thr Ser Thr Leu Pro Lys Val Arg
225                 230                 235                 240

Pro Ile Glu Arg Cys Gln Ser Ile Leu Ala Lys Leu Ala Val Ile Trp
                245                 250                 255

Val Gly Ser Met Thr Leu Ala Val Pro Glu Leu Leu Leu Trp Gln Leu
            260                 265                 270

Ala Gln Glu Pro Ala Pro Thr Met Gly Thr Leu Asp Ser Cys Ile Met
        275                 280                 285

Lys Pro Ser Ala Ser Leu Pro Glu Ser Leu Tyr Ser Leu Val Met Thr
    290                 295                 300

Tyr Gln Asn Ala Arg Met Trp Trp Tyr Phe Gly Cys Tyr Phe Cys Leu
305                 310                 315                 320

Pro Ile Leu Phe Thr Val Thr Cys Gln Leu Val Thr Trp Arg Val Arg
                325                 330                 335

Gly Pro Pro Gly Arg Lys Ser Glu Cys Arg Ala Ser Lys His Glu Gln
            340                 345                 350

Cys Glu Ser Gln Leu Lys Ser Thr Val Val Gly Leu Thr Val Val Tyr
        355                 360                 365

Ala Phe Cys Thr Leu Pro Glu Asn Val Cys Asn Ile Val Val Ala Tyr
    370                 375                 380

Leu Ser Thr Glu Leu Thr Arg Gln Thr Leu Asp Leu Leu Gly Leu Ile
385                 390                 395                 400

Asn Gln Phe Ser Thr Phe Phe Lys Gly Ala Ile Thr Pro Val Leu Leu

-continued

```
                405                 410                 415

Leu Cys Ile Cys Arg Pro Leu Gly Gln Ala Phe Leu Asp Cys Cys Cys
            420                 425                 430

Cys Cys Cys Cys Glu Glu Cys Gly Gly Ala Ser Glu Ala Ser Ala Ala
        435                 440                 445

Asn Gly Ser Asp Asn Lys Leu Lys Thr Glu Val Ser Ser Ser Ile Tyr
    450                 455                 460

Phe His Lys Pro Arg Glu Ser Pro Pro Leu Leu Pro Leu Gly Thr Pro
465                 470                 475                 480

Cys


<210> SEQ ID NO 209
<211> LENGTH: 1101
<212> TYPE: DNA
<213> ORGANISM: Homo sapiens

<400> SEQUENCE: 209

atgtggaacg cgacgcccag cgaagagccg gggttcaacc tcacactggc cgacctggac      60

tgggatgctt cccccggcaa cgactcgctg ggcgacgagc tgctgcagct cttccccgcg     120

ccgctgctgg cgggcgtcac agccacctgc gtggcactct tcgtggtggg tatcgctggc     180

aacctgctca ccatgctggt ggtgtcgcgc ttccgcgagc tgcgcaccac caccaacctc     240

tacctgtcca gcatggcctt ctccgatctg ctcatcttcc tctgcatgcc cctggacctc     300

gttcgcctct ggcagtaccg gccctggaac ttcggcgacc tcctctgcaa actcttccaa     360

ttcgtcagtg agagctgcac ctacgccacg gtgctcacca tcacagcgct gagcgtcgag     420

cgctacttcg ccatctgctt cccactccgg gccaaggtgg tggtcaccaa ggggcgggtg     480

aagctggtca tcttcgtcat ctgggccgtg gccttctgca gcgccgggcc catcttcgtg     540

ctagtcgggg tggagcacga gaacggcacc gacccttggg acaccaacga gtgccgcccc     600

accgagtttg cggtgcgctc tggactgctc acggtcatgg tgtgggtgtc cagcatcttc     660

ttcttccttc ctgtcttctg tctcacggtc ctctacagtc tcatcggcag gaagctgtgg     720

cggaggaggc gcggcgatgc tgtcgtgggt gcctcgctca gggaccagaa ccacaagcaa     780

accaagaaaa tgctggctgt agtggtgttt gccttcatcc tctgctggct ccccttccac     840

gtagggcgat atttattttc caaatccttt gagcctggct ccttggagat tgctcagatc     900

agccagtact gcaacctcgt gtcctttgtc ctcttctacc tcagtgctgc catcaacccc     960

attctgtaca acatcatgtc caagaagtac cgggtggcag tgttcagact tctgggattc    1020

gaacccttct cccagagaaa gctctccact ctgaaagatg aaagttctcg ggcctggaca    1080

gaatctagta ttaatacatg a                                              1101


<210> SEQ ID NO 210
<211> LENGTH: 366
<212> TYPE: PRT
<213> ORGANISM: Homo sapiens

<400> SEQUENCE: 210

Met Trp Asn Ala Thr Pro Ser Glu Glu Pro Gly Phe Asn Leu Thr Leu
1               5                   10                  15

Ala Asp Leu Asp Trp Asp Ala Ser Pro Gly Asn Asp Ser Leu Gly Asp
            20                  25                  30

Glu Leu Leu Gln Leu Phe Pro Ala Pro Leu Leu Ala Gly Val Thr Ala
        35                  40                  45
```

-continued

```
Thr Cys Val Ala Leu Phe Val Val Gly Ile Ala Gly Asn Leu Leu Thr
    50                  55                  60

Met Leu Val Val Ser Arg Phe Arg Glu Leu Arg Thr Thr Thr Asn Leu
65                  70                  75                  80

Tyr Leu Ser Ser Met Ala Phe Ser Asp Leu Leu Ile Phe Leu Cys Met
                85                  90                  95

Pro Leu Asp Leu Val Arg Leu Trp Gln Tyr Arg Pro Trp Asn Phe Gly
            100                 105                 110

Asp Leu Leu Cys Lys Leu Phe Gln Phe Val Ser Glu Ser Cys Thr Tyr
        115                 120                 125

Ala Thr Val Leu Thr Ile Thr Ala Leu Ser Val Glu Arg Tyr Phe Ala
    130                 135                 140

Ile Cys Phe Pro Leu Arg Ala Lys Val Val Val Thr Lys Gly Arg Val
145                 150                 155                 160

Lys Leu Val Ile Phe Val Ile Trp Ala Val Ala Phe Cys Ser Ala Gly
                165                 170                 175

Pro Ile Phe Val Leu Val Gly Val Glu His Glu Asn Gly Thr Asp Pro
            180                 185                 190

Trp Asp Thr Asn Glu Cys Arg Pro Thr Glu Phe Ala Val Arg Ser Gly
        195                 200                 205

Leu Leu Thr Val Met Val Trp Val Ser Ser Ile Phe Phe Phe Leu Pro
    210                 215                 220

Val Phe Cys Leu Thr Val Leu Tyr Ser Leu Ile Gly Arg Lys Leu Trp
225                 230                 235                 240

Arg Arg Arg Arg Gly Asp Ala Val Val Gly Ala Ser Leu Arg Asp Gln
                245                 250                 255

Asn His Lys Gln Thr Lys Lys Met Leu Ala Val Val Val Phe Ala Phe
            260                 265                 270

Ile Leu Cys Trp Leu Pro Phe His Val Gly Arg Tyr Leu Phe Ser Lys
        275                 280                 285

Ser Phe Glu Pro Gly Ser Leu Glu Ile Ala Gln Ile Ser Gln Tyr Cys
    290                 295                 300

Asn Leu Val Ser Phe Val Leu Phe Tyr Leu Ser Ala Ala Ile Asn Pro
305                 310                 315                 320

Ile Leu Tyr Asn Ile Met Ser Lys Lys Tyr Arg Val Ala Val Phe Arg
                325                 330                 335

Leu Leu Gly Phe Glu Pro Phe Ser Gln Arg Lys Leu Ser Thr Leu Lys
            340                 345                 350

Asp Glu Ser Ser Arg Ala Trp Thr Glu Ser Ser Ile Asn Thr
        355                 360                 365


<210> SEQ ID NO 211
<211> LENGTH: 1842
<212> TYPE: DNA
<213> ORGANISM: Homo sapiens

<400> SEQUENCE: 211

atgcgagccc cgggcgcgct tctcgcccgc atgtcgcggc tactgcttct gctactgctc      60

aaggtgtctg cctcttctgc cctcggggtc gcccctgcgt ccagaaacga aacttgtctg     120

ggggagagct gtgcacctac agtgatccag cgccgcggca gggacgcctg gggaccggga     180

aattctgcaa gagacgttct gcgagcccga gcacccaggg aggagcaggg ggcagcgttt     240

cttgcgggac cctcctggga cctgccggcg gccccgggcc gtgacccggc tgcaggcaga     300

ggggcggagg cgtcggcagc cggacccccg ggacctccaa ccaggccacc tggcccctgg     360
```

-continued

```
aggtggaaag gtgctcgggg tcaggagcct tctgaaactt tggggagagg gaaccccacg    420
gccctccagc tcttccttca gatctcagag gaggaagaga agggtcccag aggcgctggc    480
atttccgggc gtagccagga gcagagtgtg aagacagtcc ccggagccag cgatcttttt    540
tactggccaa ggagagccgg gaaactccag ggttcccacc acaagcccct gtccaagacg    600
gccaatggac tggcggggca cgaagggtgg acaattgcac tcccgggccg ggcgctggcc    660
cagaatggat ccttgggtga aggaatccat gagcctgggg gtccccgccg gggaaacagc    720
acgaaccggc gtgtgagact gaagaacccc ttctacccgc tgacccagga gtcctatgga    780
gcctacgcgg tcatgtgtct gtccgtggtg atcttcggga ccggcatcat tggcaacctg    840
gcggtgatgt gcatcgtgtg ccacaactac tacatgcgga gcatctccaa ctccctcttg    900
gccaacctgg ccttctggga ctttctcatc atcttcttct gccttccgct ggtcatcttc    960
cacgagctga ccaagaagtg gctgctggag gacttctcct gcaagatcgt gccctatata   1020
gaggtcgcct ctctgggagt caccactttc accttatgtg ctctgtgcat agaccgcttc   1080
cgtgctgcca ccaacgtaca gatgtactac gaaatgatcg aaaattgttc ctcaacaact   1140
gccaaacttg ctgttatatg ggtgggagct ctattgttag cacttccaga agttgttctc   1200
cgccagctga gcaaggagga tttggggttt agtggccgag ctccggcaga aaggtgcatt   1260
attaagatct ctcctgattt accagacacc atctatgttc tagccctcac ctacgacagt   1320
gcgagactgt ggtggtattt tggctgttac ttttgtttgc ccacgctttt caccatcacc   1380
tgctctctag tgactgcgag gaaaatccgc aaagcagaga aagcctgtac ccgagggaat   1440
aaacggcaga ttcaactaga gagtcagatg aagtgtacag tagtggcact gaccatttta   1500
tatggatttt gcattattcc tgaaaatatc tgcaacattg ttactgccta catggctaca   1560
ggggtttcac agcagacaat ggacctcctt aatatcatca gccagttcct tttgttcttt   1620
aagtcctgtg tcaccccagt cctccttttc tgtctctgca aacccttcag tcgggccttc   1680
atggagtgct gctgctgttg ctgtgaggaa tgcattcaga agtcttcaac ggtgaccagt   1740
gatgacaatg acaacgagta caccacggaa ctcgaactct cgcctttcag taccatacgc   1800
cgtgaaatgt ccacttttgc ttctgtcgga actcattgct ga                      1842
```

<210> SEQ ID NO 212
<211> LENGTH: 613
<212> TYPE: PRT
<213> ORGANISM: Homo sapiens

<400> SEQUENCE: 212

```
Met Arg Ala Pro Gly Ala Leu Leu Ala Arg Met Ser Arg Leu Leu Leu
1               5                   10                  15

Leu Leu Leu Leu Lys Val Ser Ala Ser Ser Ala Leu Gly Val Ala Pro
            20                  25                  30

Ala Ser Arg Asn Glu Thr Cys Leu Gly Glu Ser Cys Ala Pro Thr Val
        35                  40                  45

Ile Gln Arg Arg Gly Arg Asp Ala Trp Gly Pro Gly Asn Ser Ala Arg
    50                  55                  60

Asp Val Leu Arg Ala Arg Ala Pro Arg Glu Glu Gln Gly Ala Ala Phe
65                  70                  75                  80

Leu Ala Gly Pro Ser Trp Asp Leu Pro Ala Ala Pro Gly Arg Asp Pro
                85                  90                  95

Ala Ala Gly Arg Gly Ala Glu Ala Ser Ala Ala Gly Pro Pro Gly Pro
            100                 105                 110
```

-continued

```
Pro Thr Arg Pro Pro Gly Pro Trp Arg Trp Lys Gly Ala Arg Gly Gln
        115                 120                 125

Glu Pro Ser Glu Thr Leu Gly Arg Gly Asn Pro Thr Ala Leu Gln Leu
    130                 135                 140

Phe Leu Gln Ile Ser Glu Glu Glu Glu Lys Gly Pro Arg Gly Ala Gly
145                 150                 155                 160

Ile Ser Gly Arg Ser Gln Glu Gln Ser Val Lys Thr Val Pro Gly Ala
                165                 170                 175

Ser Asp Leu Phe Tyr Trp Pro Arg Arg Ala Gly Lys Leu Gln Gly Ser
            180                 185                 190

His His Lys Pro Leu Ser Lys Thr Ala Asn Gly Leu Ala Gly His Glu
        195                 200                 205

Gly Trp Thr Ile Ala Leu Pro Gly Arg Ala Leu Ala Gln Asn Gly Ser
    210                 215                 220

Leu Gly Glu Gly Ile His Glu Pro Gly Gly Pro Arg Arg Gly Asn Ser
225                 230                 235                 240

Thr Asn Arg Arg Val Arg Leu Lys Asn Pro Phe Tyr Pro Leu Thr Gln
                245                 250                 255

Glu Ser Tyr Gly Ala Tyr Ala Val Met Cys Leu Ser Val Val Ile Phe
            260                 265                 270

Gly Thr Gly Ile Ile Gly Asn Leu Ala Val Met Cys Ile Val Cys His
        275                 280                 285

Asn Tyr Tyr Met Arg Ser Ile Ser Asn Ser Leu Leu Ala Asn Leu Ala
    290                 295                 300

Phe Trp Asp Phe Leu Ile Ile Phe Phe Cys Leu Pro Leu Val Ile Phe
305                 310                 315                 320

His Glu Leu Thr Lys Lys Trp Leu Leu Glu Asp Phe Ser Cys Lys Ile
                325                 330                 335

Val Pro Tyr Ile Glu Val Ala Ser Leu Gly Val Thr Thr Phe Thr Leu
            340                 345                 350

Cys Ala Leu Cys Ile Asp Arg Phe Arg Ala Ala Thr Asn Val Gln Met
        355                 360                 365

Tyr Tyr Glu Met Ile Glu Asn Cys Ser Ser Thr Thr Ala Lys Leu Ala
    370                 375                 380

Val Ile Trp Val Gly Ala Leu Leu Leu Ala Leu Pro Glu Val Val Leu
385                 390                 395                 400

Arg Gln Leu Ser Lys Glu Asp Leu Gly Phe Ser Gly Arg Ala Pro Ala
                405                 410                 415

Glu Arg Cys Ile Ile Lys Ile Ser Pro Asp Leu Pro Asp Thr Ile Tyr
            420                 425                 430

Val Leu Ala Leu Thr Tyr Asp Ser Ala Arg Leu Trp Trp Tyr Phe Gly
        435                 440                 445

Cys Tyr Phe Cys Leu Pro Thr Leu Phe Thr Ile Thr Cys Ser Leu Val
    450                 455                 460

Thr Ala Arg Lys Ile Arg Lys Ala Glu Lys Ala Cys Thr Arg Gly Asn
465                 470                 475                 480

Lys Arg Gln Ile Gln Leu Glu Ser Gln Met Lys Cys Thr Val Val Ala
                485                 490                 495

Leu Thr Ile Leu Tyr Gly Phe Cys Ile Ile Pro Glu Asn Ile Cys Asn
            500                 505                 510

Ile Val Thr Ala Tyr Met Ala Thr Gly Val Ser Gln Gln Thr Met Asp
        515                 520                 525
```

-continued

```
Leu Leu Asn Ile Ile Ser Gln Phe Leu Leu Phe Phe Lys Ser Cys Val
    530                 535                 540

Thr Pro Val Leu Leu Phe Cys Leu Cys Lys Pro Phe Ser Arg Ala Phe
545                 550                 555                 560

Met Glu Cys Cys Cys Cys Cys Cys Glu Glu Cys Ile Gln Lys Ser Ser
                565                 570                 575

Thr Val Thr Ser Asp Asp Asn Asp Asn Glu Tyr Thr Thr Glu Leu Glu
            580                 585                 590

Leu Ser Pro Phe Ser Thr Ile Arg Arg Glu Met Ser Thr Phe Ala Ser
        595                 600                 605

Val Gly Thr His Cys
    610


<210> SEQ ID NO 213
<211> LENGTH: 1248
<212> TYPE: DNA
<213> ORGANISM: Homo sapiens

<400> SEQUENCE: 213

atggtttttg ctcacagaat ggataacagc aagccacatt tgattattcc tacacttctg      60

gtgcccctcc aaaaccgcag ctgcactgaa acagccacac ctctgccaag ccaatacctg     120

atggaattaa gtgaggagca cagttggatg agcaaccaaa cagaccttca ctatgtgctg     180

aaacccgggg aagtggccac agccagcatc ttctttggga ttctgtggtt gttttctatc     240

ttcggcaatt ccctggtttg tttggtcatc cataggagta ggaggactca gtctaccacc     300

aactactttg tggtctccat ggcatgtgct gaccttctca tcagcgttgc cagcacgcct     360

ttcgtcctgc tccagttcac cactggaagg tggacgctgg gtagtgcaac gtgcaaggtt     420

gtgcgatatt ttcaatatct cactccaggt gtccagatct acgttctcct ctccatctgc     480

atagaccggt tctacaccat cgtctatcct ctgagcttca aggtgtccag agaaaaagcc     540

aagaaaatga ttgcggcatc gtggatcttt gatgcaggct ttgtgacccc tgtgctcttt     600

ttctatggct ccaactggga cagtcattgt aactatttcc tcccctcctc ttgggaaggc     660

actgcctaca ctgtcatcca cttcttggtg ggctttgtga ttccatctgt cctcataatt     720

ttattttacc aaaaggtcat aaaatatatt tggagaatag gcacagatgg ccgaacggtg     780

aggaggacaa tgaacattgt ccctcggaca aaagtgaaaa ctaaaaagat gttcctcatt     840

ttaaatctgt tgtttttgct ctcctggctg ccttttcatg tagctcagct atggcacccc     900

catgaacaag actataagaa aagttccctt gttttcacag ctatcacatg gatatccttt     960

agttcttcag cctctaaacc tactctgtat tcaatttata atgccaattt tcggagaggg    1020

atgaaagaga ctttttgcat gtcctctatg aaatgttacc gaagcaatgc ctatactatc    1080

acaacaagtt caaggatggc caaaaaaaac tacgttggca tttcagaaat cccttccatg    1140

gccaaaacta ttaccaaaga ctcgatctat gactcatttg acagagaagc caaggaaaaa    1200

aagcttgctt ggcccattaa ctcaaatcca ccaaatactt ttgtctaa                 1248


<210> SEQ ID NO 214
<211> LENGTH: 415
<212> TYPE: PRT
<213> ORGANISM: Homo sapiens

<400> SEQUENCE: 214

Met Val Phe Ala His Arg Met Asp Asn Ser Lys Pro His Leu Ile Ile
1               5                   10                  15
```

-continued

```
Pro Thr Leu Leu Val Pro Leu Gln Asn Arg Ser Cys Thr Glu Thr Ala
            20                  25                  30

Thr Pro Leu Pro Ser Gln Tyr Leu Met Glu Leu Ser Glu Glu His Ser
        35                  40                  45

Trp Met Ser Asn Gln Thr Asp Leu His Tyr Val Leu Lys Pro Gly Glu
    50                  55                  60

Val Ala Thr Ala Ser Ile Phe Phe Gly Ile Leu Trp Leu Phe Ser Ile
65                  70                  75                  80

Phe Gly Asn Ser Leu Val Cys Leu Val Ile His Arg Ser Arg Arg Thr
                85                  90                  95

Gln Ser Thr Thr Asn Tyr Phe Val Val Ser Met Ala Cys Ala Asp Leu
            100                 105                 110

Leu Ile Ser Val Ala Ser Thr Pro Phe Val Leu Leu Gln Phe Thr Thr
        115                 120                 125

Gly Arg Trp Thr Leu Gly Ser Ala Thr Cys Lys Val Val Arg Tyr Phe
    130                 135                 140

Gln Tyr Leu Thr Pro Gly Val Gln Ile Tyr Val Leu Leu Ser Ile Cys
145                 150                 155                 160

Ile Asp Arg Phe Tyr Thr Ile Val Tyr Pro Leu Ser Phe Lys Val Ser
                165                 170                 175

Arg Glu Lys Ala Lys Lys Met Ile Ala Ala Ser Trp Ile Phe Asp Ala
            180                 185                 190

Gly Phe Val Thr Pro Val Leu Phe Phe Tyr Gly Ser Asn Trp Asp Ser
        195                 200                 205

His Cys Asn Tyr Phe Leu Pro Ser Ser Trp Glu Gly Thr Ala Tyr Thr
    210                 215                 220

Val Ile His Phe Leu Val Gly Phe Val Ile Pro Ser Val Leu Ile Ile
225                 230                 235                 240

Leu Phe Tyr Gln Lys Val Ile Lys Tyr Ile Trp Arg Ile Gly Thr Asp
                245                 250                 255

Gly Arg Thr Val Arg Arg Thr Met Asn Ile Val Pro Arg Thr Lys Val
            260                 265                 270

Lys Thr Lys Lys Met Phe Leu Ile Leu Asn Leu Leu Phe Leu Leu Ser
        275                 280                 285

Trp Leu Pro Phe His Val Ala Gln Leu Trp His Pro His Glu Gln Asp
    290                 295                 300

Tyr Lys Lys Ser Ser Leu Val Phe Thr Ala Ile Thr Trp Ile Ser Phe
305                 310                 315                 320

Ser Ser Ser Ala Ser Lys Pro Thr Leu Tyr Ser Ile Tyr Asn Ala Asn
                325                 330                 335

Phe Arg Arg Gly Met Lys Glu Thr Phe Cys Met Ser Ser Met Lys Cys
            340                 345                 350

Tyr Arg Ser Asn Ala Tyr Thr Ile Thr Thr Ser Ser Arg Met Ala Lys
        355                 360                 365

Lys Asn Tyr Val Gly Ile Ser Glu Ile Pro Ser Met Ala Lys Thr Ile
    370                 375                 380

Thr Lys Asp Ser Ile Tyr Asp Ser Phe Asp Arg Glu Ala Lys Glu Lys
385                 390                 395                 400

Lys Leu Ala Trp Pro Ile Asn Ser Asn Pro Pro Asn Thr Phe Val
                405                 410                 415
```

<210> SEQ ID NO 215
<211> LENGTH: 1842
<212> TYPE: DNA

-continued

<213> ORGANISM: Homo sapiens

<400> SEQUENCE: 215

```
atggggccca ccctagcggt tcccaccccc tatggctgta ttggctgtaa gctaccccag     60
ccagaatacc caccggctct aatcatcttt atgttctgcg cgatggttat caccatcgtt    120
gtagacctaa tcggcaactc catggtcatt ttggctgtga cgaagaacaa gaagctccgg    180
aattctggca acatcttcgt ggtcagtctc tctgtggccg atatgctggt ggccatctac    240
ccataccctt tgatgctgca tgccatgtcc attgggggct gggatctgag ccagttacag    300
tgccagatgg tcgggttcat cacagggctg agtgtggtcg gctccatctt caacatcgtg    360
gcaatcgcta tcaaccgtta ctgctacatc tgccacagcc tccagtacga acggatcttc    420
agtgtgcgca atacctgcat ctacctggtc atcacctgga tcatgaccgt cctggctgtc    480
ctgcccaaca tgtacattgg caccatcgag tacgatcctc gcacctacac ctgcatcttc    540
aactatctga acaaccctgt cttcactgtt accatcgtct gcatccactt cgtcctccct    600
ctcctcatcg tgggtttctg ctacgtgagg atctggacca aagtgctggc ggcccgtgac    660
cctgcagggc agaatcctga caaccaactt gctgaggttc gcaataaact aaccatgttt    720
gtgatcttcc tcctctttgc agtgtgctgg tgccctatca acgtgctcac tgtcttggtg    780
gctgtcagtc cgaaggagat ggcaggcaag atccccaact ggctttatct tgcagcctac    840
ttcatagcct acttcaacag ctgcctcaac gctgtgatct acgggctcct caatgagaat    900
ttccgaagag aatactggac catcttccat gctatgcggc accctatcat attcttctct    960
ggcctcatca gtgatattcg tgagatgcag gaggcccgta ccctggcccg cgcccgtgcc   1020
catgctcgcg accaagctcg tgaacaagac cgtgcccatg cctgtcctgc tgtggaggaa   1080
accccgatga atgtccggaa tgttccatta cctggtgatg ctgcagctgg ccaccccgac   1140
cgtgcctctg gccaccctaa gccccattcc agatcctcct ctgcctatcg caaatctgcc   1200
tctacccacc acaagtctgt ctttagccac tccaaggctg cctctggtca cctcaagcct   1260
gtctctggcc actccaagcc tgcctctggt caccccaagt ctgccactgt ctaccctaag   1320
cctgcctctg tccatttcaa ggctgactct gtccatttca agggtgactc tgtccatttc   1380
aagcctgact ctgttcattt caagcctgct tccagcaacc ccaagcccat cactggccac   1440
catgtctctg ctggcagcca ctccaagtct gccttcaatg ctgccaccag ccaccctaaa   1500
cccatcaagc cagctaccag ccatgctgag cccaccactg ctgactatcc caagcctgcc   1560
actaccagcc accctaagcc cgctgctgct gacaaccctg agctctctgc ctcccattgc   1620
cccgagatcc ctgccattgc ccaccctgtg tctgacgaca gtgacctccc tgagtcggcc   1680
tctagccctg ccgctgggcc caccaagcct gctgccagcc agctggagtc tgacaccatc   1740
gctgaccttc ctgaccctac tgtagtcact accagtacca atgattacca tgatgtcgtg   1800
gttgttgatg ttgaagatga tcctgatgaa atggctgtgt ga                      1842
```

<210> SEQ ID NO 216
<211> LENGTH: 613
<212> TYPE: PRT
<213> ORGANISM: Homo sapiens

<400> SEQUENCE: 216

```
Met Gly Pro Thr Leu Ala Val Pro Thr Pro Tyr Gly Cys Ile Gly Cys
1               5                   10                  15

Lys Leu Pro Gln Pro Glu Tyr Pro Pro Ala Leu Ile Ile Phe Met Phe
            20                  25                  30
```

-continued

```
Cys Ala Met Val Ile Thr Ile Val Val Asp Leu Ile Gly Asn Ser Met
        35                  40                  45

Val Ile Leu Ala Val Thr Lys Asn Lys Lys Leu Arg Asn Ser Gly Asn
    50                  55                  60

Ile Phe Val Val Ser Leu Ser Val Ala Asp Met Leu Val Ala Ile Tyr
65                  70                  75                  80

Pro Tyr Pro Leu Met Leu His Ala Met Ser Ile Gly Gly Trp Asp Leu
                85                  90                  95

Ser Gln Leu Gln Cys Gln Met Val Gly Phe Ile Thr Gly Leu Ser Val
            100                 105                 110

Val Gly Ser Ile Phe Asn Ile Val Ala Ile Ala Ile Asn Arg Tyr Cys
        115                 120                 125

Tyr Ile Cys His Ser Leu Gln Tyr Glu Arg Ile Phe Ser Val Arg Asn
    130                 135                 140

Thr Cys Ile Tyr Leu Val Ile Thr Trp Ile Met Thr Val Leu Ala Val
145                 150                 155                 160

Leu Pro Asn Met Tyr Ile Gly Thr Ile Glu Tyr Asp Pro Arg Thr Tyr
                165                 170                 175

Thr Cys Ile Phe Asn Tyr Leu Asn Asn Pro Val Phe Thr Val Thr Ile
            180                 185                 190

Val Cys Ile His Phe Val Leu Pro Leu Leu Ile Val Gly Phe Cys Tyr
        195                 200                 205

Val Arg Ile Trp Thr Lys Val Leu Ala Ala Arg Asp Pro Ala Gly Gln
    210                 215                 220

Asn Pro Asp Asn Gln Leu Ala Glu Val Arg Asn Lys Leu Thr Met Phe
225                 230                 235                 240

Val Ile Phe Leu Leu Phe Ala Val Cys Trp Cys Pro Ile Asn Val Leu
                245                 250                 255

Thr Val Leu Val Ala Val Ser Pro Lys Glu Met Ala Gly Lys Ile Pro
            260                 265                 270

Asn Trp Leu Tyr Leu Ala Ala Tyr Phe Ile Ala Tyr Phe Asn Ser Cys
        275                 280                 285

Leu Asn Ala Val Ile Tyr Gly Leu Leu Asn Glu Asn Phe Arg Arg Glu
    290                 295                 300

Tyr Trp Thr Ile Phe His Ala Met Arg His Pro Ile Ile Phe Phe Ser
305                 310                 315                 320

Gly Leu Ile Ser Asp Ile Arg Glu Met Gln Glu Ala Arg Thr Leu Ala
                325                 330                 335

Arg Ala Arg Ala His Ala Arg Asp Gln Ala Arg Glu Gln Asp Arg Ala
            340                 345                 350

His Ala Cys Pro Ala Val Glu Glu Thr Pro Met Asn Val Arg Asn Val
        355                 360                 365

Pro Leu Pro Gly Asp Ala Ala Ala Gly His Pro Asp Arg Ala Ser Gly
    370                 375                 380

His Pro Lys Pro His Ser Arg Ser Ser Ser Ala Tyr Arg Lys Ser Ala
385                 390                 395                 400

Ser Thr His His Lys Ser Val Phe Ser His Ser Lys Ala Ala Ser Gly
                405                 410                 415

His Leu Lys Pro Val Ser Gly His Ser Lys Pro Ala Ser Gly His Pro
            420                 425                 430

Lys Ser Ala Thr Val Tyr Pro Lys Pro Ala Ser Val His Phe Lys Ala
        435                 440                 445
```

-continued

```
Asp Ser Val His Phe Lys Gly Asp Ser Val His Phe Lys Pro Asp Ser
    450                 455                 460

Val His Phe Lys Pro Ala Ser Ser Asn Pro Lys Pro Ile Thr Gly His
465                 470                 475                 480

His Val Ser Ala Gly Ser His Ser Lys Ser Ala Phe Asn Ala Ala Thr
                485                 490                 495

Ser His Pro Lys Pro Ile Lys Pro Ala Thr Ser His Ala Glu Pro Thr
            500                 505                 510

Thr Ala Asp Tyr Pro Lys Pro Ala Thr Thr Ser His Pro Lys Pro Ala
        515                 520                 525

Ala Ala Asp Asn Pro Glu Leu Ser Ala Ser His Cys Pro Glu Ile Pro
    530                 535                 540

Ala Ile Ala His Pro Val Ser Asp Asp Ser Asp Leu Pro Glu Ser Ala
545                 550                 555                 560

Ser Ser Pro Ala Ala Gly Pro Thr Lys Pro Ala Ala Ser Gln Leu Glu
                565                 570                 575

Ser Asp Thr Ile Ala Asp Leu Pro Asp Pro Thr Val Val Thr Thr Ser
            580                 585                 590

Thr Asn Asp Tyr His Asp Val Val Val Val Asp Val Glu Asp Asp Pro
        595                 600                 605

Asp Glu Met Ala Val
    610
```

<210> SEQ ID NO 217
<211> LENGTH: 1854
<212> TYPE: DNA
<213> ORGANISM: Homo sapiens

<400> SEQUENCE: 217

```
atggggccca ccctagcggt tcccaccccc tatggctgta ttggctgtaa gctaccccag     60

ccagaatacc caccggctct aatcatcttt atgttctgcg cgatggttat caccatcgtt    120

gtagacctaa tcggcaactc catggtcatt ttggctgtga cgaagaacaa gaagctccgg    180

aattctggca acatcttcgt ggtcagtctc tctgtggccg atatgctggt ggccatctac    240

ccatacccctt tgatgctgca tgccatgtcc attgggggct gggatctgag ccagttacag    300

tgccagatgg tcgggttcat cacagggctg agtgtggtcg gctccatctt caacatcgtg    360

gcaatcgcta tcaaccgtta ctgctacatc tgccacagcc tccagtacga acggatcttc    420

agtgtgcgca atacctgcat ctacctggtc atcacctgga tcatgaccgt cctggctgtc    480

ctgcccaaca tgtacattgg caccatcgag tacgatcctc gcacctacac ctgcatcttc    540

aactatctga acaaccctgt cttcactgtt accatcgtct gcatccactt cgtcctccct    600

ctcctcatcg tgggtttctg ctacgtgagg atctggacca aagtgctggc ggcccgtgac    660

cctgcagggc agaatcctga caaccaactt gctgaggttc gcaataaact aaccatgttt    720

gtgatcttcc tcctctttgc agtgtgctgg tgccctatca acgtgctcac tgtcttggtg    780

gctgtcagtc cgaaggagat ggcaggcaag atccccaact ggctttatct tgcagcctac    840

ttcatagcct acttcaacag ctgcctcaac gctgtgatct acgggctcct caatgagaat    900

ttccgaagag aatactggac catcttccat gctatgcggc accctatcat attcttctct    960

ggcctcatca gtgatattcg tgagatgcag gaggcccgta ccctggcccg cgcccgtgcc   1020

catgctcgcg accaagctcg tgaacaagac cgtgcccatg cctgtcctgc tgtggaggaa   1080

accccgatga atgtccggaa tgttccatta cctggtgatg ctgcagctgg ccaccccgac   1140
```

-continued

```
cgtgcctctg gccaccctaa gccccattcc agatcctcct ctgcctatcg caaatctgcc   1200

tctacccacc acaagtctgt ctttagccac tccaaggctg cctctggtca cctcaagcct   1260

gtctctggcc actccaagcc tgcctctggt caccccaagt ctgccactgt ctaccctaag   1320

cctgcctctg tccatttcaa ggctgactct gtccatttca agggtgactc tgtccatttc   1380

aagcctgact ctgttcattt caagcctgct tccagcaacc ccaagcccat cactggccac   1440

catgtctctg ctggcagcca ctccaagtct gccttcagtg ctgccaccag ccaccctaaa   1500

cccaccactg gccacatcaa gccagctacc agccatgctg agcccaccac tgctgactat   1560

cccaagcctg ccactaccag ccaccctaag cccactgctg ctgacaaccc tgagctctct   1620

gcctcccatt gccccgagat ccctgccatt gcccaccctg tgtctgacga cagtgacctc   1680

cctgagtcgg cctctagccc tgccgctggg cccaccaagc ctgctgccag ccagctggag   1740

tctgacacca tcgctgacct tcctgaccct actgtagtca ctaccagtac caatgattac   1800

catgatgtcg tggttgttga tgttgaagat gatcctgatg aaatggctgt gtga         1854
```

<210> SEQ ID NO 218
<211> LENGTH: 617
<212> TYPE: PRT
<213> ORGANISM: Homo sapiens

<400> SEQUENCE: 218

```
Met Gly Pro Thr Leu Ala Val Pro Thr Pro Tyr Gly Cys Ile Gly Cys
1               5                   10                  15

Lys Leu Pro Gln Pro Glu Tyr Pro Pro Ala Leu Ile Ile Phe Met Phe
            20                  25                  30

Cys Ala Met Val Ile Thr Ile Val Val Asp Leu Ile Gly Asn Ser Met
        35                  40                  45

Val Ile Leu Ala Val Thr Lys Asn Lys Lys Leu Arg Asn Ser Gly Asn
    50                  55                  60

Ile Phe Val Val Ser Leu Ser Val Ala Asp Met Leu Val Ala Ile Tyr
65                  70                  75                  80

Pro Tyr Pro Leu Met Leu His Ala Met Ser Ile Gly Gly Trp Asp Leu
                85                  90                  95

Ser Gln Leu Gln Cys Gln Met Val Gly Phe Ile Thr Gly Leu Ser Val
            100                 105                 110

Val Gly Ser Ile Phe Asn Ile Val Ala Ile Ala Ile Asn Arg Tyr Cys
        115                 120                 125

Tyr Ile Cys His Ser Leu Gln Tyr Glu Arg Ile Phe Ser Val Arg Asn
    130                 135                 140

Thr Cys Ile Tyr Leu Val Ile Thr Trp Ile Met Thr Val Leu Ala Val
145                 150                 155                 160

Leu Pro Asn Met Tyr Ile Gly Thr Ile Glu Tyr Asp Pro Arg Thr Tyr
                165                 170                 175

Thr Cys Ile Phe Asn Tyr Leu Asn Asn Pro Val Phe Thr Val Thr Ile
            180                 185                 190

Val Cys Ile His Phe Val Leu Pro Leu Leu Ile Val Gly Phe Cys Tyr
        195                 200                 205

Val Arg Ile Trp Thr Lys Val Leu Ala Ala Arg Asp Pro Ala Gly Gln
    210                 215                 220

Asn Pro Asp Asn Gln Leu Ala Glu Val Arg Asn Lys Leu Thr Met Phe
225                 230                 235                 240

Val Ile Phe Leu Leu Phe Ala Val Cys Trp Cys Pro Ile Asn Val Leu
                245                 250                 255
```

-continued

Thr Val Leu Val Ala Val Ser Pro Lys Glu Met Ala Gly Lys Ile Pro
260 265 270

Asn Trp Leu Tyr Leu Ala Ala Tyr Phe Ile Ala Tyr Phe Asn Ser Cys
275 280 285

Leu Asn Ala Val Ile Tyr Gly Leu Leu Asn Glu Asn Phe Arg Arg Glu
290 295 300

Tyr Trp Thr Ile Phe His Ala Met Arg His Pro Ile Ile Phe Phe Ser
305 310 315 320

Gly Leu Ile Ser Asp Ile Arg Glu Met Gln Glu Ala Arg Thr Leu Ala
325 330 335

Arg Ala Arg Ala His Ala Arg Asp Gln Ala Arg Glu Gln Asp Arg Ala
340 345 350

His Ala Cys Pro Ala Val Glu Glu Thr Pro Met Asn Val Arg Asn Val
355 360 365

Pro Leu Pro Gly Asp Ala Ala Ala Gly His Pro Asp Arg Ala Ser Gly
370 375 380

His Pro Lys Pro His Ser Arg Ser Ser Ser Ala Tyr Arg Lys Ser Ala
385 390 395 400

Ser Thr His His Lys Ser Val Phe Ser His Ser Lys Ala Ala Ser Gly
405 410 415

His Leu Lys Pro Val Ser Gly His Ser Lys Pro Ala Ser Gly His Pro
420 425 430

Lys Ser Ala Thr Val Tyr Pro Lys Pro Ala Ser Val His Phe Lys Ala
435 440 445

Asp Ser Val His Phe Lys Gly Asp Ser Val His Phe Lys Pro Asp Ser
450 455 460

Val His Phe Lys Pro Ala Ser Ser Asn Pro Lys Pro Ile Thr Gly His
465 470 475 480

His Val Ser Ala Gly Ser His Ser Lys Ser Ala Phe Ser Ala Ala Thr
485 490 495

Ser His Pro Lys Pro Thr Thr Gly His Ile Lys Pro Ala Thr Ser His
500 505 510

Ala Glu Pro Thr Thr Ala Asp Tyr Pro Lys Pro Ala Thr Thr Ser His
515 520 525

Pro Lys Pro Thr Ala Ala Asp Asn Pro Glu Leu Ser Ala Ser His Cys
530 535 540

Pro Glu Ile Pro Ala Ile Ala His Pro Val Ser Asp Asp Ser Asp Leu
545 550 555 560

Pro Glu Ser Ala Ser Ser Pro Ala Ala Gly Pro Thr Lys Pro Ala Ala
565 570 575

Ser Gln Leu Glu Ser Asp Thr Ile Ala Asp Leu Pro Asp Pro Thr Val
580 585 590

Val Thr Thr Ser Thr Asn Asp Tyr His Asp Val Val Val Val Asp Val
595 600 605

Glu Asp Asp Pro Asp Glu Met Ala Val
610 615

<210> SEQ ID NO 219
<211> LENGTH: 1548
<212> TYPE: DNA
<213> ORGANISM: Homo sapiens

<400> SEQUENCE: 219
atgggacata acgggagctg gatctctcca aatgccagcg agccgcacaa cgcgtccggc 60

-continued

```
gccgaggctg cgggtgtgaa ccgcagcgcg ctcggggagt tcggcgaggc gcagctgtac    120
cgccagttca ccaccaccgt gcaggtcgtc atcttcatag gctcgctgct cggaaacttc    180
atggtgttat ggtcaacttg ccgcacaacc gtgttcaaat ctgtcaccaa caggttcatt    240
aaaaacctgg cctgctcggg gatttgtgcc agcctggtct gtgtgccctt cgacatcatc    300
ctcagcacca gtcctcactg ttgctggtgg atctacacca tgctcttctg caaggtcgtc    360
aaatttttgc acaaagtatt ctgctctgtg accatcctca gcttccctgc tattgctttg    420
gacaggtact actcagtcct ctatccactg gagaggaaaa tatctgatgc caagtcccgt    480
gaactggtga tgtacatctg ggcccatgca gtggtggcca gtgtccctgt gtttgcagta    540
accaatgtgg ctgacatcta tgccacgtcc acctgcacgg aagtctggag caactccttg    600
ggccacctgg tgtacgttct ggtgtataac atcaccacgg tcattgtgcc tgtggtggtg    660
gtgttcctct tcttgatact gatccgacgg gccctgagtg ccagccagaa gaagaaggtc    720
atcatagcag cgctccggac cccacagaac accatctcta ttccctatgc ctcccagcgg    780
gaggccgagc tgaaagccac cctgctctcc atggtgatgg tcttcatctt gtgtagcgtg    840
ccctatgcca ccctggtcgt ctaccagact gtgctcaatg tccctgacac ttccgtcttc    900
ttgctgctca ctgctgtttg gctgcccaaa gtctccctgc tggcaaaccc tgttctcttt    960
cttactgtga acaaatctgt ccgcaagtgc ttgataggga ccctggtgca actacaccac   1020
cggtacagtc gccgtaatgt ggtcagtaca gggagtggca tggctgaggc cagcctggaa   1080
cccagcatac gctcgggtag ccagctcctg gagatgttcc acattgggca gcagcagatc   1140
tttaagccca cagaggatga ggaagagagt gaggccaagt acattggctc agctgacttc   1200
caggccaagg agatatttag cacctgcctg gagggagagc aggggccaca gtttgcgccc   1260
tctgccccac ccctgagcac agtggactct gtatcccagg tggcaccggc agcccctgtg   1320
gaacctgaaa cattccctga taagtattcc ctgcagtttg gctttgggcc ttttgagttg   1380
cctcctcagt ggctctcaga gacccgaaac agcaagaagc ggctgcttcc cccccttgggc  1440
aacaccccag aagagctgat ccagacaaag gtgcccaagg taggcagggt ggagcggaag   1500
atgagcagaa acaataaagt gagcattttt ccaaaggtgg attcctag                1548
```

```
<210> SEQ ID NO 220
<211> LENGTH: 515
<212> TYPE: PRT
<213> ORGANISM: Homo sapiens

<400> SEQUENCE: 220

Met Gly His Asn Gly Ser Trp Ile Ser Pro Asn Ala Ser Glu Pro His
1               5                   10                  15

Asn Ala Ser Gly Ala Glu Ala Ala Gly Val Asn Arg Ser Ala Leu Gly
            20                  25                  30

Glu Phe Gly Glu Ala Gln Leu Tyr Arg Gln Phe Thr Thr Thr Val Gln
        35                  40                  45

Val Val Ile Phe Ile Gly Ser Leu Leu Gly Asn Phe Met Val Leu Trp
    50                  55                  60

Ser Thr Cys Arg Thr Thr Val Phe Lys Ser Val Thr Asn Arg Phe Ile
65                  70                  75                  80

Lys Asn Leu Ala Cys Ser Gly Ile Cys Ala Ser Leu Val Cys Val Pro
                85                  90                  95

Phe Asp Ile Ile Leu Ser Thr Ser Pro His Cys Cys Trp Trp Ile Tyr
            100                 105                 110
```

-continued

```
Thr Met Leu Phe Cys Lys Val Val Lys Phe Leu His Lys Val Phe Cys
        115                 120                 125

Ser Val Thr Ile Leu Ser Phe Pro Ala Ile Ala Leu Asp Arg Tyr Tyr
    130                 135                 140

Ser Val Leu Tyr Pro Leu Glu Arg Lys Ile Ser Asp Ala Lys Ser Arg
145                 150                 155                 160

Glu Leu Val Met Tyr Ile Trp Ala His Ala Val Val Ala Ser Val Pro
                165                 170                 175

Val Phe Ala Val Thr Asn Val Ala Asp Ile Tyr Ala Thr Ser Thr Cys
            180                 185                 190

Thr Glu Val Trp Ser Asn Ser Leu Gly His Leu Val Tyr Val Leu Val
        195                 200                 205

Tyr Asn Ile Thr Thr Val Ile Val Pro Val Val Val Val Phe Leu Phe
    210                 215                 220

Leu Ile Leu Ile Arg Arg Ala Leu Ser Ala Ser Gln Lys Lys Lys Val
225                 230                 235                 240

Ile Ile Ala Ala Leu Arg Thr Pro Gln Asn Thr Ile Ser Ile Pro Tyr
                245                 250                 255

Ala Ser Gln Arg Glu Ala Glu Leu Lys Ala Thr Leu Leu Ser Met Val
            260                 265                 270

Met Val Phe Ile Leu Cys Ser Val Pro Tyr Ala Thr Leu Val Val Tyr
        275                 280                 285

Gln Thr Val Leu Asn Val Pro Asp Thr Ser Val Phe Leu Leu Leu Thr
    290                 295                 300

Ala Val Trp Leu Pro Lys Val Ser Leu Leu Ala Asn Pro Val Leu Phe
305                 310                 315                 320

Leu Thr Val Asn Lys Ser Val Arg Lys Cys Leu Ile Gly Thr Leu Val
                325                 330                 335

Gln Leu His His Arg Tyr Ser Arg Arg Asn Val Val Ser Thr Gly Ser
            340                 345                 350

Gly Met Ala Glu Ala Ser Leu Glu Pro Ser Ile Arg Ser Gly Ser Gln
        355                 360                 365

Leu Leu Glu Met Phe His Ile Gly Gln Gln Gln Ile Phe Lys Pro Thr
    370                 375                 380

Glu Asp Glu Glu Glu Ser Glu Ala Lys Tyr Ile Gly Ser Ala Asp Phe
385                 390                 395                 400

Gln Ala Lys Glu Ile Phe Ser Thr Cys Leu Glu Gly Glu Gln Gly Pro
                405                 410                 415

Gln Phe Ala Pro Ser Ala Pro Pro Leu Ser Thr Val Asp Ser Val Ser
            420                 425                 430

Gln Val Ala Pro Ala Ala Pro Val Glu Pro Glu Thr Phe Pro Asp Lys
        435                 440                 445

Tyr Ser Leu Gln Phe Gly Phe Gly Pro Phe Glu Leu Pro Pro Gln Trp
    450                 455                 460

Leu Ser Glu Thr Arg Asn Ser Lys Lys Arg Leu Leu Pro Pro Leu Gly
465                 470                 475                 480

Asn Thr Pro Glu Glu Leu Ile Gln Thr Lys Val Pro Lys Val Gly Arg
                485                 490                 495

Val Glu Arg Lys Met Ser Arg Asn Asn Lys Val Ser Ile Phe Pro Lys
            500                 505                 510

Val Asp Ser
        515
```

-continued

<210> SEQ ID NO 221
<211> LENGTH: 1164
<212> TYPE: DNA
<213> ORGANISM: Homo sapiens

<400> SEQUENCE: 221

```
atgaatcggc accatctgca ggatcacttt ctggaaatag acaagaagaa ctgctgtgtg     60

ttccgagatg acttcattgc caaggtgttg ccgccggtgt tggggctgga gtttatcttt    120

gggcttctgg gcaatggcct tgccctgtgg attttctgtt tccacctcaa gtcctggaaa    180

tccagccgga ttttcctgtt caacctggca gtagctgact ttctactgat catctgcctg    240

ccgttcgtga tggactacta tgtgcggcgt tcagactgga agtttgggga catcccttgc    300

cggctggtgc tcttcatgtt tgccatgaac cgccagggca gcatcatctt cctcacggtg    360

gtggcggtag acaggtattt ccgggtggtc catccccacc acgccctgaa caagatctcc    420

aattggacag cagccatcat ctcttgcctt ctgtggggca tcactgttgg cctaacagtc    480

cacctcctga agaagaagtt gctgatccag aatggccctg caaatgtgtg catcagcttc    540

agcatctgcc ataccttccg gtggcacgaa gctatgttcc tcctggagtt cctcctgccc    600

ctgggcatca tcctgttctg ctcagccaga attatctgga gcctgcggca gagacaaatg    660

gaccggcatg ccaagatcaa gagagccaaa accttcatca tggtggtggc catcgtcttt    720

gtcatctgct tccttcccag cgtggttgtg cggatccgca tcttctggct cctgcacact    780

tcgggcacgc agaattgtga agtgtaccgc tcggtggacc tggcgttctt tatcactctc    840

agcttcacct acatgaacag catgctggac cccgtggtgt actacttctc cagcccatcc    900

tttcccaact tcttctccac tttgatcaac cgctgcctcc agaggaagat gacaggtgag    960

ccagataata accgcagcac gagcgtcgag ctcacagggg accccaacaa aaccagaggc   1020

gctccagagg cgttaatggc caactccggt gagccatgga gcccctctta tctgggccca   1080

acctcaaata accattccaa gaagggacat tgtcaccaag aaccagcatc tctggagaaa   1140

cagttgggct gttgcatcga gtaa                                          1164
```

<210> SEQ ID NO 222
<211> LENGTH: 387
<212> TYPE: PRT
<213> ORGANISM: Homo sapiens

<400> SEQUENCE: 222

```
Met Asn Arg His His Leu Gln Asp His Phe Leu Glu Ile Asp Lys Lys
1               5                   10                  15

Asn Cys Cys Val Phe Arg Asp Asp Phe Ile Ala Lys Val Leu Pro Pro
            20                  25                  30

Val Leu Gly Leu Glu Phe Ile Phe Gly Leu Leu Gly Asn Gly Leu Ala
        35                  40                  45

Leu Trp Ile Phe Cys Phe His Leu Lys Ser Trp Lys Ser Ser Arg Ile
    50                  55                  60

Phe Leu Phe Asn Leu Ala Val Ala Asp Phe Leu Leu Ile Ile Cys Leu
65                  70                  75                  80

Pro Phe Val Met Asp Tyr Tyr Val Arg Arg Ser Asp Trp Lys Phe Gly
                85                  90                  95

Asp Ile Pro Cys Arg Leu Val Leu Phe Met Phe Ala Met Asn Arg Gln
            100                 105                 110

Gly Ser Ile Ile Phe Leu Thr Val Val Ala Val Asp Arg Tyr Phe Arg
        115                 120                 125
```

-continued

```
Val Val His Pro His His Ala Leu Asn Lys Ile Ser Asn Trp Thr Ala
    130                 135                 140

Ala Ile Ile Ser Cys Leu Leu Trp Gly Ile Thr Val Gly Leu Thr Val
145                 150                 155                 160

His Leu Leu Lys Lys Lys Leu Leu Ile Gln Asn Gly Pro Ala Asn Val
                165                 170                 175

Cys Ile Ser Phe Ser Ile Cys His Thr Phe Arg Trp His Glu Ala Met
            180                 185                 190

Phe Leu Leu Glu Phe Leu Leu Pro Leu Gly Ile Ile Leu Phe Cys Ser
        195                 200                 205

Ala Arg Ile Ile Trp Ser Leu Arg Gln Arg Gln Met Asp Arg His Ala
    210                 215                 220

Lys Ile Lys Arg Ala Lys Thr Phe Ile Met Val Val Ala Ile Val Phe
225                 230                 235                 240

Val Ile Cys Phe Leu Pro Ser Val Val Val Arg Ile Arg Ile Phe Trp
                245                 250                 255

Leu Leu His Thr Ser Gly Thr Gln Asn Cys Glu Val Tyr Arg Ser Val
            260                 265                 270

Asp Leu Ala Phe Phe Ile Thr Leu Ser Phe Thr Tyr Met Asn Ser Met
        275                 280                 285

Leu Asp Pro Val Val Tyr Tyr Phe Ser Ser Pro Ser Phe Pro Asn Phe
    290                 295                 300

Phe Ser Thr Leu Ile Asn Arg Cys Leu Gln Arg Lys Met Thr Gly Glu
305                 310                 315                 320

Pro Asp Asn Asn Arg Ser Thr Ser Val Glu Leu Thr Gly Asp Pro Asn
                325                 330                 335

Lys Thr Arg Gly Ala Pro Glu Ala Leu Met Ala Asn Ser Gly Glu Pro
            340                 345                 350

Trp Ser Pro Ser Tyr Leu Gly Pro Thr Ser Asn Asn His Ser Lys Lys
        355                 360                 365

Gly His Cys His Gln Glu Pro Ala Ser Leu Glu Lys Gln Leu Gly Cys
    370                 375                 380

Cys Ile Glu
385
```

<210> SEQ ID NO 223
<211> LENGTH: 1212
<212> TYPE: DNA
<213> ORGANISM: Homo sapiens

<400> SEQUENCE: 223

```
atggcttgca atggcagtgc ggccaggggg cactttgacc ctgaggactt gaacctgact      60

gacgaggcac tgagactcaa gtacctgggg ccccagcaga cagagctgtt catgcccatc     120

tgtgccacat acctgctgat cttcgtggtg ggcgctgtgg gcaatgggct gacctgtctg     180

gtcatcctgc gccacaaggc catgcgcacg cctaccaact actacctctt cagcctggcc     240

gtgtcggacc tgctggtgct gctggtgggc ctgcccctgg agctctatga gatgtggcac     300

aactacccct tcctgctggg cgttggtggc tgctatttcc gcacgctact gtttgagatg     360

gtctgcctgg cctcagtgct caacgtcact gccctgagcg tggaacgcta tgtggccgtg     420

gtgcacccac tccaggccag gtccatggtg acgcgggccc atgtgcgccg agtgcttggg     480

gccgtctggg gtcttgccat gctctgctcc ctgcccaaca ccagcctgca cggcatccgg     540

cagctgcacg tgccctgccg gggcccagtg ccagactcag ctgtttgcat gctggtccgc     600
```

-continued

```
ccacgggccc tctacaacat ggtagtgcag accaccgcgc tgctcttctt ctgcctgccc    660

atggccatca tgagcgtgct ctacctgctc attgggctgc gactgcggcg ggagaggctg    720

ctgctcatgc aggaggccaa gggcaggggc tctgcagcag ccaggtccag atacacctgc    780

aggctccagc agcacgatcg gggccggaga caagtgaaga agatgctgtt tgtcctggtc    840

gtggtgtttg gcatctgctg ggccccgttc cacgccgacc gcgtcatgtg gagcgtcgtg    900

tcacagtgga cagatggcct gcacctggcc ttccagcacg tgcacgtcat ctccggcatc    960

ttcttctacc tgggctcggc ggccaacccc gtgctctata gcctcatgtc cagccgcttc   1020

cgagagacct tccaggaggc cctgtgcctc ggggcctgct gccatcgcct cagaccccgc   1080

cacagctccc acagcctcag caggatgacc acaggcagca ccctgtgtga tgtgggctcc   1140

ctgggcagct gggtccaccc cctggctggg aacgatggcc cagaggcgca gcaagagacc   1200

gatccatcct ga                                                       1212
```

```
<210> SEQ ID NO 224
<211> LENGTH: 403
<212> TYPE: PRT
<213> ORGANISM: Homo sapiens

<400> SEQUENCE: 224

Met Ala Cys Asn Gly Ser Ala Ala Arg Gly His Phe Asp Pro Glu Asp
1               5                   10                  15

Leu Asn Leu Thr Asp Glu Ala Leu Arg Leu Lys Tyr Leu Gly Pro Gln
            20                  25                  30

Gln Thr Glu Leu Phe Met Pro Ile Cys Ala Thr Tyr Leu Leu Ile Phe
        35                  40                  45

Val Val Gly Ala Val Gly Asn Gly Leu Thr Cys Leu Val Ile Leu Arg
    50                  55                  60

His Lys Ala Met Arg Thr Pro Thr Asn Tyr Tyr Leu Phe Ser Leu Ala
65                  70                  75                  80

Val Ser Asp Leu Leu Val Leu Leu Val Gly Leu Pro Leu Glu Leu Tyr
                85                  90                  95

Glu Met Trp His Asn Tyr Pro Phe Leu Leu Gly Val Gly Gly Cys Tyr
            100                 105                 110

Phe Arg Thr Leu Leu Phe Glu Met Val Cys Leu Ala Ser Val Leu Asn
        115                 120                 125

Val Thr Ala Leu Ser Val Glu Arg Tyr Val Ala Val Val His Pro Leu
    130                 135                 140

Gln Ala Arg Ser Met Val Thr Arg Ala His Val Arg Arg Val Leu Gly
145                 150                 155                 160

Ala Val Trp Gly Leu Ala Met Leu Cys Ser Leu Pro Asn Thr Ser Leu
                165                 170                 175

His Gly Ile Arg Gln Leu His Val Pro Cys Arg Gly Pro Val Pro Asp
            180                 185                 190

Ser Ala Val Cys Met Leu Val Arg Pro Arg Ala Leu Tyr Asn Met Val
        195                 200                 205

Val Gln Thr Thr Ala Leu Leu Phe Phe Cys Leu Pro Met Ala Ile Met
    210                 215                 220

Ser Val Leu Tyr Leu Leu Ile Gly Leu Arg Leu Arg Arg Glu Arg Leu
225                 230                 235                 240

Leu Leu Met Gln Glu Ala Lys Gly Arg Gly Ser Ala Ala Ala Arg Ser
                245                 250                 255
```

-continued

```
Arg Tyr Thr Cys Arg Leu Gln Gln His Asp Arg Gly Arg Arg Gln Val
            260                 265                 270

Lys Lys Met Leu Phe Val Leu Val Val Val Phe Gly Ile Cys Trp Ala
        275                 280                 285

Pro Phe His Ala Asp Arg Val Met Trp Ser Val Val Ser Gln Trp Thr
    290                 295                 300

Asp Gly Leu His Leu Ala Phe Gln His Val His Val Ile Ser Gly Ile
305                 310                 315                 320

Phe Phe Tyr Leu Gly Ser Ala Ala Asn Pro Val Leu Tyr Ser Leu Met
                325                 330                 335

Ser Ser Arg Phe Arg Glu Thr Phe Gln Glu Ala Leu Cys Leu Gly Ala
            340                 345                 350

Cys Cys His Arg Leu Arg Pro Arg His Ser Ser His Ser Leu Ser Arg
        355                 360                 365

Met Thr Thr Gly Ser Thr Leu Cys Asp Val Gly Ser Leu Gly Ser Trp
    370                 375                 380

Val His Pro Leu Ala Gly Asn Asp Gly Pro Glu Ala Gln Gln Glu Thr
385                 390                 395                 400

Asp Pro Ser


<210> SEQ ID NO 225
<211> LENGTH: 1098
<212> TYPE: DNA
<213> ORGANISM: Homo sapiens

<400> SEQUENCE: 225

atggggaaca tcactgcaga caactcctcg atgagctgta ccatcgacca taccatccac     60

cagacgctgg ccccggtggt ctatgttacc gtgctggtgg tgggcttccc ggccaactgc    120

ctgtccctct acttcggcta cctgcagatc aaggcccgga acgagctggg cgtgtacctg    180

tgcaacctga cggtggccga cctcttctac atctgctcgc tgcccttctg gctgcagtac    240

gtgctgcagc acgacaactg gtctcacggc gacctgtcct gccaggtgtg cggcatcctc    300

ctgtacgaga acatctacat cagcgtgggc ttcctctgct gcatctccgt ggaccgctac    360

ctggctgtgg cccatccctt ccgcttccac cagttccgga ccctgaaggc ggccgtcggc    420

gtcagcgtgg tcatctgggc caaggagctg ctgaccagca tctacttcct gatgcacgag    480

gaggtcatcg aggacgagaa ccagcaccgc gtgtgctttg agcactaccc catccaggca    540

tggcagcgcg ccatcaacta ctaccgcttc ctggtgggct tcctcttccc catctgcctg    600

ctgctggcgt cctaccaggg catcctgcgc gccgtgcgcc ggagccacgg cacccagaag    660

agccgcaagg accagatcaa gcggctggtg ctcagcaccg tggtcatctt cctggcctgc    720

ttcctgccct accacgtgtt gctgctggtg cgcagcgtct gggaggccag ctgcgacttc    780

gccaagggcg ttttcaacgc ctaccacttc tccctcctgc tcaccagctt caactgcgtc    840

gccgaccccg tgctctactg cttcgtcagc gagaccaccc accgggacct ggcccgcctc    900

cgcggggcct gcctggcctt cctcacctgc tccaggaccg gccgggccag ggaggcctac    960

ccgctgggtg cccccgaggc ctccgggaaa agcggggccc agggtgagga gcccgagctg   1020

ttgaccaagc tccacccggc cttccagacc cctaactcgc cagggtcggg cgggttcccc   1080

acgggcaggt tggcctag                                                 1098


<210> SEQ ID NO 226
<211> LENGTH: 365
<212> TYPE: PRT
```

-continued

<213> ORGANISM: Homo sapiens

<400> SEQUENCE: 226

```
Met Gly Asn Ile Thr Ala Asp Asn Ser Ser Met Ser Cys Thr Ile Asp
1               5                   10                  15

His Thr Ile His Gln Thr Leu Ala Pro Val Val Tyr Val Thr Val Leu
            20                  25                  30

Val Val Gly Phe Pro Ala Asn Cys Leu Ser Leu Tyr Phe Gly Tyr Leu
        35                  40                  45

Gln Ile Lys Ala Arg Asn Glu Leu Gly Val Tyr Leu Cys Asn Leu Thr
    50                  55                  60

Val Ala Asp Leu Phe Tyr Ile Cys Ser Leu Pro Phe Trp Leu Gln Tyr
65                  70                  75                  80

Val Leu Gln His Asp Asn Trp Ser His Gly Asp Leu Ser Cys Gln Val
                85                  90                  95

Cys Gly Ile Leu Leu Tyr Glu Asn Ile Tyr Ile Ser Val Gly Phe Leu
            100                 105                 110

Cys Cys Ile Ser Val Asp Arg Tyr Leu Ala Val Ala His Pro Phe Arg
        115                 120                 125

Phe His Gln Phe Arg Thr Leu Lys Ala Ala Val Gly Val Ser Val Val
    130                 135                 140

Ile Trp Ala Lys Glu Leu Leu Thr Ser Ile Tyr Phe Leu Met His Glu
145                 150                 155                 160

Glu Val Ile Glu Asp Glu Asn Gln His Arg Val Cys Phe Glu His Tyr
                165                 170                 175

Pro Ile Gln Ala Trp Gln Arg Ala Ile Asn Tyr Tyr Arg Phe Leu Val
            180                 185                 190

Gly Phe Leu Phe Pro Ile Cys Leu Leu Leu Ala Ser Tyr Gln Gly Ile
        195                 200                 205

Leu Arg Ala Val Arg Arg Ser His Gly Thr Gln Lys Ser Arg Lys Asp
    210                 215                 220

Gln Ile Lys Arg Leu Val Leu Ser Thr Val Val Ile Phe Leu Ala Cys
225                 230                 235                 240

Phe Leu Pro Tyr His Val Leu Leu Leu Val Arg Ser Val Trp Glu Ala
                245                 250                 255

Ser Cys Asp Phe Ala Lys Gly Val Phe Asn Ala Tyr His Phe Ser Leu
            260                 265                 270

Leu Leu Thr Ser Phe Asn Cys Val Ala Asp Pro Val Leu Tyr Cys Phe
        275                 280                 285

Val Ser Glu Thr Thr His Arg Asp Leu Ala Arg Leu Arg Gly Ala Cys
    290                 295                 300

Leu Ala Phe Leu Thr Cys Ser Arg Thr Gly Arg Ala Arg Glu Ala Tyr
305                 310                 315                 320

Pro Leu Gly Ala Pro Glu Ala Ser Gly Lys Ser Gly Ala Gln Gly Glu
                325                 330                 335

Glu Pro Glu Leu Leu Thr Lys Leu His Pro Ala Phe Gln Thr Pro Asn
            340                 345                 350

Ser Pro Gly Ser Gly Gly Phe Pro Thr Gly Arg Leu Ala
        355                 360                 365
```

<210> SEQ ID NO 227
<211> LENGTH: 1416
<212> TYPE: DNA
<213> ORGANISM: Homo sapiens -continued

<400> SEQUENCE: 227
atggatattc tttgtgaaga aaatacttct ttgagctcaa ctacgaactc cctaatgcaa 60
ttaaatgatg acaacaggct ctacagtaat gactttaact ccggagaagc taacacttct 120
gatgcattta actggacagt cgactctgaa aatcgaacca acctttcctg tgaagggtgc 180
ctctcaccgt cgtgtctctc cttacttcat ctccaggaaa aaaactggtc tgctttactg 240
acagccgtag tgattattct aactattgct ggaaacatac tcgtcatcat ggcagtgtcc 300
ctagagaaaa agctgcagaa tgccaccaac tatttcctga tgtcacttgc catagctgat 360
atgctgctgg gtttccttgt catgcccgtg tccatgttaa ccatcctgta tgggtaccgg 420
tggcctctgc cgagcaagct ttgtgcagtc tggatttacc tggacgtgct cttctccacg 480
gcctccatca tgcacctctg cgccatctcg ctggaccgct acgtcgccat ccagaatccc 540
atccaccaca gccgcttcaa ctccagaact aaggcatttc tgaaaatcat tgctgtttgg 600
accatatcag taggtatatc catgccaata ccagtctttg ggctacagga cgattcgaag 660
gtctttaagg aggggagttg cttactcgcc gatgataact ttgtcctgat cggctctttt 720
gtgtcatttt tcattccctt aaccatcatg gtgatcacct actttctaac tatcaagtca 780
ctccagaaag aagctacttt gtgtgtaagt gatcttggca cacgggccaa attagcttct 840
ttcagcttcc tccctcagag ttctttgtct tcagaaaagc tcttccagcg gtcgatccat 900
agggagccag ggtcctacac aggcaggagg actatgcagt ccatcagcaa tgagcaaaag 960
gcaaagaagg tgctgggcat cgtcttcttc ctgtttgtgg tgatgtggtg ccctttcttc 1020
atcacaaaca tcatggccgt catctgcaaa gagtcctgca atgaggatgt cattggggcc 1080
ctgctcaatg tgtttgtttg gatcggttat ctctcttcag cagtcaaccc actagtctac 1140
acactgttca acaagaccta taggtcagcc ttttcacggt atattcagtg tcagtacaag 1200
gaaaacaaaa aaccattgca gttaatttta gtgaacacaa taccggcttt ggcctacaag 1260
tctagccaac ttcaaatggg acaaaaaaag aattcaaagc aagatgccaa gacaacagat 1320
aatgactgct caatggttgc tctaggaaag cagtattctg aagaggcttc taaagacaat 1380
agcgacggag tgaatgaaaa ggtgagctgt gtgtga 1416

<210> SEQ ID NO 228
<211> LENGTH: 471
<212> TYPE: PRT
<213> ORGANISM: Homo sapiens

<400> SEQUENCE: 228

Met Asp Ile Leu Cys Glu Glu Asn Thr Ser Leu Ser Ser Thr Thr Asn
1 5 10 15

Ser Leu Met Gln Leu Asn Asp Asp Asn Arg Leu Tyr Ser Asn Asp Phe
20 25 30

Asn Ser Gly Glu Ala Asn Thr Ser Asp Ala Phe Asn Trp Thr Val Asp
35 40 45

Ser Glu Asn Arg Thr Asn Leu Ser Cys Glu Gly Cys Leu Ser Pro Ser
50 55 60

Cys Leu Ser Leu Leu His Leu Gln Glu Lys Asn Trp Ser Ala Leu Leu
65 70 75 80

Thr Ala Val Val Ile Ile Leu Thr Ile Ala Gly Asn Ile Leu Val Ile
85 90 95

Met Ala Val Ser Leu Glu Lys Lys Leu Gln Asn Ala Thr Asn Tyr Phe
100 105 110

-continued

```
Leu Met Ser Leu Ala Ile Ala Asp Met Leu Leu Gly Phe Leu Val Met
        115                 120                 125

Pro Val Ser Met Leu Thr Ile Leu Tyr Gly Tyr Arg Trp Pro Leu Pro
    130                 135                 140

Ser Lys Leu Cys Ala Val Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
            180                 185                 190

Phe Leu Lys Ile Ile Ala Val Trp Thr Ile Ser Val Gly Ile Ser Met
        195                 200                 205

Pro Ile Pro Val Phe Gly Leu Gln Asp Asp Ser Lys Val Phe Lys Glu
    210                 215                 220

Gly Ser Cys Leu Leu Ala Asp Asp Asn Phe Val Leu Ile Gly Ser Phe
225                 230                 235                 240

Val Ser Phe Phe Ile Pro Leu Thr Ile Met Val Ile Thr Tyr Phe Leu
                245                 250                 255

Thr Ile Lys Ser Leu Gln Lys Glu Ala Thr Leu Cys Val Ser Asp Leu
            260                 265                 270

Gly Thr Arg Ala Lys Leu Ala Ser Phe Ser Phe Leu Pro Gln Ser Ser
        275                 280                 285

Leu Ser Ser Glu Lys Leu Phe Gln Arg Ser Ile His Arg Glu Pro Gly
    290                 295                 300

Ser Tyr Thr Gly Arg Arg Thr Met Gln Ser Ile Ser Asn Glu Gln Lys
305                 310                 315                 320

Ala Lys Lys Val Leu Gly Ile Val Phe Phe Leu Phe Val Val Met Trp
                325                 330                 335

Cys Pro Phe Phe Ile Thr Asn Ile Met Ala Val Ile Cys Lys Glu Ser
            340                 345                 350

Cys Asn Glu Asp Val Ile Gly Ala Leu Leu Asn Val Phe Val Trp Ile
        355                 360                 365

Gly Tyr Leu Ser Ser Ala Val Asn Pro Leu Val Tyr Thr Leu Phe Asn
    370                 375                 380

Lys Thr Tyr Arg Ser Ala Phe Ser Arg Tyr Ile Gln Cys Gln Tyr Lys
385                 390                 395                 400

Glu Asn Lys Lys Pro Leu Gln Leu Ile Leu Val Asn Thr Ile Pro Ala
                405                 410                 415

Leu Ala Tyr Lys Ser Ser Gln Leu Gln Met Gly Gln Lys Lys Asn Ser
            420                 425                 430

Lys Gln Asp Ala Lys Thr Thr Asp Asn Asp Cys Ser Met Val Ala Leu
        435                 440                 445

Gly Lys Gln Tyr Ser Glu Glu Ala Ser Lys Asp Asn Ser Asp Gly Val
    450                 455                 460

Asn Glu Lys Val Ser Cys Val
465                 470
```

<210> SEQ ID NO 229
<211> LENGTH: 1377
<212> TYPE: DNA
<213> ORGANISM: Homo sapiens

<400> SEQUENCE: 229

```
atggtgaacc tgaggaatgc ggtgcattca ttccttgtgc acctaattgg cctattggtt      60
```

-continued

```
tggcaatgtg atatttctgt gagcccagta gcagctatag taactgacat tttcaatacc    120

tccgatggtg gacgcttcaa attcccagac ggggtacaaa actggccagc actttcaatc    180

gtcatcataa taatcatgac aataggtggc aacatccttg tgatcatggc agtaagcatg    240

gaaaagaaac tgcacaatgc caccaattac ttcttaatgt ccctagccat tgctgatatg    300

ctagtgggac tacttgtcat gcccctgtct ctcctggcaa tcctttatga ttatgtctgg    360

ccactaccta gatatttgtg ccccgtctgg atttctttag atgttttatt ttcaacagcg    420

tccatcatgc acctctgcgc tatatcgctg gatcggtatg tagcaatacg taatcctatt    480

gagcatagcc gtttcaattc gcggactaag gccatcatga agattgctat tgtttgggca    540

atttctatag gtgtatcagt tcctatccct gtgattggac tgagggacga agaaaaggtg    600

ttcgtgaaca acacgacgtg cgtgctcaac gacccaaatt tcgttcttat tgggtccttc    660

gtagctttct tcataccgct gacgattatg gtgattacgt attgcctgac catctacgtt    720

ctgcgccgac aagctttgat gttactgcac ggccacaccg aggaaccgcc tggactaagt    780

ctggatttcc tgaagtgctg caagaggaat acggccgagg aagagaactc tgcaaaccct    840

aaccaagacc agaacgcacg ccgaagaaag aagaaggaga gacgtcctag ggcaccatg     900

caggctatca acaatgaaag aaaagctaag aaagtccttg ggattgtttt ctttgtgttt    960

ctgatcatgt ggtgcccatt tttcattacc aatattctgt ctgttctttg tgagaagtcc   1020

tgtaaccaaa agctcatgga aaagcttctg aatgtgtttg tttggattgg ctatgtttgt   1080

tcaggaatca atcctctggt gtatactctg ttcaacaaaa tttaccgaag ggcattctcc   1140

aactatttgc gttgcaatta taaggtagag aaaaagcctc ctgtcaggca gattccaaga   1200

gttgccgcca ctgctttgtc tgggagggag cttaatgtta acatttatcg gcataccaat   1260

gaaccggtga tcgagaaagc cagtgacaat gagcccggta tagagatgca agttgagaat   1320

ttagagttac cagtaaatcc ctccagtgtg gttagcgaaa ggattagcag tgtgtga      1377


<210> SEQ ID NO 230
<211> LENGTH: 458
<212> TYPE: PRT
<213> ORGANISM: Homo sapiens

<400> SEQUENCE: 230

Met Val Asn Leu Arg Asn Ala Val His Ser Phe Leu Val His Leu Ile
1               5                   10                  15

Gly Leu Leu Val Trp Gln Cys Asp Ile Ser Val Ser Pro Val Ala Ala
            20                  25                  30

Ile Val Thr Asp Ile Phe Asn Thr Ser Asp Gly Gly Arg Phe Lys Phe
        35                  40                  45

Pro Asp Gly Val Gln Asn Trp Pro Ala Leu Ser Ile Val Ile Ile Ile
    50                  55                  60

Ile Met Thr Ile Gly Gly Asn Ile Leu Val Ile Met Ala Val Ser Met
65                  70                  75                  80

Glu Lys Lys Leu His Asn Ala Thr Asn Tyr Phe Leu Met Ser Leu Ala
                85                  90                  95

Ile Ala Asp Met Leu Val Gly Leu Leu Val Met Pro Leu Ser Leu Leu
            100                 105                 110

Ala Ile Leu Tyr Asp Tyr Val Trp Pro Leu Pro Arg Tyr Leu Cys Pro
        115                 120                 125

Val Trp Ile Ser Leu Asp Val Leu Phe Ser Thr Ala Ser Ile Met His
    130                 135                 140
```

-continued

```
Leu Cys Ala Ile Ser Leu Asp Arg Tyr Val Ala Ile Arg Asn Pro Ile
145                 150                 155                 160

Glu His Ser Arg Phe Asn Ser Arg Thr Lys Ala Ile Met Lys Ile Ala
                165                 170                 175

Ile Val Trp Ala Ile Ser Ile Gly Val Ser Val Pro Ile Pro Val Ile
            180                 185                 190

Gly Leu Arg Asp Glu Glu Lys Val Phe Val Asn Asn Thr Thr Cys Val
        195                 200                 205

Leu Asn Asp Pro Asn Phe Val Leu Ile Gly Ser Phe Val Ala Phe Phe
    210                 215                 220

Ile Pro Leu Thr Ile Met Val Ile Thr Tyr Cys Leu Thr Ile Tyr Val
225                 230                 235                 240

Leu Arg Arg Gln Ala Leu Met Leu Leu His Gly His Thr Glu Glu Pro
                245                 250                 255

Pro Gly Leu Ser Leu Asp Phe Leu Lys Cys Cys Lys Arg Asn Thr Ala
            260                 265                 270

Glu Glu Glu Asn Ser Ala Asn Pro Asn Gln Asp Gln Asn Ala Arg Arg
        275                 280                 285

Arg Lys Lys Lys Glu Arg Arg Pro Arg Gly Thr Met Gln Ala Ile Asn
    290                 295                 300

Asn Glu Arg Lys Ala Lys Lys Val Leu Gly Ile Val Phe Phe Val Phe
305                 310                 315                 320

Leu Ile Met Trp Cys Pro Phe Phe Ile Thr Asn Ile Leu Ser Val Leu
                325                 330                 335

Cys Glu Lys Ser Cys Asn Gln Lys Leu Met Glu Lys Leu Leu Asn Val
            340                 345                 350

Phe Val Trp Ile Gly Tyr Val Cys Ser Gly Ile Asn Pro Leu Val Tyr
        355                 360                 365

Thr Leu Phe Asn Lys Ile Tyr Arg Arg Ala Phe Ser Asn Tyr Leu Arg
    370                 375                 380

Cys Asn Tyr Lys Val Glu Lys Lys Pro Pro Val Arg Gln Ile Pro Arg
385                 390                 395                 400

Val Ala Ala Thr Ala Leu Ser Gly Arg Glu Leu Asn Val Asn Ile Tyr
                405                 410                 415

Arg His Thr Asn Glu Pro Val Ile Glu Lys Ala Ser Asp Asn Glu Pro
            420                 425                 430

Gly Ile Glu Met Gln Val Glu Asn Leu Glu Leu Pro Val Asn Pro Ser
        435                 440                 445

Ser Val Val Ser Glu Arg Ile Ser Ser Val
    450                 455
```

<210> SEQ ID NO 231
<211> LENGTH: 1068
<212> TYPE: DNA
<213> ORGANISM: Homo sapiens

<400> SEQUENCE: 231

```
atggatcagt tccctgaatc agtgacagaa aactttgagt acgatgattt ggctgaggcc     60

tgttatattg ggacatcgt  ggtctttggg actgtgttcc tgtccatatt ctactccgtc    120

atctttgcca ttggcctggt gggaaatttg ttggtagtgt ttgccctcac caacagcaag    180

aagcccaaga gtgtcaccga catttacctc ctgaacctgg ccttgtctga tctgctgttt    240

gtagccactt tgcccttctg gactcactat ttgataaatg aaaagggcct ccacaatgcc    300

atgtgcaaat tcactaccgc cttcttcttc atcggctttt ttggaagcat attcttcatc    360
```

-continued

```
accgtcatca gcattgatag gtacctggcc atcgtcctgg ccgccaactc catgaacaac    420

cggaccgtgc agcatggcgt caccatcagc ctaggcgtct gggcagcagc cattttggtg    480

gcagcacccc agttcatgtt cacaaagcag aaagaaaatg aatgccttgg tgactacccc    540

gaggtcctcc aggaaatctg gcccgtgctc cgcaatgtgg aaacaaattt tcttggcttc    600

ctactccccc tgctcattat gagttattgc tacttcagaa tcatccagac gctgttttcc    660

tgcaagaacc acaagaaagc caaagccaag aaactgatcc ttctggtggt catcgtgttt    720

ttcctcttct ggacacccta caacgttatg attttcctgg agacgcttaa gctctatgac    780

ttctttccca gttgtgacat gaggaaggat ctgaggctgg ccctcagtgt gactgagacg    840

gttgcattta gccattgttg cctgaatcct ctcatctatg catttgctgg ggagaagttc    900

agaagatacc tttaccacct gtatgggaaa tgcctggctg tcctgtgtgg gcgctcagtc    960

cacgttgatt tctcctcatc tgaatcacaa aggagcaggc atggaagtgt tctgagcagc   1020

aattttactt accacacgag tgatggagat gcattgctcc ttctctga                1068


<210> SEQ ID NO 232
<211> LENGTH: 355
<212> TYPE: PRT
<213> ORGANISM: Homo sapiens

<400> SEQUENCE: 232

Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Val Phe Gly Thr Val
            20                  25                  30

Phe Leu Ser Ile Phe Tyr Ser Val Ile Phe Ala Ile Gly Leu Val Gly
        35                  40                  45

Asn Leu Leu Val Val Phe Ala Leu Thr Asn Ser Lys Lys Pro Lys Ser
    50                  55                  60

Val Thr Asp Ile Tyr Leu Leu Asn Leu Ala Leu Ser Asp Leu Leu Phe
65                  70                  75                  80

Val Ala Thr Leu Pro Phe Trp Thr His Tyr Leu Ile Asn Glu Lys Gly
                85                  90                  95

Leu His Asn Ala Met Cys Lys Phe Thr Thr Ala Phe Phe Phe Ile Gly
            100                 105                 110

Phe Phe Gly Ser Ile Phe Phe Ile Thr Val Ile Ser Ile Asp Arg Tyr
        115                 120                 125

Leu Ala Ile Val Leu Ala Ala Asn Ser Met Asn Asn Arg Thr Val Gln
    130                 135                 140

His Gly Val Thr Ile Ser Leu Gly Val Trp Ala Ala Ala Ile Leu Val
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Phe Leu Gly Phe Leu Leu Pro Leu Leu Ile Met Ser
        195                 200                 205

Tyr Cys Tyr Phe Arg Ile Ile Gln Thr Leu Phe Ser Cys Lys Asn His
    210                 215                 220

Lys Lys Ala Lys Ala Lys Lys Leu Ile Leu Leu Val Val Ile Val Phe
225                 230                 235                 240

Phe Leu Phe Trp Thr Pro Tyr Asn Val Met Ile Phe Leu Glu Thr Leu
```

-continued

```
                245                 250                 255

Lys Leu Tyr Asp Phe Phe Pro Ser Cys Asp Met Arg Lys Asp Leu Arg
            260                 265                 270

Leu Ala Leu Ser Val Thr Glu Thr Val Ala Phe Ser His Cys Cys Leu
        275                 280                 285

Asn Pro Leu Ile Tyr Ala Phe Ala Gly Glu Lys Phe Arg Arg Tyr Leu
    290                 295                 300

Tyr His Leu Tyr Gly Lys Cys Leu Ala Val Leu Cys Gly Arg Ser Val
305                 310                 315                 320

His Val Asp Phe Ser Ser Ser Glu Ser Gln Arg Ser Arg His Gly Ser
                325                 330                 335

Val Leu Ser Ser Asn Phe Thr Tyr His Thr Ser Asp Gly Asp Ala Leu
            340                 345                 350

Leu Leu Leu
        355


<210> SEQ ID NO 233
<211> LENGTH: 29
<212> TYPE: DNA
<213> ORGANISM: Artificial Sequence
<220> FEATURE:
<223> OTHER INFORMATION: Novel Sequence

<400> SEQUENCE: 233

ggcttaagag catcatcgtg gtgctggtg                                         29


<210> SEQ ID NO 234
<211> LENGTH: 34
<212> TYPE: DNA
<213> ORGANISM: Artificial Sequence
<220> FEATURE:
<223> OTHER INFORMATION: Novel Sequence

<400> SEQUENCE: 234

gtcaccacca gcaccacgat gatgctctta agcc                                   34


<210> SEQ ID NO 235
<211> LENGTH: 31
<212> TYPE: DNA
<213> ORGANISM: Artificial Sequence
<220> FEATURE:
<223> OTHER INFORMATION: Novel Sequence

<400> SEQUENCE: 235

caaagaaagt actgggcatc gtcttcttcc t                                      31


<210> SEQ ID NO 236
<211> LENGTH: 30
<212> TYPE: DNA
<213> ORGANISM: Artificial Sequence
<220> FEATURE:
<223> OTHER INFORMATION: Novel Sequence

<400> SEQUENCE: 236

tgctctagat tccagatagg tgaaaacttg                                        30


<210> SEQ ID NO 237
<211> LENGTH: 50
<212> TYPE: DNA
<213> ORGANISM: Artificial Sequence
<220> FEATURE:
<223> OTHER INFORMATION: Novel Sequence
```

-continued

<400> SEQUENCE: 237
ctaggggcac catgcaggct atcaacaatg aaagaaaagc taagaaagtc 50

<210> SEQ ID NO 238
<211> LENGTH: 50
<212> TYPE: DNA
<213> ORGANISM: Artificial Sequence
<220> FEATURE:
<223> OTHER INFORMATION: Novel Sequence
<220> FEATURE:
<221> NAME/KEY: misc_feature
<223> OTHER INFORMATION: Novel Sequence

<400> SEQUENCE: 238
caaggacttt cttagctttt ctttcattgt tgatagcctg catggtgccc 50

<210> SEQ ID NO 239
<211> LENGTH: 35
<212> TYPE: DNA
<213> ORGANISM: Artificial Sequence
<220> FEATURE:
<223> OTHER INFORMATION: Novel Sequence

<400> SEQUENCE: 239
cggcggcaga aggcgaaacg catgatcctc gcggt 35

<210> SEQ ID NO 240
<211> LENGTH: 35
<212> TYPE: DNA
<213> ORGANISM: Artificial Sequence
<220> FEATURE:
<223> OTHER INFORMATION: Novel Sequence

<400> SEQUENCE: 240
accgcgagga tcatgcgttt cgccttctgc cgccg 35

<210> SEQ ID NO 241
<211> LENGTH: 24
<212> TYPE: DNA
<213> ORGANISM: Artificial Sequence
<220> FEATURE:
<223> OTHER INFORMATION: Novel Sequence

<400> SEQUENCE: 241
gagacatatt atctgccacg gagg 24

<210> SEQ ID NO 242
<211> LENGTH: 24
<212> TYPE: DNA
<213> ORGANISM: Artificial Sequence
<220> FEATURE:
<223> OTHER INFORMATION: Novel Sequence

<400> SEQUENCE: 242
ttggcataga aaccggaccc aagg 24

<210> SEQ ID NO 243
<211> LENGTH: 28
<212> TYPE: DNA
<213> ORGANISM: Artificial Sequence
<220> FEATURE:
<223> OTHER INFORMATION: Novel Sequence

<400> SEQUENCE: 243
taagaattcc ataaaaatta tggaatgg 28

-continued

<210> SEQ ID NO 244
<211> LENGTH: 30
<212> TYPE: DNA
<213> ORGANISM: Artificial Sequence
<220> FEATURE:
<223> OTHER INFORMATION: Novel Sequence

<400> SEQUENCE: 244
ccaggatcca gctgaagtct tccatcattc 30

<210> SEQ ID NO 245
<211> LENGTH: 1071
<212> TYPE: DNA
<213> ORGANISM: Homo sapiens

<400> SEQUENCE: 245
atgaatgggg tctcggaggg gaccagaggc tgcagtgaca ggcaacctgg ggtcctgaca 60
cgtgatcgct cttgttccag gaagatgaac tcttccggat gcctgtctga ggaggtgggg 120
tccctccgcc cactgactgt ggttatcctg tctgcgtcca ttgtcgtcgg agtgctgggc 180
aatgggctgg tgctgtggat gactgtcttc cgtatggcac gcacggtctc caccgtctgc 240
ttcttccacc tggcccttgc cgatttcatg ctctcactgt ctctgcccat tgccatgtac 300
tatattgtct ccaggcagtg gctcctcgga gagtgggcct gcaaactcta catcaccttt 360
gtgttcctca gctactttgc cagtaactgc ctccttgtct tcatctctgt ggaccgttgc 420
atctctgtcc tctaccccgt ctgggccctg aaccaccgca ctgtgcagcg ggcgagctgg 480
ctggcctttg ggggtgtggct cctggccgcc gccttgtgct ctgcgcacct gaaattccgg 540
acaaccagaa aatggaatgg ctgtacgcac tgctacttgg cgttcaactc tgacaatgag 600
actgcccaga tttggattga aggggtcgtg gagggacaca ttatagggac cattggccac 660
ttcctgctgg gcttcctggg gcccttagca atcataggca cctgcgccca cctcatccgg 720
gccaagctct tgcgggaggg ctgggtccat gccaaccggc ccgcgaggct gctgctggtg 780
ctggtgagcg ctttctttat cttctggtcc ccgtttaacg tggtgctgtt ggtccatctg 840
tggcgacggg tgatgctcaa ggaaatctac cacccccgga tgctgctcat cctccaggct 900
agctttgcct tgggctgtgt caacagcagc ctcaacccct tcctctacgt cttcgttggc 960
agagatttcc aagaaaagtt tttccagtct ttgacttctg ccctggcgag ggcgtttgga 1020
gaggaggagt ttctgtcatc ctgtccccgt ggcaacgccc cccgggaatg a 1071

<210> SEQ ID NO 246
<211> LENGTH: 356
<212> TYPE: PRT
<213> ORGANISM: Homo sapiens

<400> SEQUENCE: 246

Met Asn Gly Val Ser Glu Gly Thr Arg Gly Cys Ser Asp Arg Gln Pro
1               5                   10                  15

Gly Val Leu Thr Arg Asp Arg Ser Cys Ser Arg Lys Met Asn Ser Ser
            20                  25                  30

Gly Cys Leu Ser Glu Glu Val Gly Ser Leu Arg Pro Leu Thr Val Val
        35                  40                  45

Ile Leu Ser Ala Ser Ile Val Val Gly Val Leu Gly Asn Gly Leu Val
    50                  55                  60

Leu Trp Met Thr Val Phe Arg Met Ala Arg Thr Val Ser Thr Val Cys
65                  70                  75                  80

-continued

```
Phe Phe His Leu Ala Leu Ala Asp Phe Met Leu Ser Leu Ser Leu Pro
                85                  90                  95

Ile Ala Met Tyr Tyr Ile Val Ser Arg Gln Trp Leu Leu Gly Glu Trp
            100                 105                 110

Ala Cys Lys Leu Tyr Ile Thr Phe Val Phe Leu Ser Tyr Phe Ala Ser
        115                 120                 125

Asn Cys Leu Leu Val Phe Ile Ser Val Asp Arg Cys Ile Ser Val Leu
    130                 135                 140

Tyr Pro Val Trp Ala Leu Asn His Arg Thr Val Gln Arg Ala Ser Trp
145                 150                 155                 160

Leu Ala Phe Gly Val Trp Leu Leu Ala Ala Ala Leu Cys Ser Ala His
                165                 170                 175

Leu Lys Phe Arg Thr Thr Arg Lys Trp Asn Gly Cys Thr His Cys Tyr
            180                 185                 190

Leu Ala Phe Asn Ser Asp Asn Glu Thr Ala Gln Ile Trp Ile Glu Gly
        195                 200                 205

Val Val Glu Gly His Ile Ile Gly Thr Ile Gly His Phe Leu Leu Gly
    210                 215                 220

Phe Leu Gly Pro Leu Ala Ile Ile Gly Thr Cys Ala His Leu Ile Arg
225                 230                 235                 240

Ala Lys Leu Leu Arg Glu Gly Trp Val His Ala Asn Arg Pro Ala Arg
                245                 250                 255

Leu Leu Leu Val Leu Val Ser Ala Phe Phe Ile Phe Trp Ser Pro Phe
            260                 265                 270

Asn Val Val Leu Leu Val His Leu Trp Arg Arg Val Met Leu Lys Glu
        275                 280                 285

Ile Tyr His Pro Arg Met Leu Leu Ile Leu Gln Ala Ser Phe Ala Leu
    290                 295                 300

Gly Cys Val Asn Ser Ser Leu Asn Pro Phe Leu Tyr Val Phe Val Gly
305                 310                 315                 320

Arg Asp Phe Gln Glu Lys Phe Phe Gln Ser Leu Thr Ser Ala Leu Ala
                325                 330                 335

Arg Ala Phe Gly Glu Glu Glu Phe Leu Ser Ser Cys Pro Arg Gly Asn
            340                 345                 350

Ala Pro Arg Glu
        355
```

<210> SEQ ID NO 247
<211> LENGTH: 32
<212> TYPE: DNA
<213> ORGANISM: Artificial Sequence
<220> FEATURE:
<223> OTHER INFORMATION: Novel Sequence

<400> SEQUENCE: 247
gcagaattcg gcggccccat ggacctgccc cc 32

<210> SEQ ID NO 248
<211> LENGTH: 30
<212> TYPE: DNA
<213> ORGANISM: Artificial Sequence
<220> FEATURE:
<223> OTHER INFORMATION: Novel Sequence

<400> SEQUENCE: 248
gctggatccc ccgagcagtg gcgttacttc 30

-continued

<210> SEQ ID NO 249
<211> LENGTH: 903
<212> TYPE: DNA
<213> ORGANISM: Homo sapiens

<400> SEQUENCE: 249

```
atggacctgc ccccgcagct ctccttcggc ctctatgtgg ccgcctttgc gctgggcttc     60

ccgctcaacg tcctggccat ccgaggcgcg acggcccacg cccggctccg tctcacccct    120

agcctggtct acgccctgaa cctgggctgc tccgacctgc tgctgacagt ctctctgccc    180

ctgaaggcgg tggaggcgct agcctccggg gcctggcctc tgccggcctc gctgtgcccc    240

gtcttcgcgg tggcccactt cttcccactc tatgccggcg gggcttcct ggccgccctg     300

agtgcaggcc gctacctggg agcagccttc cccttgggct accaagcctt ccggaggccg    360

tgctattcct ggggggtgtg cgcggccatc tgggccctcg tcctgtgtca cctgggtctg    420

gtctttgggt tggaggctcc aggaggctgg ctggaccaca gcaacacctc cctgggcatc    480

aacacaccgg tcaacggctc tccggtctgc ctggaggcct gggacccggc ctctgccggc    540

ccggcccgct tcagcctctc tctcctgctc ttttttctgc ccttggccat cacagccttc    600

tgctacgtgg gctgcctccg ggcactggcc cgctccggcc tgacgcacag gcggaagctg    660

cgggccgcct gggtggccgg cggggccctc ctcacgctgc tgctctgcgt aggaccctac    720

aacgcctcca acgtggccag cttcctgtac cccaatctag gaggctcctg gcggaagctg    780

gggctcatca cgggtgcctg gagtgtggtg cttaatccgc tggtgaccgg ttacttggga    840

aggggtcctg gcctgaagac agtgtgtgcg gcaagaacgc aagggggcaa gtcccagaag    900

taa                                                                  903
```

<210> SEQ ID NO 250
<211> LENGTH: 300
<212> TYPE: PRT
<213> ORGANISM: Homo sapiens

<400> SEQUENCE: 250

```
Met Asp Leu Pro Pro Gln Leu Ser Phe Gly Leu Tyr Val Ala Ala Phe
1               5                   10                  15

Ala Leu Gly Phe Pro Leu Asn Val Leu Ala Ile Arg Gly Ala Thr Ala
            20                  25                  30

His Ala Arg Leu Arg Leu Thr Pro Ser Leu Val Tyr Ala Leu Asn Leu
        35                  40                  45

Gly Cys Ser Asp Leu Leu Leu Thr Val Ser Leu Pro Leu Lys Ala Val
    50                  55                  60

Glu Ala Leu Ala Ser Gly Ala Trp Pro Leu Pro Ala Ser Leu Cys Pro
65                  70                  75                  80

Val Phe Ala Val Ala His Phe Phe Pro Leu Tyr Ala Gly Gly Gly Phe
                85                  90                  95

Leu Ala Ala Leu Ser Ala Gly Arg Tyr Leu Gly Ala Ala Phe Pro Leu
            100                 105                 110

Gly Tyr Gln Ala Phe Arg Arg Pro Cys Tyr Ser Trp Gly Val Cys Ala
        115                 120                 125

Ala Ile Trp Ala Leu Val Leu Cys His Leu Gly Leu Val Phe Gly Leu
    130                 135                 140

Glu Ala Pro Gly Gly Trp Leu Asp His Ser Asn Thr Ser Leu Gly Ile
145                 150                 155                 160

Asn Thr Pro Val Asn Gly Ser Pro Val Cys Leu Glu Ala Trp Asp Pro
                165                 170                 175
```

-continued

```
Ala Ser Ala Gly Pro Ala Arg Phe Ser Leu Ser Leu Leu Leu Phe Phe
            180                 185                 190

Leu Pro Leu Ala Ile Thr Ala Phe Cys Tyr Val Gly Cys Leu Arg Ala
        195                 200                 205

Leu Ala Arg Ser Gly Leu Thr His Arg Arg Lys Leu Arg Ala Ala Trp
    210                 215                 220

Val Ala Gly Gly Ala Leu Leu Thr Leu Leu Leu Cys Val Gly Pro Tyr
225                 230                 235                 240

Asn Ala Ser Asn Val Ala Ser Phe Leu Tyr Pro Asn Leu Gly Gly Ser
                245                 250                 255

Trp Arg Lys Leu Gly Leu Ile Thr Gly Ala Trp Ser Val Val Leu Asn
            260                 265                 270

Pro Leu Val Thr Gly Tyr Leu Gly Arg Gly Pro Gly Leu Lys Thr Val
        275                 280                 285

Cys Ala Ala Arg Thr Gln Gly Gly Lys Ser Gln Lys
    290                 295                 300
```

<210> SEQ ID NO 251
<211> LENGTH: 31
<212> TYPE: DNA
<213> ORGANISM: Artificial Sequence
<220> FEATURE:
<223> OTHER INFORMATION: Novel Sequence

<400> SEQUENCE: 251
ctcaagctta ctctctctca ccagtggcca c 31

<210> SEQ ID NO 252
<211> LENGTH: 24
<212> TYPE: DNA
<213> ORGANISM: Artificial Sequence
<220> FEATURE:
<223> OTHER INFORMATION: Novel Sequence

<400> SEQUENCE: 252
ccctcctccc ccggaggacc tagc 24

<210> SEQ ID NO 253
<211> LENGTH: 1041
<212> TYPE: DNA
<213> ORGANISM: Homo sapiens

<400> SEQUENCE: 253
atggatacag gccccgacca gtcctacttc tccggcaatc actggttcgt cttctcggtg 60
taccttctca ctttcctggt ggggctcccc ctcaacctgc tggccctggt ggtcttcgtg 120
ggcaagctgc agcgccgccc ggtggccgtg gacgtgctcc tgctcaacct gaccgcctcg 180
gacctgctcc tgctgctgtt cctgcctttc cgcatggtgg aggcagccaa tggcatgcac 240
tggcccctgc ccttcatcct ctgcccactc tctggattca tcttcttcac caccatctat 300
ctcaccgccc tcttcctggc agctgtgagc attgaacgct tcctgagtgt ggcccaccca 360
ctgtggtaca agacccggcc gaggctgggg caggcaggtc tggtgagtgt ggcctgctgg 420
ctgttggcct ctgctcactg cagcgtggtc tacgtcatag aattctcagg ggacatctcc 480
cacagccagg gcaccaatgg gacctgctac ctggagttcc ggaaggacca gctagccatc 540
ctcctgcccg tgcggctgga gatggctgtg gtcctctttg tggtcccgct gatcatcacc 600
agctactgct acagccgcct ggtgtggatc ctcggcagag gggcagccca ccgccggcag 660

-continued

```
aggagggtgg cggggctgtt ggcggccacg ctgctcaact tccttgtctg ctttgggccc    720

tacaacgtgt cccatgtcgt gggctatatc tgcggtgaaa gcccggcatg gaggatctac    780

gtgacgcttc tcagcaccct gaactcctgt gtcgacccct ttgtctacta cttctcctcc    840

tccgggttcc aagccgactt tcatgagctg ctgaggaggt tgtgtgggct ctggggccag    900

tggcagcagg agagcagcat ggagctgaag gagcagaagg gaggggagga gcagagagcg    960

gaccgaccag ctgaaagaaa gaccagtgaa cactcacagg gctgtggaac tggtggccag   1020

gtggcctgtg ctgaaagcta g                                              1041
```

<210> SEQ ID NO 254
<211> LENGTH: 346
<212> TYPE: PRT
<213> ORGANISM: Homo sapiens

<400> SEQUENCE: 254

```
Met Asp Thr Gly Pro Asp Gln Ser Tyr Phe Ser Gly Asn His Trp Phe
1               5                   10                  15

Val Phe Ser Val Tyr Leu Leu Thr Phe Leu Val Gly Leu Pro Leu Asn
            20                  25                  30

Leu Leu Ala Leu Val Val Phe Val Gly Lys Leu Gln Arg Arg Pro Val
        35                  40                  45

Ala Val Asp Val Leu Leu Leu Asn Leu Thr Ala Ser Asp Leu Leu Leu
    50                  55                  60

Leu Leu Phe Leu Pro Phe Arg Met Val Glu Ala Ala Asn Gly Met His
65                  70                  75                  80

Trp Pro Leu Pro Phe Ile Leu Cys Pro Leu Ser Gly Phe Ile Phe Phe
                85                  90                  95

Thr Thr Ile Tyr Leu Thr Ala Leu Phe Leu Ala Ala Val Ser Ile Glu
            100                 105                 110

Arg Phe Leu Ser Val Ala His Pro Leu Trp Tyr Lys Thr Arg Pro Arg
        115                 120                 125

Leu Gly Gln Ala Gly Leu Val Ser Val Ala Cys Trp Leu Leu Ala Ser
    130                 135                 140

Ala His Cys Ser Val Val Tyr Val Ile Glu Phe Ser Gly Asp Ile Ser
145                 150                 155                 160

His Ser Gln Gly Thr Asn Gly Thr Cys Tyr Leu Glu Phe Arg Lys Asp
                165                 170                 175

Gln Leu Ala Ile Leu Leu Pro Val Arg Leu Glu Met Ala Val Val Leu
            180                 185                 190

Phe Val Val Pro Leu Ile Ile Thr Ser Tyr Cys Tyr Ser Arg Leu Val
        195                 200                 205

Trp Ile Leu Gly Arg Gly Gly Ser His Arg Arg Gln Arg Arg Val Ala
    210                 215                 220

Gly Leu Leu Ala Ala Thr Leu Leu Asn Phe Leu Val Cys Phe Gly Pro
225                 230                 235                 240

Tyr Asn Val Ser His Val Val Gly Tyr Ile Cys Gly Glu Ser Pro Ala
                245                 250                 255

Trp Arg Ile Tyr Val Thr Leu Leu Ser Thr Leu Asn Ser Cys Val Asp
            260                 265                 270

Pro Phe Val Tyr Tyr Phe Ser Ser Ser Gly Phe Gln Ala Asp Phe His
        275                 280                 285

Glu Leu Leu Arg Arg Leu Cys Gly Leu Trp Gly Gln Trp Gln Gln Glu
    290                 295                 300
```

-continued

```
Ser Ser Met Glu Leu Lys Glu Gln Lys Gly Gly Glu Glu Gln Arg Ala
305                 310                 315                 320

Asp Arg Pro Ala Glu Arg Lys Thr Ser Glu His Ser Gln Gly Cys Gly
                325                 330                 335

Thr Gly Gly Gln Val Ala Cys Ala Glu Ser
            340                 345


<210> SEQ ID NO 255
<211> LENGTH: 31
<212> TYPE: DNA
<213> ORGANISM: Artificial Sequence
<220> FEATURE:
<223> OTHER INFORMATION: Novel Sequence

<400> SEQUENCE: 255

tttaagcttc ccctccagga tgctgccgga c                                    31


<210> SEQ ID NO 256
<211> LENGTH: 31
<212> TYPE: DNA
<213> ORGANISM: Artificial Sequence
<220> FEATURE:
<223> OTHER INFORMATION: Novel Sequence

<400> SEQUENCE: 256

ggcgaattct gaaggtccag ggaaactgct a                                    31


<210> SEQ ID NO 257
<211> LENGTH: 993
<212> TYPE: DNA
<213> ORGANISM: Homo sapiens

<400> SEQUENCE: 257

atgctgccgg actggaagag ctccttgatc ctcatggctt acatcatcat cttcctcact      60

ggcctccctg ccaacctcct ggccctgcgg gcctttgtgg ggcggatccg ccagccccag     120

cctgcacctg tgcacatcct cctgctgagc ctgacgctgg ccgacctcct cctgctgctg     180

ctgctgccct tcaagatcat cgaggctgcg tcgaacttcc gctggtacct gcccaaggtc     240

gtctgcgccc tcacgagttt tggcttctac agcagcatct actgcagcac gtggctcctg     300

gcgggcatca gcatcgagcg ctacctggga gtggctttcc ccgtgcagta caagctctcc     360

cgccggcctc tgtatggagt gattgcagct ctggtggcct gggttatgtc ctttggtcac     420

tgcaccatcg tgatcatcgt tcaatacttg aacacgactg agcaggtcag aagtggcaat     480

gaaattacct gctacgagaa cttcaccgat aaccagttgg acgtggtgct gcccgtgcgg     540

ctggagctgt gcctggtgct cttcttcatc cccatggcag tcaccatctt ctgctactgg     600

cgttttgtgt ggatcatgct ctcccagccc cttgtggggg cccagaggcg gcgccgagcc     660

gtggggctgg ctgtggtgac gctgctcaat ttcctggtgt gcttcggacc ttacaacgtg     720

tcccacctgg tggggtatca ccagagaaaa agcccctggt ggcggtcaat agccgtggtg     780

ttcagttcac tcaacgccag tctggacccc ctgctcttct atttctcttc ttcagtggtg     840

cgcagggcat ttgggagagg gctgcaggtg ctgcggaatc agggctcctc cctgttggga     900

cgcagaggca aagacacagc agaggggaca aatgaggaca ggggtgtggg tcaaggagaa     960

gggatgccaa gttcggactt cactacagag tag                                 993


<210> SEQ ID NO 258
<211> LENGTH: 330
<212> TYPE: PRT
```

-continued

<213> ORGANISM: Homo sapiens

<400> SEQUENCE: 258

```
Met Leu Pro Asp Trp Lys Ser Ser Leu Ile Leu Met Ala Tyr Ile Ile
1               5                   10                  15

Ile Phe Leu Thr Gly Leu Pro Ala Asn Leu Leu Ala Leu Arg Ala Phe
            20                  25                  30

Val Gly Arg Ile Arg Gln Pro Gln Pro Ala Pro Val His Ile Leu Leu
        35                  40                  45

Leu Ser Leu Thr Leu Ala Asp Leu Leu Leu Leu Leu Leu Leu Pro Phe
    50                  55                  60

Lys Ile Ile Glu Ala Ala Ser Asn Phe Arg Trp Tyr Leu Pro Lys Val
65                  70                  75                  80

Val Cys Ala Leu Thr Ser Phe Gly Phe Tyr Ser Ser Ile Tyr Cys Ser
                85                  90                  95

Thr Trp Leu Leu Ala Gly Ile Ser Ile Glu Arg Tyr Leu Gly Val Ala
            100                 105                 110

Phe Pro Val Gln Tyr Lys Leu Ser Arg Arg Pro Leu Tyr Gly Val Ile
        115                 120                 125

Ala Ala Leu Val Ala Trp Val Met Ser Phe Gly His Cys Thr Ile Val
    130                 135                 140

Ile Ile Val Gln Tyr Leu Asn Thr Thr Glu Gln Val Arg Ser Gly Asn
145                 150                 155                 160

Glu Ile Thr Cys Tyr Glu Asn Phe Thr Asp Asn Gln Leu Asp Val Val
                165                 170                 175

Leu Pro Val Arg Leu Glu Leu Cys Leu Val Leu Phe Phe Ile Pro Met
            180                 185                 190

Ala Val Thr Ile Phe Cys Tyr Trp Arg Phe Val Trp Ile Met Leu Ser
        195                 200                 205

Gln Pro Leu Val Gly Ala Gln Arg Arg Arg Arg Ala Val Gly Leu Ala
    210                 215                 220

Val Val Thr Leu Leu Asn Phe Leu Val Cys Phe Gly Pro Tyr Asn Val
225                 230                 235                 240

Ser His Leu Val Gly Tyr His Gln Arg Lys Ser Pro Trp Trp Arg Ser
                245                 250                 255

Ile Ala Val Val Phe Ser Ser Leu Asn Ala Ser Leu Asp Pro Leu Leu
            260                 265                 270

Phe Tyr Phe Ser Ser Ser Val Val Arg Arg Ala Phe Gly Arg Gly Leu
        275                 280                 285

Gln Val Leu Arg Asn Gln Gly Ser Ser Leu Leu Gly Arg Arg Gly Lys
    290                 295                 300

Asp Thr Ala Glu Gly Thr Asn Glu Asp Arg Gly Val Gly Gln Gly Glu
305                 310                 315                 320

Gly Met Pro Ser Ser Asp Phe Thr Thr Glu
                325                 330
```

<210> SEQ ID NO 259
<211> LENGTH: 30
<212> TYPE: DNA
<213> ORGANISM: Artificial Sequence
<220> FEATURE:
<223> OTHER INFORMATION: Novel Sequence

<400> SEQUENCE: 259
cccaagcttc gggcaccatg gacacctccc 30

-continued

<210> SEQ ID NO 260
<211> LENGTH: 30
<212> TYPE: DNA
<213> ORGANISM: Artificial Sequence
<220> FEATURE:
<223> OTHER INFORMATION: Novel Sequence

<400> SEQUENCE: 260
acaggatcca aatgcacagc actggtaagc 30

<210> SEQ ID NO 261
<211> LENGTH: 25
<212> TYPE: DNA
<213> ORGANISM: Artificial Sequence
<220> FEATURE:
<223> OTHER INFORMATION: Novel Sequence

<400> SEQUENCE: 261
ctataactgg gttacatggt ttaac 25

<210> SEQ ID NO 262
<211> LENGTH: 30
<212> TYPE: DNA
<213> ORGANISM: Artificial Sequence
<220> FEATURE:
<223> OTHER INFORMATION: Novel Sequence
<220> FEATURE:
<221> NAME/KEY: misc_feature
<223> OTHER INFORMATION: Novel Sequence

<400> SEQUENCE: 262
tttgaattca catattaatt agagacatgg 30

<210> SEQ ID NO 263
<211> LENGTH: 2724
<212> TYPE: DNA
<213> ORGANISM: Homo sapiens

<400> SEQUENCE: 263
atggacacct cccggctcgg tgtgctcctg tccttgcctg tgctgctgca gctggcgacc 60
gggggcagct ctcccaggtc tggtgtgttg ctgaggggct gccccacaca ctgtcattgc 120
gagcccgacg gcaggatgtt gctcagggtg gactgctccg acctggggct ctcggagctg 180
ccttccaacc tcagcgtctt cacctcctac ctagacctca gtatgaacaa catcagtcag 240
ctgctcccga atcccctgcc cagtctccgc ttcctggagg agttacgtct tgcgggaaac 300
gctctgacat acattcccaa gggagcattc actggccttt acagtcttaa agttcttatg 360
ctgcagaata atcagctaag acacgtaccc acagaagctc tgcagaattt gcgaagcctt 420
caatccctgc gtctggatgc taaccacatc agctatgtgc ccccaagctg tttcagtggc 480
ctgcattccc tgaggcacct gtggctggat gacaatgcgt taacagaaat ccccgtccag 540
gcttttagaa gtttatcggc attgcaagcc atgaccttgg ccctgaacaa aatacaccac 600
ataccagact atgcctttgg aaacctctcc agcttggtag ttctacatct ccataacaat 660
agaatccact ccctgggaaa gaaatgcttt gatgggctcc acagcctaga gactttagat 720
ttaaattaca ataaccttga tgaattcccc actgcaatta ggacactctc caaccttaaa 780
gaactaggat ttcatagcaa caatatcagg tcgatacctg agaaagcatt tgtaggcaac 840
ccttctctta ttacaataca tttctatgac aatcccatcc aatttgttgg gagatctgct 900
tttcaacatt tacctgaact aagaacactg actctgaatg gtgcctcaca aataactgaa 960

-continued

```
tttcctgatt taactggaac tgcaaacctg gagagtctga ctttaactgg agcacagatc   1020

tcatctcttc ctcaaaccgt ctgcaatcag ttacctaatc tccaagtgct agatctgtct   1080

tacaacctat tagaagattt acccagtttt tcagtctgcc aaaagcttca gaaaattgac   1140

ctaagacata atgaaatcta cgaaattaaa gttgacactt tccagcagtt gcttagcctc   1200

cgatcgctga atttggcttg gaacaaaatt gctattattc accccaatgc attttccact   1260

ttgccatccc taataaagct ggacctatcg tccaacctcc tgtcgtcttt tcctataact   1320

gggttacatg gtttaactca cttaaaatta acaggaaatc atgccttaca gagcttgata   1380

tcatctgaaa actttccaga actcaaggtt atagaaatgc cttatgctta ccagtgctgt   1440

gcatttggag tgtgtgagaa tgcctataag atttctaatc aatggaataa aggtgacaac   1500

agcagtatgg acgaccttca taagaaagat gctggaatgt ttcaggctca agatgaacgt   1560

gaccttgaag atttcctgct tgactttgag gaagacctga aagcccttca ttcagtgcag   1620

tgttcacctt ccccaggccc cttcaaaccc tgtgaacacc tgcttgatgg ctggctgatc   1680

agaattggag tgtggaccat agcagttctg gcacttactt gtaatgcttt ggtgacttca   1740

acagttttca gatcccctct gtacatttcc cccattaaac tgttaattgg ggtcatcgca   1800

gcagtgaaca tgctcacggg agtctccagt gccgtgctgg ctggtgtgga tgcgttcact   1860

tttggcagct ttgcacgaca tggtgcctgg tgggagaatg gggttggttg ccatgtcatt   1920

ggtttttgt ccatttttgc ttcagaatca tctgttttcc tgcttactct ggcagccctg   1980

gagcgtgggt tctctgtgaa atattctgca aaatttgaaa cgaaagctcc attttctagc   2040

ctgaaagtaa tcattttgct ctgtgccctg ctggccttga ccatggccgc agttcccctg   2100

ctgggtggca gcaagtatgg cgcctcccct ctctgcctgc ctttgccttt tggggagccc   2160

agcaccatgg gctacatggt cgctctcatc ttgctcaatt ccctttgctt cctcatgatg   2220

accattgcct acaccaagct ctactgcaat ttggacaagg gagacctgga gaatatttgg   2280

gactgctcta tggtaaaaca cattgccctg ttgctcttca ccaactgcat cctaaactgc   2340

cctgtggctt tcttgtcctt ctcctcttta ataaacctta catttatcag tcctgaagta   2400

attaagttta tccttctggt ggtagtccca cttcctgcat gtctcaatcc ccttctctac   2460

atcttgttca atcctcactt taaggaggat ctggtgagcc tgagaaagca aacctacgtc   2520

tggacaagat caaaacaccc aagcttgatg tcaattaact ctgatgatgt cgaaaaacag   2580

tcctgtgact caactcaagc cttggtaacc tttaccagct ccagcatcac ttatgacctg   2640

cctcccagtt ccgtgccatc accagcttat ccagtgactg agagctgcca tctttcctct   2700

gtggcatttg tcccatgtct ctaa                                           2724
```

<210> SEQ ID NO 264
<211> LENGTH: 907
<212> TYPE: PRT
<213> ORGANISM: Homo sapiens

<400> SEQUENCE: 264

```
Met Asp Thr Ser Arg Leu Gly Val Leu Leu Ser Leu Pro Val Leu Leu
1               5                   10                  15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
        35                  40                  45

Arg Val Asp Cys Ser Asp Leu Gly Leu Ser Glu Leu Pro Ser Asn Leu
    50                  55                  60
```

-continued

```
Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
            100                 105                 110

Leu Tyr Ser Leu Lys Val Leu Met Leu Gln Asn Asn Gln Leu Arg His
        115                 120                 125

Val Pro Thr Glu Ala Leu Gln Asn Leu Arg Ser Leu Gln Ser Leu Arg
    130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
            180                 185                 190

Leu Ala Leu Asn Lys Ile His His Ile Pro Asp Tyr Ala Phe Gly Asn
        195                 200                 205

Leu Ser Ser Leu Val Val Leu His Leu His Asn Asn Arg Ile His Ser
    210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
                245                 250                 255

Ser Asn Leu Lys Glu Leu Gly Phe His Ser Asn Asn Ile Arg Ser Ile
            260                 265                 270

Pro Glu Lys Ala Phe Val Gly Asn Pro Ser Leu Ile Thr Ile His Phe
        275                 280                 285

Tyr Asp Asn Pro Ile Gln Phe Val Gly Arg Ser Ala Phe Gln His Leu
    290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
                325                 330                 335

Gly Ala Gln Ile Ser Ser Leu Pro Gln Thr Val Cys Asn Gln Leu Pro
            340                 345                 350

Asn Leu Gln Val Leu Asp Leu Ser Tyr Asn Leu Leu Glu Asp Leu Pro
        355                 360                 365

Ser Phe Ser Val Cys Gln Lys Leu Gln Lys Ile Asp Leu Arg His Asn
    370                 375                 380

Glu Ile Tyr Glu Ile Lys Val Asp Thr Phe Gln Gln Leu Leu Ser Leu
385                 390                 395                 400

Arg Ser Leu Asn Leu Ala Trp Asn Lys Ile Ala Ile Ile His Pro Asn
                405                 410                 415

Ala Phe Ser Thr Leu Pro Ser Leu Ile Lys Leu Asp Leu Ser Ser Asn
            420                 425                 430

Leu Leu Ser Ser Phe Pro Ile Thr Gly Leu His Gly Leu Thr His Leu
        435                 440                 445

Lys Leu Thr Gly Asn His Ala Leu Gln Ser Leu Ile Ser Ser Glu Asn
    450                 455                 460

Phe Pro Glu Leu Lys Val Ile Glu Met Pro Tyr Ala Tyr Gln Cys Cys
465                 470                 475                 480
```

-continued

```
Ala Phe Gly Val Cys Glu Asn Ala Tyr Lys Ile Ser Asn Gln Trp Asn
                485                 490                 495

Lys Gly Asp Asn Ser Ser Met Asp Asp Leu His Lys Lys Asp Ala Gly
            500                 505                 510

Met Phe Gln Ala Gln Asp Glu Arg Asp Leu Glu Asp Phe Leu Leu Asp
        515                 520                 525

Phe Glu Glu Asp Leu Lys Ala Leu His Ser Val Gln Cys Ser Pro Ser
    530                 535                 540

Pro Gly Pro Phe Lys Pro Cys Glu His Leu Leu Asp Gly Trp Leu Ile
545                 550                 555                 560

Arg Ile Gly Val Trp Thr Ile Ala Val Leu Ala Leu Thr Cys Asn Ala
                565                 570                 575

Leu Val Thr Ser Thr Val Phe Arg Ser Pro Leu Tyr Ile Ser Pro Ile
            580                 585                 590

Lys Leu Leu Ile Gly Val Ile Ala Ala Val Asn Met Leu Thr Gly Val
        595                 600                 605

Ser Ser Ala Val Leu Ala Gly Val Asp Ala Phe Thr Phe Gly Ser Phe
    610                 615                 620

Ala Arg His Gly Ala Trp Trp Glu Asn Gly Val Gly Cys His Val Ile
625                 630                 635                 640

Gly Phe Leu Ser Ile Phe Ala Ser Glu Ser Ser Val Phe Leu Leu Thr
                645                 650                 655

Leu Ala Ala Leu Glu Arg Gly Phe Ser Val Lys Tyr Ser Ala Lys Phe
            660                 665                 670

Glu Thr Lys Ala Pro Phe Ser Ser Leu Lys Val Ile Ile Leu Leu Cys
        675                 680                 685

Ala Leu Leu Ala Leu Thr Met Ala Ala Val Pro Leu Leu Gly Gly Ser
    690                 695                 700

Lys Tyr Gly Ala Ser Pro Leu Cys Leu Pro Leu Pro Phe Gly Glu Pro
705                 710                 715                 720

Ser Thr Met Gly Tyr Met Val Ala Leu Ile Leu Leu Asn Ser Leu Cys
                725                 730                 735

Phe Leu Met Met Thr Ile Ala Tyr Thr Lys Leu Tyr Cys Asn Leu Asp
            740                 745                 750

Lys Gly Asp Leu Glu Asn Ile Trp Asp Cys Ser Met Val Lys His Ile
        755                 760                 765

Ala Leu Leu Leu Phe Thr Asn Cys Ile Leu Asn Cys Pro Val Ala Phe
    770                 775                 780

Leu Ser Phe Ser Ser Leu Ile Asn Leu Thr Phe Ile Ser Pro Glu Val
785                 790                 795                 800

Ile Lys Phe Ile Leu Leu Val Val Val Pro Leu Pro Ala Cys Leu Asn
                805                 810                 815

Pro Leu Leu Tyr Ile Leu Phe Asn Pro His Phe Lys Glu Asp Leu Val
            820                 825                 830

Ser Leu Arg Lys Gln Thr Tyr Val Trp Thr Arg Ser Lys His Pro Ser
        835                 840                 845

Leu Met Ser Ile Asn Ser Asp Asp Val Glu Lys Gln Ser Cys Asp Ser
    850                 855                 860

Thr Gln Ala Leu Val Thr Phe Thr Ser Ser Ser Ile Thr Tyr Asp Leu
865                 870                 875                 880

Pro Pro Ser Ser Val Pro Ser Pro Ala Tyr Pro Val Thr Glu Ser Cys
                885                 890                 895

His Leu Ser Ser Val Ala Phe Val Pro Cys Leu
```

-continued 900 905

<210> SEQ ID NO 265
<211> LENGTH: 30
<212> TYPE: DNA
<213> ORGANISM: Artificial Sequence
<220> FEATURE:
<223> OTHER INFORMATION: Novel Sequence

<400> SEQUENCE: 265
cggaagctgc gggccaaatg ggtggccggc 30

<210> SEQ ID NO 266
<211> LENGTH: 27
<212> TYPE: DNA
<213> ORGANISM: Artificial Sequence
<220> FEATURE:
<223> OTHER INFORMATION: Novel Sequence

<400> SEQUENCE: 266
cagaggaggg tgaaggggct gttggcg 27

<210> SEQ ID NO 267
<211> LENGTH: 30
<212> TYPE: DNA
<213> ORGANISM: Artificial Sequence
<220> FEATURE:
<223> OTHER INFORMATION: Novel Sequence

<400> SEQUENCE: 267
ggcggcgccg agccaagggg ctggctgtgg 30

<210> SEQ ID NO 268
<211> LENGTH: 32
<212> TYPE: DNA
<213> ORGANISM: Artificial Sequence
<220> FEATURE:
<223> OTHER INFORMATION: Novel Sequence

<400> SEQUENCE: 268
gggactgctc tatgaaaaaa cacattgccc tg 32

<210> SEQ ID NO 269
<211> LENGTH: 1071
<212> TYPE: DNA
<213> ORGANISM: Homo sapiens

<400> SEQUENCE: 269
atgaatgggg tctcggaggg gaccagaggc tgcagtgaca ggcaacctgg ggtcctgaca 60
cgtgatcgct cttgttccag gaagatgaac tcttccggat gcctgtctga ggaggtgggg 120
tccctccgcc cactgactgt ggttatcctg tctgcgtcca ttgtcgtcgg agtgctgggc 180
aatgggctgg tgctgtggat gactgtcttc cgtatggcac gcacggtctc caccgtctgc 240
ttcttccacc tggcccttgc cgatttcatg ctctcactgt ctctgcccat tgccatgtac 300
tatattgtct ccaggcagtg gctcctcgga gagtgggcct gcaaactcta catcaccttt 360
gtgttcctca gctactttgc cagtaactgc ctccttgtct tcatctctgt ggaccgttgc 420
atctctgtcc tctaccccgt ctgggccctg aaccaccgca ctgtgcagcg ggcgagctgg 480
ctggcctttg gggtgtggct cctggccgcc gccttgtgct ctgcgcacct gaaattccgg 540
acaaccagaa aatggaatgg ctgtacgcac tgctacttgg cgttcaactc tgacaatgag 600
actgcccaga tttggattga aggggtcgtg gagggacaca ttatagggac cattggccac 660

-continued

```
ttcctgctgg gcttcctggg gcccttagca atcataggca cctgcgccca cctcatccgg    720

gccaagctct tgcgggaggg ctgggtccat gccaaccggc ccaagaggct gctgctggtg    780

ctggtgagcg ctttctttat cttctggtcc ccgtttaacg tggtgctgtt ggtccatctg    840

tggcgacggg tgatgctcaa ggaaatctac cacccccgga tgctgctcat cctccaggct    900

agctttgcct tgggctgtgt caacagcagc ctcaacccct tcctctacgt cttcgttggc    960

agagatttcc aagaaaagtt tttccagtct ttgacttctg ccctggcgag ggcgtttgga   1020

gaggaggagt ttctgtcatc ctgtccccgt ggcaacgccc cccgggaatg a            1071
```

```
<210> SEQ ID NO 270
<211> LENGTH: 356
<212> TYPE: PRT
<213> ORGANISM: Homo sapiens

<400> SEQUENCE: 270

Met Asn Gly Val Ser Glu Gly Thr Arg Gly Cys Ser Asp Arg Gln Pro
1               5                   10                  15

Gly Val Leu Thr Arg Asp Arg Ser Cys Ser Arg Lys Met Asn Ser Ser
            20                  25                  30

Gly Cys Leu Ser Glu Glu Val Gly Ser Leu Arg Pro Leu Thr Val Val
        35                  40                  45

Ile Leu Ser Ala Ser Ile Val Val Gly Val Leu Gly Asn Gly Leu Val
    50                  55                  60

Leu Trp Met Thr Val Phe Arg Met Ala Arg Thr Val Ser Thr Val Cys
65                  70                  75                  80

Phe Phe His Leu Ala Leu Ala Asp Phe Met Leu Ser Leu Ser Leu Pro
                85                  90                  95

Ile Ala Met Tyr Tyr Ile Val Ser Arg Gln Trp Leu Leu Gly Glu Trp
            100                 105                 110

Ala Cys Lys Leu Tyr Ile Thr Phe Val Phe Leu Ser Tyr Phe Ala Ser
        115                 120                 125

Asn Cys Leu Leu Val Phe Ile Ser Val Asp Arg Cys Ile Ser Val Leu
    130                 135                 140

Tyr Pro Val Trp Ala Leu Asn His Arg Thr Val Gln Arg Ala Ser Trp
145                 150                 155                 160

Leu Ala Phe Gly Val Trp Leu Leu Ala Ala Ala Leu Cys Ser Ala His
                165                 170                 175

Leu Lys Phe Arg Thr Thr Arg Lys Trp Asn Gly Cys Thr His Cys Tyr
            180                 185                 190

Leu Ala Phe Asn Ser Asp Asn Glu Thr Ala Gln Ile Trp Ile Glu Gly
        195                 200                 205

Val Val Glu Gly His Ile Ile Gly Thr Ile Gly His Phe Leu Leu Gly
    210                 215                 220

Phe Leu Gly Pro Leu Ala Ile Ile Gly Thr Cys Ala His Leu Ile Arg
225                 230                 235                 240

Ala Lys Leu Leu Arg Glu Gly Trp Val His Ala Asn Arg Pro Lys Arg
                245                 250                 255

Leu Leu Leu Val Leu Val Ser Ala Phe Phe Ile Phe Trp Ser Pro Phe
            260                 265                 270

Asn Val Val Leu Leu Val His Leu Trp Arg Arg Val Met Leu Lys Glu
        275                 280                 285

Ile Tyr His Pro Arg Met Leu Leu Ile Leu Gln Ala Ser Phe Ala Leu
    290                 295                 300
```

-continued

```
Gly Cys Val Asn Ser Ser Leu Asn Pro Phe Leu Tyr Val Phe Val Gly
305                 310                 315                 320

Arg Asp Phe Gln Glu Lys Phe Phe Gln Ser Leu Thr Ser Ala Leu Ala
                325                 330                 335

Arg Ala Phe Gly Glu Glu Glu Phe Leu Ser Ser Cys Pro Arg Gly Asn
            340                 345                 350

Ala Pro Arg Glu
        355
```

<210> SEQ ID NO 271
<211> LENGTH: 903
<212> TYPE: DNA
<213> ORGANISM: Homo sapiens

<400> SEQUENCE: 271

```
atggacctgc ccccgcagct ctccttcggc ctctatgtgg ccgcctttgc gctgggcttc     60

ccgctcaacg tcctggccat ccgaggcgcg acggcccacg cccggctccg tctcacccct    120

agcctggtct acgccctgaa cctgggctgc tccgacctgc tgctgacagt ctctctgccc    180

ctgaaggcgg tggaggcgct agcctccggg gcctggcctc tgccggcctc gctgtgcccc    240

gtcttcgcgg tggcccactt cttcccactc tatgccggcg ggggcttcct ggccgccctg    300

agtgcaggcc gctacctggg agcagccttc cccttgggct accaagcctt ccggaggccg    360

tgctattcct ggggggtgtg cgcggccatc tgggccctcg tcctgtgtca cctgggtctg    420

gtctttgggt tggaggctcc aggaggctgg ctggaccaca gcaacacctc cctgggcatc    480

aacacaccgg tcaacggctc tccggtctgc ctggaggcct gggacccggc ctctgccggc    540

ccggcccgct tcagcctctc tctcctgctc ttttttctgc ccttggccat cacagccttc    600

tgctacgtgg gctgcctccg ggcactggcc cgctccggcc tgacgcacag gcggaagctg    660

cgggccaaat gggtggccgg cggggccctc ctcacgctgc tgctctgcgt aggaccctac    720

aacgcctcca acgtggccag cttcctgtac cccaatctag gaggctcctg gcggaagctg    780

gggctcatca cgggtgcctg gagtgtggtg cttaatccgc tggtgaccgg ttacttggga    840

aggggtcctg gcctgaagac agtgtgtgcg gcaagaacgc aagggggcaa gtcccagaag    900

taa                                                                  903
```

<210> SEQ ID NO 272
<211> LENGTH: 300
<212> TYPE: PRT
<213> ORGANISM: Homo sapiens

<400> SEQUENCE: 272

```
Met Asp Leu Pro Pro Gln Leu Ser Phe Gly Leu Tyr Val Ala Ala Phe
1               5                   10                  15

Ala Leu Gly Phe Pro Leu Asn Val Leu Ala Ile Arg Gly Ala Thr Ala
            20                  25                  30

His Ala Arg Leu Arg Leu Thr Pro Ser Leu Val Tyr Ala Leu Asn Leu
        35                  40                  45

Gly Cys Ser Asp Leu Leu Leu Thr Val Ser Leu Pro Leu Lys Ala Val
    50                  55                  60

Glu Ala Leu Ala Ser Gly Ala Trp Pro Leu Pro Ala Ser Leu Cys Pro
65                  70                  75                  80

Val Phe Ala Val Ala His Phe Phe Pro Leu Tyr Ala Gly Gly Gly Phe
                85                  90                  95
```

-continued

```
Leu Ala Ala Leu Ser Ala Gly Arg Tyr Leu Gly Ala Ala Phe Pro Leu
            100                 105                 110

Gly Tyr Gln Ala Phe Arg Arg Pro Cys Tyr Ser Trp Gly Val Cys Ala
        115                 120                 125

Ala Ile Trp Ala Leu Val Leu Cys His Leu Gly Leu Val Phe Gly Leu
    130                 135                 140

Glu Ala Pro Gly Gly Trp Leu Asp His Ser Asn Thr Ser Leu Gly Ile
145                 150                 155                 160

Asn Thr Pro Val Asn Gly Ser Pro Val Cys Leu Glu Ala Trp Asp Pro
                165                 170                 175

Ala Ser Ala Gly Pro Ala Arg Phe Ser Leu Ser Leu Leu Leu Phe Phe
            180                 185                 190

Leu Pro Leu Ala Ile Thr Ala Phe Cys Tyr Val Gly Cys Leu Arg Ala
        195                 200                 205

Leu Ala Arg Ser Gly Leu Thr His Arg Arg Lys Leu Arg Ala Lys Trp
    210                 215                 220

Val Ala Gly Gly Ala Leu Leu Thr Leu Leu Leu Cys Val Gly Pro Tyr
225                 230                 235                 240

Asn Ala Ser Asn Val Ala Ser Phe Leu Tyr Pro Asn Leu Gly Gly Ser
                245                 250                 255

Trp Arg Lys Leu Gly Leu Ile Thr Gly Ala Trp Ser Val Val Leu Asn
            260                 265                 270

Pro Leu Val Thr Gly Tyr Leu Gly Arg Gly Pro Gly Leu Lys Thr Val
        275                 280                 285

Cys Ala Ala Arg Thr Gln Gly Gly Lys Ser Gln Lys
    290                 295                 300
```

<210> SEQ ID NO 273
<211> LENGTH: 1041
<212> TYPE: DNA
<213> ORGANISM: Homo sapiens

<400> SEQUENCE: 273

```
atggatacag gccccgacca gtcctacttc tccggcaatc actggttcgt cttctcggtg     60

taccttctca ctttcctggt ggggctcccc ctcaacctgc tggccctggt ggtcttcgtg    120

ggcaagctgc agcgccgccc ggtggccgtg gacgtgctcc tgctcaacct gaccgcctcg    180

gacctgctcc tgctgctgtt cctgcctttc cgcatggtgg aggcagccaa tggcatgcac    240

tggcccctgc ccttcatcct ctgcccactc tctggattca tcttcttcac caccatctat    300

ctcaccgccc tcttcctggc agctgtgagc attgaacgct tcctgagtgt ggcccaccca    360

ctgtggtaca agacccggcc gaggctgggg caggcaggtc tggtgagtgt ggcctgctgg    420

ctgttggcct ctgctcactg cagcgtggtc tacgtcatag aattctcagg ggacatctcc    480

cacagccagg gcaccaatgg gacctgctac ctggagttcc ggaaggacca gctagccatc    540

ctcctgcccg tgcggctgga gatggctgtg gtcctctttg tggtcccgct gatcatcacc    600

agctactgct acagccgcct ggtgtggatc ctcggcagag gggcagccca ccgccggcag    660

aggagggtga aggggctgtt ggcggccacg ctgctcaact tccttgtctg ctttgggccc    720

tacaacgtgt cccatgtcgt gggctatatc tgcggtgaaa gcccggcatg gaggatctac    780

gtgacgcttc tcagcaccct gaactcctgt gtcgacccct ttgtctacta cttctcctcc    840

tccgggttcc aagccgactt tcatgagctg ctgaggaggt tgtgtgggct ctggggccag    900

tggcagcagg agagcagcat ggagctgaag gagcagaagg gaggggagga gcagagagcg    960
```

-continued

```
gaccgaccag ctgaaagaaa gaccagtgaa cactcacagg gctgtggaac tggtggccag   1020

gtggcctgtg ctgaaagcta g                                             1041


<210> SEQ ID NO 274
<211> LENGTH: 346
<212> TYPE: PRT
<213> ORGANISM: Homo sapiens

<400> SEQUENCE: 274

Met Asp Thr Gly Pro Asp Gln Ser Tyr Phe Ser Gly Asn His Trp Phe
1               5                   10                  15

Val Phe Ser Val Tyr Leu Leu Thr Phe Leu Val Gly Leu Pro Leu Asn
            20                  25                  30

Leu Leu Ala Leu Val Val Phe Val Gly Lys Leu Gln Arg Arg Pro Val
        35                  40                  45

Ala Val Asp Val Leu Leu Leu Asn Leu Thr Ala Ser Asp Leu Leu Leu
    50                  55                  60

Leu Leu Phe Leu Pro Phe Arg Met Val Glu Ala Ala Asn Gly Met His
65                  70                  75                  80

Trp Pro Leu Pro Phe Ile Leu Cys Pro Leu Ser Gly Phe Ile Phe Phe
                85                  90                  95

Thr Thr Ile Tyr Leu Thr Ala Leu Phe Leu Ala Ala Val Ser Ile Glu
            100                 105                 110

Arg Phe Leu Ser Val Ala His Pro Leu Trp Tyr Lys Thr Arg Pro Arg
        115                 120                 125

Leu Gly Gln Ala Gly Leu Val Ser Val Ala Cys Trp Leu Leu Ala Ser
    130                 135                 140

Ala His Cys Ser Val Val Tyr Val Ile Glu Phe Ser Gly Asp Ile Ser
145                 150                 155                 160

His Ser Gln Gly Thr Asn Gly Thr Cys Tyr Leu Glu Phe Arg Lys Asp
                165                 170                 175

Gln Leu Ala Ile Leu Leu Pro Val Arg Leu Glu Met Ala Val Val Leu
            180                 185                 190

Phe Val Val Pro Leu Ile Ile Thr Ser Tyr Cys Tyr Ser Arg Leu Val
        195                 200                 205

Trp Ile Leu Gly Arg Gly Gly Ser His Arg Arg Gln Arg Arg Val Lys
    210                 215                 220

Gly Leu Leu Ala Ala Thr Leu Leu Asn Phe Leu Val Cys Phe Gly Pro
225                 230                 235                 240

Tyr Asn Val Ser His Val Val Gly Tyr Ile Cys Gly Glu Ser Pro Ala
                245                 250                 255

Trp Arg Ile Tyr Val Thr Leu Leu Ser Thr Leu Asn Ser Cys Val Asp
            260                 265                 270

Pro Phe Val Tyr Tyr Phe Ser Ser Ser Gly Phe Gln Ala Asp Phe His
        275                 280                 285

Glu Leu Leu Arg Arg Leu Cys Gly Leu Trp Gly Gln Trp Gln Gln Glu
    290                 295                 300

Ser Ser Met Glu Leu Lys Glu Gln Lys Gly Gly Glu Glu Gln Arg Ala
305                 310                 315                 320

Asp Arg Pro Ala Glu Arg Lys Thr Ser Glu His Ser Gln Gly Cys Gly
                325                 330                 335

Thr Gly Gly Gln Val Ala Cys Ala Glu Ser
            340                 345
```

-continued

<210> SEQ ID NO 275
<211> LENGTH: 993
<212> TYPE: DNA
<213> ORGANISM: Homo sapiens

<400> SEQUENCE: 275
atgctgccgg actggaagag ctccttgatc ctcatggctt acatcatcat cttcctcact 60
ggcctccctg ccaacctcct ggccctgcgg gcctttgtgg ggcggatccg ccagccccag 120
cctgcacctg tgcacatcct cctgctgagc ctgacgctgg ccgacctcct cctgctgctg 180
ctgctgccct tcaagatcat cgaggctgcg tcgaacttcc gctggtacct gcccaaggtc 240
gtctgcgccc tcacgagttt tggcttctac agcagcatct actgcagcac gtggctcctg 300
gcgggcatca gcatcgagcg ctacctggga gtggctttcc ccgtgcagta caagctctcc 360
cgccggcctc tgtatggagt gattgcagct ctggtggcct gggttatgtc ctttggtcac 420
tgcaccatcg tgatcatcgt tcaatacttg aacacgactg agcaggtcag aagtggcaat 480
gaaattacct gctacgagaa cttcaccgat aaccagttgg acgtggtgct gcccgtgcgg 540
ctggagctgt gcctggtgct cttcttcatc cccatggcag tcaccatctt ctgctactgg 600
cgttttgtgt ggatcatgct ctcccagccc cttgtggggg cccagaggcg gcgccgagcc 660
aaggggctgg ctgtggtgac gctgctcaat ttcctggtgt gcttcggacc ttacaacgtg 720
tcccacctgg tggggtatca ccagagaaaa agcccctggt ggcggtcaat agccgtggtg 780
ttcagttcac tcaacgccag tctggacccc ctgctcttct atttctcttc ttcagtggtg 840
cgcagggcat ttgggagagg gctgcaggtg ctgcggaatc agggctcctc cctgttggga 900
cgcagaggca aagacacagc agaggggaca aatgaggaca ggggtgtggg tcaaggagaa 960
gggatgccaa gttcggactt cactacagag tag 993

<210> SEQ ID NO 276
<211> LENGTH: 330
<212> TYPE: PRT
<213> ORGANISM: Homo sapiens

<400> SEQUENCE: 276

Met Leu Pro Asp Trp Lys Ser Ser Leu Ile Leu Met Ala Tyr Ile Ile
1 5 10 15

Ile Phe Leu Thr Gly Leu Pro Ala Asn Leu Leu Ala Leu Arg Ala Phe
20 25 30

Val Gly Arg Ile Arg Gln Pro Gln Pro Ala Pro Val His Ile Leu Leu
35 40 45

Leu Ser Leu Thr Leu Ala Asp Leu Leu Leu Leu Leu Leu Leu Pro Phe
50 55 60

Lys Ile Ile Glu Ala Ala Ser Asn Phe Arg Trp Tyr Leu Pro Lys Val
65 70 75 80

Val Cys Ala Leu Thr Ser Phe Gly Phe Tyr Ser Ser Ile Tyr Cys Ser
85 90 95

Thr Trp Leu Leu Ala Gly Ile Ser Ile Glu Arg Tyr Leu Gly Val Ala
100 105 110

Phe Pro Val Gln Tyr Lys Leu Ser Arg Arg Pro Leu Tyr Gly Val Ile
115 120 125

Ala Ala Leu Val Ala Trp Val Met Ser Phe Gly His Cys Thr Ile Val
130 135 140

Ile Ile Val Gln Tyr Leu Asn Thr Thr Glu Gln Val Arg Ser Gly Asn
145 150 155 160

-continued

```
Glu Ile Thr Cys Tyr Glu Asn Phe Thr Asp Asn Gln Leu Asp Val Val
                165                 170                 175

Leu Pro Val Arg Leu Glu Leu Cys Leu Val Leu Phe Phe Ile Pro Met
            180                 185                 190

Ala Val Thr Ile Phe Cys Tyr Trp Arg Phe Val Trp Ile Met Leu Ser
        195                 200                 205

Gln Pro Leu Val Gly Ala Gln Arg Arg Arg Arg Ala Lys Gly Leu Ala
    210                 215                 220

Val Val Thr Leu Leu Asn Phe Leu Val Cys Phe Gly Pro Tyr Asn Val
225                 230                 235                 240

Ser His Leu Val Gly Tyr His Gln Arg Lys Ser Pro Trp Trp Arg Ser
                245                 250                 255

Ile Ala Val Val Phe Ser Ser Leu Asn Ala Ser Leu Asp Pro Leu Leu
            260                 265                 270

Phe Tyr Phe Ser Ser Ser Val Val Arg Arg Ala Phe Gly Arg Gly Leu
        275                 280                 285

Gln Val Leu Arg Asn Gln Gly Ser Ser Leu Leu Gly Arg Arg Gly Lys
    290                 295                 300

Asp Thr Ala Glu Gly Thr Asn Glu Asp Arg Gly Val Gly Gln Gly Glu
305                 310                 315                 320

Gly Met Pro Ser Ser Asp Phe Thr Thr Glu
                325                 330


<210> SEQ ID NO 277
<211> LENGTH: 2724
<212> TYPE: DNA
<213> ORGANISM: Homo sapiens

<400> SEQUENCE: 277

atggacacct cccggctcgg tgtgctcctg tccttgcctg tgctgctgca gctggcgacc      60

gggggcagct ctcccaggtc tggtgtgttg ctgaggggct gccccacaca ctgtcattgc     120

gagcccgacg gcaggatgtt gctcagggtg gactgctccg acctggggct ctcggagctg     180

ccttccaacc tcagcgtctt cacctcctac ctagacctca gtatgaacaa catcagtcag     240

ctgctcccga atcccctgcc cagtctccgc ttcctggagg agttacgtct tgcgggaaac     300

gctctgacat acattcccaa gggagcattc actggccttt acagtcttaa agttcttatg     360

ctgcagaata atcagctaag acacgtaccc acagaagctc tgcagaattt gcgaagcctt     420

caatccctgc gtctggatgc taaccacatc agctatgtgc ccccaagctg tttcagtggc     480

ctgcattccc tgaggcacct gtggctggat gacaatgcgt taacagaaat ccccgtccag     540

gcttttagaa gtttatcggc attgcaagcc atgaccttgg ccctgaacaa aatacaccac     600

ataccagact atgcctttgg aaacctctcc agcttggtag ttctacatct ccataacaat     660

agaatccact ccctgggaaa gaaatgcttt gatgggctcc acagcctaga gactttagat     720

ttaaattaca ataaccttga tgaattcccc actgcaatta ggacactctc caaccttaaa     780

gaactaggat ttcatagcaa caatatcagg tcgatacctg agaaagcatt tgtaggcaac     840

ccttctctta ttacaataca tttctatgac aatcccatcc aatttgttgg gagatctgct     900

tttcaacatt tacctgaact aagaacactg actctgaatg gtgcctcaca aataactgaa     960

tttcctgatt taactggaac tgcaaacctg gagagtctga ctttaactgg agcacagatc    1020

tcatctcttc ctcaaaccgt ctgcaatcag ttacctaatc tccaagtgct agatctgtct    1080

tacaacctat tagaagattt acccagtttt tcagtctgcc aaaagcttca gaaaattgac    1140
```

-continued

```
ctaagacata atgaaatcta cgaaattaaa gttgacactt tccagcagtt gcttagcctc   1200

cgatcgctga atttggcttg gaacaaaatt gctattattc accccaatgc attttccact   1260

ttgccatccc taataaagct ggacctatcg tccaacctcc tgtcgtcttt tcctataact   1320

gggttacatg gtttaactca cttaaaatta acaggaaatc atgccttaca gagcttgata   1380

tcatctgaaa actttccaga actcaaggtt atagaaatgc cttatgctta ccagtgctgt   1440

gcatttggag tgtgtgagaa tgcctataag atttctaatc aatggaataa aggtgacaac   1500

agcagtatgg acgaccttca taagaaagat gctggaatgt ttcaggctca agatgaacgt   1560

gaccttgaag atttcctgct tgactttgag gaagacctga aagcccttca ttcagtgcag   1620

tgttcacctt ccccaggccc cttcaaaccc tgtgaacacc tgcttgatgg ctggctgatc   1680

agaattggag tgtggaccat agcagttctg gcacttactt gtaatgcttt ggtgacttca   1740

acagttttca gatcccctct gtacatttcc cccattaaac tgttaattgg ggtcatcgca   1800

gcagtgaaca tgctcacggg agtctccagt gccgtgctgg ctggtgtgga tgcgttcact   1860

tttggcagct ttgcacgaca tggtgcctgg tgggagaatg gggttggttg ccatgtcatt   1920

ggtttttttgt ccatttttgc ttcagaatca tctgttttcc tgcttactct ggcagccctg   1980

gagcgtgggt tctctgtgaa atattctgca aaatttgaaa cgaaagctcc attttctagc   2040

ctgaaagtaa tcattttgct ctgtgccctg ctggccttga ccatggccgc agttcccctg   2100

ctgggtggca gcaagtatgg cgcctcccct ctctgcctgc ctttgccttt tggggagccc   2160

agcaccatgg gctacatggt cgctctcatc ttgctcaatt ccctttgctt cctcatgatg   2220

accattgcct acaccaagct ctactgcaat ttggacaagg gagacctgga gaatatttgg   2280

gactgctcta tgaaaaaaca cattgccctg ttgctcttca ccaactgcat cctaaactgc   2340

cctgtggctt tcttgtcctt ctcctcttta ataaacctta catttatcag tcctgaagta   2400

attaagttta tccttctggt ggtagtccca cttcctgcat gtctcaatcc ccttctctac   2460

atcttgttca atcctcactt taaggaggat ctggtgagcc tgagaaagca aacctacgtc   2520

tggacaagat caaaacaccc aagcttgatg tcaattaact ctgatgatgt cgaaaaacag   2580

tcctgtgact caactcaagc cttggtaacc tttaccagct ccagcatcac ttatgacctg   2640

cctcccagtt ccgtgccatc accagcttat ccagtgactg agagctgcca tctttcctct   2700

gtggcatttg tcccatgtct ctaa                                          2724
```

<210> SEQ ID NO 278
<211> LENGTH: 907
<212> TYPE: PRT
<213> ORGANISM: Homo sapiens

<400> SEQUENCE: 278

```
Met Asp Thr Ser Arg Leu Gly Val Leu Leu Ser Leu Pro Val Leu Leu
1               5                   10                  15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
        35                  40                  45

Arg Val Asp Cys Ser Asp Leu Gly Leu Ser Glu Leu Pro Ser Asn Leu
    50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95
```

-continued

```
Leu Ala Gly Asn Ala Leu Thr Tyr Ile Pro Lys Gly Ala Phe Thr Gly
            100                 105                 110

Leu Tyr Ser Leu Lys Val Leu Met Leu Gln Asn Asn Gln Leu Arg His
        115                 120                 125

Val Pro Thr Glu Ala Leu Gln Asn Leu Arg Ser Leu Gln Ser Leu Arg
    130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
            180                 185                 190

Leu Ala Leu Asn Lys Ile His His Ile Pro Asp Tyr Ala Phe Gly Asn
        195                 200                 205

Leu Ser Ser Leu Val Val Leu His Leu His Asn Asn Arg Ile His Ser
    210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
                245                 250                 255

Ser Asn Leu Lys Glu Leu Gly Phe His Ser Asn Asn Ile Arg Ser Ile
            260                 265                 270

Pro Glu Lys Ala Phe Val Gly Asn Pro Ser Leu Ile Thr Ile His Phe
        275                 280                 285

Tyr Asp Asn Pro Ile Gln Phe Val Gly Arg Ser Ala Phe Gln His Leu
    290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
                325                 330                 335

Gly Ala Gln Ile Ser Ser Leu Pro Gln Thr Val Cys Asn Gln Leu Pro
            340                 345                 350

Asn Leu Gln Val Leu Asp Leu Ser Tyr Asn Leu Leu Glu Asp Leu Pro
        355                 360                 365

Ser Phe Ser Val Cys Gln Lys Leu Gln Lys Ile Asp Leu Arg His Asn
    370                 375                 380

Glu Ile Tyr Glu Ile Lys Val Asp Thr Phe Gln Gln Leu Leu Ser Leu
385                 390                 395                 400

Arg Ser Leu Asn Leu Ala Trp Asn Lys Ile Ala Ile Ile His Pro Asn
                405                 410                 415

Ala Phe Ser Thr Leu Pro Ser Leu Ile Lys Leu Asp Leu Ser Ser Asn
            420                 425                 430

Leu Leu Ser Ser Phe Pro Ile Thr Gly Leu His Gly Leu Thr His Leu
        435                 440                 445

Lys Leu Thr Gly Asn His Ala Leu Gln Ser Leu Ile Ser Ser Glu Asn
    450                 455                 460

Phe Pro Glu Leu Lys Val Ile Glu Met Pro Tyr Ala Tyr Gln Cys Cys
465                 470                 475                 480

Ala Phe Gly Val Cys Glu Asn Ala Tyr Lys Ile Ser Asn Gln Trp Asn
                485                 490                 495

Lys Gly Asp Asn Ser Ser Met Asp Asp Leu His Lys Lys Asp Ala Gly
            500                 505                 510
```

-continued

```
Met Phe Gln Ala Gln Asp Glu Arg Asp Leu Glu Asp Phe Leu Leu Asp
        515                 520                 525

Phe Glu Glu Asp Leu Lys Ala Leu His Ser Val Gln Cys Ser Pro Ser
    530                 535                 540

Pro Gly Pro Phe Lys Pro Cys Glu His Leu Leu Asp Gly Trp Leu Ile
545                 550                 555                 560

Arg Ile Gly Val Trp Thr Ile Ala Val Leu Ala Leu Thr Cys Asn Ala
                565                 570                 575

Leu Val Thr Ser Thr Val Phe Arg Ser Pro Leu Tyr Ile Ser Pro Ile
            580                 585                 590

Lys Leu Leu Ile Gly Val Ile Ala Ala Val Asn Met Leu Thr Gly Val
        595                 600                 605

Ser Ser Ala Val Leu Ala Gly Val Asp Ala Phe Thr Phe Gly Ser Phe
    610                 615                 620

Ala Arg His Gly Ala Trp Trp Glu Asn Gly Val Gly Cys His Val Ile
625                 630                 635                 640

Gly Phe Leu Ser Ile Phe Ala Ser Glu Ser Ser Val Phe Leu Leu Thr
                645                 650                 655

Leu Ala Ala Leu Glu Arg Gly Phe Ser Val Lys Tyr Ser Ala Lys Phe
            660                 665                 670

Glu Thr Lys Ala Pro Phe Ser Ser Leu Lys Val Ile Ile Leu Leu Cys
        675                 680                 685

Ala Leu Leu Ala Leu Thr Met Ala Ala Val Pro Leu Leu Gly Gly Ser
    690                 695                 700

Lys Tyr Gly Ala Ser Pro Leu Cys Leu Pro Leu Pro Phe Gly Glu Pro
705                 710                 715                 720

Ser Thr Met Gly Tyr Met Val Ala Leu Ile Leu Leu Asn Ser Leu Cys
                725                 730                 735

Phe Leu Met Met Thr Ile Ala Tyr Thr Lys Leu Tyr Cys Asn Leu Asp
            740                 745                 750

Lys Gly Asp Leu Glu Asn Ile Trp Asp Cys Ser Met Lys Lys His Ile
        755                 760                 765

Ala Leu Leu Leu Phe Thr Asn Cys Ile Leu Asn Cys Pro Val Ala Phe
    770                 775                 780

Leu Ser Phe Ser Ser Leu Ile Asn Leu Thr Phe Ile Ser Pro Glu Val
785                 790                 795                 800

Ile Lys Phe Ile Leu Leu Val Val Val Pro Leu Pro Ala Cys Leu Asn
                805                 810                 815

Pro Leu Leu Tyr Ile Leu Phe Asn Pro His Phe Lys Glu Asp Leu Val
            820                 825                 830

Ser Leu Arg Lys Gln Thr Tyr Val Trp Thr Arg Ser Lys His Pro Ser
        835                 840                 845

Leu Met Ser Ile Asn Ser Asp Asp Val Glu Lys Gln Ser Cys Asp Ser
    850                 855                 860

Thr Gln Ala Leu Val Thr Phe Thr Ser Ser Ser Ile Thr Tyr Asp Leu
865                 870                 875                 880

Pro Pro Ser Ser Val Pro Ser Pro Ala Tyr Pro Val Thr Glu Ser Cys
                885                 890                 895

His Leu Ser Ser Val Ala Phe Val Pro Cys Leu
            900                 905
```

<210> SEQ ID NO 279
<211> LENGTH: 32
<212> TYPE: DNA

-continued

<213> ORGANISM: Artificial Sequence
<220> FEATURE:
<223> OTHER INFORMATION: Novel Sequence

<400> SEQUENCE: 279
catgccaacc ggcccgcgag gctgctgctg gt 32

<210> SEQ ID NO 280
<211> LENGTH: 32
<212> TYPE: DNA
<213> ORGANISM: Artificial Sequence
<220> FEATURE:
<223> OTHER INFORMATION: Novel Sequence

<400> SEQUENCE: 280
accagcagca gcctcgcggg ccggttggca tg 32

<210> SEQ ID NO 281
<211> LENGTH: 17
<212> TYPE: PRT
<213> ORGANISM: Artificial Sequence
<220> FEATURE:
<223> OTHER INFORMATION: Novel Sequence

<400> SEQUENCE: 281

Pro Ala Ala Cys Cys Thr Thr Gly Gly Arg Arg Arg Asp Asp Asp Glu
1 5 10 15

Gln

<210> SEQ ID NO 282
<211> LENGTH: 17
<212> TYPE: PRT
<213> ORGANISM: Artificial Sequence
<220> FEATURE:
<223> OTHER INFORMATION: Novel Sequence

<400> SEQUENCE: 282

Pro Ala Ala Cys Cys Thr Thr Gly Gly Arg Arg Arg Asp Asp Asp Glu
1 5 10 15

Lys

<210> SEQ ID NO 283
<211> LENGTH: 17
<212> TYPE: PRT
<213> ORGANISM: Artificial Sequence
<220> FEATURE:
<223> OTHER INFORMATION: Novel Sequence

<400> SEQUENCE: 283

Pro Ala Ala Cys Cys Thr Thr His Ile Gly Arg Arg Asp Asp Asp Glu
1 5 10 15

Lys

<210> SEQ ID NO 284
<211> LENGTH: 17
<212> TYPE: PRT
<213> ORGANISM: Artificial Sequence
<220> FEATURE:
<223> OTHER INFORMATION: Novel Sequence

<400> SEQUENCE: 284

Pro Ala Asp Glu Glu Thr Thr Gly Gly Arg Arg Arg Asp Asp Asp Glu
1 5 10 15

Ala

<210> SEQ ID NO 285
<211> LENGTH: 16
<212> TYPE: PRT
<213> ORGANISM: Artificial Sequence
<220> FEATURE:
<223> OTHER INFORMATION: Novel Sequence

<400> SEQUENCE: 285

Pro Leu Leu Lys Phe Met Ser Thr Trp Leu Val Ala Ala Pro Gln Lys
1 5 10 15

<210> SEQ ID NO 286
<211> LENGTH: 17
<212> TYPE: PRT
<213> ORGANISM: Artificial Sequence
<220> FEATURE:
<223> OTHER INFORMATION: Novel Sequence

<400> SEQUENCE: 286

Ala Leu Leu Lys Phe Met Ser Thr Trp Glx Leu Val Ala Ala Pro Gln
1 5 10 15

Lys

<210> SEQ ID NO 287
<211> LENGTH: 4069
<212> TYPE: DNA
<213> ORGANISM: Homo sapiens

<400> SEQUENCE: 287
aagcttgata tcgaattcct gcagcccggg ggatccacta gttctagagc ggccgccacc 60
gcggtggagc tccagctttt gttcccttta gtgagggtta attgcgcgct agaggatctt 120
tgtgaaggaa ccttacttct gtggtgtgac ataattggac aaactaccta cagagattta 180
aagctctaag gtaaatataa aatttttaag tgtataatgt gttaaactac tgattctaat 240
tgtttgtgta ttttagattc caacctatgg aactgatgaa tgggagcagt ggtggaatgc 300
ctttaatgag gaaaacctgt tttgctcaga agaaatgcca tctagtgatg atgaggctac 360
tgctgactct caacattcta ctcctccaaa aaagaagaga aaggtagaag accccaagga 420
ctttccttca gaattgctaa gtttttgag tcatgctgtg tttagtaata gaactcttgc 480
ttgctttgct atttacacca caaaggaaaa agctgcactg ctatacaaga aaattatgga 540
aaaatattct gtaaccttta taagtaggca taacagttat aatcataaca tactgttttt 600
tcttactcca cacaggcata gagtgtctgc tattaataac tatgctcaaa aattgtgtac 660
ctttagcttt ttaatttgta aaggggttaa taaggaatat ttgatgtata gtgccttgac 720
tagagatcat aatcagccat accacatttg tagaggtttt acttgcttta aaaaacctcc 780
cacacctccc cctgaacctg aaacataaaa tgaatgcaat tgttgttgtt aacttgttta 840
ttgcagctta taatggttac aaataaagca atagcatcac aaatttcaca aataaagcat 900 tttttcact gcattctagt tgtggtttgt ccaaactcat caatgtatct tatcatgtct 960
agatcttccg aaatgtgtgt cagttagggt gtggaaagtc cccaggctcc ccagcaggca 1020
gaagtatgca aagcatgcat ctcaattagt cagcaaccag gtgtggaaag tccccaggct 1080
ccccagcagg cagaagtatg caaagcatgc atctcaatta gtcagcaacc atagtcccgc 1140
ccctaactcc gcccatcccg cccctaactc cgcccagttc cgcccattct ccgccccatg 1200
gctgactaat tttttttatt tatgcagagg ccgaggccgc ctcggcctct gagctattcc 1260

-continued

```
agaagtagtg aggaggcttt tttggaggcc taggcttttg caaaaagctc cctcgagagc   1320
ttggcgtaat catggtcata gctgtttcct gtgtgaaatt gttatccgct cacaattcca   1380
cacaacatac gagccggaag cataaagtgt aaagcctggg gtgcctaatg agtgagctaa   1440
ctcacattaa ttgcgttgcg ctcactgccc gctttccagt cgggaaacct gtcgtgccag   1500
ctgcattaat gaatcggcca acgcgcgggg agaggcggtt tgcgtattgg gcgctcttcc   1560
gcttcctcgc tcactgactc gctgcgctcg gtcgttcggc tgcggcgagc ggtatcagct   1620
cactcaaagg cggtaatacg gttatccaca gaatcagggg ataacgcagg aaagaacatg   1680
tgagcaaaag gccagcaaaa ggccaggaac cgtaaaaagg ccgcgttgct ggcgtttttc   1740
cataggctcc gcccccctga cgagcatcac aaaaatcgac gctcaagtca gaggtggcga   1800
aacccgacag gactataaag ataccaggcg tttccccctg gaagctccct cgtgcgctct   1860
cctgttccga ccctgccgct taccggatac ctgtccgcct ttctcccttc gggaagcgtg   1920
gcgctttctc aatgctcacg ctgtaggtat ctcagttcgg tgtaggtcgt tcgctccaag   1980
ctgggctgtg tgcacgaacc ccccgttcag cccgaccgct gcgccttatc cggtaactat   2040
cgtcttgagt ccaacccggt aagacacgac ttatcgccac tggcagcagc cactggtaac   2100
aggattagca gagcgaggta tgtaggcggt gctacagagt tcttgaagtg gtggcctaac   2160
tacggctaca ctagaaggac agtatttggt atctgcgctc tgctgaagcc agttaccttc   2220
ggaaaaagag ttggtagctc ttgatccggc aaacaaacca ccgctggtag cggtggtttt   2280
tttgtttgca agcagcagat tacgcgcaga aaaaaaggat ctcaagaaga tcctttgatc   2340
ttttctacgg ggtctgacgc tcagtggaac gaaaactcac gttaagggat tttggtcatg   2400
agattatcaa aaaggatctt cacctagatc cttttaaatt aaaaatgaag ttttaaatca   2460
atctaaagta tatatgagta aacttggtct gacagttacc aatgcttaat cagtgaggca   2520
cctatctcag cgatctgtct atttcgttca tccatagttg cctgactccc cgtcgtgtag   2580
ataactacga tacgggaggg cttaccatct ggccccagtg ctgcaatgat accgcgagac   2640
ccacgctcac cggctccaga tttatcagca ataaaccagc cagccggaag ggccgagcgc   2700
agaagtggtc ctgcaacttt atccgcctcc atccagtcta ttaattgttg ccgggaagct   2760
agagtaagta gttcgccagt taatagtttg cgcaacgttg ttgccattgc tacaggcatc   2820
gtggtgtcac gctcgtcgtt tggtatggct tcattcagct ccggttccca acgatcaagg   2880
cgagttacat gatcccccat gttgtgcaaa aaagcggtta gctccttcgg tcctccgatc   2940
gttgtcagaa gtaagttggc cgcagtgtta tcactcatgg ttatggcagc actgcataat   3000
tctcttactg tcatgccatc cgtaagatgc ttttctgtga ctggtgagta ctcaaccaag   3060
tcattctgag aatagtgtat gcggcgaccg agttgctctt gcccggcgtc aacacgggat   3120
aataccgcgc cacatagcag aactttaaaa gtgctcatca ttggaaaacg ttcttcgggg   3180
cgaaaactct caaggatctt accgctgttg agatccagtt cgatgtaacc cactcgtgca   3240
cccaactgat cttcagcatc ttttactttc accagcgttt ctgggtgagc aaaaacagga   3300
aggcaaaatg ccgcaaaaaa gggaataagg gcgacacgga aatgttgaat actcatactc   3360
ttcctttttc aatattattg aagcatttat cagggttatt gtctcatgcg cgttgacatt   3420
gattattgac tagttattaa tagtaatcaa ttacggggtc attagttcat agcccatata   3480
tggagttccg cgttacataa cttacggtaa atggcccgcc tggctgaccg cccaacgacc   3540
cccgcccatt gacgtcaata atgacgtatg ttcccatagt aacgccaata gggactttcc   3600
attgacgtca atgggtggac tatttacggt aaactgccca cttggcagta catcaagtgt   3660
```

-continued atcatatgcc aagtacgccc cctattgacg tcaatgacgg taaatggccc gcctggcatt 3720
atgcccagta catgacctta tgggactttc ctacttggca gtacatctac gtattagtca 3780
tcgctattac catggtgatg cggttttggc agtacatcaa tgggcgtgga tagcggtttg 3840
actcacgggg atttccaagt ctccacccca ttgacgtcaa tgggagtttg ttttggcacc 3900
aaaatcaacg ggactttcca aaatgtcgta acaactccgc cccattgacg caaatgggcg 3960
gtaggcgtgt acggtgggag gtctatataa gcagagctct ctggctaact agagaaccca 4020
ctgcttaact ggcttatcga aattaatacg actcactata gggagaccc 4069

<210> SEQ ID NO 288
<211> LENGTH: 4069
<212> TYPE: DNA
<213> ORGANISM: Homo sapiens

<400> SEQUENCE: 288
gggtctccct atagtgagtc gtattaattt cgataagcca gttaagcagt gggttctcta 60
gttagccaga gagctctgct tatatagacc tcccaccgta cacgcctacc gcccatttgc 120
gtcaatgggg cggagttgtt acgacatttt ggaaagtccc gttgattttg gtgccaaaac 180
aaactcccat tgacgtcaat ggggtggaga cttggaaatc cccgtgagtc aaaccgctat 240
ccacgcccat tgatgtactg ccaaaaccgc atcaccatgg taatagcgat gactaatacg 300
tagatgtact gccaagtagg aaagtcccat aaggtcatgt actgggcata atgccaggcg 360
ggccatttac cgtcattgac gtcaataggg ggcgtacttg gcatatgata cacttgatgt 420
actgccaagt gggcagttta ccgtaaatag tccacccatt gacgtcaatg gaaagtccct 480
attggcgtta ctatgggaac atacgtcatt attgacgtca atgggcgggg gtcgttgggc 540
ggtcagccag gcgggccatt taccgtaagt tatgtaacgc ggaactccat atatgggcta 600
tgaactaatg accccgtaat tgattactat taataactag tcaataatca atgtcaacgc 660
gcatgagaca ataaccctga taaatgcttc aataatattg aaaaaggaag agtatgagta 720
ttcaacattt ccgtgtcgcc cttattccct tttttgcggc attttgcctt cctgtttttg 780
ctcacccaga aacgctggtg aaagtaaaag atgctgaaga tcagttgggt gcacgagtgg 840
gttacatcga actggatctc aacagcggta agatccttga gagttttcgc cccgaagaac 900
gttttccaat gatgagcact tttaaagttc tgctatgtgg cgcggtatta tcccgtgttg 960
acgccgggca agagcaactc ggtcgccgca tacactattc tcagaatgac ttggttgagt 1020
actcaccagt cacagaaaag catcttacgg atggcatgac agtaagagaa ttatgcagtg 1080
ctgccataac catgagtgat aacactgcgg ccaacttact tctgacaacg atcggaggac 1140
cgaaggagct aaccgctttt ttgcacaaca tgggggatca tgtaactcgc cttgatcgtt 1200
gggaaccgga gctgaatgaa gccataccaa acgacgagcg tgacaccacg atgcctgtag 1260
caatggcaac aacgttgcgc aaactattaa ctggcgaact acttactcta gcttcccggc 1320
aacaattaat agactggatg gaggcggata aagttgcagg accacttctg cgctcggccc 1380
ttccggctgg ctggtttatt gctgataaat ctggagccgg tgagcgtggg tctcgcggta 1440
tcattgcagc actggggcca gatggtaagc cctcccgtat cgtagttatc tacacgacgg 1500
ggagtcaggc aactatggat gaacgaaata gacagatcgc tgagataggt gcctcactga 1560
ttaagcattg gtaactgtca gaccaagttt actcatatat actttagatt gatttaaaac 1620
ttcattttta atttaaaagg atctaggtga agatcctttt tgataatctc atgaccaaaa 1680

-continued

```
tcccttaacg tgagttttcg ttccactgag cgtcagaccc cgtagaaaag atcaaaggat   1740
cttcttgaga tccttttttt ctgcgcgtaa tctgctgctt gcaaacaaaa aaaccaccgc   1800
taccagcggt ggtttgtttg ccggatcaag agctaccaac tctttttccg aaggtaactg   1860
gcttcagcag agcgcagata ccaaatactg tccttctagt gtagccgtag ttaggccacc   1920
acttcaagaa ctctgtagca ccgcctacat acctcgctct gctaatcctg ttaccagtgg   1980
ctgctgccag tggcgataag tcgtgtctta ccgggttgga ctcaagacga tagttaccgg   2040
ataaggcgca gcggtcgggc tgaacggggg gttcgtgcac acagcccagc ttggagcgaa   2100
cgacctacac cgaactgaga tacctacagc gtgagcattg agaaagcgcc acgcttcccg   2160
aagggagaaa ggcggacagg tatccggtaa gcggcagggt cggaacagga gagcgcacga   2220
gggagcttcc agggggaaac gcctggtatc tttatagtcc tgtcgggttt cgccacctct   2280
gacttgagcg tcgatttttg tgatgctcgt caggggggcg gagcctatgg aaaaacgcca   2340
gcaacgcggc ctttttacgg ttcctggcct tttgctggcc ttttgctcac atgttctttc   2400
ctgcgttatc ccctgattct gtggataacc gtattaccgc ctttgagtga gctgataccg   2460
ctcgccgcag ccgaacgacc gagcgcagcg agtcagtgag cgaggaagcg gaagagcgcc   2520
caatacgcaa accgcctctc cccgcgcgtt ggccgattca ttaatgcagc tggcacgaca   2580
ggtttcccga ctggaaagcg ggcagtgagc gcaacgcaat taatgtgagt tagctcactc   2640
attaggcacc ccaggcttta cactttatgc ttccggctcg tatgttgtgt ggaattgtga   2700
gcggataaca atttcacaca ggaaacagct atgaccatga ttacgccaag ctctcgaggg   2760
agctttttgc aaaagcctag gcctccaaaa aagcctcctc actacttctg gaatagctca   2820
gaggccgagg cggcctcggc ctctgcataa ataaaaaaaa ttagtcagcc atggggcgga   2880
gaatgggcgg aactgggcgg agttaggggc gggatgggcg gagttagggg cgggactatg   2940
gttgctgact aattgagatg catgctttgc atacttctgc ctgctgggga gcctggggac   3000
tttccacacc tggttgctga ctaattgaga tgcatgcttt gcatacttct gcctgctggg   3060
gagcctgggg actttccaca ccctaactga cacacatttc ggaagatcta gacatgataa   3120
gatacattga tgagtttgga caaaccacaa ctagaatgca gtgaaaaaaa tgctttattt   3180
gtgaaatttg tgatgctatt gctttatttg taaccattat aagctgcaat aaacaagtta   3240
acaacaacaa ttgcattcat tttatgtttc aggttcaggg ggaggtgtgg gaggtttttt   3300
aaagcaagta aaacctctac aaatgtggta tggctgatta tgatctctag tcaaggcact   3360
atacatcaaa tattccttat taaccccttt acaaattaaa aagctaaagg tacacaattt   3420
ttgagcatag ttattaatag cagacactct atgcctgtgt ggagtaagaa aaaacagtat   3480
gttatgatta taactgttat gcctacttat aaaggttaca gaatattttt ccataatttt   3540
cttgtatagc agtgcagctt tttcctttgt ggtgtaaata gcaaagcaag caagagttct   3600
attactaaac acagcatgac tcaaaaaact tagcaattct gaaggaaagt ccttggggtc   3660
ttctaccttt ctcttctttt ttggaggagt agaatgttga gagtcagcag tagcctcatc   3720
atcactagat ggcatttctt ctgagcaaaa caggttttcc tcattaaagg cattccacca   3780
ctgctcccat tcatcagttc cataggttgg aatctaaaat acacaaacaa ttagaatcag   3840
tagtttaaca cattatacac ttaaaaattt tatatttacc ttagagcttt aaatctctgt   3900
aggtagtttg tccaattatg tcacaccaca gaagtaaggt tccttcacaa agatcctcta   3960
gcgcgcaatt aaccctcact aaagggaaca aaagctggag ctccaccgcg gtggcggccg   4020
ctctagaact agtggatccc ccgggctgca ggaattcgat atcaagctt              4069
```

-continued

<210> SEQ ID NO 289
<211> LENGTH: 1273
<212> TYPE: PRT
<213> ORGANISM: Homo sapiens

<400> SEQUENCE: 289

```
Lys Leu Asp Ile Glu Phe Leu Gln Pro Gly Gly Ser Thr Ser Ser Arg
1               5                   10                  15

Ala Ala Ala Thr Ala Val Glu Leu Gln Leu Leu Phe Pro Leu Val Arg
            20                  25                  30

Val Asn Cys Ala Leu Glu Asp Leu Cys Glu Gly Thr Leu Leu Leu Trp
        35                  40                  45

Cys Asp Ile Ile Gly Gln Thr Thr Tyr Arg Asp Leu Lys Leu Gly Lys
    50                  55                  60

Tyr Lys Ile Phe Lys Cys Ile Met Cys Thr Thr Asp Ser Asn Cys Leu
65                  70                  75                  80

Cys Ile Leu Asp Ser Asn Leu Trp Asn Met Gly Ala Val Val Glu Cys
                85                  90                  95

Leu Gly Lys Pro Val Leu Leu Arg Arg Asn Ala Ile Gly Tyr Cys Leu
            100                 105                 110

Ser Thr Phe Tyr Ser Ser Lys Lys Glu Glu Lys Gly Arg Arg Pro Gln
        115                 120                 125

Gly Leu Ser Phe Arg Ile Ala Lys Phe Phe Glu Ser Cys Cys Val Asn
    130                 135                 140

Ser Cys Leu Leu Cys Tyr Leu His His Lys Gly Lys Ser Cys Thr Ala
145                 150                 155                 160

Ile Gln Glu Asn Tyr Gly Lys Ile Phe Cys Asn Leu Tyr Lys Ala Gln
                165                 170                 175

Leu His Thr Val Phe Ser Tyr Ser Thr Gln Ala Ser Val Cys Tyr Leu
            180                 185                 190

Cys Ser Lys Ile Val Tyr Leu Leu Phe Asn Leu Arg Gly Gly Ile Phe
        195                 200                 205

Asp Val Cys Leu Asp Arg Ser Ser Ala Ile Pro His Leu Arg Phe Tyr
    210                 215                 220

Leu Leu Lys Thr Ser His Thr Ser Pro Thr Asn Ile Lys Met Gln Leu
225                 230                 235                 240

Leu Leu Leu Thr Cys Leu Leu Gln Leu Ile Met Val Thr Asn Lys Ala
                245                 250                 255

Ile Ala Ser Gln Ile Ser Gln Ile Lys His Phe Phe His Cys Ile Leu
            260                 265                 270

Val Val Val Cys Pro Asn Ser Ser Met Tyr Leu Ile Met Ser Arg Ser
        275                 280                 285

Ser Glu Met Cys Val Ser Gly Val Glu Ser Pro Gln Ala Pro Gln Gln
    290                 295                 300

Ala Glu Val Cys Lys Ala Cys Ile Ser Ile Ser Gln Gln Pro Gly Val
305                 310                 315                 320

Glu Ser Pro Gln Ala Pro Gln Gln Ala Glu Val Cys Lys Ala Cys Ile
                325                 330                 335

Ser Ile Ser Gln Gln Pro Ser Arg Pro Leu Arg Pro Ser Arg Pro Leu
            340                 345                 350

Arg Pro Val Pro Pro Ile Leu Arg Pro Met Ala Asp Phe Phe Leu Phe
        355                 360                 365

Met Gln Arg Pro Arg Pro Pro Arg Pro Leu Ser Tyr Ser Arg Ser Ser
```

-continued

```
    370                 375                 380

Glu Glu Ala Phe Leu Glu Ala Ala Phe Ala Lys Ser Ser Leu Glu Ser
385                 390                 395                 400

Leu Ala Ser Trp Ser Leu Phe Pro Val Asn Cys Tyr Pro Leu Thr Ile
                405                 410                 415

Pro His Asn Ile Arg Ala Gly Ser Ile Lys Cys Lys Ala Trp Gly Ala
            420                 425                 430

Val Ser Leu Thr Leu Ile Ala Leu Arg Ser Leu Pro Ala Phe Gln Ser
        435                 440                 445

Gly Asn Leu Ser Cys Gln Leu His Ile Gly Gln Arg Ala Gly Arg Gly
    450                 455                 460

Gly Leu Arg Ile Gly Arg Ser Ser Ala Ser Ser Leu Thr Asp Ser Leu
465                 470                 475                 480

Arg Ser Val Val Arg Leu Arg Arg Ala Val Ser Ala His Ser Lys Ala
                485                 490                 495

Val Ile Arg Leu Ser Thr Glu Ser Gly Asp Asn Ala Gly Lys Asn Met
            500                 505                 510

Ala Lys Gly Gln Gln Lys Ala Arg Asn Arg Lys Lys Ala Ala Leu Leu
        515                 520                 525

Ala Phe Phe His Arg Leu Arg Pro Pro Asp Glu His His Lys Asn Arg
    530                 535                 540

Arg Ser Ser Gln Arg Trp Arg Asn Pro Thr Gly Leu Arg Tyr Gln Ala
545                 550                 555                 560

Phe Pro Pro Gly Ser Ser Leu Val Arg Ser Pro Val Pro Thr Leu Pro
                565                 570                 575

Leu Thr Gly Tyr Leu Ser Ala Phe Leu Pro Ser Gly Ser Val Ala Leu
            580                 585                 590

Ser Gln Cys Ser Arg Cys Arg Tyr Leu Ser Ser Val Val Val Arg Ser
        595                 600                 605

Lys Leu Gly Cys Val His Glu Pro Pro Val Gln Pro Asp Arg Cys Ala
    610                 615                 620

Leu Ser Gly Asn Tyr Arg Leu Glu Ser Asn Pro Val Arg His Asp Leu
625                 630                 635                 640

Ser Pro Leu Ala Ala Ala Thr Gly Asn Arg Ile Ser Arg Ala Arg Tyr
                645                 650                 655

Val Gly Gly Ala Thr Glu Phe Leu Lys Trp Trp Pro Asn Tyr Gly Tyr
            660                 665                 670

Thr Arg Arg Thr Val Phe Gly Ile Cys Ala Leu Leu Lys Pro Val Thr
        675                 680                 685

Phe Gly Lys Arg Val Gly Ser Ser Ser Gly Lys Gln Thr Thr Ala Gly
    690                 695                 700

Ser Gly Gly Phe Phe Val Cys Lys Gln Gln Ile Thr Arg Arg Lys Lys
705                 710                 715                 720

Gly Ser Gln Glu Asp Pro Leu Ile Phe Ser Thr Gly Ser Asp Ala Gln
                725                 730                 735

Trp Asn Glu Asn Ser Arg Gly Ile Leu Val Met Arg Leu Ser Lys Arg
            740                 745                 750

Ile Phe Thr Ile Leu Leu Asn Lys Ser Phe Lys Ser Ile Ser Ile Tyr
        755                 760                 765

Glu Thr Trp Ser Asp Ser Tyr Gln Cys Leu Ile Ser Glu Ala Pro Ile
    770                 775                 780

Ser Ala Ile Cys Leu Phe Arg Ser Ser Ile Val Ala Leu Pro Val Val
785                 790                 795                 800
```

-continued

```
Ile Thr Thr Ile Arg Glu Gly Leu Pro Ser Gly Pro Ser Ala Ala Met
                805                 810                 815

Ile Pro Arg Asp Pro Arg Ser Pro Ala Pro Asp Leu Ser Ala Ile Asn
            820                 825                 830

Gln Pro Ala Gly Arg Ala Glu Arg Arg Ser Gly Pro Ala Thr Leu Ser
        835                 840                 845

Ala Ser Ile Gln Ser Ile Asn Cys Cys Arg Glu Ala Arg Val Ser Ser
    850                 855                 860

Ser Pro Val Asn Ser Leu Arg Asn Val Val Ala Ile Ala Thr Gly Ile
865                 870                 875                 880

Val Val Ser Arg Ser Ser Phe Gly Met Ala Ser Phe Ser Ser Gly Ser
                885                 890                 895

Gln Arg Ser Arg Arg Val Thr Ser Pro Met Leu Cys Lys Lys Ala Val
            900                 905                 910

Ser Ser Phe Gly Pro Pro Ile Val Val Arg Ser Lys Leu Ala Ala Val
        915                 920                 925

Leu Ser Leu Met Val Met Ala Ala Leu His Asn Ser Leu Thr Val Met
    930                 935                 940

Pro Ser Val Arg Cys Phe Ser Val Thr Gly Glu Tyr Ser Thr Lys Ser
945                 950                 955                 960

Phe Glu Cys Met Arg Arg Pro Ser Cys Ser Cys Pro Ala Ser Thr Arg
                965                 970                 975

Asp Asn Thr Ala Pro His Ser Arg Thr Leu Lys Val Leu Ile Ile Gly
            980                 985                 990

Lys Arg Ser Ser Gly Arg Lys Leu  Ser Arg Ile Leu Pro  Leu Leu Arg
        995                 1000                1005

Ser Ser  Ser Met Pro Thr Arg  Ala Pro Asn Ser Ser  Ala Ser Phe
    1010                1015                1020

Thr Phe  Thr Ser Val Ser Gly  Ala Lys Thr Gly Arg  Gln Asn Ala
    1025                1030                1035

Ala Lys  Lys Gly Ile Arg Ala  Thr Arg Lys Cys Ile  Leu Ile Leu
    1040                1045                1050

Phe Leu  Phe Gln Tyr Tyr Ser  Ile Tyr Gln Gly Tyr  Cys Leu Met
    1055                1060                1065

Arg Val  Asp Ile Asp Tyr Leu  Val Ile Asn Ser Asn  Gln Leu Arg
    1070                1075                1080

Gly His  Phe Ile Ala His Ile  Trp Ser Ser Ala Leu  His Asn Leu
    1085                1090                1095

Arg Met  Ala Arg Leu Ala Asp  Arg Pro Thr Thr Pro  Ala His Arg
    1100                1105                1110

Gln Arg  Met Phe Pro Arg Gln  Gly Leu Ser Ile Asp  Val Asn Gly
    1115                1120                1125

Trp Thr  Ile Tyr Gly Lys Leu  Pro Thr Trp Gln Tyr  Ile Lys Cys
    1130                1135                1140

Ile Ile  Cys Gln Val Arg Pro  Leu Leu Thr Ser Met  Thr Val Asn
    1145                1150                1155

Gly Pro  Pro Gly Ile Met Pro  Ser Thr Pro Tyr Gly  Thr Phe Leu
    1160                1165                1170

Leu Gly  Ser Thr Ser Thr Tyr  Ser Ser Leu Leu Pro  Trp Cys Gly
    1175                1180                1185

Phe Gly  Ser Thr Ser Met Gly  Val Asp Ser Gly Leu  Thr His Gly
    1190                1195                1200
```

-continued

```
Asp Phe  Gln Val Ser Thr Pro  Leu Thr Ser Met Gly  Val Cys Phe
    1205                 1210                 1215

Gly Thr  Lys Ile Asn Gly Thr  Phe Gln Asn Val Val  Thr Thr Pro
    1220                 1225                 1230

Pro His  Arg Lys Trp Ala Val  Gly Val Tyr Gly Gly  Arg Ser Ile
    1235                 1240                 1245

Ala Glu  Leu Ser Gly Leu Glu  Asn Pro Leu Leu Asn  Trp Leu Ile
    1250                 1255                 1260

Glu Ile  Asn Thr Thr His Tyr  Arg Glu Thr
    1265                 1270


<210> SEQ ID NO 290
<211> LENGTH: 1310
<212> TYPE: PRT
<213> ORGANISM: Homo sapiens

<400> SEQUENCE: 290

Ser Leu Ile Ser Asn Ser Cys Ser Pro Gly Asp Pro Leu Val Leu Glu
1               5                   10                  15

Arg Pro Pro Pro Arg Trp Ser Ser Ser Phe Cys Ser Leu Gly Leu Ile
            20                  25                  30

Ala Arg Arg Ile Phe Val Lys Glu Pro Tyr Phe Cys Gly Val Thr Leu
        35                  40                  45

Asp Lys Leu Pro Thr Glu Ile Ser Ser Lys Val Asn Ile Lys Phe Leu
    50                  55                  60

Ser Val Cys Val Lys Leu Leu Ile Leu Ile Val Cys Val Phe Ile Pro
65                  70                  75                  80

Thr Tyr Gly Thr Asp Glu Trp Glu Gln Trp Trp Asn Ala Phe Asn Glu
                85                  90                  95

Glu Asn Leu Phe Cys Ser Glu Glu Met Pro Ser Ser Asp Asp Glu Ala
            100                 105                 110

Thr Ala Asp Ser Gln His Ser Thr Pro Pro Lys Lys Lys Arg Lys Val
        115                 120                 125

Glu Asp Pro Lys Asp Phe Pro Ser Glu Leu Leu Ser Phe Leu Ser His
    130                 135                 140

Ala Val Phe Ser Asn Arg Thr Leu Ala Cys Phe Ala Ile Tyr Thr Thr
145                 150                 155                 160

Lys Glu Lys Ala Ala Leu Leu Tyr Lys Lys Ile Met Glu Lys Tyr Ser
                165                 170                 175

Val Thr Phe Ile Ser Arg His Asn Ser Tyr Asn His Asn Ile Leu Phe
            180                 185                 190

Phe Leu Thr Pro His Arg His Arg Val Ser Ala Ile Asn Asn Tyr Ala
        195                 200                 205

Gln Lys Leu Cys Thr Phe Ser Phe Leu Ile Cys Lys Gly Val Asn Lys
    210                 215                 220

Glu Tyr Leu Met Tyr Ser Ala Leu Thr Arg Asp His Asn Gln Pro Tyr
225                 230                 235                 240

His Ile Cys Arg Gly Phe Thr Cys Phe Lys Lys Pro Pro Thr Pro Pro
                245                 250                 255

Pro Glu Pro Glu Thr Asn Glu Cys Asn Cys Cys Cys Leu Val Tyr Cys
            260                 265                 270

Ser Leu Trp Leu Gln Ile Lys Gln His His Lys Phe His Lys Ser Ile
        275                 280                 285

Phe Phe Thr Ala Phe Leu Trp Phe Val Gln Thr His Gln Cys Ile Leu
    290                 295                 300
```

-continued

Ser Cys Leu Asp Leu Pro Lys Cys Val Ser Val Arg Val Trp Lys Val
305 310 315 320

Pro Arg Leu Pro Ser Arg Gln Lys Tyr Ala Lys His Ala Ser Gln Leu
325 330 335

Val Ser Asn Gln Val Trp Lys Val Pro Arg Leu Pro Ser Arg Gln Lys
340 345 350

Tyr Ala Lys His Ala Ser Gln Leu Val Ser Asn His Ser Pro Ala Pro
355 360 365

Asn Ser Ala His Pro Ala Pro Asn Ser Ala Gln Phe Arg Pro Phe Ser
370 375 380

Ala Pro Trp Leu Thr Asn Phe Phe Tyr Leu Cys Arg Gly Arg Gly Arg
385 390 395 400

Leu Gly Leu Ala Ile Pro Glu Val Val Arg Arg Leu Phe Trp Arg Pro
405 410 415

Arg Leu Leu Gln Lys Ala Pro Ser Arg Ala Trp Arg Asn His Gly His
420 425 430

Ser Cys Phe Leu Cys Glu Ile Val Ile Arg Ser Gln Phe His Thr Thr
435 440 445

Tyr Glu Pro Glu Ala Ser Val Lys Pro Gly Val Pro Asn Glu Ala Asn
450 455 460

Ser His Leu Arg Cys Ala His Cys Pro Leu Ser Ser Arg Glu Thr Cys
465 470 475 480

Arg Ala Ser Cys Ile Asn Glu Ser Ala Asn Ala Arg Gly Glu Ala Val
485 490 495

Cys Val Leu Gly Ala Leu Pro Leu Pro Arg Ser Leu Thr Arg Cys Ala
500 505 510

Arg Ser Phe Gly Cys Gly Glu Arg Tyr Gln Leu Thr Gln Arg Arg Tyr
515 520 525

Gly Tyr Pro Gln Asn Gln Gly Ile Thr Gln Glu Arg Thr Cys Glu Gln
530 535 540

Lys Ala Ser Lys Arg Pro Gly Thr Val Lys Arg Pro Arg Cys Trp Arg
545 550 555 560

Phe Ser Ile Gly Ser Ala Pro Leu Thr Ser Ile Thr Lys Ile Asp Ala
565 570 575

Gln Val Arg Gly Gly Glu Thr Arg Gln Asp Tyr Lys Asp Thr Arg Arg
580 585 590

Phe Pro Leu Glu Ala Pro Ser Cys Ala Leu Leu Phe Arg Pro Cys Arg
595 600 605

Leu Pro Asp Thr Cys Pro Pro Phe Ser Leu Arg Glu Ala Trp Arg Phe
610 615 620

Leu Asn Ala His Ala Val Gly Ile Ser Val Arg Cys Arg Ser Phe Ala
625 630 635 640

Pro Ser Trp Ala Val Cys Thr Asn Pro Pro Phe Ser Pro Thr Ala Ala
645 650 655

Pro Tyr Pro Val Thr Ile Val Leu Ser Pro Thr Arg Asp Thr Thr Tyr
660 665 670

Arg His Trp Gln Gln Pro Leu Val Thr Gly Leu Ala Glu Arg Gly Met
675 680 685

Ala Val Leu Gln Ser Ser Ser Gly Gly Leu Thr Thr Ala Thr Leu Glu
690 695 700

Gly Gln Tyr Leu Val Ser Ala Leu Cys Ser Gln Leu Pro Ser Glu Lys
705 710 715 720

-continued

```
Glu Leu Val Ala Leu Asp Pro Ala Asn Lys Pro Pro Leu Val Ala Val
                725                 730                 735

Val Phe Leu Phe Ala Ser Ser Arg Leu Arg Ala Glu Lys Lys Asp Leu
            740                 745                 750

Lys Lys Ile Leu Ser Phe Leu Arg Gly Leu Thr Leu Ser Gly Thr Lys
        755                 760                 765

Thr His Val Lys Gly Phe Trp Ser Asp Tyr Gln Lys Gly Ser Ser Pro
    770                 775                 780

Arg Ser Phe Ile Lys Asn Glu Val Leu Asn Gln Ser Lys Val Tyr Met
785                 790                 795                 800

Ser Lys Leu Gly Leu Thr Val Thr Asn Ala Ser Val Arg His Leu Ser
                805                 810                 815

Gln Arg Ser Val Tyr Phe Val His Pro Leu Pro Asp Ser Pro Ser Cys
            820                 825                 830

Arg Leu Arg Tyr Gly Arg Ala Tyr His Leu Ala Pro Val Leu Gln Tyr
        835                 840                 845

Arg Glu Thr His Ala His Arg Leu Gln Ile Tyr Gln Gln Thr Ser Gln
    850                 855                 860

Pro Glu Gly Pro Ser Ala Glu Val Val Leu Gln Leu Tyr Pro Pro Pro
865                 870                 875                 880

Ser Ser Leu Leu Ile Val Ala Gly Lys Leu Glu Val Val Arg Gln Leu
                885                 890                 895

Ile Val Cys Ala Thr Leu Leu Pro Leu Leu Gln Ala Ser Trp Cys His
            900                 905                 910

Ala Arg Arg Leu Val Trp Leu His Ser Ala Pro Val Pro Asn Asp Gln
        915                 920                 925

Gly Glu Leu His Asp Pro Pro Cys Cys Ala Lys Lys Arg Leu Ala Pro
    930                 935                 940

Ser Val Leu Arg Ser Leu Ser Glu Val Ser Trp Pro Gln Cys Tyr His
945                 950                 955                 960

Ser Trp Leu Trp Gln His Cys Ile Ile Leu Leu Leu Ser Cys His Pro
                965                 970                 975

Asp Ala Phe Leu Leu Val Ser Thr Gln Pro Ser His Ser Glu Asn Ser
            980                 985                 990

Val Cys Gly Asp Arg Val Ala Leu  Ala Arg Arg Gln His  Gly Ile Ile
        995                 1000                1005

Pro Arg  His Ile Ala Glu Leu  Lys Cys Ser Ser Leu  Glu Asn Val
    1010                1015                1020

Leu Arg  Gly Glu Asn Ser Gln  Gly Ser Tyr Arg Cys  Asp Pro Val
    1025                1030                1035

Arg Cys  Asn Pro Leu Val His  Pro Thr Asp Leu Gln  His Leu Leu
    1040                1045                1050

Leu Ser  Pro Ala Phe Leu Gly  Glu Gln Lys Gln Glu  Gly Lys Met
    1055                1060                1065

Pro Gln  Lys Arg Glu Gly Arg  His Gly Asn Val Glu  Tyr Ser Tyr
    1070                1075                1080

Ser Ser  Phe Phe Asn Ile Ile  Glu Ala Phe Ile Arg  Val Ile Val
    1085                1090                1095

Ser Cys  Ala Leu Thr Leu Ile  Ile Asp Leu Leu Ile  Val Ile Asn
    1100                1105                1110

Tyr Gly  Val Ile Ser Ser Pro  Ile Tyr Gly Val Pro  Arg Tyr Ile
    1115                1120                1125

Thr Tyr  Gly Lys Trp Pro Ala  Trp Leu Thr Ala Gln  Arg Pro Pro
```

-continued

```
    1130                1135                1140

Pro Ile  Asp Val Asn Asn Asp  Val Cys Ser His Ser  Asn Ala Asn
    1145                1150                1155

Arg Asp  Phe Pro Leu Thr Ser  Met Gly Gly Leu Phe  Thr Val Asn
    1160                1165                1170

Cys Pro  Leu Gly Ser Thr Ser  Ser Val Ser Tyr Ala  Lys Tyr Ala
    1175                1180                1185

Pro Tyr  Arg Gln Arg Met Ala  Arg Leu Ala Leu Cys  Pro Val His
    1190                1195                1200

Asp Leu  Met Gly Leu Ser Tyr  Leu Ala Val His Leu  Arg Ile Ser
    1205                1210                1215

His Arg  Tyr Tyr His Gly Asp  Ala Val Leu Ala Val  His Gln Trp
    1220                1225                1230

Ala Trp  Ile Ala Val Leu Thr  Gly Ile Ser Lys Ser  Pro Pro His
    1235                1240                1245

Arg Gln  Trp Glu Phe Val Leu  Ala Pro Lys Ser Thr  Gly Leu Ser
    1250                1255                1260

Lys Met  Ser Gln Leu Arg Pro  Ile Asp Ala Asn Gly  Arg Ala Cys
    1265                1270                1275

Thr Val  Gly Gly Leu Tyr Lys  Gln Ser Ser Leu Ala  Asn Arg Thr
    1280                1285                1290

His Cys  Leu Thr Gly Leu Ser  Lys Leu Ile Arg Leu  Thr Ile Gly
    1295                1300                1305

Arg Pro
    1310


<210> SEQ ID NO 291
<211> LENGTH: 1286
<212> TYPE: PRT
<213> ORGANISM: Homo sapiens

<400> SEQUENCE: 291

Gln Ala Tyr Arg Ile Pro Ala Ala Arg Gly Ile His Phe Ser Gly Arg
1               5                   10                  15

His Arg Gly Gly Ala Pro Ala Phe Val Pro Phe Ser Glu Gly Leu Arg
            20                  25                  30

Ala Arg Gly Ser Leu Arg Asn Leu Thr Ser Val Val His Asn Trp Thr
        35                  40                  45

Asn Tyr Leu Gln Arg Phe Lys Ala Leu Arg Ile Asn Phe Val Tyr Asn
    50                  55                  60

Val Leu Asn Tyr Phe Leu Phe Val Tyr Phe Arg Phe Gln Pro Met Glu
65                  70                  75                  80

Leu Met Asn Gly Ser Ser Gly Gly Met Pro Leu Met Arg Lys Thr Cys
                85                  90                  95

Phe Ala Gln Lys Lys Cys His Leu Val Met Met Arg Leu Leu Leu Thr
            100                 105                 110

Leu Asn Ile Leu Leu Leu Gln Lys Arg Arg Glu Arg Lys Thr Pro Arg
        115                 120                 125

Thr Phe Leu Gln Asn Cys Val Phe Val Met Leu Cys Leu Val Ile Glu
    130                 135                 140

Leu Leu Leu Ala Leu Leu Phe Thr Pro Gln Arg Lys Lys Leu His Cys
145                 150                 155                 160

Tyr Thr Arg Lys Leu Trp Lys Asn Ile Leu Pro Leu Val Gly Ile Thr
                165                 170                 175
```

-continued

```
Val Ile Ile Ile Thr Tyr Cys Phe Phe Leu Leu His Thr Gly Ile Glu
            180                 185                 190

Cys Leu Leu Leu Ile Thr Met Leu Lys Asn Cys Val Pro Leu Ala Phe
        195                 200                 205

Phe Val Lys Gly Leu Ile Arg Asn Ile Cys Ile Val Pro Leu Glu Ile
    210                 215                 220

Ile Ile Ser His Thr Thr Phe Val Glu Val Leu Leu Ala Leu Lys Asn
225                 230                 235                 240

Leu Pro His Leu Pro Leu Asn Leu Lys His Lys Met Asn Ala Ile Val
                245                 250                 255

Val Val Asn Leu Phe Ile Ala Ala Tyr Asn Gly Tyr Lys Ser Asn Ser
            260                 265                 270

Ile Thr Asn Phe Thr Asn Lys Ala Phe Phe Ser Leu His Ser Ser Cys
        275                 280                 285

Gly Leu Ser Lys Leu Ile Asn Val Ser Tyr His Val Ile Phe Arg Asn
    290                 295                 300

Val Cys Gln Leu Gly Cys Gly Lys Ser Pro Gly Ser Pro Ala Gly Arg
305                 310                 315                 320

Ser Met Gln Ser Met His Leu Asn Ser Ala Thr Arg Cys Gly Lys Ser
                325                 330                 335

Pro Gly Ser Pro Ala Gly Arg Ser Met Gln Ser Met His Leu Asn Ser
            340                 345                 350

Ala Thr Ile Val Pro Pro Leu Thr Pro Pro Ile Pro Pro Leu Thr Pro
        355                 360                 365

Pro Ser Ser Ala His Ser Pro Pro His Gly Leu Ile Phe Phe Ile Tyr
    370                 375                 380

Ala Glu Ala Glu Ala Ala Ser Ala Ser Glu Leu Phe Gln Lys Gly Gly
385                 390                 395                 400

Phe Phe Gly Gly Leu Gly Phe Cys Lys Lys Leu Pro Arg Glu Leu Gly
                405                 410                 415

Val Ile Met Val Ile Ala Val Ser Cys Val Lys Leu Leu Ser Ala His
            420                 425                 430

Asn Ser Thr Gln His Thr Ser Arg Lys His Lys Val Ser Leu Gly Cys
        435                 440                 445

Leu Met Ser Glu Leu Thr His Ile Asn Cys Val Ala Leu Thr Ala Arg
    450                 455                 460

Phe Pro Val Gly Lys Pro Val Val Pro Ala Ala Leu Met Asn Arg Pro
465                 470                 475                 480

Thr Arg Gly Glu Arg Arg Phe Ala Tyr Trp Ala Leu Phe Arg Phe Leu
                485                 490                 495

Ala His Leu Ala Ala Leu Gly Arg Ser Ala Ala Ala Ser Gly Ile Ser
            500                 505                 510

Ser Leu Lys Gly Gly Asn Thr Val Ile His Arg Ile Arg Gly Arg Arg
        515                 520                 525

Lys Glu His Val Ser Lys Arg Pro Ala Lys Gly Gln Glu Pro Lys Gly
    530                 535                 540

Arg Val Ala Gly Val Phe Pro Ala Pro Pro Pro Arg Ala Ser Gln Lys
545                 550                 555                 560

Ser Thr Leu Lys Ser Glu Val Ala Lys Pro Asp Arg Thr Ile Lys Ile
                565                 570                 575

Pro Gly Val Ser Pro Trp Lys Leu Pro Arg Ala Leu Ser Cys Ser Asp
            580                 585                 590

Pro Ala Ala Tyr Arg Ile Pro Val Arg Leu Ser Pro Phe Gly Lys Arg
```

-continued

```
        595                 600                 605

Gly Ala Phe Ser Met Leu Thr Leu Val Ser Gln Phe Gly Val Gly Arg
    610                 615                 620

Ser Leu Gln Ala Gly Leu Cys Ala Arg Thr Pro Arg Ser Ala Arg Pro
625                 630                 635                 640

Leu Arg Leu Ile Arg Leu Ser Ser Val Gln Pro Gly Lys Thr Arg Leu
                645                 650                 655

Ile Ala Thr Gly Ser Ser His Trp Gln Asp Gln Ser Glu Val Cys Arg
            660                 665                 670

Arg Cys Tyr Arg Val Leu Glu Val Val Ala Leu Arg Leu His Lys Asp
        675                 680                 685

Ser Ile Trp Tyr Leu Arg Ser Ala Glu Ala Ser Tyr Leu Arg Lys Lys
    690                 695                 700

Ser Trp Leu Leu Ile Arg Gln Thr Asn His Arg Trp Arg Trp Phe Phe
705                 710                 715                 720

Cys Leu Gln Ala Ala Asp Tyr Ala Gln Lys Lys Arg Ile Ser Arg Arg
                725                 730                 735

Ser Phe Asp Leu Phe Tyr Gly Val Arg Ser Val Glu Arg Lys Leu Thr
            740                 745                 750

Leu Arg Asp Phe Gly His Glu Ile Ile Lys Lys Asp Leu His Leu Asp
        755                 760                 765

Pro Phe Lys Leu Lys Met Lys Phe Ile Asn Leu Lys Tyr Ile Val Asn
    770                 775                 780

Leu Val Gln Leu Pro Met Leu Asn Gln Gly Thr Tyr Leu Ser Asp Leu
785                 790                 795                 800

Ser Ile Ser Phe Ile His Ser Cys Leu Thr Pro Arg Arg Val Asp Asn
                805                 810                 815

Tyr Asp Thr Gly Gly Leu Thr Ile Trp Pro Gln Cys Cys Asn Asp Thr
            820                 825                 830

Ala Arg Pro Thr Leu Thr Gly Ser Arg Phe Ile Ser Asn Lys Pro Ala
        835                 840                 845

Ser Arg Lys Gly Arg Ala Gln Lys Trp Ser Cys Asn Phe Ile Arg Leu
    850                 855                 860

His Pro Val Tyr Leu Leu Pro Gly Ser Ser Lys Phe Ala Ser Phe Ala
865                 870                 875                 880

Gln Arg Cys Cys His Cys Tyr Arg His Arg Gly Val Thr Leu Val Val
                885                 890                 895

Trp Tyr Gly Phe Ile Gln Leu Arg Phe Pro Thr Ile Lys Ala Ser Tyr
            900                 905                 910

Met Ile Pro His Val Val Gln Lys Ser Gly Leu Leu Arg Ser Ser Asp
        915                 920                 925

Arg Cys Gln Lys Val Gly Arg Ser Val Ile Thr His Gly Tyr Gly Ser
    930                 935                 940

Thr Ala Phe Ser Tyr Cys His Ala Ile Arg Lys Met Leu Phe Cys Asp
945                 950                 955                 960

Trp Val Leu Asn Gln Val Ile Leu Arg Ile Val Tyr Ala Ala Thr Glu
                965                 970                 975

Leu Leu Leu Pro Gly Val Asn Thr Gly Tyr Arg Ala Thr Gln Asn Phe
            980                 985                 990

Lys Ser Ala His His Trp Lys Thr  Phe Phe Gly Ala Lys  Thr Leu Lys
        995                 1000                1005

Asp Leu  Thr Ala Val Glu Ile  Gln Phe Asp Val Thr  His Ser Cys
    1010                1015                1020
```

-continued

```
Thr Gln  Leu Ile Phe Ser Ile  Phe Tyr Phe His Gln  Arg Phe Trp
    1025                 1030                 1035

Val Ser  Lys Asn Arg Lys Ala  Lys Cys Arg Lys Lys  Gly Asn Lys
    1040                 1045                 1050

Gly Asp  Thr Glu Met Leu Asn  Thr His Thr Leu Pro  Phe Ser Ile
    1055                 1060                 1065

Leu Leu  Lys His Leu Ser Gly  Leu Leu Ser His Ala  Arg His Leu
    1070                 1075                 1080

Leu Thr  Ser Tyr Ser Ile Thr  Gly Ser Leu Val His  Ser Pro Tyr
    1085                 1090                 1095

Met Glu  Phe Arg Val Thr Leu  Thr Val Asn Gly Pro  Pro Gly Pro
    1100                 1105                 1110

Pro Asn  Asp Pro Arg Pro Leu  Thr Ser Ile Met Thr  Tyr Val Pro
    1115                 1120                 1125

Ile Val  Thr Pro Ile Gly Thr  Phe His Arg Gln Trp  Val Asp Tyr
    1130                 1135                 1140

Leu Arg  Thr Ala His Leu Ala  Val His Gln Val Tyr  His Met Pro
    1145                 1150                 1155

Ser Thr  Pro Pro Ile Asp Val  Asn Asp Gly Lys Trp  Pro Ala Trp
    1160                 1165                 1170

His Tyr  Ala Gln Tyr Met Thr  Leu Trp Asp Phe Pro  Thr Trp Gln
    1175                 1180                 1185

Tyr Ile  Tyr Val Leu Val Ile  Ala Ile Thr Met Val  Met Arg Phe
    1190                 1195                 1200

Trp Gln  Tyr Ile Asn Gly Arg  Gly Arg Phe Asp Ser  Arg Gly Phe
    1205                 1210                 1215

Pro Ser  Leu His Pro Ile Asp  Val Asn Gly Ser Leu  Phe Trp His
    1220                 1225                 1230

Gln Asn  Gln Arg Asp Phe Pro  Lys Cys Arg Asn Asn  Ser Ala Pro
    1235                 1240                 1245

Leu Thr  Gln Met Gly Gly Arg  Arg Val Arg Trp Glu  Val Tyr Ile
    1250                 1255                 1260

Ser Arg  Ala Leu Trp Leu Thr  Arg Glu Pro Thr Ala  Leu Ala Tyr
    1265                 1270                 1275

Arg Asn  Tyr Asp Ser Leu Gly  Asp
    1280                 1285


<210> SEQ ID NO 292
<211> LENGTH: 1293
<212> TYPE: PRT
<213> ORGANISM: Homo sapiens

<400> SEQUENCE: 292

Trp Val Ser Leu Val Val Leu Ile Ser Ile Ser Gln Leu Ser Ser Gly
1               5                   10                  15

Phe Ser Ser Pro Glu Ser Ser Ala Tyr Ile Asp Leu Pro Pro Tyr Thr
            20                  25                  30

Pro Thr Ala His Leu Arg Gln Trp Gly Gly Val Val Thr Thr Phe Trp
        35                  40                  45

Lys Val Pro Leu Ile Leu Val Pro Lys Gln Thr Pro Ile Asp Val Asn
    50                  55                  60

Gly Val Glu Thr Trp Lys Ser Pro Val Lys Pro Leu Ser Thr Pro Ile
65                  70                  75                  80

Asp Val Leu Pro Lys Pro His His His Gly Asn Ser Asp Asp Tyr Val
```

-continued

```
                85                  90                  95

Asp Val Leu Pro Ser Arg Lys Val Pro Gly His Val Leu Gly Ile Met
            100                 105                 110

Pro Gly Gly Pro Phe Thr Val Ile Asp Val Asn Arg Gly Arg Thr Trp
        115                 120                 125

His Met Ile His Leu Met Tyr Cys Gln Val Gly Ser Leu Pro Ile Val
    130                 135                 140

His Pro Leu Thr Ser Met Glu Ser Pro Tyr Trp Arg Tyr Tyr Gly Asn
145                 150                 155                 160

Ile Arg His Tyr Arg Gln Trp Ala Gly Val Val Gly Arg Ser Ala Arg
                165                 170                 175

Arg Ala Ile Tyr Arg Lys Leu Cys Asn Ala Glu Leu His Ile Trp Ala
            180                 185                 190

Met Asn Pro Arg Asn Leu Leu Leu Ile Thr Ser Gln Ser Met Ser Thr
        195                 200                 205

Arg Met Arg Gln Pro Met Leu Gln Tyr Lys Arg Lys Ser Met Ser Ile
    210                 215                 220

Gln His Phe Arg Val Ala Leu Ile Pro Phe Phe Ala Ala Phe Cys Leu
225                 230                 235                 240

Pro Val Phe Ala His Pro Glu Thr Leu Val Lys Val Lys Asp Ala Glu
                245                 250                 255

Asp Gln Leu Gly Ala Arg Val Gly Tyr Ile Glu Leu Asp Leu Asn Ser
            260                 265                 270

Gly Lys Ile Leu Glu Ser Phe Arg Pro Glu Glu Arg Phe Pro Met Met
        275                 280                 285

Ser Thr Phe Lys Val Leu Leu Cys Gly Ala Val Leu Ser Arg Val Asp
    290                 295                 300

Ala Gly Gln Glu Gln Leu Gly Arg Arg Ile His Tyr Ser Gln Asn Asp
305                 310                 315                 320

Leu Val Glu Tyr Ser Pro Val Thr Glu Lys His Leu Thr Asp Gly Met
                325                 330                 335

Thr Val Arg Glu Leu Cys Ser Ala Ala Ile Thr Met Ser Asp Asn Thr
            340                 345                 350

Ala Ala Asn Leu Leu Leu Thr Thr Ile Gly Gly Pro Lys Glu Leu Thr
        355                 360                 365

Ala Phe Leu His Asn Met Gly Asp His Val Thr Arg Leu Asp Arg Trp
    370                 375                 380

Glu Pro Glu Leu Asn Glu Ala Ile Pro Asn Asp Glu Arg Asp Thr Thr
385                 390                 395                 400

Met Pro Val Ala Met Ala Thr Thr Leu Arg Lys Leu Leu Thr Gly Glu
                405                 410                 415

Leu Leu Thr Leu Ala Ser Arg Gln Gln Leu Ile Asp Trp Met Glu Ala
            420                 425                 430

Asp Lys Val Ala Gly Pro Leu Leu Arg Ser Ala Leu Pro Ala Gly Trp
        435                 440                 445

Phe Ile Ala Asp Lys Ser Gly Ala Gly Glu Arg Gly Ser Arg Gly Ile
    450                 455                 460

Ile Ala Ala Leu Gly Pro Asp Gly Lys Pro Ser Arg Ile Val Val Ile
465                 470                 475                 480

Tyr Thr Thr Gly Ser Gln Ala Thr Met Asp Glu Arg Asn Arg Gln Ile
                485                 490                 495

Ala Glu Ile Gly Ala Ser Leu Ile Lys His Trp Leu Ser Asp Gln Val
            500                 505                 510
```

-continued

```
Tyr Ser Tyr Ile Leu Ile Asp Leu Lys Leu His Phe Phe Lys Arg Ile
        515                 520                 525

Val Lys Ile Leu Phe Asp Asn Leu Met Thr Lys Ile Pro Arg Glu Phe
    530                 535                 540

Ser Phe His Ala Ser Asp Pro Val Glu Lys Ile Lys Gly Ser Ser Asp
545                 550                 555                 560

Pro Phe Phe Leu Arg Val Ile Cys Cys Leu Gln Thr Lys Lys Pro Pro
                565                 570                 575

Leu Pro Ala Val Val Cys Leu Pro Asp Gln Glu Leu Pro Thr Leu Phe
            580                 585                 590

Pro Lys Val Thr Gly Phe Ser Arg Ala Gln Ile Pro Asn Thr Val Leu
        595                 600                 605

Leu Val Pro Leu Gly His His Phe Lys Asn Ser Val Ala Pro Pro Thr
    610                 615                 620

Tyr Leu Ala Leu Leu Ile Leu Leu Pro Val Ala Ala Ala Ser Gly Asp
625                 630                 635                 640

Lys Ser Cys Leu Thr Gly Leu Asp Ser Arg Arg Leu Pro Asp Lys Ala
                645                 650                 655

Gln Arg Ser Gly Thr Gly Gly Ser Cys Thr Gln Pro Ser Leu Glu Arg
            660                 665                 670

Thr Thr Tyr Thr Glu Leu Arg Tyr Leu Gln Arg Glu His Glu Ser Ala
        675                 680                 685

Thr Leu Pro Glu Gly Arg Lys Ala Asp Arg Tyr Pro Val Ser Gly Arg
    690                 695                 700

Val Gly Thr Gly Glu Arg Thr Arg Glu Leu Pro Gly Gly Asn Ala Trp
705                 710                 715                 720

Tyr Leu Tyr Ser Pro Val Gly Phe Arg His Leu Leu Glu Arg Arg Phe
                725                 730                 735

Leu Cys Ser Ser Gly Gly Arg Ser Leu Trp Lys Asn Ala Ser Asn Ala
            740                 745                 750

Ala Phe Leu Arg Phe Leu Ala Phe Cys Trp Pro Phe Ala His Met Phe
        755                 760                 765

Phe Pro Ala Leu Ser Pro Asp Ser Val Asp Asn Arg Ile Thr Ala Phe
    770                 775                 780

Glu Ala Asp Thr Ala Arg Arg Ser Arg Thr Thr Glu Arg Ser Glu Ser
785                 790                 795                 800

Val Ser Glu Glu Ala Glu Glu Arg Pro Ile Arg Lys Pro Pro Leu Pro
                805                 810                 815

Ala Arg Trp Pro Ile His Cys Ser Trp His Asp Arg Phe Pro Asp Trp
            820                 825                 830

Lys Ala Gly Ser Glu Arg Asn Ala Ile Asn Val Ser Leu Thr His Ala
        835                 840                 845

Pro Gln Ala Leu His Phe Met Leu Pro Ala Arg Met Leu Cys Gly Ile
    850                 855                 860

Val Ser Gly Gln Phe His Thr Gly Asn Ser Tyr Asp His Asp Tyr Ala
865                 870                 875                 880

Lys Leu Ser Arg Glu Leu Phe Ala Lys Ala Ala Ser Lys Lys Ala Ser
                885                 890                 895

Ser Leu Leu Leu Glu Leu Arg Gly Arg Gly Gly Leu Gly Leu Cys Ile
            900                 905                 910

Asn Lys Lys Asn Ser Ala Met Gly Arg Arg Met Gly Gly Thr Gly Arg
        915                 920                 925
```

-continued

```
Ser Gly Arg Asp Gly Arg Ser Gly Arg Asp Tyr Gly Cys Leu Ile Glu
    930                 935                 940

Met His Ala Leu His Thr Ser Ala Cys Trp Gly Ala Trp Gly Leu Ser
945                 950                 955                 960

Thr Pro Gly Cys Leu Ile Glu Met His Ala Leu His Thr Ser Ala Cys
                965                 970                 975

Trp Gly Ala Trp Gly Leu Ser Thr Pro Leu Thr His Ile Ser Glu Asp
            980                 985                 990

Leu Asp Met Ile Arg Tyr Ile Asp  Glu Phe Gly Gln Thr  Thr Thr Arg
        995                 1000                 1005

Met Gln  Lys Lys Cys Phe Ile  Cys Glu Ile Cys Asp  Ala Ile Ala
    1010                 1015                 1020

Leu Phe  Val Thr Ile Ile Ser  Cys Asn Lys Gln Val  Asn Asn Asn
    1025                 1030                 1035

Asn Cys  Ile His Phe Met Phe  Gln Val Gln Gly Glu  Val Trp Glu
    1040                 1045                 1050

Val Phe  Ser Lys Asn Leu Tyr  Lys Cys Gly Met Ala  Asp Tyr Asp
    1055                 1060                 1065

Leu Ser  Arg His Tyr Thr Ser  Asn Ile Pro Tyr Pro  Leu Tyr Lys
    1070                 1075                 1080

Leu Lys  Ser Arg Tyr Thr Ile  Phe Glu His Ser Tyr  Gln Thr Leu
    1085                 1090                 1095

Tyr Ala  Cys Val Glu Glu Lys  Thr Val Cys Tyr Asp  Tyr Asn Cys
    1100                 1105                 1110

Tyr Ala  Tyr Leu Arg Leu Gln  Asn Ile Phe Pro Phe  Ser Cys Ile
    1115                 1120                 1125

Ala Val  Gln Leu Phe Pro Leu  Trp Cys Lys Gln Ser  Lys Gln Glu
    1130                 1135                 1140

Phe Tyr  Tyr Thr Gln His Asp  Ser Lys Asn Leu Ala  Ile Leu Lys
    1145                 1150                 1155

Glu Ser  Pro Trp Gly Leu Leu  Pro Phe Ser Ser Phe  Leu Glu Glu
    1160                 1165                 1170

Asn Val  Glu Ser Gln Gln Pro  His His His Met Ala  Phe Leu Leu
    1175                 1180                 1185

Ser Lys  Thr Gly Phe Pro His  Arg His Ser Thr Thr  Ala Pro Ile
    1190                 1195                 1200

His Gln  Phe His Arg Leu Glu  Ser Lys Ile His Lys  Gln Leu Glu
    1205                 1210                 1215

Ser Val  Val His Ile Ile His  Leu Lys Ile Leu Tyr  Leu Pro Ser
    1220                 1225                 1230

Phe Lys  Ser Leu Val Val Cys  Pro Ile Met Ser His  His Arg Ser
    1235                 1240                 1245

Lys Val  Pro Ser Gln Arg Ser  Ser Ser Ala Gln Leu  Thr Leu Thr
    1250                 1255                 1260

Lys Gly  Asn Lys Ser Trp Ser  Ser Thr Ala Val Ala  Ala Ala Leu
    1265                 1270                 1275

Glu Leu  Val Asp Pro Pro Gly  Cys Arg Asn Ser Ile  Ser Ser Leu
    1280                 1285                 1290
```

<210> SEQ ID NO 293
<211> LENGTH: 1279
<212> TYPE: PRT
<213> ORGANISM: Homo sapiens

<400> SEQUENCE: 293

-continued

```
Gly Leu Pro Ile Val Ser Arg Ile Asn Phe Asp Lys Pro Val Lys Gln
1               5                   10                  15

Trp Val Leu Leu Ala Arg Glu Leu Cys Leu Tyr Arg Pro Pro Thr Val
            20                  25                  30

His Ala Tyr Arg Pro Phe Ala Ser Met Gly Arg Ser Cys Tyr Asp Ile
        35                  40                  45

Leu Glu Ser Pro Val Asp Phe Gly Ala Lys Thr Asn Ser His Arg Gln
    50                  55                  60

Trp Gly Gly Asp Leu Glu Ile Pro Val Ser Gln Thr Ala Ile His Ala
65                  70                  75                  80

His Cys Thr Ala Lys Thr Ala Ser Pro Trp Arg Leu Ile Arg Arg Cys
                85                  90                  95

Thr Ala Lys Glu Ser Pro Ile Arg Ser Cys Thr Gly His Asn Ala Arg
            100                 105                 110

Arg Ala Ile Tyr Arg His Arg Gln Gly Ala Tyr Leu Ala Tyr Asp Thr
        115                 120                 125

Leu Asp Val Leu Pro Ser Gly Gln Phe Thr Val Asn Ser Pro Pro Ile
    130                 135                 140

Asp Val Asn Gly Lys Ser Leu Leu Ala Leu Leu Trp Glu His Thr Ser
145                 150                 155                 160

Leu Leu Thr Ser Met Gly Gly Gly Arg Trp Ala Val Ser Gln Ala Gly
                165                 170                 175

His Leu Pro Val Met Arg Gly Thr Pro Tyr Met Gly Tyr Glu Leu Met
            180                 185                 190

Thr Pro Leu Ile Thr Ile Asn Asn Ser Ile Ile Asn Val Asn Ala His
        195                 200                 205

Glu Thr Ile Thr Leu Ile Asn Ala Ser Ile Ile Leu Lys Lys Glu Glu
    210                 215                 220

Tyr Glu Tyr Ser Thr Phe Pro Cys Arg Pro Tyr Ser Leu Phe Cys Gly
225                 230                 235                 240

Ile Leu Pro Ser Cys Phe Cys Ser Pro Arg Asn Ala Gly Glu Ser Lys
                245                 250                 255

Arg Cys Arg Ser Val Gly Cys Thr Ser Gly Leu His Arg Thr Gly Ser
            260                 265                 270

Gln Gln Arg Asp Pro Glu Phe Ser Pro Arg Arg Thr Phe Ser Asn Asp
        275                 280                 285

Glu His Phe Ser Ser Ala Met Trp Arg Gly Ile Ile Pro Cys Arg Arg
    290                 295                 300

Ala Arg Ala Thr Arg Ser Pro His Thr Leu Phe Ser Glu Leu Gly Val
305                 310                 315                 320

Leu Thr Ser His Arg Lys Ala Ser Tyr Gly Trp His Asp Ser Lys Arg
                325                 330                 335

Ile Met Gln Cys Cys His Asn His Glu His Cys Gly Gln Leu Thr Ser
            340                 345                 350

Asp Asn Asp Arg Arg Thr Glu Gly Ala Asn Arg Phe Phe Ala Gln His
        355                 360                 365

Gly Gly Ser Cys Asn Ser Pro Ser Leu Gly Thr Gly Ala Glu Ser His
    370                 375                 380

Thr Lys Arg Arg Ala His His Asp Ala Cys Ser Asn Gly Asn Asn Val
385                 390                 395                 400

Ala Gln Thr Ile Asn Trp Arg Thr Thr Tyr Ser Ser Phe Pro Ala Thr
                405                 410                 415
```

-continued

```
Ile Asn Arg Leu Asp Gly Gly Gly Ser Cys Arg Thr Thr Ser Ala Leu
            420                 425                 430

Gly Pro Ser Gly Trp Leu Val Tyr Cys Ile Trp Ser Arg Ala Trp Val
        435                 440                 445

Ser Arg Tyr His Cys Ser Thr Gly Ala Arg Trp Ala Leu Pro Tyr Arg
    450                 455                 460

Ser Tyr Leu His Asp Gly Glu Ser Gly Asn Tyr Gly Thr Lys Thr Asp
465                 470                 475                 480

Arg Asp Arg Cys Leu Thr Asp Ala Leu Val Thr Val Arg Pro Ser Leu
                485                 490                 495

Leu Ile Tyr Thr Leu Asp Phe Lys Thr Ser Phe Leu Ile Lys Asp Leu
            500                 505                 510

Gly Glu Asp Pro Phe Ser His Asp Gln Asn Pro Leu Thr Val Phe Val
        515                 520                 525

Pro Leu Ser Val Arg Pro Arg Arg Lys Asp Gln Arg Ile Phe Leu Arg
    530                 535                 540

Ser Phe Phe Ser Ala Arg Asn Leu Leu Leu Ala Asn Lys Lys Thr Thr
545                 550                 555                 560

Ala Thr Ser Gly Gly Leu Phe Ala Gly Ser Arg Ala Thr Asn Ser Phe
                565                 570                 575

Ser Glu Gly Asn Trp Leu Gln Gln Ser Ala Asp Thr Lys Tyr Cys Pro
            580                 585                 590

Ser Ser Val Ala Val Val Arg Pro Pro Leu Gln Glu Leu Cys Ser Thr
        595                 600                 605

Ala Tyr Ile Pro Arg Ser Ala Asn Pro Val Thr Ser Gly Cys Cys Gln
    610                 615                 620

Trp Arg Val Val Ser Tyr Arg Val Gly Leu Lys Thr Ile Val Thr Gly
625                 630                 635                 640

Gly Ala Ala Val Gly Leu Asn Gly Gly Phe Val His Thr Ala Gln Leu
                645                 650                 655

Gly Ala Asn Asp Leu His Arg Thr Glu Ile Pro Thr Ala Ala Leu Arg
            660                 665                 670

Lys Arg His Ala Ser Arg Arg Glu Lys Gly Gly Gln Val Ser Gly Lys
        675                 680                 685

Arg Gln Gly Arg Asn Arg Arg Ala His Glu Gly Ala Ser Arg Gly Lys
    690                 695                 700

Arg Leu Val Ser Leu Ser Cys Arg Val Ser Pro Pro Leu Thr Ala Ser
705                 710                 715                 720

Ile Phe Val Met Leu Val Arg Gly Ala Glu Pro Met Glu Lys Arg Gln
                725                 730                 735

Gln Arg Gly Leu Phe Thr Val Pro Gly Leu Leu Leu Ala Phe Cys Ser
            740                 745                 750

His Val Leu Ser Cys Val Ile Pro Phe Cys Gly Pro Tyr Tyr Arg Leu
        755                 760                 765

Val Ser Tyr Arg Ser Pro Gln Pro Asn Asp Arg Ala Gln Arg Val Ser
    770                 775                 780

Glu Arg Gly Ser Gly Arg Ala Pro Asn Thr Gln Thr Ala Ser Pro Arg
785                 790                 795                 800

Ala Leu Ala Asp Ser Leu Met Gln Leu Ala Arg Gln Val Ser Arg Leu
                805                 810                 815

Glu Ser Gly Gln Ala Gln Arg Asn Cys Glu Leu Ala His Ser Leu Gly
            820                 825                 830

Thr Pro Gly Phe Thr Leu Tyr Ala Ser Gly Ser Tyr Val Val Trp Asn
```

-continued

```
        835                 840                 845

Cys Glu Arg Ile Thr Ile Ser His Arg Lys Gln Leu Pro Leu Arg Gln
    850                 855                 860

Ala Leu Glu Gly Ala Phe Cys Lys Ser Leu Gly Leu Gln Lys Ser Leu
865                 870                 875                 880

Leu Thr Thr Ser Gly Ile Ala Gln Arg Pro Arg Arg Pro Arg Pro Leu
                885                 890                 895

His Lys Lys Lys Leu Val Ser His Gly Ala Glu Asn Gly Arg Asn Trp
            900                 905                 910

Ala Glu Leu Gly Ala Gly Trp Ala Glu Leu Gly Ala Gly Leu Trp Leu
        915                 920                 925

Leu Thr Asn Asp Ala Cys Phe Ala Tyr Phe Cys Leu Leu Gly Ser Leu
    930                 935                 940

Gly Thr Phe His Thr Trp Leu Leu Thr Asn Asp Ala Cys Phe Ala Tyr
945                 950                 955                 960

Phe Cys Leu Leu Gly Ser Leu Gly Thr Phe His Thr Leu Thr Asp Thr
                965                 970                 975

His Phe Gly Arg Ser Arg His Asp Lys Ile His Val Trp Thr Asn His
            980                 985                 990

Asn Asn Ala Val Lys Lys Met Leu  Tyr Leu Asn Leu Cys  Tyr Cys Phe
        995                 1000                1005

Ile Cys  Asn His Tyr Lys Leu  Gln Thr Ser Gln Gln  Gln Leu His
    1010                 1015                 1020

Ser Phe  Tyr Val Ser Gly Ser  Gly Gly Gly Val Gly  Gly Phe Leu
    1025                 1030                 1035

Lys Gln  Val Lys Pro Leu Gln  Met Trp Tyr Gly Leu  Ser Leu Val
    1040                 1045                 1050

Lys Ala  Leu Tyr Ile Lys Tyr  Ser Leu Leu Thr Pro  Leu Gln Ile
    1055                 1060                 1065

Lys Lys  Leu Lys Val His Asn  Phe Ala Leu Leu Ile  Ala Asp Thr
    1070                 1075                 1080

Leu Cys  Leu Cys Gly Val Arg  Lys Asn Ser Met Leu  Leu Leu Leu
    1085                 1090                 1095

Cys Leu  Leu Ile Lys Val Thr  Glu Tyr Phe Ser Ile  Ile Phe Leu
    1100                 1105                 1110

Tyr Ser  Ser Ala Ala Phe Ser  Phe Val Val Ile Ala  Lys Gln Ala
    1115                 1120                 1125

Arg Val  Leu Leu Leu Asn Thr  Ala Leu Lys Lys Leu  Ser Asn Ser
    1130                 1135                 1140

Glu Gly  Lys Ser Leu Gly Ser  Ser Thr Phe Leu Phe  Phe Phe Gly
    1145                 1150                 1155

Gly Val  Glu Cys Glu Ser Ala  Val Ala Ser Ser Ser  Leu Asp Gly
    1160                 1165                 1170

Ile Ser  Ser Glu Gln Asn Arg  Phe Ser Ser Leu Lys  Ala Phe His
    1175                 1180                 1185

His Cys  Ser His Ser Ser Val  Pro Val Gly Ile Asn  Thr Gln Thr
    1190                 1195                 1200

Ile Arg  Ile Ser Ser Leu Thr  His Tyr Thr Leu Lys  Asn Phe Ile
    1205                 1210                 1215

Phe Thr  Leu Glu Leu Ile Ser  Val Gly Ser Leu Ser  Asn Tyr Val
    1220                 1225                 1230

Thr Pro  Gln Lys Gly Ser Phe  Thr Lys Ile Leu Arg  Ala Ile Asn
    1235                 1240                 1245
```

-continued

Pro His Arg Glu Gln Lys Leu Glu Leu His Arg Gly Gly Gly Arg
1250 1255 1260

Ser Arg Thr Ser Gly Ser Pro Gly Leu Gln Glu Phe Asp Ile Lys
1265 1270 1275

Leu

<210> SEQ ID NO 294
<211> LENGTH: 1284
<212> TYPE: PRT
<213> ORGANISM: Homo sapiens

<400> SEQUENCE: 294

Gly Ser Pro Tyr Ser Glu Ser Tyr Phe Arg Ala Ser Ala Val Gly Ser
1 5 10 15

Leu Val Ser Gln Arg Ala Leu Leu Ile Thr Ser His Arg Thr Arg Leu
20 25 30

Pro Pro Ile Cys Val Asn Gly Ala Glu Leu Leu Arg His Phe Gly Lys
35 40 45

Ser Arg Phe Trp Cys Gln Asn Lys Leu Pro Leu Thr Ser Met Gly Trp
50 55 60

Arg Leu Gly Asn Pro Arg Glu Ser Asn Arg Tyr Pro Arg Pro Leu Met
65 70 75 80

Tyr Cys Gln Asn Arg Ile Thr Met Val Ile Ala Met Thr Asn Thr Met
85 90 95

Tyr Cys Gln Val Gly Lys Ser His Lys Val Met Tyr Trp Ala Cys Gln
100 105 110

Ala Gly His Leu Pro Ser Leu Thr Ser Ile Gly Gly Val Leu Gly Ile
115 120 125

Tyr Thr Cys Thr Ala Lys Trp Ala Val Tyr Arg Lys Ser Thr His Arg
130 135 140

Gln Trp Lys Val Pro Ile Gly Val Thr Met Gly Thr Tyr Val Ile Ile
145 150 155 160

Asp Val Asn Gly Arg Gly Ser Leu Gly Gly Gln Pro Gly Gly Pro Phe
165 170 175

Thr Val Ser Tyr Val Thr Arg Asn Ser Ile Tyr Gly Leu Thr Asn Asp
180 185 190

Pro Val Ile Asp Tyr Tyr Leu Val Asn Asn Gln Cys Gln Arg Ala Asp
195 200 205

Asn Asn Pro Asp Lys Cys Phe Asn Asn Ile Glu Lys Gly Arg Val Val
210 215 220

Phe Asn Ile Ser Val Ser Pro Leu Phe Pro Phe Leu Arg His Phe Ala
225 230 235 240

Phe Leu Phe Leu Leu Thr Gln Lys Arg Trp Lys Lys Met Leu Lys Ile
245 250 255

Ser Trp Val His Glu Trp Val Thr Ser Asn Trp Ile Ser Thr Ala Val
260 265 270

Arg Ser Leu Arg Val Phe Ala Pro Lys Asn Val Phe Gln Ala Leu Leu
275 280 285

Lys Phe Cys Tyr Val Ala Arg Tyr Tyr Pro Val Leu Thr Pro Gly Lys
290 295 300

Ser Asn Ser Val Ala Ala Tyr Thr Ile Leu Arg Met Thr Trp Leu Ser
305 310 315 320

Thr His Gln Ser Gln Lys Ser Ile Leu Arg Met Ala Gln Glu Asn Tyr
325 330 335

-continued

```
Ala Val Leu Pro Pro Val Ile Thr Leu Arg Pro Thr Tyr Phe Gln Arg
            340                 345                 350

Ser Glu Asp Arg Arg Ser Pro Leu Phe Cys Thr Thr Trp Gly Ile Met
        355                 360                 365

Leu Ala Leu Ile Val Gly Asn Arg Ser Met Lys Pro Tyr Gln Thr Thr
    370                 375                 380

Ser Val Thr Pro Arg Cys Leu Gln Trp Gln Gln Arg Cys Ala Asn Tyr
385                 390                 395                 400

Leu Ala Asn Tyr Leu Leu Leu Pro Gly Asn Asn Thr Gly Trp Arg Arg
                405                 410                 415

Ile Lys Leu Gln Asp His Phe Cys Ala Arg Pro Phe Arg Leu Ala Gly
            420                 425                 430

Leu Leu Leu Ile Asn Leu Glu Pro Val Ser Val Gly Leu Ala Val Ser
        435                 440                 445

Leu Gln His Trp Gly Gln Met Val Ser Pro Pro Val Ser Leu Ser Thr
    450                 455                 460

Arg Arg Gly Val Arg Gln Leu Trp Met Asn Glu Ile Asp Arg Ser Leu
465                 470                 475                 480

Arg Val Pro His Leu Ser Ile Gly Asn Cys Gln Thr Lys Phe Thr His
                485                 490                 495

Ile Tyr Phe Arg Leu Ile Asn Phe Ile Phe Asn Leu Lys Gly Ser Arg
            500                 505                 510

Arg Ser Phe Leu Ile Ile Ser Pro Lys Ser Leu Asn Val Ser Phe Arg
        515                 520                 525

Ser Thr Glu Arg Gln Thr Pro Lys Arg Ser Lys Asp Leu Leu Glu Ile
    530                 535                 540

Leu Phe Phe Cys Ala Ser Ala Ala Cys Lys Gln Lys Asn His Arg Tyr
545                 550                 555                 560

Gln Arg Trp Phe Val Cys Arg Ile Lys Ser Tyr Gln Leu Phe Phe Arg
                565                 570                 575

Arg Leu Ala Ser Ala Glu Arg Arg Tyr Gln Ile Leu Ser Phe Cys Ser
            580                 585                 590

Arg Ser Ala Thr Thr Ser Arg Thr Leu His Arg Leu His Thr Ser Leu
        595                 600                 605

Cys Ser Cys Tyr Gln Trp Leu Leu Pro Val Ala Ile Ser Arg Val Leu
    610                 615                 620

Pro Gly Trp Thr Gln Asp Asp Ser Tyr Arg Ile Arg Arg Ser Gly Arg
625                 630                 635                 640

Ala Glu Arg Gly Val Arg Ala His Ser Pro Ala Trp Ser Glu Arg Pro
                645                 650                 655

Thr Pro Asn Asp Thr Tyr Ser Val Ser Ile Glu Lys Ala Pro Arg Phe
            660                 665                 670

Pro Lys Gly Glu Arg Arg Thr Gly Ile Arg Ala Ala Gly Ser Glu Gln
        675                 680                 685

Glu Ser Ala Arg Gly Ser Phe Gln Gly Glu Thr Pro Gly Ile Phe Ile
    690                 695                 700

Val Leu Ser Gly Phe Ala Thr Ser Asp Leu Ser Val Asp Phe Cys Asp
705                 710                 715                 720

Ala Arg Gln Gly Gly Gly Ala Tyr Gly Lys Thr Pro Ala Thr Arg Pro
                725                 730                 735

Phe Tyr Gly Ser Trp Pro Phe Ala Gly Leu Leu Leu Thr Cys Ser Phe
            740                 745                 750
```

-continued

```
Leu Arg Tyr Pro Leu Ile Leu Trp Ile Thr Val Leu Pro Pro Leu Ser
        755                 760                 765

Glu Leu Ile Pro Leu Ala Ala Ala Glu Arg Pro Ser Ala Ala Ser Gln
    770                 775                 780

Ala Arg Lys Arg Lys Ser Ala Gln Tyr Ala Asn Arg Leu Ser Pro Arg
785                 790                 795                 800

Val Gly Arg Phe Ile Asn Ala Ala Gly Thr Thr Gly Phe Pro Thr Gly
                805                 810                 815

Lys Arg Ala Val Ser Ala Thr Gln Leu Met Val Ser Ser Leu Ile Arg
            820                 825                 830

His Pro Arg Leu Tyr Thr Leu Cys Phe Arg Leu Val Cys Cys Val Glu
        835                 840                 845

Leu Ala Asp Asn Asn Phe Thr Gln Glu Thr Ala Met Thr Met Ile Thr
    850                 855                 860

Pro Ser Ser Arg Gly Ser Phe Leu Gln Lys Pro Arg Pro Pro Lys Lys
865                 870                 875                 880

Pro Pro His Tyr Phe Trp Asn Ser Ser Glu Ala Glu Ala Ala Ser Ala
                885                 890                 895

Ser Ala Ile Lys Lys Ile Ser Gln Pro Trp Gly Gly Glu Trp Ala Glu
            900                 905                 910

Leu Gly Gly Val Arg Gly Gly Met Gly Gly Val Arg Gly Gly Thr Met
        915                 920                 925

Val Ala Asp Leu Arg Cys Met Leu Cys Ile Leu Leu Pro Ala Gly Glu
    930                 935                 940

Pro Gly Asp Phe Pro His Leu Val Ala Asp Leu Arg Cys Met Leu Cys
945                 950                 955                 960

Ile Leu Leu Pro Ala Gly Glu Pro Gly Asp Phe Pro His Pro Asn His
                965                 970                 975

Thr Phe Arg Lys Ile Thr Asp Thr Leu Met Ser Leu Asp Lys Pro Gln
            980                 985                 990

Leu Glu Cys Ser Glu Lys Asn Ala  Leu Phe Val Lys Phe  Val Met Leu
        995                 1000                1005

Leu Leu  Tyr Leu Pro Leu Ala  Ala Ile Asn Lys Leu  Thr Thr Thr
    1010                 1015                 1020

Ile Ala  Phe Ile Leu Cys Phe  Arg Phe Arg Gly Arg  Cys Gly Arg
    1025                 1030                 1035

Phe Phe  Lys Ala Ser Lys Thr  Ser Thr Asn Val Val  Trp Leu Ile
    1040                 1045                 1050

Met Ile  Ser Ser Gln Gly Thr  Ile His Gln Ile Phe  Leu Ile Asn
    1055                 1060                 1065

Pro Phe  Thr Asn Lys Ala Lys  Gly Thr Gln Phe Leu  Ser Ile Val
    1070                 1075                 1080

Ile Asn  Ser Arg His Ser Met  Pro Val Trp Ser Lys  Lys Lys Gln
    1085                 1090                 1095

Tyr Val  Met Ile Ile Thr Val  Met Pro Thr Tyr Lys  Gly Tyr Arg
    1100                 1105                 1110

Ile Phe  Phe His Asn Phe Leu  Val Gln Cys Ser Phe  Phe Leu Cys
    1115                 1120                 1125

Gly Val  Asn Ser Lys Ala Ser  Lys Ser Ser Ile Thr  Lys His Ser
    1130                 1135                 1140

Met Thr  Gln Lys Thr Gln Phe  Arg Lys Val Leu Gly  Val Phe Tyr
    1145                 1150                 1155
```

-continued

```
Leu Ser  Leu Leu Phe Trp Arg  Ser Arg Met Leu Arg  Val Ser Ser
    1160                 1165                 1170

Ser Leu  Ile Ile Thr Arg Trp  His Phe Phe Ala Lys  Gln Val Phe
    1175                 1180                 1185

Leu Ile  Lys Gly Ile Pro Pro  Leu Leu Pro Phe Ile  Ser Ser Ile
    1190                 1195                 1200

Gly Trp  Asn Leu Lys Tyr Thr  Asn Asn Asn Gln Phe  Asn Thr Leu
    1205                 1210                 1215

Tyr Thr  Lys Phe Tyr Ile Tyr  Leu Arg Ala Leu Asn  Leu Cys Arg
    1220                 1225                 1230

Phe Val  Gln Leu Cys His Thr  Thr Glu Val Arg Phe  Leu His Lys
    1235                 1240                 1245

Asp Pro  Leu Ala Arg Asn Pro  Ser Leu Lys Gly Thr  Lys Ala Gly
    1250                 1255                 1260

Ala Pro  Pro Arg Trp Arg Pro  Leu Asn Trp Ile Pro  Arg Ala Ala
    1265                 1270                 1275

Gly Ile  Arg Tyr Gln Ala
    1280
```